United States Patent [19]

Levitt

[11] Patent Number: 4,599,103

[45] Date of Patent: Jul. 8, 1986

[54] AGRICULTURAL UREAS AND ISOUREAS

[75] Inventor: George Levitt, Wilmington, Del.

[73] Assignee: E. I. Du Pont de Nemours and Company, Wilmington, Del.

[21] Appl. No.: 662,444

[22] Filed: Oct. 15, 1984

Related U.S. Application Data

[60] Division of Ser. No. 450,214, Dec. 16, 1982, Pat. No. 4,481,029, which is a continuation-in-part of Ser. No. 196,276, Oct. 22, 1980, abandoned, which is a continuation-in-part of Ser. No. 96,723, Nov. 30, 1979, abandoned.

[51] Int. Cl.$^4$ .................. A01N 47/36; C07D 405/12; C07D 409/12

[52] U.S. Cl. ............................................ 71/90; 71/92; 71/93; 544/182; 544/253; 544/278; 544/310; 544/317; 544/320; 544/321; 544/324; 544/327; 544/331

[58] Field of Search ............... 71/90, 92, 93; 544/320, 544/321, 324, 331, 278, 253, 327, 310, 317, 182

[56] References Cited

U.S. PATENT DOCUMENTS

| | | | |
|---|---|---|---|
| 4,214,890 | 7/1980 | Levitt | 71/90 |
| 4,339,266 | 7/1982 | Levitt | 71/90 |
| 4,441,910 | 4/1984 | Shapiro | 71/90 |

FOREIGN PATENT DOCUMENTS

| | | |
|---|---|---|
| 64804 | 11/1982 | European Pat. Off. |
| 2078728 | 1/1982 | United Kingdom |

*Primary Examiner*—Robert Gerstl

[57] ABSTRACT

This invention relates to ureas and isoureas which are useful as herbicides and plant growth regulants. In particular, compounds of the instant invention have demonstrated great selectivity.

53 Claims, No Drawings

AGRICULTURAL UREAS AND ISOUREAS

CROSS-REFERENCE TO RELATED APPLICATION

This is a division of application Ser. No. 450,214, filed Dec. 16, 1982, now U.S. Pat. No. 4,481,029, which is a continuation-in-part of my copending application U.S. Ser. No. 196,276, filed Oct. 22, 1980 now abandoned which is a continuation-in-part of my copending application U.S. Ser. No. 096,723 filed Nov. 30, 1979 now abandoned.

BACKGROUND OF THE INVENTION

This invention relates to ureas and isoureas and in particular their use as agricultural chemicals and particularly as herbicides.

U.S. Pat. No. 4,127,405 teaches compounds which are useful for controlling weeds in wheat having the formula

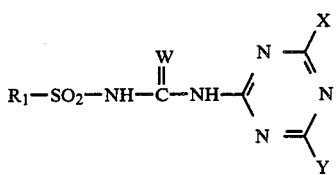

wherein
$R_1$ is

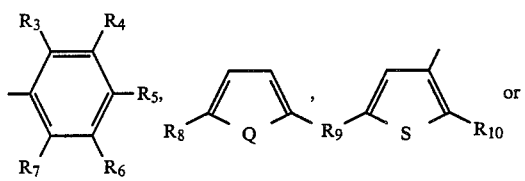

$R_3$ and $R_6$ are independently hydrogen, fluorine, chlorine, bromine, iodine, alkyl of 1-4 carbon atoms, alkoxy of 1-4 carbon atoms, nitro, trifluoromethyl, cyano, $CH_3S(O)_n-$ or $CH_3CH_2S(O)_n-$;

$R_4$ is hydrogen, fluorine, chlorine, bromine or methyl;

$R_5$ is hydrogen, fluorine, chlorine, bromine, methyl or methoxy;

$R_7$ is hydrogen, fluorine, chlorine, bromine, alkyl of 1-2 carbon atoms or alkoxy of 1-2 carbon atoms;

$R_8$ is hydrogen, methyl, chlorine or bromine;

$R_9$ and $R_{10}$ are independently hydrogen, methyl, chlorine or bromine;

W and Q are independently oxygen or sulfur;

n is 0, 1 or 2;

X is hydrogen, chlorine, bromine, methyl, ethyl, alkoxy of 1-3 carbon atoms, trifluoromethyl, $CH_3S-$ or $CH_3OCH_2-$; and Y is methyl or methoxy; or their agriculturally suitable salts; provided that:

(a) when $R_5$ is other than hydrogen, at least one of $R_3$, $R_4$, $R_6$ and $R_7$ is other than hydrogen and at least two of $R_3$, $R_4$, $R_6$ and $R_7$ must be hydrogen;

(b) when $R_5$ is hydrogen and all of $R_3$, $R_4$, $R_6$ and $R_7$ are other than hydrogen, then all of $R_3$, $R_4$, $R_6$ and $R_7$ must be either chlorine or methyl; and (c) when $R_3$ and $R_7$ are both hydrogen, at least one of $R_4$, $R_5$ or $R_6$ must be hydrogen.

French Patent No. 1,468,747 discloses the following para-substituted phenylsulfonamides, useful as antidiabetic agents:

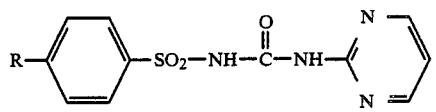

wherein R=H, halogen, $CF_3$ or alkyl.

Logemann et al. chem. Ab., 53, 18052 g (1959), disclose a number of sulfonamides, including uracil derivatives and those having the formula:

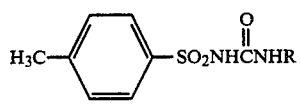

wherein R is butyl, phenyl or

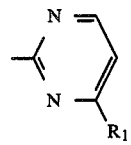

and $R_1$ is hydrogen or methyl. When tested for hypoglycemic effect in rats (oral doses of 25 mg/100 g), the compounds in which R is butyl and phenyl were most potent. The others were of low potency or inactive.

Wojciechowski, J. Acta. Polon. Pharm. 19, p. 121-5 (1962) [Chem Ab., 59 1633 e] describes the synthesis of N-[(2,6-dimethoxypyrimidin-4-yl)aminocarbonyl]-4-methylbenzenesulfonamide:

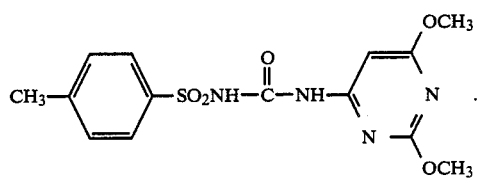

Based upon similarity to a known compound, the author predicted hypoglycemic activity for the foregoing compound.

Netherlands Patent No. 121,788, published Sept. 15, 1966, teaches the preparation of compounds of Formula (i), and their use as general or selective herbicides,

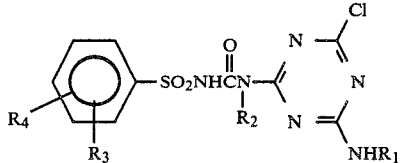

wherein
R₁ and R₂ may independently be alkyl of 1–4 carbon atoms; and
R₃ and R₄ may independently be hydrogen, chlorine or alkyl of 1–4 carbon atoms.

Compounds of Formula (ii), and their use as antidiabetic agents, are reported in *J. Drug. Res.* 6, 123 (1974),

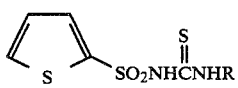

wherein R is pyridyl.

The presence of undesired vegetation causes substantial damage to useful crops, especially agricultural products that satisfy man's basic food needs, such as soybeans, barley, wheat, and the like. The current population explosion and concomitant world food shortage demand improvements in the efficiency of producing these crops. Prevention or minimizing the loss of a portion of such valuable crops by killing, or inhibiting the growth of undesired vegetation is one way of improving this efficiency.

A wide variety of materials useful for killing, or inhibiting (controlling) the growth of undesired vegetation is available; such materials are commonly referred to as herbicides. The need exists, however, for still more effective herbicides that destroy or retard weeds without causing significant damage to useful crops.

SUMMARY OF THE INVENTION

This invention relates to novel compounds of Formulas I, II, and III and their agriculturally suitable salts, suitable agricultural compositions containing them, and methods of using them as selective, as well as general herbicides having both pre-emergence and post-emergence activity. Some of the compounds are especially useful for controlling weeds in crops such as soybeans:

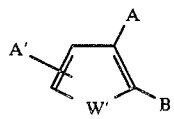

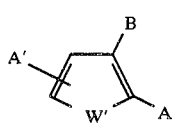

or

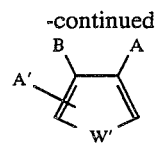

wherein
W' is O or S;
A' is H, Cl, Br, $C_1-C_4$ alkyl, $OCH_3$, $NO_2$ or $CF_3$;
A is

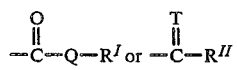

where
Q is O, S or

T is O or

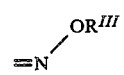

where
$R^{III}$ is H, $C_1-C_4$ alkyl or $C_3-C_4$ alkenyl;
when
Q is O or S then
$R^I$ is $C_1-C_6$ alkyl; $C_3-C_6$ alkenyl; $C_3-C_6$ alkynyl; $C_2-C_6$ alkyl substituted with 1–3Cl, F or Br, or one of CN or $OCH_3$; $C_3-C_6$ alkenyl substituted with 1–3 Cl; $C_3-C_6$ alkynyl substituted with Cl; $C_5-C_6$ cycloalkyl; cyclohexenyl; cyclohexyl substituted with 1–3 $CH_3$; $C_4-C_7$ cycloalkylalkyl or

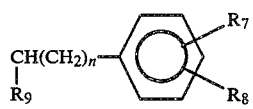

where
$R_7$ and $R_8$ are independently H, Cl, $CH_3$ or $OCH_3$;
n is 0 or 1; and
$R_9$ is H or $CH_3$;
when Q is O then $R^I$ is $CH_2CH_2OR_{15}$; $CH_2CH_2CH_2OR_{15}$;

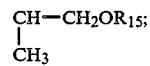

where $R_{15}$ is $C_2H_5$, $CH(CH_3)_2$, phenyl, $CH_2CH_2Cl$, $CH_2CCl_3$; $-CH_2CH_2O-_{n'}R_{16}$,

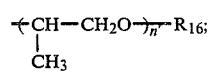

where $R_{16}$ is $CH_3$, $C_2H_5$, $CH(CH_3)_2$, phenyl, $CH_2CH_2Cl$, $CH_2CCl_3$, and n' is 2 or 3; $CH_2CN$;

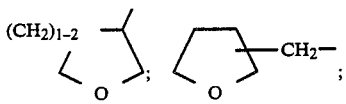
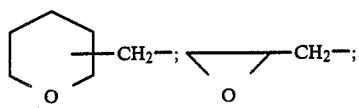

$CH_2OR_6'$; where $R_6'$ is $C_1$-$C_4$ alkyl; provided $R^I$ has a total of $\leq 13$ carbon atoms; when
Q is

then
$R^I$ is H; $C_1$-$C_6$ alkyl; —$CH_2CH_2OR_{10}$; —$CH_2CH_2CH_2OR_{10}$; where $R_{10}$ is $CH_3$, $CH_3CH_2$, $CH(CH_3)_2$, or phenyl; $C_3$-$C_6$ alkenyl; $C_3$-$C_6$ cycloalkyl; $C_5$-$C_6$ cycloalkenyl; $C_6$ cycloalkyl substituted with any one of 1-2 $OCH_3$, 1-3 $CH_3$, —$CH_2CH_3$ or $CF_3$; $C_4$-$C_7$ cycloalkylalkyl;

—$CH_2CN$; —$CH_2CH_2CN$; —C(CH_3)_2—CN; $OCH_3$; $OCH_2CH_3$;

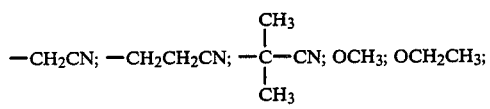

where
R' is H, $C_1$-$C_4$ alkyl, $OCH_3$, F, Cl, Br, CN, $NO_2$ or $CF_3$;
R'' is H, $CH_3$, Cl, F or Br;
$R_7$, $R_8$ and $R_9$ are as previously defined; $R_6$ is H, $C_1$-$C_3$ alkyl; $CH_2CN$; $CH_2CH_2$—CN or —$CH_2$—CH=$CH_2$ and $R_6$ and $R^I$ may be taken together to form —$(CH_2)_4$—, —$(CH_2)_5$— or —$CH_2CH_2O$—$CH_2CH_2$—;
with the proviso that when $R_6$ is $CH_2CH_2CN$ or $CH_2CN$, then $R^I$ is $CH_2CH_2CN$ or $CH_2CN$; and $R^I$ and $R_6$ have a total carbon atom count of $\leq 13$; and when $R^I$ is $OCH_3$ or $OCH_2CH_3$ then $R_6$ is $CH_3$ or H;
when
A is

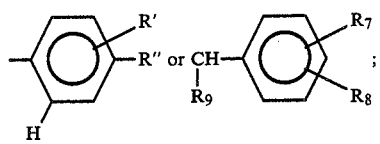

then
$R^{II}$ is H, $C_1$-$C_6$ alkyl; $C_3$-$C_6$ alkenyl; phenyl; benzyl; benzyl or phenyl substituted with 1-2 Cl, 1-2 $OCH_3$, 1-2 $CH_3$; $C_5$-$C_6$ cycloalkyl; $C_4$-$C_7$ cycloalkylalkyl with the proviso that when T is =N—$OR^{III}$, then $R^{II}$ must be $C_1$-$C_6$ alkyl or $C_3$-$C_6$ alkenyl;
B is

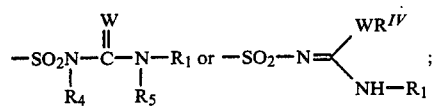

where
$R_4$ is H or $CH_3$; W is O or S;
$R_5$ is H, or $CH_3$; with the proviso that either $R_4$ or $R_5$ must be H;
$R^{IV}$ is $C_1$-$C_6$ alkyl or $C_3$-$C_4$ alkenyl;
$R_1$ is

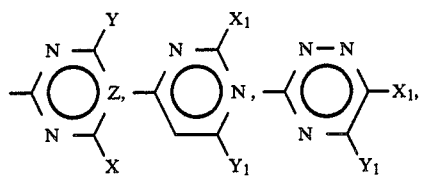

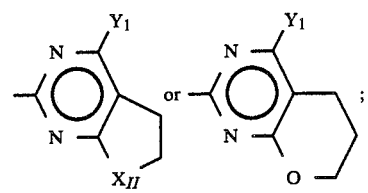

where
Z is N, CH or C—F;
X=H, Cl, —$CH_3$, —$OCH_3$ or —$OCH_2CH_3$;
Y=H; Cl; $C_1$-$C_4$ alkyl; $C_1$-$C_4$ alkyl substituted with —$OCH_3$, —$OC_2H_5$, —CN, —$CO_2CH_3$, —$CO_2C_2H_5$,

or 1-3 atoms of F, Cl, Br; $C_3$-$C_4$ alkenyl;
—O—$(CH_2)_{n'}$O—($C_1$-$C_3$ alkyl) where n' is 2 or 3;

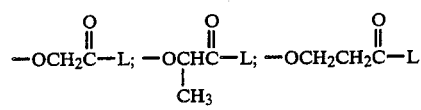

where L is OH, —$NH_2$,

—NH($C_1$-$C_4$ alkyl), —N($C_1$-$C_4$ alkyl)$_2$ or $C_1$-$C_6$ alkoxy; SCN; —$N_3$; $NR_{11}R_{12}$ where $R_{11}$ is H or $CH_3$ and $R_{12}$ is H, —$OCH_3$, $C_1$-$C_4$ alkyl, $C_3$-$C_6$ cycloalkyl, $C_3$-$C_4$ alkenyl, $C_2$-$C_3$ alkyl substituted with $OCH_3$ or $OC_2H_5$, $C_1$-$C_2$ alkyl substituted with —CN, $CO_2H$, $CO_2CH_3$ or $CO_2C_2H_5$, and $R_{11}$ and $R_{12}$ can be taken together to form —$CH_2CH_2CH_2CH_2$— or $CH_2CH_2OCH_2CH_2$—;
—O—$R_9$ where $R_9$ is $C_1$-$C_4$ alkyl, $C_2$-$C_4$ alkyl substituted with 1-3 atoms of F, Cl or Br, $C_1$-$C_2$ alkyl substituted with cyano, $C_3$-$C_4$ alkenyl, —$CH_2C\equiv CR_{13}$,

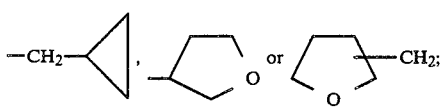

$R_{13}$ is H, $CH_3$ or $CH_2Cl$; $SR_{14}$;
where $R_{14}$ is $C_1-C_4$ alkyl, allyl, propargyl or $C_1-C_2$ alkyl substituted with CN; with the proviso that when X and Y are both H, then $R^I$ and $R^{II}$ are less than 5 carbons;
$X_1$ = H, Cl, $OCH_3$, $OCH_2CH_3$ or $CH_3$;
$Y_1$ = H, $OCH_3$ or $CH_3$; and
$X_{II}$ = O or $CH_2$
and further provided that when A contains greater than 5 carbon atoms, then Y must contain ≦4 carbon atoms, and their agriculturally suitable salts.

Preferred Compounds

Preferred for reasons of higher activity and/or lower cost and/or greater ease of synthesis are compounds:
(1) Of the Generic scope in which B is

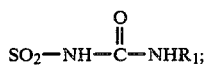

More Preferred and in increasing order for reasons of higher activity and/or even lower cost and/or even greater ease of synthesis are compounds:
(2) Preferred (1) in which W' is sulfur;
(2a) Most Preferred (2) in which T is oxygen;
(3) More Preferred (2a) in which $R_1$ is

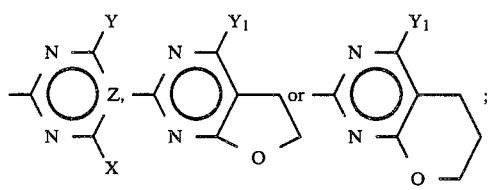

(4) More Preferred (3) where Q is O or S and $R^I$ is $C_1-C_4$ alkyl; $C_3-C_4$ alkenyl; $C_3-C_4$ alkynyl; $C_2-C_3$ alkyl substituted with CN, $OCH_3$ or 1-3 F, Cl or Br; $C_3-C_4$ alkenyl substituted with 1-3 Cl; $C_3-C_4$ alkynyl substituted with Cl;
(5) More Preferred (3) in which Q is oxygen and $R^I$ is $CH_2CH_2OR_{15}$; $CH_2CH_2CH_2OR_{15}$;

$$\begin{array}{c} CHOR_{15} \\ | \\ CH_3 \end{array}$$

where $R_{15}$ is $CH_2CH_3$; $CH_2CN$; $CH_2OR_6'$ where $R_6'$ is $CH_3$ or $CH_3CH_2$;

(6) More Preferred (3) in which Q is

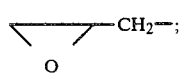

and $R^I$ is H, $C_1-C_4$ alkyl, $CH_2CH_2OR_{10}$, $CH_2CH_2CH_2OR_{10}$ where $R_{10}$ is $CH_3$ or $CH_3CH_2$; $C_3-C_4$ alkenyl; $CH_2CN$; $CH_2CH_2CN$; $OCH_3$ or $OCH_2CH_3$; $R^6$ is H, $C_1-C_2$ alkyl, $CH_2CN$ or $CH_2CH_2CN$ and $R_6$ and $R^I$ can be taken together to form $-CH_2-_4$.
(7) More preferred (3) in which $R^{II}$ is H or $C_1-C_3$ alkyl;
(8) More preferred (4), (5), (6) and (7) in which
Z is CH or N;
X is $CH_3$ or $CH_3O$; and
Y is $C_1-C_2$ alkyl; $C_1-C_2$ alkyl substituted with $OCH_3$; $OCH_2CH_3$, CN or 1-3 atoms of F, Cl or Br;

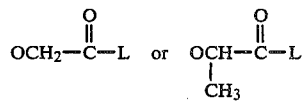

where L is $NH_2$, OH,

$N(CH_3)_2$, $NHCH_3$, $C_1-C_2$ alkoxy; SCN; $N_3$; $NR_{11}R_{12}$ where $R_{11}$ is H or $CH_3$; $R_{12}$ is H, $CH_3$, $CH_3CH_2$, $OCH_3$; $OR_9$ where $R_9$ is $CH_3$, $CH_3CH_2$; $CH_2CH=CH_2$ or $CH_2C\equiv CH$; $R_9$ is also $C_2$ alkyl substituted with 1-3 F, Cl or Br; $CH_3S$;
(9) More Preferred (3) in which A' is H, Cl or Br;
(10) More Preferred (9) in which Q is O or S and $R^I$ is $C_1-C_4$ alkyl, $CH_2CH=CH_2$ or $CH_2CH_2Cl$;
(11) More Preferred (9) in which Q is O and $R^I$ is $CH_2CH_2OCH_3$, $$\begin{array}{c} CH-OCH_3 \\ | \\ CH_3 \end{array}$$

$CH_2OCH_3$ or $CH_2OCH_2CH_3$;
(12) More Preferred (9) in which Q is

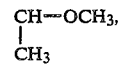

and $R^I$ is H, $C_1-C_3$ alkyl, $OCH_3$ or $OCH_2CH_3$ and $R_6$ is H or $C_1-C_2$ alkyl;
(13) More Preferred (9) in which $R^{II}$ is H or $CH_3$;
(14) More Preferred (10), (11), (12) and (13) in which A' is H; Y is $CH_3$, $OCH_3$, $OCH_2CH_3$, $OCH_2CF_3$, $OCH_2CH=CH_2$ or $OCH_2C\equiv CH$;
(15) More Preferred (8) in which A is

and Q is oxygen or sulfur and $R^I$ is $CH_3$ or $CH_2CH_3$;
Q is

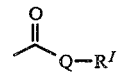

and $R^I$ is H, $CH_3$ or $OCH_3$ and $R_6$ is $CH_3$;
$R_1$ is

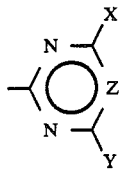

and Y is $CH_3$ or $OCH_3$;

(16) More Preferred (15) of Formula I;
(17) More Preferred (15) of Formula II;
(18) More Preferred (15) of Formula III.

Equally More Preferred in increasing order and for reasons of higher activity and/or even lower cost and/or even greater ease of synthesis are:

(19) Compounds of Preferred 1 in which W' is oxygen;

(20) Compounds of More Preferred (19) in which T is oxygen;

(21) More Preferred (20) in which $R_1$ is

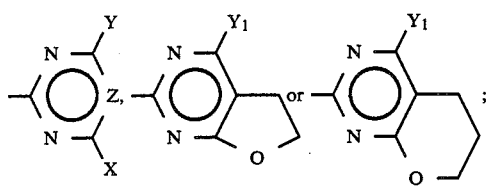

(22) More Preferred (21) where Q is O or S and $R_1$ is $C_1$-$C_4$ alkyl; $C_3$-$C_4$ alkenyl; $C_3$-$C_4$ alkynyl; $C_2$-$C_3$ alkyl substituted with CN, $OCH_3$ or 1-3 F, Cl or Br; $C_3$-$C_4$ alkenyl substituted with 1-3 Cl; $C_3$-$C_4$ alkynyl substituted with Cl;

(23) More Preferred (21) in which Q is oxygen and $R^I$ is $CH_2CH_2OR_{15}$; $CH_2CH_2CH_2OR_{15}$;

$$\begin{array}{c} CHOR_{15} \\ | \\ CH_3 \end{array}$$

where $R_{15}$ is $CH_2CH_3$; $CH_2CN$; $CH_2OR_6'$ where $R_6'$ is $CH_3$ or $CH_3CH_2$;

(24) More Preferred (21) in which Q is

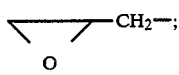

and $R^I$ is H, $C_1$-$C_4$ alkyl, $CH_2CH_2OR_{10}$, $CH_2CH_2CH_2OR_{10}$ where $R_{10}$ is $CH_3$ or $CH_3CH_2$; $C_3$-$C_4$ alkenyl; $CH_2CN$; $CH_2CH_2CN$; $OCH_3$ or $OCH_2CH_3$; $R^6$ is H, $C_1$-$C_2$ alkyl, $CH_2CN$ or $CH_2CH_2CN$ and $R_6$ and $R^I$ can be taken together to form $-CH_2-_4$.

(25) More Preferred (21) in which $R^{II}$ is H or $C_1$-$C_3$ alkyl;

(26) More Preferred (22), (23), (24) and (25) in which Z is CH or N;
X is $CH_3$ or $CH_3O$; and
Y is $C_1$-$C_2$ alkyl; $C_1$-$C_2$ alkyl substituted with $OCH_3$; $OCH_2CH_3$, CN or 1-3 atoms of F, Cl or Br;

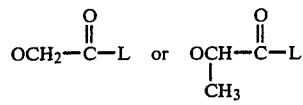

where L is $NH_2$, OH,

$N(CH_3)_2$, $NHCH_3$, $C_1$-$C_2$ alkoxy; SCN; $N_3$; $NR_{11}R_{12}$ where $R_{11}$ is H or $CH_3$; $R_{12}$ is H, $CH_3$, $CH_3CH_2$, $OCH_3$; $OR_9$ where $R_9$ is $CH_3$, $CH_3CH_2$, $CH_2CH=CH_2$ or $CH_2C\equiv CH$; $R_9$ is also $C_2$ alkyl substituted with 1-3 F, Cl or Br; $CH_3S$;

(27) Preferred (21) in which A' is H, Cl or Br;
(28) More Preferred (27) in which Q is O or S and $R^I$ is $C_1$-$C_4$ alkyl, $CH_2CH=CH_2$ or $CH_2CH_2Cl$;
(29) More Preferred (27) in which Q is O and $R^I$ is $CH_2CH_2OCH_3$, $$\begin{array}{c} CH-OCH_3, \\ | \\ CH_3 \end{array}$$

$CH_2OCH_3$ or $CH_2OCH_2CH_3$;

(30) More Preferred (27) in which Q is

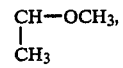

and $R^I$ is H, $C_1$-$C_3$ alkyl, $OCH_3$ or $OCH_2CH_3$ and $R_6$ is H or $C_1$-$C_2$ alkyl;

(31) More Preferred (27) in which $R^{II}$ is H or $CH_3$;
(32) More Preferred (28), (29), (30) and (31) in which A' is H; Y is $CH_3$, $OCH_3$, $OCH_2CH_3$, $OCH_2CF_3$, $OCH_2CH=CH_2$ or $OCH_2C\equiv CH$;

(33) More Preferred (27) in which A is

and Q is oxygen or sulfur and $R^I$ is $CH_3$ or $CH_2CH_3$;
Q is

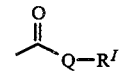

and $R^I$ is H, $CH_3$ or $OCH_3$ and $R_6$ is $CH_3$;
$R_1$ is

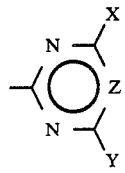

and Y is $CH_3$ or $OCH_3$;
(34) More Preferred (33) of Formula I;
(35) More Preferred (33) of Formula II;
(36) More Preferred (33) of Formula III.

Specifically Preferred for reasons of highest activity and/or lowest cost and/or greatest ease of synthesis are:

methyl 3-[[(4,6-dimethoxypyrimidin-2-yl)aminocarbonyl]aminosulfonyl]-2-thiophenecarboxylate
methyl 3-[[(4,6-dimethylpyrimidin-2-yl)aminocarbonyl]aminosulfonyl]-2-thiophenecarboxylate
methyl 3-[[(4-methoxy-6-methylpyrimidin-2-yl)aminocarbonyl]aminosulfonyl]-2-thiophenecarboxylate
methyl 3-[[(4,6-dimethoxy-1,3,5-triazin-2-yl)aminocarbonyl]aminosulfonyl]-2-thiophenecarboxylate
methyl 3-[[(4,6-dimethyl-1,3,5-triazin-2-yl)aminocarbonyl]aminosulfonyl]-2-thiophenecarboxylate
methyl 3-[[(4-methoxy-6-methyl-1,3,5-triazin-2-yl)aminocarbonyl]aminosulfonyl]-2-thiophenecarboxylate
methyl 3-[[(4,6-dimethoxypyrimidin-2-yl)aminocarbonyl]aminosulfonyl]-2-furancarboxylate
methyl 3-[[(4,6-dimethylpyrimidin-2-yl)aminocarbonyl]aminosulfonyl]-2-furancarboxylate
methyl 3-[[(4-methoxy-6-methylpyrimidin-2-yl)aminocarbonyl]aminosulfonyl]-2-furancarboxylate
methyl 3-[[(4,6-dimethoxy-1,3,5-triazin-2-yl)aminocarbonyl]aminosulfonyl]-2-furancarboxylate
methyl 3-[[(4,6-dimethyl-1,3,5-triazin-2-yl)aminocarbonyl]aminosulfonyl]-2-furancarboxylate
methyl 3-[[(4-methoxy-6-methyl-1,3,5-triazin-2-yl)aminocarbonyl]aminosulfonyl]-2-furancarboxylate
methyl 2-[[(4,6-dimethoxypyrimidin-2-yl)aminocarbonyl]aminosulfonyl]-3-thiophenecarboxylate
methyl 2-[[(4,6-dimethylpyrimidin-2-yl)aminocarbonyl]aminosulfonyl]-3-thiophenecarboxylate
methyl 2-[[(4-methoxy-6-methylpyrimidin-2-yl)aminocarbonyl]aminosulfonyl]-3-thiophenecarboxylate
methyl 2-[[(4,6-dimethoxy-1,3,5-triazin-2-yl)aminocarbonyl]aminosulfonyl]-3-thiophenecarboxylate
methyl 2-[[(4,6-dimethyl-1,3,5-triazin-2-yl)aminocarbonyl]aminosulfonyl]-3-thiophenecarboxylate
methyl 2-[[(4-methoxy-6-methyl-1,3,5-triazin-2-yl)aminocarbonyl]aminosulfonyl]-3-thiophenecarboxylate
methyl 2-[[(4,6-dimethoxypyrimidin-2-yl)aminocarbonyl]aminosulfonyl]-3-furancarboxylate
methyl 2-[[(4,6-dimethylpyrimidin-2-yl)aminocarbonyl]aminosulfonyl]-3-furancarboxylate
methyl 2-[[4-methoxy-6-methylpyrimidin-2-yl)aminocarbonyl]aminosulfonyl]-3-furancarboxylate
methyl 2-[[(4,6-dimethoxy-1,3,5-triazin-2-yl)aminocarbonyl]aminosulfonyl]-3-furancarboxylate
methyl 2-[[(4,6-dimethyl-1,3,5-triazin-2-yl)aminocarbonyl]-aminosulfonyl]-3-furancarboxylate
methyl 2-[[(4-methoxy-6-methyl-1,3,5-triazin-2-yl)aminocarbonyl]aminosulfonyl]-3-furancarboxylate
N-[(4-methoxy-6-methylpyrimidin-2-yl)aminocarbonyl]-2-(1-pyrrolidinylcarbonyl)-3-thiophenesulfonamide
1-methylethyl 3-[[(4,6-dimethoxypyrimidin-2-yl)aminocarbonyl]aminosulfonyl]-2-thiophenecarboxylate
2-propenyl 3-[[(4-methoxy-6-methylpyrimidin-2-ylaminocarbonyl]aminosulfonyl]-2-thiophenecarboxylate
1-methylethyl 3-[[(4-methoxy-6-methylpyrimidin-2-yl)aminocarbonyl]aminosulfonyl]-2-thiophenecarboxylate.

Novel Intermediates

Also novel and useful for the preparation of compounds of Formulas I, II and III are compounds of Formulas I', II' and III'.

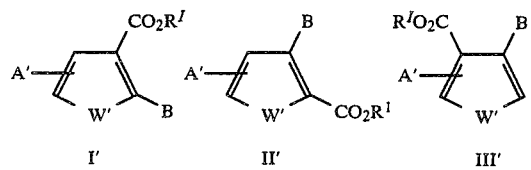

wherein
$R^I$ is H or M;
M is a cation of an alkalii metal or of a tertiary amine of up to 12 carbon atoms;
A', W', B, are as previously defined.

Preferred and in increasing order for reasons of lower cost and/or greater ease of synthesis and/or higher activity of derived compounds are those intermediate (1) Compounds of formulas I', II' and III' in which W' is is sulfur, B is SO$_2$NHCONHR$_1$, A' is H, Cl or Br and R$_1$ is

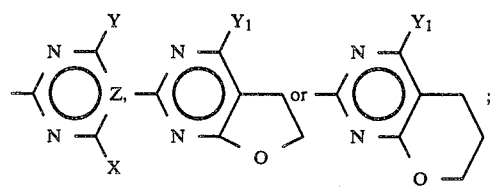

(2) Compounds of Preferred (1) in which X is CH$_3$ or OCH$_3$; Y is CH$_3$, OCH$_3$, OCH$_2$CH$_3$, OCH$_2$CF$_3$, OCH$_2$CH=CH$_2$ or OCH$_2$—C≡C—H; Z is CH or N;

(3) Compounds of Preferred (2) in which Y is CH$_3$ or OCH$_3$; R$_1$ is

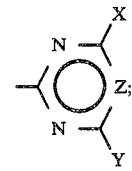

A' is H;
(4) Compounds of Preferred (3) of Formula I';
(5) Compounds of Preferred (4) of Formula II';
(6) Compounds of Preferred (5) of Formula III';

Equally Preferred in increasing order, for reasons of lower cost and/or greater ease of synethesis and/or higher activity of derived compound are those intermediate:

(7) Compounds of formulas I', II' and III' in which W' is oxygen; B is SO$_2$NHCONHR$_1$, A' is H, Cl or Br, and R$_1$ is

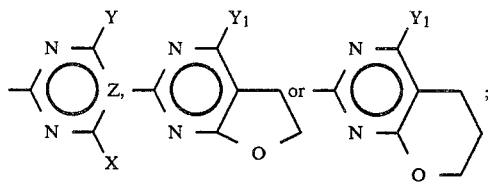

(8) Compounds of Preferred (7) in which X is CH₃ or OCH₃; Y is CH₃, OCH₃, OCH₂CH₃, OCH₂CF₃, OCH₂CH=CH₂ or OCH₂C≡C—H; and Z is CH or N;

(9) Compounds of Preferred (8) in which Y is CH₃ or OCH₃; R₁ is

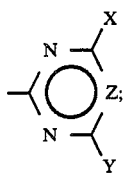

A' is H;

(10) Compounds of Preferred (9) of Formula I';
(11) Compounds of Preferred (9) of Formula II';
(12) Compounds of Preferred (9) of Formula III';

Specifically Preferred for reasons of lowest cost and/or greatest ease of synthesis and/or highest activity of desired compounds are:

3-[[(4,6-dimethoxypyrimidin-2-yl)aminocarbonyl]aminosulfonyl]-2-thiophenecarboxylic acid
3-[[(4,6-dimethylpyrimidin-2-yl)aminocarbonyl]aminosulfonyl]-2-thiophenecarboxylic acid
3-[[(4-methoxy-6-methylpyrimidin-2-yl)aminocarbonyl]aminosulfonyl]-2-thiophenecarboxylic acid
3-[[(4,6-dimethoxy-1,3,5-triazin-2-yl)aminocarbonyl]aminosulfonyl]-2-thiophenecarboxylic acid
3-[[(4,6-dimethyl-1,3,5-triazin-2-yl)aminocarbonyl]aminosulfonyl]-2-thiophenecarboxylic acid
3-[[(4-methoxy-6-methyl-1,3,5-triazin-2-yl)aminocarbonyl]aminosulfonyl]-2-thiophenecarboxylic acid
3-[[(4,6-dimethoxypyrimidin-2-yl)aminocarbonyl]aminosulfonyl]-2-furancarboxylic acid
3-[[(4,6-dimethylpyrimidin-2-yl)aminocarbonyl]aminosulfonyl]-2-furancarboxylic acid
3-[[(4-methoxy-6-methylpyrimidin-2-yl)aminocarbonyl]aminosulfonyl]-2-furancarboxylic acid
3-[[(4,6-dimethoxy-1,3,5-triazin-2-yl)aminocarbonyl]aminosulfonyl]-2-furancarboxylic acid
3-[[(4,6-dimethyl-1,3,5-triazin-2-yl)aminocarbonyl]aminosulfonyl]-2-furancarboxylic acid
3-[[(4-methoxy-6-methyl-1,3,5-triazin-2-yl)aminocarbonyl]aminosulfonyl]-2-furancarboxylic acid
2-[[(4,6-dimethoxypyrimidin-2-yl)aminocarbonyl]aminosulfonyl]-3-thiophenecarboxylic acid
2-[[(4,6-dimethylpyrimidin-2-yl)aminocarbonyl]aminosulfonyl]-3-thiophenecarboxylic acid
2-[[(4-methoxy-6-methylpyrimidin-2-yl)aminocarbonyl]aminosulfonyl]-3-thiophenecarboxylic acid
2-[[(4,6-dimethoxy-1,3,5-triazin-2-yl)aminocarbonyl]aminosulfonyl]-3-thiophenecarboxylic acid
2-[[(4,6-dimethyl-1,3,5-triazin-2-yl)aminocarbonyl]aminosulfonyl]-3-thiophenecarboxylic acid
2-[[(4-methoxy-6-methyl-1,3,5-triazin-2-yl)aminocarbonyl]aminosulfonyl]-3-thiophenecarboxylic acid
2-[[(4,6-dimethoxypyrimidin-2-yl)aminocarbonyl]aminosulfonyl]-3-furancarboxylic acid
2-[[(4,6-dimethylpyrimidin-2-yl)aminocarbonyl]aminosulfonyl]-3-furancarboxylic acid
2-[[(4-methoxy-6-methylpyrimidin-2-yl)aminocarbonyl]aminosulfonyl]-3-furancarboxylic acid
2-[[(4,6-dimethoxy-1,3,5-triazin-2-yl)aminocarbonyl]aminosulfonyl]-3-furancarboxylic acid
2-[[(4,6-dimethyl-1,3,5-triazin-2-yl)aminocarbonyl]aminosulfonyl]-3-furancarboxylic acid
2-[[(4-methoxy-6-methyl-1,3,5-triazin-2-yl)aminocarbonyl]aminosulfonyl]-3-furancarboxylic acid Also novel and useful for the preparation of compounds of Formulas I, II and III are compounds of Formulas I'', II'' and III''

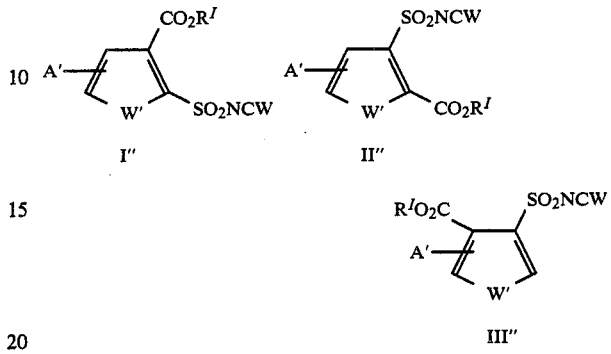

wherein
W is oxygen or sulfur;
W' is oxygen or sulfur;
A' is H, Cl, Br, C₁–C₄ alkyl, OCH₃, NO₂ or CF₃;
R^I is C₁–C₆ alkyl; C₃–C₆ alkenyl; C₃–C₆ alkynyl; C₂–C₆ alkyl substituted with Cl, CN or OCH₃; C₃–C₆ alkenyl substituted with 1–3 Cl; C₃–C₆ alkynyl substituted with Cl; C₅–C₆ cycloalkyl; cyclohexenyl; cyclohexyl substituted with 1–3 CH₃; C₄–C₇ cycloalkylalkyl or

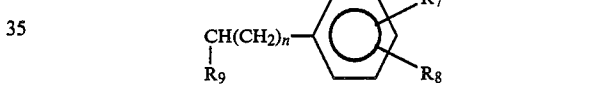

where R₇ and R₈ are independently H, Cl, CH₃ or OCH₃;
n is 0 or 1; and
R₉ is H or CH₃; CH₂CH₂OR₁₅, CH₂CH₂CH₂OR₁₅,

where R₁₅ is C₂H₅, CH(CH₃)₂, phenyl, CH₂CH₂Cl, CH₂CCl₃; —CH₂CH₂O—ₙ, R₁₆,

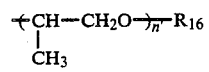

where R₁₆ is CH₃, C₂H₅, CH(CH₃)₂, phenyl, CH₂CH₂Cl, CH₂CCl₃, and n' is 2 or 3; CH₂CN;

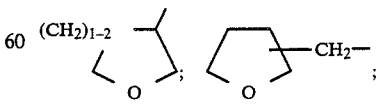

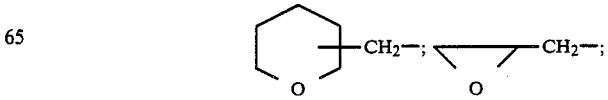

$CH_2OR_6'$; where $R_6'$ is $C_1$–$C_4$ alkyl; provided $R^J$ has a total of $\leq 13$ carbon atoms.

Preferred in increasing order for reasons of lower cost and/or greater ease of synthesis and/or higher activity of desired compounds are those intermediate:

(1) Compounds of formulas I″, II″ and III″ in which W′ is sulfur; W is oxygen; A′ is H, Cl or Br; and $R^J$ is $C_1$–$C_4$ alkyl; $CH_2CH=CH_2$; or $CH_2CH_2Cl$; $CH_2CH_2OCH_3$; or

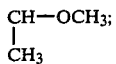

(2) Compounds of Preferred (1) in which $R^J$ is $CH_3$ or $CH_2CH_3$; $A^J$ is H;

(3) Compounds of Preferred (2) of Formula I″;
(4) Compounds of Preferred (2) of Formula II″;
(5) Compounds of Preferred (2) of Formula III″.

Equally Preferred in increasing order for reasons of lower cost and/or greater ease of synthesis and/or higher activity of derived compounds are those intermediate:

(6) Compounds of formulas I″, II″, and III″ in which W′ is oxygen; W is oxygen; A′ is H, Cl or Br;

(7) Compounds of Preferred (6) in which $R^J$ is $CH_3$ or $CH_2CH_3$; $A^J$ is H;

(8) Compounds of Preferred (7) of Formula I″.
(9) Compounds of Preferred (7) of Formula II″.
(10) Compounds of Preferred (7) of Formula III″.

Specifically Preferred for reasons of lowest cost and/or greatest ease of synthesis and/or highest activity of desired compounds are:

methyl 3-(isocyanatosulfonyl)-2-thiophenecarboxylate
methyl 2-(isocyanatosulfonyl)-3-thiophenecarboxylate
methyl 4-(isocyanatosulfonyl)-3-thiophenecarboxylate
methyl 3-(isocyanatosulfonyl)-2-furancarboxylate
methyl 2-(isocyanatosulfonyl)-3-furancarboxylate
methyl 4-(isocyanatosulfonyl)-3-furancarboxylate Synthesis Many of the compounds of Formulas I–III are prepared as shown in Equation 3 by the reaction of an appropriately substituted alkoxycarbonylthiophene or furan sulfonylisocyanate or sulfonylisothiocyanate with an appropriate aminopyrimidine or aminotriazine. These compounds of Formulas I–III can be converted to other compounds of Formulas I–III as will be shown in subsequent equations.

The novel sulfonylisocyanates are important intermediates for the preparation of the compounds of this invention. Their synthesis is described in Equations 1 and 2.

Equation 1

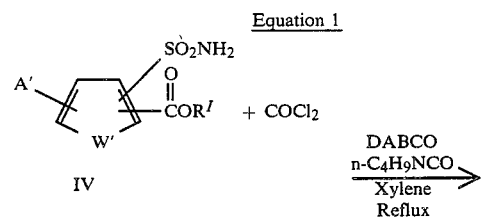

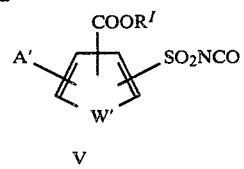

A mixture of the appropriate sulfonamide, e.g. an 2-alkoxycarbonyl-3-thiophene sulfonamide IV such as the methyl ester, which is known in the art, an alkyl isocyanate such as butyl isocyanate and a catalytic amount of 1,4-diaza[2.2.2]bicyclooctane (DABCO) in xylene or other inert solvent of sufficiently high boiling point (e.g. >135°) is heated to approximately 130°–150° C. Phosgene is added to the mixture until an excess of phosgene is present as indicated by a drop in the boiling point. After the mixture is cooled and filtered to remove a small amount of insoluble by-products, the solvent and alkyl isocyanate are distilled off in-vacuo leaving a residue which is the crude sulfonyl isocyanate V. In Equation 1, A′, W′ and $CO_2R^J$ are as defined previously for structures I″, II″ and III″.

The novel sulfonylisothiocyanate intermediates of Formula $V^a$, prepared according to Equations 2 and 2′, are useful for the preparation of compounds of Formulas I–III where W=S.

Equation 2

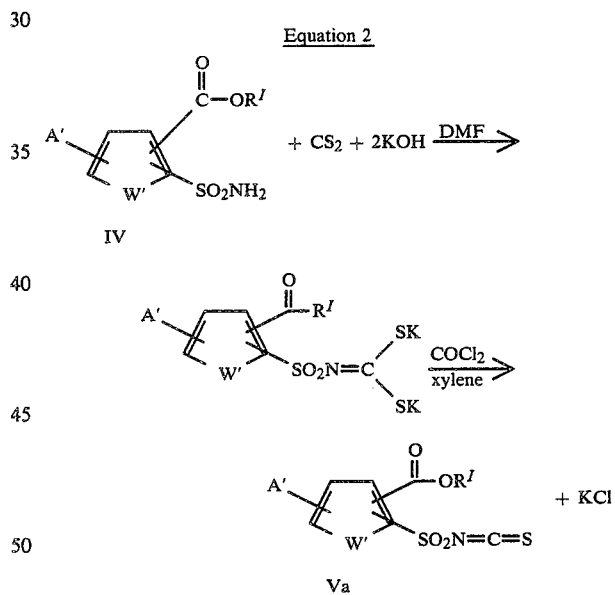

The alkoxycarbonyl substituted sulfonamide is dissolved in dimethylformamide (DMF) with an equivalent amount of carbon disulfide and two equivalents of potassium hydroxide are added portionwise at room temperature. The mixture is stirred for 1–8 hours and diluted with ethylacetate, ethyl ether or similar aprotic solvent to cause the dipotassium salt of the dithiocarbamic acid to precipitate. The salt is isolated, dried and suspended in an inert solvent such as xylene, benzene, carbon tetrachloride or methylene chloride. Phosgene is added to the stirred suspension at below room temperature and the mixture stirred for 1–3 hours. In place of phosgene, a chloroformic ester (e.g. methyl chloroformate), phosphorous pentachloride, sulfuryl chloride or thionyl chloride can be used.

The sulfonylisothiocyanate which is formed is usually soluble in the solvent and is isolated by filtering off the insoluble potassium chloride and concentrating the filtrate. These isothiocyanates tend to be unstable and dimerize readily, (Equation 2') however, the dimers can be used Alternate routes to prepare sulfonylisothiocyanates are described by M. O. Lozinskii et al. in Organic Compounds: Reactions and Methods, Ed. by B. A. Kazanskii et al., Vol 22, p 188–197, Plenum Press, 1973 (Engl. Trans.)

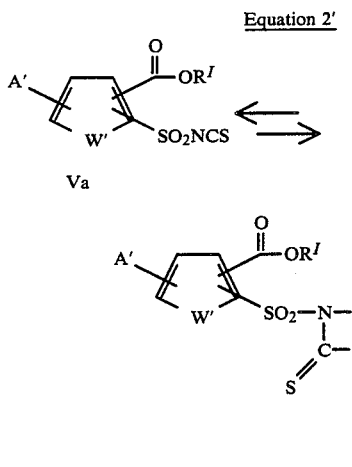

Equation 2' in the same manner as the present isothiocyanates for the purposes of this invention.

The synthetic method chosen for the preparation of compounds of Formulas I–III depends largely on the substituents $QR^I$ and $R_4$. As shown in Equation 3, compounds of Formulas I–III wherein $R^I$ or A' are as defined for Equation 1, are conveniently prepared by reacting an appropriately substituted carbonyl thiophene or furan sulfonyl isocyanate or isothiocyanate of Formula V with an appropriately substituted aminopyrimidine or aminotriazine of Formula VI:

Equation 3

The reaction of Equation 3 is best carried out in inert aprotic organic solvents such as methylene chloride, tetrahydrofuran or acetonitrile, at ambient pressure and temperature. The mode of addition is not critical; however, it is often convenient to add the sulfonyl isocyanate or isothiocyanate to a stirred suspension of amine VI. Since such isocyanates and isothiocyanates are liquids, low melting solids or are readily soluble in solvents such as those listed above, their addition can be easily controlled.

The reaction is generally exothermic. In some cases, the desired product is soluble in the warm reaction medium and on cooling crystallizes in pure form. Other products which are soluble in the reaction medium are isolated by evaporation of the solvent, trituration of the solid residue with solvents such as 1-chlorobutane or ethyl ether, and filtration.

As shown in Equation 4, compounds of Formulas I–III, wherein W is S, A and A' are as previously defined and $R_5$ is H, are altervatively prepared by the reaction of an appropriately substituted thiophene or furan sulfonamide with the appropriate triazine or pyrimidine isothiocyanate of Formula VIa.

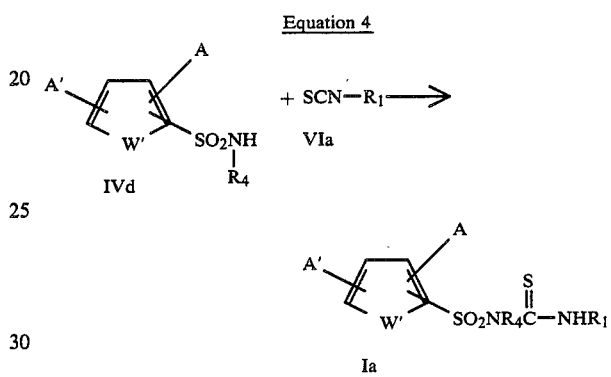

Equation 4

The reaction of Equation 4 is best carried out by dissolving or suspending the sulfonamide and isothiocyanate in a polar solvent such as acetone, acetonitrile, ethyl acetate or methylethylketone, adding an equivalent of a base such as potassium carbonate and stirring the mixture at a temperature from ambient up to the reflux temperature for one to twenty-four hours. In some cases, the product precipitates from the reaction mixture and can be removed by filtration. The product is stirred in dilute mineral acid, filtered and washed with cold water. If the product does not precipitate from the reaction mixture, it can be isolated by evaporation of the solvent, trituration of the residue with dilute mineral acid and filtering off the insoluble product.

The heterocyclic isothiocyanates which are used in the procedure of Equation 4 are prepared, for example, according to the method of Japan patent application Pub: Kokai No. 51-143686, June 5, 1976, or that of W. Abraham and G. Barnikow, Tetrahedron 29, 691–7 (1973).

As shown in Equation 5, compounds of Formulas I–III, wherein A, A', $R_1$, W', and $R_5$ are as defined previously, and W is O, can be prepared by methylation of salts VII wherein M is an alkali metal cation such as sodium (derived from compounds of Formulas I–III wherein $R_4$ is hydrogen):

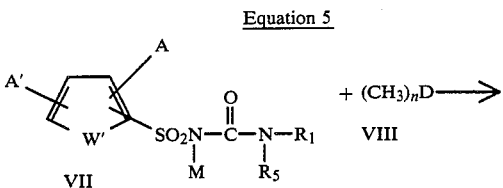

Equation 5

-continued

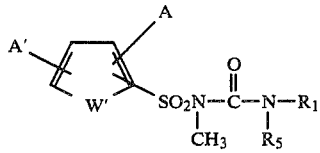

D being an incipient anion and n being an integer corresponding to the valence of D.

The reaction of Equation 5 is best carried out in aprotic organic solvents such as tetrahydrofuran, dimethylformamide, or dimethylacetamide, at ambient pressure and temperature. Methylating agents VIII such as dimethyl sulfate or methyl iodide, can be employed. The desired product can be isolated by pouring the reaction mixture into water and filtering off the precipitated solid.

As shown in Equation 6, compounds of Formulas I-III wherein A, A', $R_1$, W', and $R_5$ are as defined for Equation 5, and W is O or S, can also be prepared by the reaction of an appropriately substituted sulfonyl-N-methylcarbamyl chloride or sulfonyl-N-methylthiocarbamyl chloride of Formula IX with an appropriate aminopyrimidine or aminotriazine of Formula VI;

Equation 6

The preparation of ureas and thioureas, like those of Formula Ic, from amines and carbamyl chlorides and thiocarbamyl chlorides is well known to the art. The reaction can best be carried out by adding equivalent amounts of chloride IX and amine VI to an inert organic solvent, such as tetrahydrofuran, xylene, or methylene chloride, in the presence of an acid acceptor, such as triethylamine, pyridine, or sodium carbonate employing temperatures from 20°-130°. Soluble products can be isolated by filtering off the precipitated salts and concentration of the filtrate. Insoluble products can be filtered off and washed free of salts with water.

The chlorides of Formula IX can be prepared by phosgenation or thiophosgenation of N-methylsulfonamide salts. The sulfonamide salt is added to an excess of phosgene or thiophosgene in an inert organic solvent, such as tetrahydrofuran, toluene, or xylene, whereupon, after removal of the excess phosgene, the chloride IX can be isolated or reacted in situ with the amine VI.

The esters of Formulas I-III hydrolyze to the parent acid as shown in Equation 7. Alkali metal base catalyzed hydrolysis in aqueous methanol produces the alkali metal carboxylate from which the carboxylic acid is obtained by treatment with mineral acids such as HCl:

Equation 7

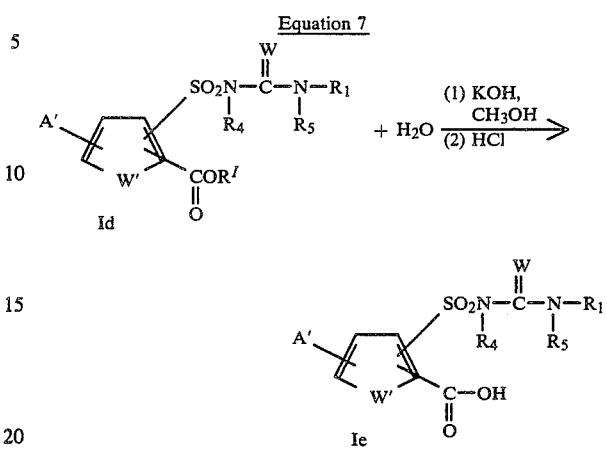

The reaction of Equation 7 is best carried out in a solution containing the compound being hydrolyzed, 2 to 10 parts of methanol, 10-50 parts of water and 2-10 equivalents of a base such as sodium or potassium hydroxide maintaining the temperature at 30°-90° C. for 3-24 hours. The reaction yields the soluble alkali metal salt of the carboxylic acid, which is suitable for the purposes of this invention. Conversion of these salts to the acid form is easily carried out by addition to the reaction medium of strong mineral acids, such as hydrochloric or sulfuric acid, causing the desired carboxylic acids to precipitate from solution.

The acids of Formula Ie prepared as in Equation 7 wherein W is O can be converted to compounds of this invention where $R^I$ is a higher alkyl or substituted hydrocarbyl group, as already disclosed herein, by the reaction of salts of the parent acid with $R^I$-halogen as shown in Equation 8.

Equation 8

The reaction of Equation 8 is of use where the intermediate compound $R^I$-halogen contains a readily replaceable halogen as is the case for substituted or unsubstituted allylic or benzylic halides, α-halonitriles, or α-halocarbonyl compounds.

The procedure of Equation 8 is best carried out in inert polar solvents such as tetrahydrofuran, acetonitrile or acetone by combining the appropriately substituted carboxylic acid and base such as triethylamine 1,4-diaza[2,2,2]bicyclooctane adding the appropriate halide and heating the mixture to reflux with stirring for 1 to 16 hours. The reaction mixture can be evaporated to dryness and the residue triturated with water, filtered and washed with water to separate the desired product from the water soluble salt.

The procedure of Equation 8 can also be used for the synthesis of compounds wherein $R^I$-halogen of Equation 8 is of a less reactive species than described above. In these cases, the silver salt of the carboxylic acid is used rather than the amine salt. The silver salt which is precipitated by adding silver nitrate to an aqueous solution of the sodium salt of the acid of Formula Ie is combined with the appropriate $R^I$-halide using the same solvents and conditions as shown above for the amine salt.

When Q is $NR_6$, the compounds can be prepared from the esters of this invention where $R^I$ is $C_1$-$C_4$ (preferably $C_1$) by the reaction of the esters with dialkylaluminum-N-alkylamide derivatives according to Equation 9; $R^I$, A', W', $R_1$, $R_4$, $R_5$ and $R_6$ being as previously defined.

Equation 9

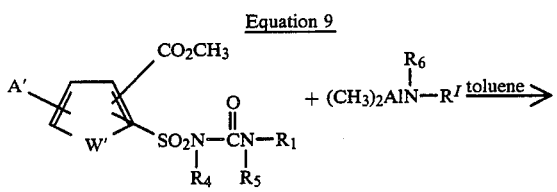

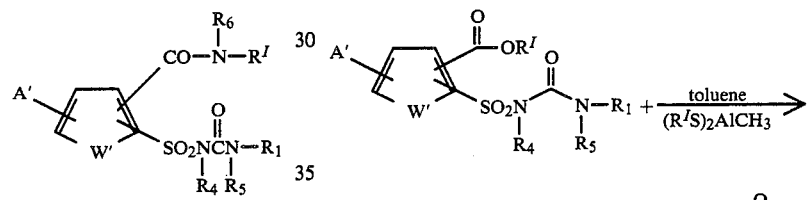

The intermediate alkylaminoaluminum compounds prepared according to A. Basha, M. Lipton and S. W. Weinreb, *Tetrahedron Letters* 4171 (1977), are comingled with a suspension of the esters in toluene or similar inert solvent and the mixture is refluxed for one to six hours. The product can be isolated by evaporation of the solvent, addition of methylene chloride and aqueous hydrochloric acid to decompose the residual reaction mass and extracting the desired product into methylene chloride. Evaporation of the methylene chloride yields the desired product in sufficiently pure form for the purpose of this invention.

Compounds of Formula X, wherein Q is $$\begin{array}{c} R^I \\ | \\ NR_6, \end{array}$$

A', W' and $R_4$ are as previously defined in the general formula, which are useful as intermediates in Equation 4, are prepared as shown in Equation 10.

Equation 10

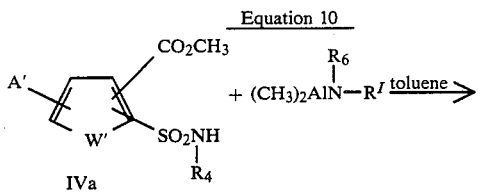

-continued

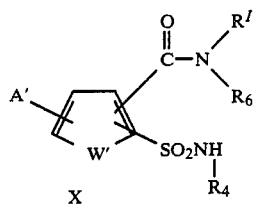

The conditions described for Equation 8 are suitable for the conversion of the esters of Formula IVa to the carboxamides as shown in Equation 10.

The products of Equation 10 are especially useful for the preparation of compounds of Formulas I-III wherein Y has an ester substituent $CO_2(C_1$-$C_6)$, by the route described in Equation 4.

When Q is S, these compounds can be prepared from the esters of this invention wherein $QR^I$ is $O(C_1$-$C_4$ alkyl) (preferably $C_1$) by the reaction of the esters with the appropriate dialkylaluminum alkylthiolate according to Equation 11.

Equation 11

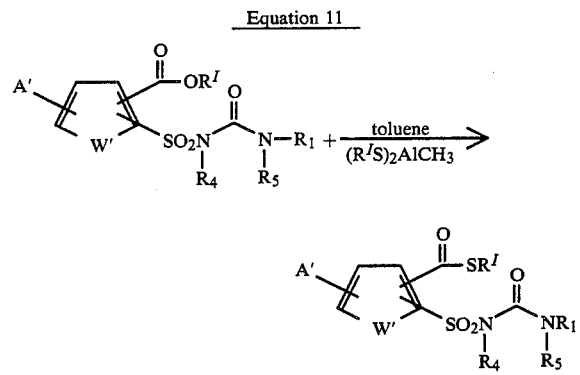

The intermediate aluminum thiolates can be prepared according to R. P. Hatch and S. W. Weinreb, *Journal of Organic Chemistry*, Vol. 42, 3960 (1977). The reaction of the thiolate with the ester of this invention is best carried out in a neutral solvent such as toluene or xylene at reflux for one to three hours. Best results are obtained when the aluminum thiolate compound is present in excess of the stoichiometric amount required.

Sulfonamides of Formula IVc are also converted from carboxylic acid esters to the thiolesters as shown in Equation 12 according to the method of R. P. Hatch and S. W. Weinreb as described for Equation 11 wherein $R^I$, A', W' and $R_4$ are as previously defined.

Equation 12

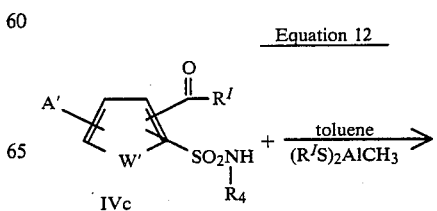

-continued

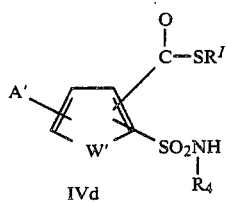
IVd

The conditions described for Equation 11 are suitable for the conversion of the sulfonamides of Formula IVc as shown in Equation 12.

The products obtained by the procedure of Equation 12 are especially useful for the preparation of compounds of formulas I–III where Y has a substituent ($CO_2C_1$–$C_6$) by the route described for Equation 4 and Q=S.

An alternate route to prepare compounds where $R^I$ is bonded to Q (Q=O) at a secondary carbon involves the reaction of the appropriate dialkylaluminum alcoholate and an ester of this invention wherein $R^I$ is a lower primary alkyl group, preferably methyl, according to Equation 13.

Equation 13

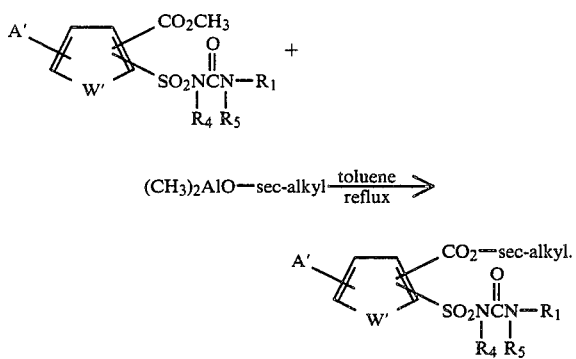

The reaction is carried out in a neutral solvent such as toluene with a boiling point sufficiently high to bring about the desired reaction during reflux. The dialkylaluminum alcoholate being present in greater than an equivalent amount to the ester for best yields. After refluxing for 1–15 hours, the reaction mixture is decomposed with dilute hydrochloric acid and the product extracted into methylene chloride. Evaporation of the methylene chloride yields the desired compound sufficiently pure for the purposes of this invention. The product can be triturated with a solvent, e.g. 1-chlorobutane to remove impurities.

Ketones wherein A is

and A', W', W, $R_1$, $R_4$ and $R_5$ are as defined by the scope of this invention, are prepared according to Equation 14, from the carboxylic acids of Formula Ie whose preparation is described in Equation 7.

Equation 14

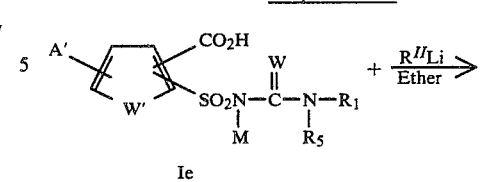
Ie

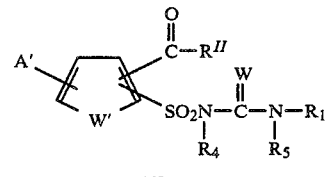
XI

The reaction of an organolithium compound with a carboxylic acid to yield a ketone as in Equation 14 is described in the work of H. Gilman and P. R. Van Ess, JACS, 55, 1258 (1933); H. Gilman, W. Langham and F. W. Moore, ibid., 62 (1940); C. Tegner, Chem. Scand., 6, 782 (1952); J. F. Arens and D. A. Van Dorp, Rec. Trav., 65 338 (1946); 66, 759 (1947); C. H. Depuy, G. M. Dappen, K. L. Eilers and R. A. Klein, J. Org., 29, 2813 (1964).

An excess of the organolithium compound in a suitable solvent such as diethyl ether, hexane, pentane or benzene is added to a solution or slurry of XI in a similar solvent at temperatures between $-100°$ and $0°$ C. The mixture is allowed to warm to room temperature and stir for 30 minutes. Aqueous acid is then added and the ketosulfonamide extracted into a suitable solvent to free it from salts followed by evaporation of the solvent.

The synthesis of a wide variety of organolithium compounds by many different procedures is known in the art. A summary of methods with bibliography is contained in Organo-Metallic Compounds, G. E. Coates, John Wiley and Sons, 1960, p. 3–21.

Oximes of the ketones of Formula XI, for example, can be prepared from the appropriate hydroxylamine derivative, wherein $R^{III}$ is as previously defined, and the ketone of Formula XI according to Equation 15.

Equation 15

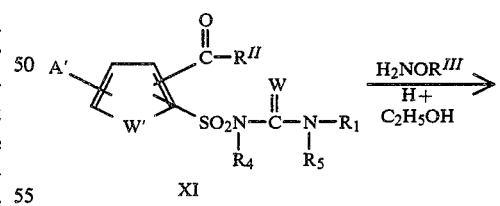
XI

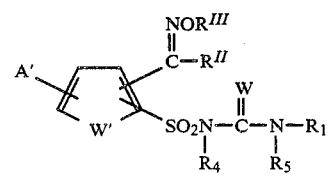

A procedure such as that described in Preparative Organic Chemistry by G. Hilgetag and A. Martini, Ed., John Wiley and Sons, p. 513 is suitable for the preparation of the oximes of this invention.

Compounds of Formulas I–III wherein B is $$\underset{\mid}{SO_2-N=C-NH-R_1}^{WR^{IV}}$$

and W is O, are prepared by the sequence of reactions shown in Equation 16.

Equation 16

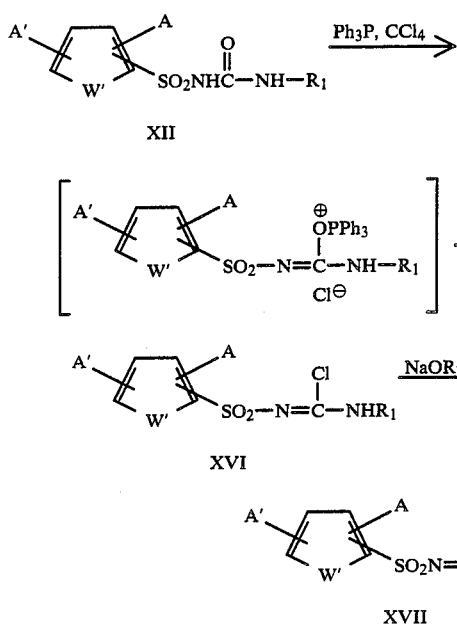

The compounds of Formula XVII are prepared by adding an appropriate carbon tetrahalide to a solution of a compound of Formula XII and triphenyl phosphine in an inert aprotic solvent such as acetonitrile at about $-10°$ to 25° and stirring at the designated temperature for 10 to 48 hours. The carbamimidoyl halides of Formula XVI thus formed may be isolated by passing the reaction solution through a silica gel column to remove the triphenyl phosphine oxide and removal of the solvent by evaporation under reduced pressure.

The compounds of Formula XVI can be converted to the corresponding compounds of Formula XVII by treating reaction mixture with a metal alkoxide, NaO-$R^{III}$, at $-10°$ to 25° and stirring at ambient temperature for 2 to 24 hours. The crude products of Formula XVII are isolated by filtering off the precipitated metal halide and removing the solvent by evaporation under reduced pressure. Further purification may be accomplished by recrystallization or by column chromatography over silica gel.

It will be understood that the compounds of Formula XVI are not necessarily converted directly to the compounds of Formula XVII, but may first form the carbodiimides of Formula XVIII.

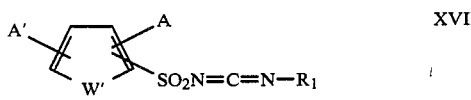

XVIII

Many compounds, particularly compounds in which the heterocyclic moiety is pyrimidinyl, may be prepared by the sequence of reactions shown in Equation 17.

Equation 17

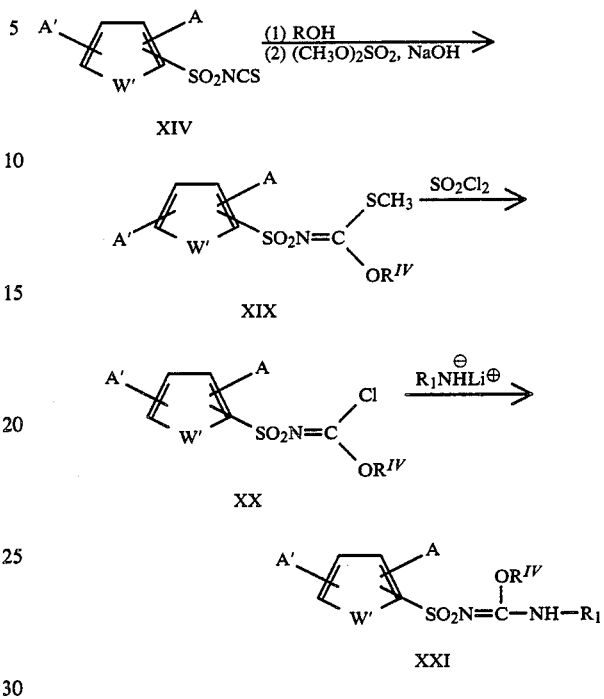

The compounds of Formula XIX are prepared according to the procedure or R. Gompper and W. Hägele in Chemische Berichte 99, 2885–2899 (1966).

The compounds of Formula XX are prepared from the compounds of Formula XIX with sulfuryl chloride in an inert organic solvent such as methylene chloride or chloroform at temperatures between $-10°$ and 80°. They are isolated by removing the solvent under reduced pressure, and can be used without further purification.

The compounds of Formula XXI are prepared in the following manner: The lithium salt of the appropriate aminoheterocycle is prepared from the aminoheterocycle with n-butyl lithium in a solvent such as tetrahydrofuran. To this salt solution is added the compound of Formula XX in tetrahydrofuran at a temperature of about $-10°$ to 10°. The reaction mixture is then stirred at about 0°–10° for ½–2 hours and at ambient temperature for ½–4 hours. The products of Formula XXI are isolated by filtering off the inorganic salts and removing the solvent under reduced pressure. Further purification can be done by recrystallization or by column chromatography on silica gel using a suitable eluent such as ethyl acetate.

As shown in Equation 18, the compounds of Formula XXIV, wherein

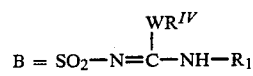

and W=S can be prepared by reacting an appropriately substituted carbamimidothioic acid salt of Formula XXII with an alkylating agent of Formula XXIII.

Equation 18

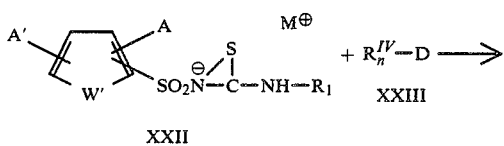

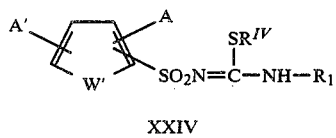

wherein D is a sulfate or halogen, such as Cl, Br or I; M is an alkali or alkaline earth metal, and n is an integer corresponding to the valence of D.

The reaction is best carried out in inert aprotic organic solvents such as tetrahydrofuran or diethyl ether at temperatures between 25° and 100° C. and ambient pressure. The mode of addition is not critical; however, it is often convenient to add the alkylating agent in solution to a stirred suspension of the salt of Formula XXII. The product is isolated by evaporation of the solvent and can be purified by recrystallization from a solvent such as acetonitrile or ethanol.

The metal salts of Formula XXII can be prepared by treating the corresponding sulfonylthiourea with a solution of an alkali metal or alkaline earth metal salt having an anion sufficiently basic to the proton (e.g. hydroxide, alkoxide, carbonate or hydride).

When Z is N, the preferred procedure for the preparation of compounds of Formula XXIV is that shown in Equation 19.

Equation 19

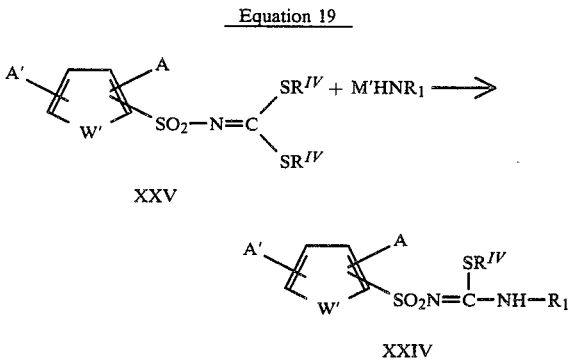

A compound of Formula XXV is treated with an alkali metal (M') salt of the appropriately substituted heterocyclic amine at temperatures of 0° to 100° C. in a solvent such as dimethylformamide, dimethylsulfoxide or an ethereal solvent, such as tetrahydrofuran.

Compounds of Formula XXV can be prepared according to the procedure of Chem. Ber. 99, 2885 (1966).

Compounds of Formulas I-III wherein Y of group $R_1$ contains

and L is OH can be prepared according to the procedure of Equation 20 wherein A', W', X, $R_4$, W and $R_5$ are as defined previously; and Q' is $C_1$-$C_4$ alkyl, $OCH_2$, $OCH_2CH_2$, $$\begin{array}{ccc} OCH, & N, & \text{or } NCH_2 \\ | & | & | \\ CH_3 & R_{11} & R_{11} \end{array}$$

where $R_{11}$ is as previously defined.

Equation 20

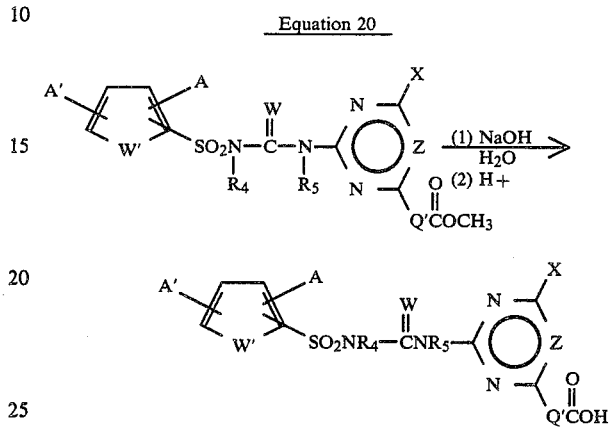

The reaction of Equation 20 is best carried out by suspending the compound being hydrolyzed in 10 to 100 parts of water with enough of a base such as sodium hydroxide or potassium hydroxide to obtain a pH 10 to 14, ideally a pH of 12, heating until a clear solution is obtained and then adjusting the pH to 1–3, preferably 3. The product is thus caused to precipitate in some instances and can be removed by filtration or it can be extracted into a polar organic solvent such as methylene chloride and isolated by evaporation of the solvent.

Thiophene derivatives with sulfamoyl and alkoxycarbonyl substituents on adjacent carbon atoms are prepared by the methods taught by O. Hromatka and D. Binder, U.S. Pat. No. 4,028,373 and P. A. Rossy et al., U.S. Pat. No. 4,143,050. The analogous furan derivatives are prepared similarly or as taught in Belgian Pat. No. 871,772.

Alternate methods of preparation of thiophene and furan sulfonamides with alkoxycarbonyl substituents adjacent to the sulfonamide are preferable in certain circumstances. For example, if one of the α-carbons is not substituted, chlorosulfonation of a furan or thiophene may give the undesired substituted sulfonyl chloride or a mixture of isomers. Regiospecific introduction of substituents may be achieved in many cases via ring metalation reactions. The use of such reactions has been reviewed by H. Gschwend and H. Rodriguez in "Organic Reactions", Vol. 26 (John Wiley & Sons, Inc., New York, 1979). Using these methods, the 2-lithio-3-furancarboxylates or -thiophenecarboxylates may be generated from the corresponding acid and two equivalents of an alkyllithium in an inert, aprotic solvent such as an ether solvent. These intermediates are described in

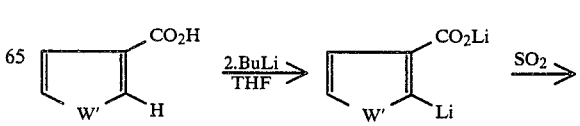

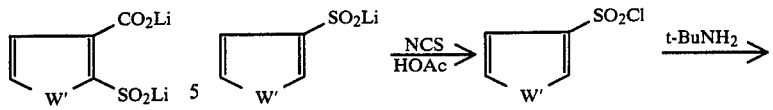

Tetrahedron Letters 5051 (1980) and references therein. Treatment of these organolithium species with sulfur dioxide afford the corresponding 2-sulfinate-3-carboxylate salts which are conveniently isolated by evaporation of the solvent. The lithium sulfinates are converted to the sulfonamides by reaction with an excess of chloramine in aqueous solution and isolated by acidification and extraction

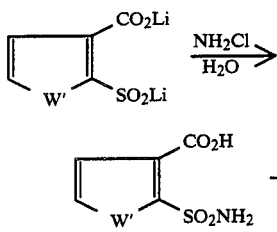

into an organic solvent. Esterification of the resulting acids under standard conditions (e.g., methanol, sulfuric acid catalyst, 25°–65° C., 1–24 h) yield the appropriate alkoxycarbonyl sulfonamides.

Other isomeric furan and thiophene sulfonamides may be prepared through a sequence of these metalation reactions as shown below. The reaction of 3-bromofurans or -thiophenes with alkyllithium reagents at low temperatures (preferably below −40°) in an aprotic, inert solvent afford the corresponding 3-lithiofurans and -thiophenes via halogen-metal exchange. These may be quenched with sulfur dioxide to yield the 3-sulfinic acid salts. They may be subsequently

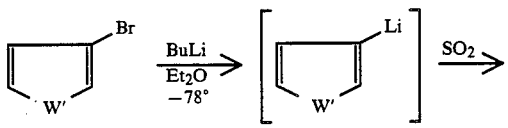

converted to sulfonyl chlorides with a chlorinating agent, conveniently with a reagent such as N-chlorosuccinimide (NCS) in a suitable solvent such as acetic acid, preferably at ambient temperature. The

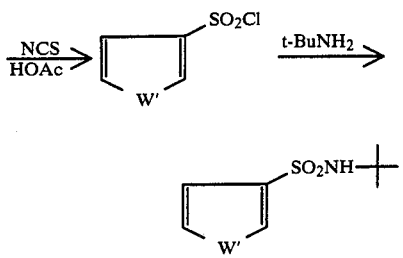

3-t-butylsulfonamide is then prepared upon reaction of the sulfonyl chloride with excess t-butylamine. Reaction of the sulfonamide with

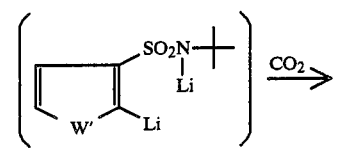

two equivalents of an alkyllithium, as described above for the 3-carboxylic acids, yield specifically the 2-lithio intermediates which are quenched with carbon dioxide to afford the 2-carboxylic acid salts. Esterification of the carboxylic acid and removal of the t-butyl group may be accomplished in one reaction by heating the above products in an alcohol solvent with acid catalyst (e.g. methanol, sulfuric acid).

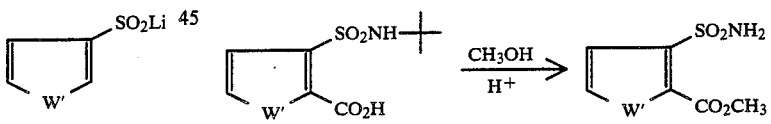

For 3,4-disubstituted furan and thiophene sulfonamides, a modification of the above sequence is appropriate. A 4-bromo-3-t-butylsulfamoylthiophene or furan intermediate may be prepared by the methods outlined above beginning with the 3,4-dibromo compound. Reaction of these sulfonamides with

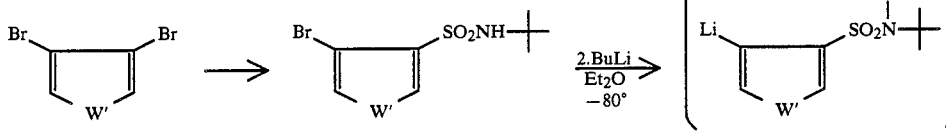

-continued

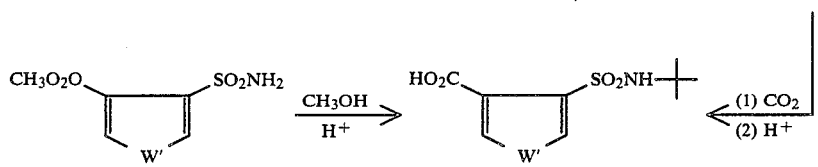

two equivalents of alkyllithium in preferably an ether solvent at low temperature (preferably less than −40°) will afford the 3-lithio species via halogen-metal exchange. These may be subsequently quenched with carbon dioxide to yield the carboxylic acids which are then converted to the free sulfonamideesters as outlined above for the 2,3-disubstituted isomers.

Compounds of structure XXIX wherein A is an aldehyde group and A' does not equal —NO₂ are prepared by the procedure of Equation 21.

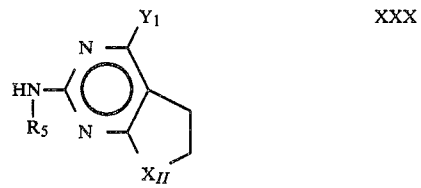

XXX

Braker, Sheehan, Spitzmiller and Lott, *J. Am. Chem.*

Equation 21

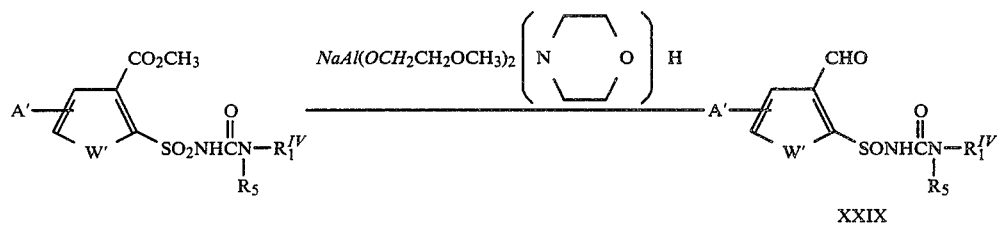

XXIX

Following the procedure of R. Kanazawa and T. Tokoroyama, *Synthesis*, 526 (1976), a solution of sodium bis-(2-methoxyethoxy)aluminum hydride in THF is reacted with one equivalent of morpholine. To this solution at −40° C. is added a methyl ester of Formula XXVIII and the solution is allowed to warm to 25° C. The product is isolated by addition of aqueous acid and extraction into ether or methylene chloride. Evaporation of the solvent and crystallization or column chromatography on silica gel affords the aldehyde XXX.

Aldehydes of Formula XXX may also be prepared from the esters of treatment with diisobutylaluminum hydride according to the procedures of E. Winterfeldt, *Synthesis*, 617 (1975).

Compounds of Formulas I, II and III may also be prepared by the reaction of the appropriately substituted thiophene or furan sulfonamides with the appropriate heterocyclic isocyanate using the methods described in co-pending applications U.S. Ser. No. 098,725 and U.S. Ser. No. 098,722, filed Nov. 30, 1979.

The synthesis of heterocyclic amines has been reviewed in "The Chemistry of Heterocyclic Compounds" a series published by Interscience Publ., New York and London. 2-Aminopyrimidines are described by D. J. Brown in The Pyrimidines, Vol. XVI of this series. The 2-amino-1,3,5-triazines are reviewed by K. R. Huffman and in The Triazines of this same series. The synthesis of triazines are also described by F. C. Schaefer, U.S. Pat. No. 3,154,547 and by K. R. Huffman and F. C. Schaeffer, J. Org. Chem. 28, 1816–1821 (1963).

The preparation of the aminoheterocycles described by Formula XXX varies according to the definition of Y₁ and X$_{II}$.

*Soc.* 69, 3072 (1947) describe the preparation of 6,7-dihydro-4-methoxy-5H-cyclopentapyrimidin-2-amine by the following sequence of reactions.

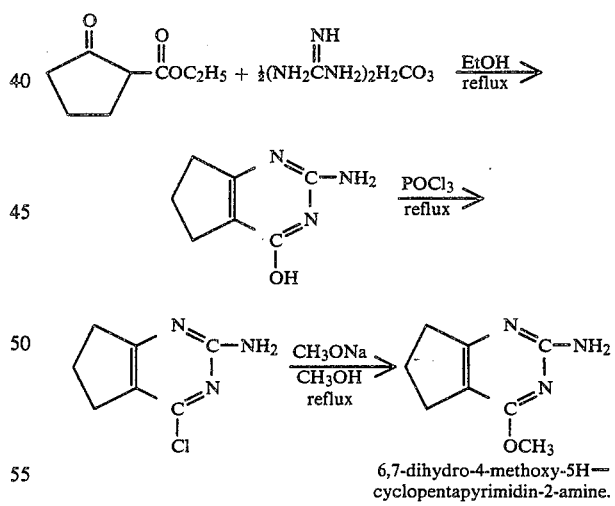

6,7-dihydro-4-methoxy-5H—cyclopentapyrimidin-2-amine.

Similarly, 6,7-dihydro-4-methyl-5H-cyclopentapyrimidin-2-amine can be prepared by the condensation of 2-acetylcyclopentanone with guanidine carbonate, but preferably under acidic conditions, removing the water formed.

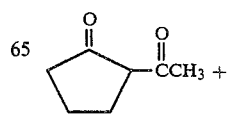

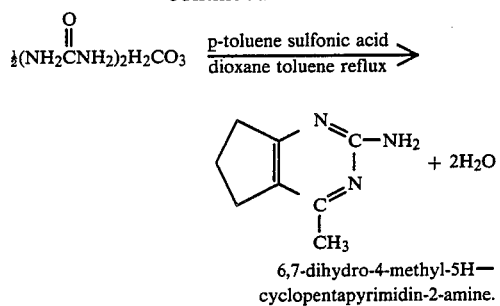

6,7-dihydro-4-methyl-5H—
cyclopentapyrimidin-2-amine.

Shrage and Hitchings, *J. Org. Chem.* 16, 1153 (1951) describe the preparation of 5,6-dihydro-4-methyl-furo[2,3-d]pyrimidin-2-amine by the following sequence of reactions.

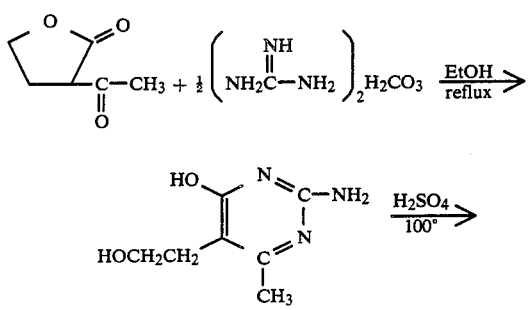

5,6-Dihydro-4-methoxyfuro[2,3-d]pyrimidin-2-amine can be prepared by the method of Braker et al. *J. Am. Chem. Soc.* 69, 3072 (1947), using 5,6-dihydro-4-hydroxyfuro[2,3-d]pyrimidin-2-amine [Svab, Budesinski and Vavrina, *Collection Czech. Chem. Commun.* 32, 1582 (1967)].

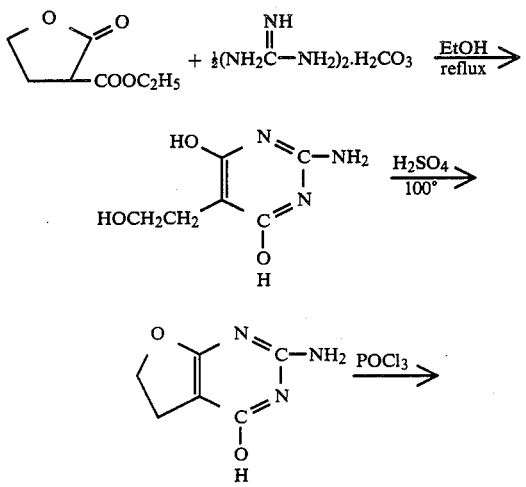

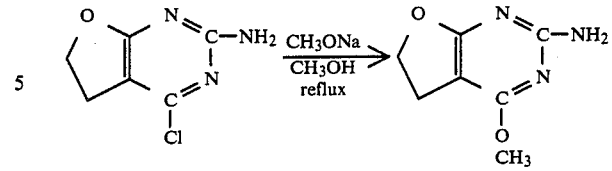

Caldwell, Kornfeld and Donnell, *J. Am. Chem. Soc.* 63, 2188 (1941), describe the preparation of 6,7-dihydro-5H-cyclopentapyrimidin-2-amine by the following sequence of reactions.

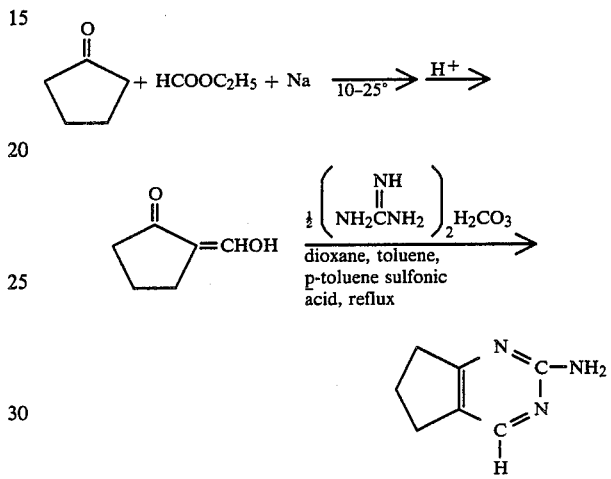

Fissekis, Myles and Brown, *J. Org. Chem.* 29, 2670 (1964), describe the preparation of 2-amino-4-hydroxy-5-(2-hydroxyethyl)pyrimidine which can be converted to 5,6-dihydrofuro[2,3-d]pyrimidin-2-amine by dehydration.

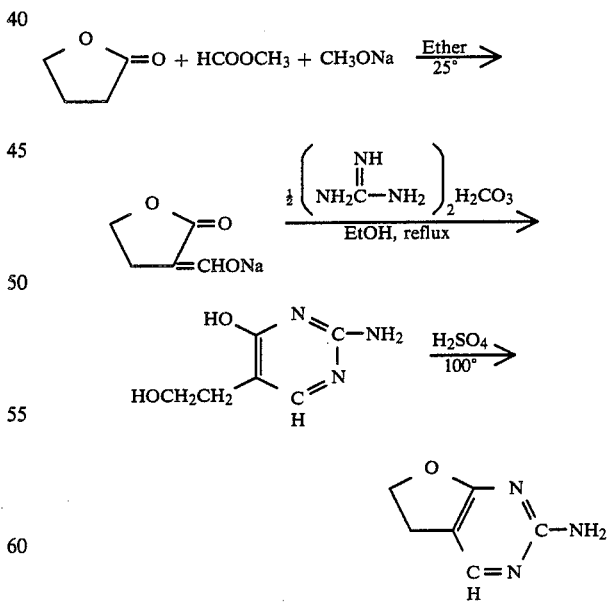

Agriculturally suitable salts of compounds of Formulas I–III are also useful herbicides and can be prepared by a number of ways known to the art. For example, metal salts can be made by treating compounds of Formulas I–III with a solution of alkali or alkaline earth metal salt having a sufficiently basic anion (e.g., hydroxide, alkoxide, carbonate or hydride). Quaternary amine salts can be made by similar techniques.

Salts of compounds of Formulas I–III can also be prepared by exchange of one cation to another. Cationic exchange can be effected by direct treatment of an aqueous solution of a salt of a compound of Formulas I–III (e.g., alkali metal or quuaternary amine salt) with a solution containing the cation to be exchanged. This method is most effective when the desired salt containing the exchanged cation is insoluble in water, e.g., a copper salt, and can be separated by filtration.

Exchange may also be effected by passing an aqueous solution of a salt of a compound of Formulas I–III (e.g., an alkali metal or quaternary amine salt) through a column packed with a cation exchange resin containing the cation to be exchanged. In this method, the cation of the resin is exchanged for that of the original salt and the desired product is eluted from the column. This method is particularly useful when the desired salt is water soluble, e.g., a potassium, sodium or calcium salt.

Acid addition salts, useful in this invention, can be obtained by reacting a compound of Formulas I–III with a suitable acid, e.g., p-toluenesulfonic acid, trichloroacetic acid or the like.

The compounds of this invention and their preparation are further illustrated by the following examples wherein temperatures are given in degrees centigrade.

The desired product is underscored at the top of each example.

EXAMPLE 1

2-Methoxycarbonyl-3-thiophenesulfonyl isocyanate

A mixture containing 22.1 g of methyl-3-sulfamoyl-thiophene-2-carboxylate, 9.9 g of n-butyl isocyanate, 0.3 g of 1,4-diaza[2,2,2]bicyclooctane and 150 ml of dry xylene was placed in a 4 neck round bottom flask equipped with a gas inlet tube, mechanical stirrer, thermometer and dry ice cooled reflux condenser. This mixture was heated to 135° C. and phosgene was passed into the flask so that after several minutes, the reflux temperature dropped to 120°. The phosgene addition was halted until the temperature rose to 130° and then additional phosgene was added to cause the temperature to drop again to 120°. The phosgene addition cycle was repeated until the reflux temperature of the reaction mixture remained at 120° with no further phosgene addition.

Cooling the reaction mixture caused a small amount of a precipitate to form which was removed by filtration and the filtrate was concentrated in-vacuo to yield an oil which showed a strong absorption peak in the infrared region at 2200 cm$^{-1}$ consistent for the desired sulfonyl isocyanate. This highly reactive intermediate was used without further purification.

EXAMPLE 2

Methyl 3-[[(4,6-dimethylpyrimidin-2-yl)aminocarbonyl-]aminosulfonyl]-2-thiophenecarboxylate To 1.23 g of 2-amino-4,6-dimethyl pyrimidine in 30 ml of anhydrous acetonitrile was added with stirring 2.7 g of 2-methoxycarbonyl-3-thiophenesulfonylisocyanate. The mixture was heated to the boiling point, whereupon all of the insoluble material dissolved and the mixture was allowed to cool. After stirring for two hours the mixture was filtered to remove the desired product which had precipitated as a white solid. After washing with anhydrous ethyl ether the product melted at 191°–193° with decomposition and showed absorption peaks by nuclear magnetic resonance at 3.8 ppm for the methxy group, 2.44 ppm for the two methyl groups on the pyrimidine ring, a peak at 7.0 consistent for the hydrogen in the pyrimidine ring and a peak at 7.42 for the hydrogens on the thiophene ring. The infrared absorption spectrum showed absorption peaks at 1720 and 1700 cm$^{-1}$ consistent for the two carbonyl groups present in the desired product.

EXAMPLE 3

Methyl 3[[(4,6-dimethoxypyrimidin-2-yl)aminocarbonyl-]aminosulfonyl]-2-thiophenecarboxylate To 1.5 g of 2-amino-4,6-dimethoxypyrimidine in 30 ml of anhydrous acetonitrile was added 2.7 g of 2-methoxycarbonyl-3-thiophenesulfonyl isocyanate with stirring at ambient temperature. All of the solid reactant dissolved and after twenty minutes of stirring a precipitate started to form. After two hours the mixture was filtered and the solid which was washed with anhydrous ethyl ether, melted at 191°–193°. The solid showed peaks by nuclear magnetic resonance spectroscopy at 4.0 ppm and 3.8 ppm for the methoxy groups, 6.0 ppm for the H of pyrimidine and 7.6 ppm for the hydrogens on thiophene. The infrared absorption spectrum showed absorption peaks at 1730 and 1700 cm$^{-1}$ consistent for the two carbonyl peaks in the desired product.

EXAMPLE 4

Methyl 3-[[(4-methoxy-6-methylpyrimidin-2-yl)aminocarbonyl-]aminosulfonyl]-2-thiophenecarboxylate To 1.4 g of 2-amino-4-methoxy-6-methylpyrimidine in 30 ml of anhydrous acetonitrile was added at ambient temperature, with stirring 3.6 g of 2-methoxycarbonyl-3-thiophenesulfonylisocyanate. The mixture was heated to the boiling point and then allowed to cool to ambient temperature. After stirring for sixteen hours the precipitate present in the mixture was filtered off and washed with anhydrous ethyl ether. The product thus obtained which melted at 165°–173° showed absorption peaks by infrared spectroscopy at 1720 and 1700 cm$^{-1}$, consistent for the carbonyl groups in the desired product.

EXAMPLE 5

Methyl 3-[[(4,6-dimethyl-1,3,5-triazin-2-yl)aminocarbonyl-]aminosulfonyl]-2-thiophenecarboxylate To 1.23 g of 2-amino-4,6-dimethyl-1,3,5-triazine in 30 ml of anhydrous methylene chloride was added with stirring 2.7 g of 2-methoxycarbonyl-3-thiophenesulfonylisocyanate. The mixture was heated to the boiling point and allowed to cool and stir at ambient temperature for sixteen hours. The solid thus obtained was removed by filtration to yield 2.3 g of the crude desired product melting at 158°–178°. The product showed peaks at 1720 and 1710 cm$^{-1}$, by infrared absorption spectroscopy, consistent for the desired product.

EXAMPLE 6

Methyl 3-[[(5,6 dimethyl-1,2,4-triazinyl-2-yl)aminocarbonyl]aminosulfonyl]-2-thiophenecarboxylate To 1.2 g of 3-amino-5,6-dimethyl-1,2,4-traizine in 30 ml of anhydrous methylene chloride was added with stirring 2.7 g of 2-methoxycarbonyl-3-thiophenesulfonylisocyanate. After stirring for 16 hours at ambient temperature the solution was filtered to remove some insoluble material and the filtrate evaporated to dryness. The residue thus obtained was triturated with ethyl ether and the insoluble product filtered to yield 2.9 g of the desired compound melting at 129° with decomposition. Infrared analysis of this product showed absorption peaks at 1730 and 1700 cm$^{-1}$ as expected for the desired product.

EXAMPLE 7

3-[[(4,6-Dimethylpyrimidin-2-yl)aminocarbonyl]amino sulfonyl]-2-thiophene carboxylic acid A solution of 1.0 g of methyl 3-[[(4,6-dimethylpyrimidin-2-yl)aminocarbonyl]aminosulfonyl]-2-thiophenecarboxylate in 10 ml of ethanol and 1 ml of 50% sodium hydroxide in water was stirred overnight at room temperature. To this was added ice-water and aqueous hydrochloric acid until acidic, and the precipitate was filtered and washed first with acetone and then with methylene chloride. The product, 0.8 g, melted at 127°.

EXAMPLE 8

1-[3-[[(4-methoxy-6-methylpyrimidin-2-yl)aminocarbonyl]aminosulfonyl]thiene-2-yl carbonyl]pyrrolidone To 2.5 ml of a 2M-solution of trimethylaluminum in toluene was added 20 ml of methylene chloride and 400 μl of pyrrolidine. To this solution was added 0.66 g of methyl 3-[[(4-methoxy-6-methylpyrimidin-2-yl)amino carbonyl]aminosulfonyl]-2-thiophenecarboxylate. The resulting solution was stirred under nitrogen overnight at room temperature, quenched with 5N aqueous hydrochloric acid, and extracted with ethyl acetate. The residue obtained from evaporation of solvent was washed with ether to afford 0.6 g of product, mp 184°-5°, which showed absorption peaks at 1.8-2.2 ppm and 3.2-3.8 ppm for the pyrrolidine ring and no methyl ester peak, and all other signals indicative of the desired product.

TABLE I-a

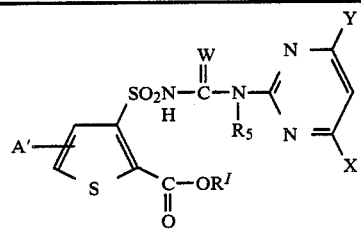

| A' | R$^I$ | W | R$_5$ | X | Y | m.p. (°C.) |
|---|---|---|---|---|---|---|
| H | CH$_3$ | O | H | CH$_3$ | Cl | |
| H | CH$_3$ | O | H | H | H | |
| H | CH$_3$ | O | H | Cl | Cl | |
| H | CH$_3$ | O | H | OCH$_2$CH$_3$ | CH$_2$CH$_3$ | |
| H | CH$_3$ | O | H | CH$_3$ | CH$_2$CH$_3$ | |
| H | CH$_3$ | O | H | CH$_3$ | CH$_3$CH$_2$OCH$_3$ | |
| H | CH$_3$ | O | H | CH$_3$ | (CH$_2$)$_4$OCH$_3$ | |
| H | CH$_3$ | O | H | CH$_3$ | (CH$_2$)$_2$OC$_2$H$_5$ | |
| H | CH$_3$ | O | H | OCH$_3$ | CH$_2$CN | |
| H | CH$_3$ | O | H | OCH$_3$ | CH—CN<br>\|<br>CH$_3$ | |
| H | CH$_3$ | O | H | OCH$_3$ | (CH$_2$)$_3$CO$_2$CH$_3$ | |
| H | CH$_3$ | O | H | OCH$_3$ | CH$_2$CO$_2$C$_2$H$_5$ | |
| H | CH$_3$ | O | H | OCH$_3$ | CH$_2$CF$_3$ | |
| H | CH$_3$ | O | H | OCH$_3$ | CH$_2$CH$_2$Cl | |
| H | CH$_3$ | O | H | OCH$_3$ | CF$_3$ | |
| H | CH$_3$ | O | H | OCH$_3$ | CH$_2$CCl$_3$ | |
| H | CH$_3$ | O | H | OCH$_3$ | (CH$_2$)$_4$Cl | |
| H | CH$_3$ | O | H | OCH$_3$ | (CH$_2$)$_3$Br | |
| H | CH$_3$ | O | H | OCH$_3$ | CH$_2$CH=CH$_2$ | |
| H | CH$_3$ | O | H | OCH$_3$ | CH$_2$CH=CHCH$_2$ | |
| H | CH$_3$ | O | H | CH$_3$ | O(CH$_2$)$_2$OCH$_3$ | |
| H | CH$_3$ | O | H | CH$_3$ | O(CH$_2$)$_3$OC$_2$H$_5$ | |
| H | CH$_3$ | O | H | CH$_3$ | O(CH$_2$)$_2$OCH(CH$_3$)$_2$ | |
| H | CH$_3$ | O | H | CH$_3$ | O(CH$_2$)$_3$O(CH$_2$)$_2$CH$_3$ | |
| H | CH$_3$ | O | H | CH$_3$ | OCH$_2$—C(=O)—OH | |
| H | CH$_3$ | O | H | CH$_3$ | OCH$_2$C(=O)—NH$_2$ | |

TABLE I-a-continued

| A' | R$^I$ | W | R$_5$ | X | Y | m.p. (°C.) |
|---|---|---|---|---|---|---|
| H | CH$_3$ | O | H | CH$_3$ | OCH$_2$CH$_2$C(=O)-N(OCH$_3$)(CH$_3$) | |
| H | CH$_3$ | O | H | CH$_3$ | OCH$_2$-C(=O)-N(CH$_3$)(H) | |
| H | CH$_3$ | O | H | CH$_3$ | OCH(CH$_3$)-C(=O)-N(CH(CH$_3$)$_2$)(H) | |
| H | CH$_3$ | O | H | CH$_3$ | OCH$_2$C(=O)-N(C$_2$H$_5$)(C$_2$H$_5$) | |
| H | CH$_3$ | O | H | CH$_3$ | OCH(CH$_3$)-C(=O)-N(CH$_3$)((CH$_2$)$_3$CH$_3$) | |
| H | CH$_3$ | O | H | CH$_3$ | OCH$_2$C(=O)-O-C$_2$H$_5$ | |
| H | CH$_3$ | O | H | CH$_3$ | OCH$_2$C(=O)-O-CH(CH$_3$)$_2$ | |
| H | CH$_3$ | O | H | CH$_3$ | OCH(CH$_3$)-C(=O)-O-(CH$_2$)$_3$CH$_3$ | |
| H | CH$_3$ | O | H | CH$_3$ | OCH(CH$_3$)-C(=O)-O-CH(CH$_3$)(CH$_2$)$_3$CH$_3$ | |
| H | CH$_3$ | O | H | CH$_3$ | SCN | |
| H | CH$_3$ | O | H | CH$_3$ | N$_3$ | |
| H | CH$_3$ | O | H | CH$_3$ | NH$_2$ | |
| H | CH$_3$ | O | H | CH$_3$ | NHCH$_3$ | |
| H | CH$_3$ | O | H | CH$_3$ | N(CH$_3$)(C$_2$H$_5$) | |
| H | CH$_3$ | O | H | CH$_3$ | N(CH$_3$)((CH$_2$)$_3$CH$_3$) | |
| H | CH$_3$ | O | H | CH$_3$ | NH-cyclobutyl | |

TABLE I-a-continued

[Structure shown at top of table with substituents A', R^I, W, R_5, X, Y]

| A' | R^I | W | R_5 | X | Y | m.p. (°C.) |
|----|-----|---|-----|---|---|------------|
| H | CH$_3$ | O | H | CH$_3$ | NH—(tetrahydrothiopyranyl) | |
| H | CH$_3$ | O | H | CH$_3$ | NH—CH$_2$CH=CH$_2$ | |
| H | CH$_3$ | O | H | CH$_3$ | NH—CH$_2$CH=CHCH$_2$ | |
| H | CH$_3$ | O | H | CH$_3$ | N(CH$_3$)—(CH$_2$)$_2$OCH$_3$ | |
| H | CH$_3$ | O | H | CH$_3$ | N(CH$_3$)—CH(CH$_3$)—CH$_2$OCH$_3$ | |
| H | CH$_3$ | O | H | CH$_3$ | NH—(CH$_2$)$_2$OC$_2$H$_5$ | |
| H | CH$_3$ | O | H | CH$_3$ | N(CH$_3$)—CH$_2$CN | |
| H | CH$_3$ | O | H | CH$_3$ | NH—CH(CH$_3$)—CN | |
| H | CH$_3$ | O | H | CH$_3$ | N(CH$_3$)—CH(CH$_3$)—CO$_2$H | |
| H | CH$_3$ | O | H | CH$_3$ | NH—CH(CH$_3$)—CO$_2$CH$_3$ | |
| H | CH$_3$ | O | H | CH$_3$ | N(CH$_3$)—CH$_2$CO$_2$C$_2$H$_5$ | |
| H | CH$_3$ | O | H | CH$_3$ | piperidino | |
| H | CH$_3$ | O | H | CH$_3$ | morpholino | |
| H | CH$_3$ | O | H | CH$_3$ | O—C$_2$H$_5$ | |
| H | CH$_3$ | O | H | CH$_3$ | O—n-C$_3$H$_7$ | |
| H | CH$_3$ | O | H | CH$_3$ | O—CH(CH$_3$)$_2$ | |
| H | CH$_3$ | O | H | CH$_3$ | O—CH(CH$_3$)—C$_2$H$_5$ | |
| H | CH$_3$ | O | H | CH$_3$ | O—CH$_2$CF$_3$ | |
| H | CH$_3$ | O | H | CH$_3$ | O—CH$_2$CH$_2$Cl | |
| H | CH$_3$ | O | H | CH$_3$ | O—CH$_2$CH$_2$Br | |
| H | CH$_3$ | O | H | CH$_3$ | O—CH$_2$CCl$_3$ | |
| H | CH$_3$ | O | H | CH$_3$ | O—CH$_2$CN | |

TABLE I-a-continued

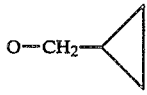

| A' | R¹ | W | R₅ | X | Y | m.p. (°C.) |
|---|---|---|---|---|---|---|
| H | CH₃ | O | H | CH₃ | O—CH—CN<br>    CH₃ | |
| H | CH₃ | O | H | CH₃ | O—CH₂—CH=CH—CH₃ | |
| H | CH₃ | O | H | CH₃ | O—CH₂—C≡CH | |
| H | CH₃ | O | H | CH₃ | O—CH₂—C≡C—CH₂Cl | |
| H | CH₃ | O | H | CH₃ | O—CH₂—<cyclopropyl> | |
| H | CH₃ | O | H | CH₃ | O—<tetrahydrofuran-3-yl> | |
| H | CH₃ | O | H | CH₃ | S—CH₃ | |
| H | CH₃ | O | H | CH₃ | S—CH(CH₃)₂ | |
| H | CH₃ | O | H | CH₃ | S—n-C₄H₉ | |
| H | CH₃ | O | H | CH₃ | S—CH₂CH=CH₂ | |
| 5-CH₃ | CH₃ | O | H | CH₃ | OCH₃ | |
| 5-CH₃ | CH₃ | O | H | CH₃ | OCH₃ | |
| 5-Cl | CH₃ | O | H | CH₃ | OCH₃ | |
| 5-Cl | CH₃ | O | H | CH₃ | OCH₃ | |
| 5-Cl | CH₃ | O | H | CH₃ | OCH₃ | |
| 5-Br | CH₃ | O | H | CH₃ | OCH₃ | |
| 5-Br | CH₃ | O | H | CH₃ | OCH₃ | |
| 5-Br | CH₃ | O | H | CH₃ | OCH₃ | |
| 5-C₂H₅ | CH₃ | O | H | CH₃ | OCH₃ | |
| 5-n-C₄H₉ | CH₃ | O | H | CH₃ | OCH₃ | |
| H | (CH₂)₅CN | O | H | CH₃ | OCH₃ | |
| H | CH₂CH=CHCH₂Cl | O | H | CH₃ | OCH₃ | |
| H | CH₂CH=CH(CH₂)₂Cl | O | H | CH₃ | OCH₃ | |
| H | CH₂C≡CCH₂Cl | O | H | CH₃ | OCH₃ | |
| H | CH₂C≡C(CH₂)₃Cl | O | H | CH₃ | OCH₃ | |
| H | cyclopentyl | O | H | CH₃ | OCH₃ | |
| H | cyclohexyl | O | H | CH₃ | OCH₃ | |
| H | cyclohexenyl | O | H | CH₃ | OCH₃ | |
| H | methylcyclohexyl | O | H | CH₃ | OCH₃ | |

TABLE I-a-continued

Structure: A'-thiophene with SO₂NH-C(=W)-N(R₅)-pyrimidine(X,Y), and C(=O)-OR^I on thiophene

| A' | R^I | W | R₅ | X | Y | m.p. (°C.) |
|---|---|---|---|---|---|---|
| H | H₃C-cyclohexyl(2,5-diCH₃) | O | H | CH₃ | OCH₃ | |
| H | CH₂-cyclohexyl | O | H | CH₃ | OCH₃ | |
| H | CH₂-cyclopentyl | O | H | CH₃ | OCH₃ | |
| H | CH₂-cyclopropyl | O | H | CH₃ | OCH₃ | |
| H | CH₂-cyclohexenyl | O | H | CH₃ | OCH₃ | |
| H | CH₂CH₂-(4-Cl-C₆H₄) | O | H | CH₃ | OCH₃ | |
| H | CHCH₂(CH₃)-(3-OCH₃-C₆H₄) | O | H | CH₃ | OCH₃ | |
| H | CH₃ | O | H | OCH₃ | S—CH₂—C≡CH | |
| H | CH₃ | O | H | OCH₃ | S—CH(CH₃)—CN | |
| H | CH₃ | O | H | OCH₃ | S—CH₂CN | |
| H | CH₃ | S | H | OCH₃ | CH₃ | |
| H | CH₃ | S | H | CH₃ | CH₃ | |
| H | CH₃ | S | H | OCH₃ | CH₃ | |
| H | CH₃ | S | H | OCH₃ | CH₃ | |
| H | CH₃ | S | CH₃ | OCH₃ | OCH₃ | |
| H | CH₃ | S | CH₃ | CH₃ | OCH₃ | |
| H | CH₃ | S | H | OCH₃ | OC₂H₅ | |
| H | CH₃ | O | CH₃ | OCH₃ | OCH₃ | |
| H | CH₃ | O | CH₃ | CH₃ | OCH₃ | |
| H | CH₃ | O | CH₃ | CH₃ | CH₃ | |
| H | CH₃ | O | CH₃ | CH₃ | OCH₂CO₂CH₃ | |
| 4-Cl | CH₃ | O | H | OCH₃ | OCH₃ | |
| 4-Cl | CH(CH₃)₂ | O | H | CH₃ | OCH₃ | |
| 4-Cl | CH₂CH=CH₂ | O | H | CH₃ | OCH₃ | |
| 4-Br | C₂H₅ | O | H | CH₃ | OCH₃ | |

TABLE I-a-continued

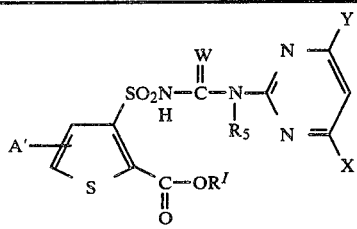

| A' | R$^I$ | W | R$_5$ | X | Y | m.p. (°C.) |
|---|---|---|---|---|---|---|
| 4-CH$_3$ | CH$_2$CH$_2$Cl | O | H | CH$_3$ | OCH$_3$ | |
| 4-C$_2$H$_5$ | CH(CH$_3$)$_2$ | O | H | CH$_3$ | OCH$_3$ | |
| 4-n-C$_4$H$_9$ | CH$_2$CH=CH$_2$ | O | H | CH$_3$ | OCH$_3$ | |
| 4-i-C$_3$H$_7$ | CH$_3$ | O | H | CH$_3$ | OCH$_3$ | |
| 5-Cl | C$_2$H$_5$ | O | H | CH$_3$ | OCH$_3$ | |
| 5-Br | CH$_3$ | O | H | CH$_3$ | OCH$_3$ | |
| 5-CH$_3$ | CH(CH$_3$)$_2$ | O | H | CH$_3$ | OCH$_3$ | |
| H | C$_2$H$_5$ | O | H | CH$_3$ | OCH$_3$ | |
| H | CH$_2$CH=CH$_2$ | O | H | OCH$_3$ | OCH$_3$ | |
| H | (CH$_2$)$_3$CH$_3$ | O | H | OCH$_3$ | OCH$_3$ | |
| H | (CH$_2$)$_4$CH$_3$ | O | H | OCH$_3$ | OCH$_3$ | |
| H | CH(CH$_2$)$_2$CH$_3$ \| CH$_3$ | O | H | OCH$_3$ | OCH$_3$ | |
| H | (CH$_2$)$_3$CH$_3$ | O | H | OCH$_3$ | OCH$_3$ | |
| H | CH$_2$CH=CHCH$_3$ | O | H | OCH$_3$ | OCH$_3$ | |
| H | CH$_2$CH=CHC$_2$H$_5$ | O | H | OCH$_3$ | OCH$_3$ | |
| H | CH$_2$CH=CHCH(CH$_3$)$_2$ | O | H | OCH$_3$ | OCH$_3$ | |
| H | (CH$_2$)$_3$Cl | O | H | OCH$_3$ | OCH$_3$ | |
| H | (CH$_2$)$_5$Cl | O | H | OCH$_3$ | OCH$_3$ | |
| H | (CH$_2$)$_6$OCH$_3$ | O | H | OCH$_3$ | OCH$_3$ | |
| H | CH$_2$CN | O | H | OCH$_3$ | OCH$_3$ | |
| 4-OCH$_3$ | CH$_3$ | O | H | CH$_3$ | CH$_3$ | |
| 5-OCH$_3$ | CH$_3$ | O | H | CH$_3$ | OCH$_3$ | |
| 4-NO$_2$ | CH$_3$ | O | H | CH$_3$ | OCH$_3$ | |
| 5-NO$_2$ | CH$_3$ | O | H | CH$_3$ | OCH$_3$ | |
| 4-CF$_3$ | CH$_3$ | O | H | CH$_3$ | OCH$_3$ | |
| 5-CF$_3$ | CH$_3$ | O | H | CH$_3$ | OCH$_3$ | |
| H | CH$_2$CH$_2$CH$_2$Cl | O | H | CH$_3$ | OCH$_3$ | |
| H | CH$_2$CCl$_3$ | O | H | CH$_3$ | OCH$_3$ | |
| H | (CH$_2$)$_6$Cl | O | H | CH$_3$ | OCH$_3$ | |
| H | (CH$_2$)$_4$Cl | O | H | CH$_3$ | OCH$_3$ | |
| H | CH$_2$CBr$_3$ | O | H | CH$_3$ | OCH$_3$ | |
| H | (CH$_2$)$_4$Br | O | H | CH$_3$ | OCH$_3$ | |
| H | (CH$_2$)$_6$Br | O | H | CH$_3$ | OCH$_3$ | |
| H | (CH$_2$)$_6$F | O | H | CH$_3$ | OCH$_3$ | |
| H | (CH$_2$)$_4$F | O | H | CH$_3$ | OCH$_3$ | |
| H | (CH$_2$)$_3$F | O | H | CH$_3$ | OCH$_3$ | |
| H | CH$_2$CF$_3$ | O | H | CH$_3$ | OCH$_3$ | |
| H | CH$_2$CN | O | H | CH$_3$ | OCH$_3$ | |
| H | 3-tetrahydrofuryl | O | H | CH$_3$ | OCH$_3$ | |
| H | 3-tetrahydrofuryl | O | H | CH$_3$ | OCH$_3$ | |
| H | (3-tetrahydrofuryl)methyl | O | H | CH$_3$ | OCH$_3$ | |
| H | (2-tetrahydrofuryl)methyl | O | H | CH$_3$ | OCH$_3$ | |

TABLE I-a-continued

| A' | R^I | W | R_5 | X | Y | m.p. (°C.) |
|---|---|---|---|---|---|---|
| H | (tetrahydropyran-2-yl)CH₂— | O | H | $CH_3$ | $OCH_3$ | |
| H | (tetrahydropyran-3-yl)CH₂— | O | H | $CH_3$ | $OCH_3$ | |
| H | (tetrahydrofuran-3-yl)CH₂— | O | H | $CH_3$ | $OCH_3$ | |
| H | (oxiranyl)CH₂— | O | H | $CH_3$ | $OCH_3$ | |
| H | —$CH_2OCH_3$ | O | H | $CH_3$ | $OCH_3$ | |
| H | —$CH_2OC_2H_5$ | O | H | $CH_3$ | $OCH_3$ | |
| H | —$CH_2OCH(CH_3)_2$ | O | H | $CH_3$ | $OCH_3$ | |
| H | —$CH_2O$—n-$C_4H_9$ | O | H | $CH_3$ | $OCH_3$ | |
| H | H | O | H | $CH_3$ | $CH_3$ | |
| H | H | O | H | $CH_3$ | $OCH_3$ | |
| H | H | O | H | $OCH_3$ | $OCH_3$ | |
| H | $CH_3$ | O | H | $CH_3$ | $CH_3$ | 191–193 |
| H | $CH_3$ | O | H | $OCH_3$ | $OCH_3$ | 191–193 |
| H | $CH_3$ | O | H | $OCH_3$ | $CH_3$ | 165–173 |
| H | $CH_2C_6H_5$ | O | H | $CH_3$ | $CH_3$ | 133–136 |
| H | $CH(CH_3)_2$ | O | H | $OCH_3$ | $OCH_3$ | 155–160 |
| H | $CH_2CH=CH_2$ | O | H | $CH_3$ | $OCH_3$ | 164–165 |
| H | $CH(CH_3)_2$ | O | H | $CH_3$ | $OCH_3$ | 153–161 |
| H | $CH(CH_3)C_2H_5$ | O | H | $CH_3$ | $OCH_3$ | 146–156 |
| H | $CH(CH_3)CH=CH_2$ | O | H | $CH_3$ | $OCH_3$ | 152–154 |
| H | $CH(CH_3)C\equiv CH$ | O | H | $CH_3$ | $OCH_3$ | 167–173 |
| H | $CH_3$ | O | H | $CH_3$ | $CF_3$ | 171–175 |
| H | $CH_3$ | O | H | $CH_3$ | $SCH_3$ | 128–142 |
| H | $CH_3$ | O | H | $CH_3$ | $CH_2OCH_3$ | 183–187 |
| H | $CH_3$ | O | H | $CH_3$ | Cl | 155–158 |
| H | $CH_3$ | O | H | $CH_3$ | $N(CH_3)_2$ | 225–228 |
| H | $CH_3$ | O | H | Cl | $N(CH_3)_2$ | 205–207 |
| H | $CH_3$ | O | H | $CH_3$ | $CH_3$ | 198–199 |
| H | $CH_2CH=CH_2$ | O | H | $CH_3$ | $CH_3$ | 173–175(d) |
| H | $CH_2CH=CH_2$ | O | H | $OCH_3$ | $OCH_3$ | 140–145(d) |
| H | $CH_3$ | O | H | $CH_3$ | H | 184–185(d) |
| H | $CH_3$ | O | H | $CH_3$ | $C_2H_5$ | 160–169 |
| H | $CH_3$ | O | H | $CH_3$ | $CH(CH_3)_2$ | 130–139 |
| H | $CH(CH_3)C\equiv CH$ | O | H | $CH_3$ | $CH_3$ | — |
| H | $CH_3$ | O | H | $CH_3$ | $N(CH_3)OCH_3$ | 150–154(d) |

TABLE I-b

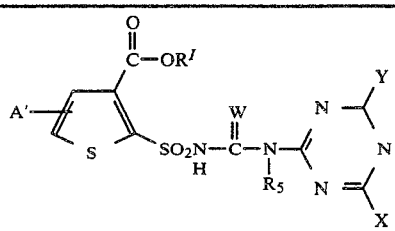

| A' | R^I | W | R_5 | X | Y | m.p. (°C.) |
|---|---|---|---|---|---|---|
| H | CH_3 | O | H | CH_3 | Cl | |
| H | CH_3 | O | H | H | H | |
| H | CH_3 | O | H | Cl | Cl | |
| H | CH_3 | O | H | OCH_2CH_3 | CH_2CH_3 | |
| H | CH_3 | O | H | CH_3 | CH(CH_3)_2 | |
| H | CH_3 | O | H | CH_3 | CH_2CH_3 | |
| H | CH_3 | O | H | CH_3 | CH_2OCH_3 | |
| H | CH_3 | O | H | CH_3 | CH_3CH_2OCH_3 | |
| H | CH_3 | O | H | CH_3 | (CH_2)_4OCH_3 | |
| H | CH_3 | O | H | CH_3 | (CH_2)_2OC_2H_5 | |
| H | CH_3 | O | H | OCH_3 | CH_2CN | |
| H | CH_3 | O | H | OCH_3 | CH—CN<br>    |<br>    CH_3 | |
| H | CH_3 | O | H | OCH_3 | (CH_2)_3CO_2CH_3 | |
| H | CH_3 | O | H | OCH_3 | CH_2CO_2C_2H_5 | |
| H | CH_3 | O | H | OCH_3 | CH_2CH_3 | |
| H | CH_3 | O | H | OCH_3 | CH_2CH_2Cl | |
| H | CH_3 | O | H | OCH_3 | CH_3 | |
| H | CH_3 | O | H | OCH_3 | CH_2CCl_3 | |
| H | CH_3 | O | H | OCH_3 | (CH_2)_4Cl | |
| H | CH_3 | O | H | OCH_3 | (CH_2)_3Br | |
| H | CH_3 | O | H | OCH_3 | CH_2CH=CH_2 | |
| H | CH_3 | O | H | OCH_3 | CH_2CH=CHCH_2 | |
| H | CH_3 | O | H | CH_3 | O(CH_2)_2OCH_3 | |
| H | CH_3 | O | H | CH_3 | O(CH_2)_3OC_2H_5 | |
| H | CH_3 | O | H | CH_3 | O(CH_2)_2OCH(CH_3)_2 | |
| H | CH_3 | O | H | CH_3 | CH_3 | 179–181(d) |
| H | CH_3 | O | H | OCH_3 | CH_3 | 149–159(d) |
| H | CH_3 | O | H | OCH_3 | OCH_3 | 189–190(d) |

TABLE I-c

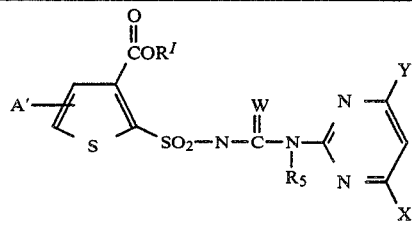

| A' | R^I | W | R_5 | X | Y | m.p. (°C.) |
|---|---|---|---|---|---|---|
| H | CH_3 | O | H | CH_3 | Cl | |
| H | CH_3 | O | H | H | H | |
| H | CH_3 | O | H | Cl | Cl | |
| H | CH_3 | O | H | OCH_2CH_3 | CH_2CH_3 | |
| H | CH_3 | O | H | CH_3 | CH(CH_3)_2 | |
| H | CH_3 | O | H | CH_3 | CH_2CH_3 | |
| H | CH_3 | O | H | CH_3 | CH_3CH_2OCH_3 | |
| H | CH_3 | O | H | CH_3 | (CH_2)_4OCH_3 | |
| H | CH_3 | O | H | CH_3 | (CH_2)_2OC_2H_5 | |
| H | CH_3 | O | H | OCH_3 | CH_2CN | |
| H | CH_3 | O | H | OCH_3 | CH—CN<br>    |<br>    CH_3 | |
| H | CH_3 | O | H | OCH_3 | (CH_2)_3CO_2CH_3 | |
| H | CH_3 | O | H | OCH_3 | CH_2CO_2C_2H_5 | |
| H | CH_3 | O | H | OCH_3 | CH_2CH_3 | |
| H | CH_3 | O | H | OCH_3 | CH_2CH_2Cl | |
| H | CH_3 | O | H | OCH_3 | CH_3 | |
| H | CH_3 | O | H | OCH_3 | CH_2CCl_3 | |
| H | CH_3 | O | H | OCH_3 | (CH_2)_4Cl | |
| H | CH_3 | O | H | OCH_3 | (CH_2)_3Br | |
| H | CH_3 | O | H | OCH_3 | CH_2CH=CH_2 | |
| H | CH_3 | O | H | OCH_3 | CH_2CH=CHCH_2 | |
| H | CH_3 | O | H | CH_3 | O(CH_2)_2OCH_3 | |
| H | CH_3 | O | H | CH_3 | O(CH_2)_3OC_2H_5 | |
| H | CH_3 | O | H | CH_3 | O(CH_2)_2OCH(CH_3)_2 | |
| H | CH_3 | O | H | CH_3 | OCH_3 | 182–183.5 |
| H | CH_3 | O | H | CH_3 | CH_3 | 169–172(d) |
| H | CH_3 | O | H | OCH_3 | OCH_3 | 179–181 |
| H | CH_3 | O | H | CH_3 | CH_2OCH_3 | 154–157(d) |
| 5-C_2H_5 | CH_3 | O | H | CH_3 | CH_3 | 180–185 |
| 5-C_2H_5 | CH_3 | O | H | CH_3 | OCH_3 | 150–154(d) |
| 5-C_2H_5 | CH_3 | O | H | OCH_3 | OCH_3 | 158–161 |

TABLE I-d

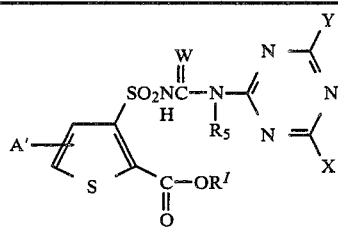

| A' | R^I | W | R_5 | X | Y | m.p. (°C.) |
|---|---|---|---|---|---|---|
| H | CH_3 | O | H | CH_3 | Cl | |
| H | CH_3 | O | H | H | H | |
| H | CH_3 | O | H | Cl | Cl | |
| H | CH_3 | O | H | OCH_2CH_3 | CH_2CH_3 | |
| H | CH_3 | O | H | CH_3 | CH(CH_3)_2 | |
| H | CH_3 | O | H | CH_3 | CH_2CH_3 | |
| H | CH_3 | O | H | CH_3 | CH_2OCH_3 | |
| H | CH_3 | O | H | CH_3 | CH_3CH_2OCH_3 | |

TABLE I-d-continued

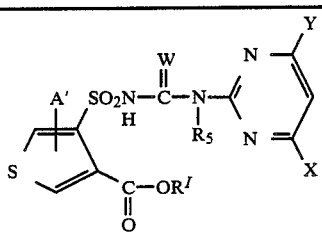

| A' | R$^I$ | W | R$_5$ | X | Y | m.p. (°C.) |
|---|---|---|---|---|---|---|
| H | CH$_3$ | O | H | CH$_3$ | (CH$_2$)$_4$OCH$_3$ | |
| H | CH$_3$ | O | H | CH$_3$ | (CH$_2$)$_2$OC$_2$H$_5$ | |
| H | CH$_3$ | O | H | OCH$_3$ | CH$_2$CN | |
| H | CH$_3$ | O | H | OCH$_3$ | CH—CN<br>\|<br>CH$_3$ | |
| H | CH$_3$ | O | H | OCH$_3$ | (CH$_2$)$_3$CO$_2$CH$_3$ | |
| H | CH$_3$ | O | H | OCH$_3$ | CH$_2$CO$_2$C$_2$H$_5$ | |
| H | CH$_3$ | O | H | OCH$_3$ | CH$_2$CF$_3$ | |
| H | CH$_3$ | O | H | OCH$_3$ | CH$_2$CH$_2$Cl | |
| H | CH$_3$ | O | H | OCH$_3$ | CF$_3$ | |
| H | CH$_3$ | O | H | OCH$_3$ | CH$_2$CCl$_3$ | |
| H | CH$_3$ | O | H | OCH$_3$ | (CH$_2$)$_4$Cl | |
| H | CH$_3$ | O | H | OCH$_3$ | (CH$_2$)$_3$Br | |
| H | CH$_3$ | O | H | OCH$_3$ | CH$_2$CH=CH$_2$ | |
| H | CH$_3$ | O | H | OCH$_3$ | CH$_2$CH=CHCH$_3$ | |
| H | CH$_3$ | O | H | CH$_3$ | O(CH$_2$)$_2$OCH$_3$ | |
| H | CH$_3$ | O | H | CH$_3$ | O(CH$_2$)$_3$OC$_2$H$_5$ | |
| H | CH$_3$ | O | H | CH$_3$ | O(CH$_2$)$_2$OCH(CH$_3$)$_2$ | |
| H | CH$_3$ | O | H | CH$_3$ | CH$_3$ | 158–171 |
| H | CH$_3$ | O | H | OCH$_3$ | OCH$_3$ | 181–183 |
| H | CH$_3$ | O | H | CH$_3$ | OCH$_3$ | 166–170 |
| H | CH(CH$_3$)$_2$ | O | H | CH$_3$ | CH$_3$ | 195–196(d) |
| H | CH(CH$_3$)$_2$ | O | H | CH$_3$ | OCH$_3$ | 179–181(d) |
| H | CH(CH$_3$)$_2$ | O | H | OCH$_3$ | OCH$_3$ | 178–180(d) |
| H | CH$_2$CH=CH$_2$ | O | H | CH$_3$ | OCH$_3$ | 142–146(d) |
| H | CH$_2$CH=CH$_2$ | O | H | OCH$_3$ | OCH$_3$ | 151–155(d) |
| H | CH$_3$ | O | H | OCH$_3$ | N(CH$_3$)$_2$ | 173–175 |
| H | CH$_3$ | O | H | OCH$_3$ | CH$_2$OCH$_3$ | 179–181 |
| H | CH$_3$ | O | CH$_3$ | OCH$_3$ | OCH$_3$ | 185–187 |
| H | CH$_3$ | O | CH$_3$ | OCH$_3$ | Cl | 134–138 |
| H | CH$_3$ | O | CH$_3$ | OCH$_3$ | CH$_3$ | 139–145 |
| H | CH$_3$ | O | OCH$_3$ | OCH$_3$ | OCH$_3$ | 175–177 |

TABLE I-e

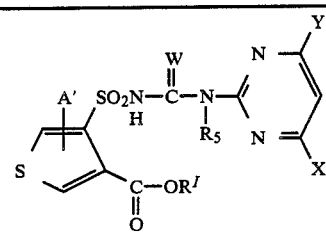

| A' | R$^I$ | W | R$_5$ | X | Y | m.p. (°C.) |
|---|---|---|---|---|---|---|
| H | CH$_3$ | O | H | CH$_3$ | Cl | |
| H | CH$_3$ | O | H | H | H | |
| H | CH$_3$ | O | H | Cl | Cl | |
| H | CH$_3$ | O | H | OCH$_2$CH$_3$ | CH$_2$CH$_3$ | |
| H | CH$_3$ | O | H | CH$_3$ | CH(CH$_3$)$_2$ | |
| H | CH$_3$ | O | H | CH$_3$ | CH$_2$CH$_3$ | |
| H | CH$_3$ | O | H | CH$_3$ | CH$_2$OCH$_3$ | |
| H | CH$_3$ | O | H | CH$_3$ | CH$_3$CH$_2$OCH$_3$ | |
| H | CH$_3$ | O | H | CH$_3$ | (CH$_2$)$_4$OCH$_3$ | |
| H | CH$_3$ | O | H | CH$_3$ | (CH$_2$)$_2$OC$_2$H$_5$ | |
| H | CH$_3$ | O | H | OCH$_3$ | CH$_2$CN | |
| H | CH$_3$ | O | H | OCH$_3$ | CH—CN<br>\|<br>CH$_3$ | |

TABLE I-e-continued

| A' | R$^I$ | W | R$_5$ | X | Y | m.p. (°C.) |
|---|---|---|---|---|---|---|
| H | CH$_3$ | O | H | OCH$_3$ | (CH$_2$)$_3$CO$_2$CH$_3$ | |
| H | CH$_3$ | O | H | OCH$_3$ | CH$_2$CO$_2$C$_2$H$_5$ | |
| H | CH$_3$ | O | H | OCH$_3$ | CH$_2$CH$_3$ | |
| H | CH$_3$ | O | H | OCH$_3$ | CH$_2$CH$_2$Cl | |
| H | CH$_3$ | O | H | OCH$_3$ | CF$_3$ | |
| H | CH$_3$ | O | H | OCH$_3$ | CH$_2$CCl$_3$ | |
| H | CH$_3$ | O | H | OCH$_3$ | (CH$_2$)$_4$Cl | |
| H | CH$_3$ | O | H | OCH$_3$ | (CH$_2$)$_3$Br | |
| H | CH$_3$ | O | H | OCH$_3$ | CH$_2$CH=CH$_2$ | |
| H | CH$_3$ | O | H | OCH$_3$ | CH$_2$CH=CHCH$_3$ | |
| H | CH$_3$ | O | H | CH$_3$ | O(CH$_2$)$_2$OCH$_3$ | |
| H | CH$_3$ | O | H | CH$_3$ | O(CH$_2$)$_3$OC$_2$H$_5$ | |
| H | CH$_3$ | O | H | CH$_3$ | O(CH$_2$)$_2$OCH(CH$_3$)$_2$ | |
| H | CH$_3$ | O | H | CH$_3$ | CH$_3$ | 184– |

TABLE I-e-continued

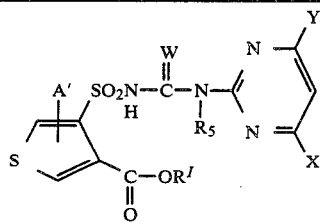

| A' | R^I | W | R_5 | X | Y | m.p. (°C.) |
|---|---|---|---|---|---|---|
| H | CH_3 | O | H | CH_3 | OCH_3 | 187(d) 196–198(d) |
| H | CH_3 | O | H | OCH_3 | OCH_3 | 192–195 |
| H | CH(CH_3)_2 | O | H | CH_3 | CH_3 | 155–157 |
| H | CH(CH_3)_2 | O | H | CH_3 | OCH_3 | 166–170 |
| H | CH(CH_3)_2 | O | H | OCH_3 | OCH_3 | 176–177 |

TABLE I-f

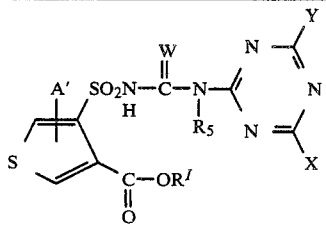

| A' | R^I | W | R_5 | X | Y | m.p. (°C.) |
|---|---|---|---|---|---|---|
| H | CH_3 | O | H | CH_3 | Cl | |
| H | CH_3 | O | H | H | H | |
| H | CH_3 | O | H | Cl | Cl | |
| H | CH_3 | O | H | OCH_2CH_3 | CH_2CH_3 | |
| H | CH_3 | O | H | CH_3 | CH(CH_3)_2 | |
| H | CH_3 | O | H | CH_3 | CH_2CH_3 | |
| H | CH_3 | O | H | CH_3 | CH_2OCH_3 | |
| H | CH_3 | O | H | CH_3 | CH_3CH_2OCH_3 | |
| H | CH_3 | O | H | CH_3 | (CH_2)_4OCH_3 | |
| H | CH_3 | O | H | CH_3 | (CH_2)_2OC_2H_5 | |
| H | CH_3 | O | H | OCH_3 | CH_2CN | |
| H | CH_3 | O | H | OCH_3 | CH—CN \| CH_3 | |
| H | CH_3 | O | H | OCH_3 | (CH_2)_3CO_2CH_3 | |
| H | CH_3 | O | H | OCH_3 | CH_2CO_2C_2H_5 | |
| H | CH_3 | O | H | OCH_3 | CH_2CH_3 | |
| H | CH_3 | O | H | OCH_3 | CH_2CH_2Cl | |
| H | CH_3 | O | H | OCH_3 | CF_3 | |
| H | CH_3 | O | H | OCH_3 | CH_2CCl_3 | |
| H | CH_3 | O | H | OCH_3 | (CH_2)_4Cl | |
| H | CH_3 | O | H | OCH_3 | (CH_2)_3Br | |
| H | CH_3 | O | H | OCH_3 | CH_2CH=CH_2 | |
| H | CH_3 | O | H | OCH_3 | CH_2CH=CHCH_2 | |
| H | CH_3 | O | H | CH_3 | O(CH_2)_2OCH_3 | |
| H | CH_3 | O | H | CH_3 | O(CH_2)_3OC_2H_5 | |
| H | CH_3 | O | H | CH_3 | O(CH_2)_2OCH(CH_3)_2 | |
| H | CH_3 | O | H | CH_3 | CH_3 | 165–175 |
| H | CH_3 | O | H | CH_3 | OCH_3 | 170–72(d) |
| H | CH_3 | O | H | OCH_3 | OCH_3 | — |
| H | CH(CH_3)_2 | O | H | CH_3 | CH_3 | 158–160 |
| H | CH(CH_3)_2 | O | H | CH_3 | OCH_3 | 106–111 |
| H | CH(CH_3)_2 | O | H | OCH_3 | OCH_3 | 165– |

TABLE I-f-continued

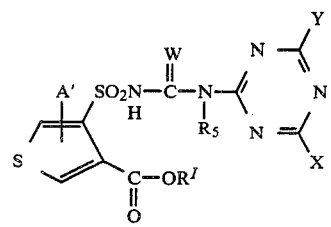

| A' | R^I | W | R_5 | X | Y | m.p. (°C.) |
|---|---|---|---|---|---|---|
| | | | | | | 167 |

TABLE I-g

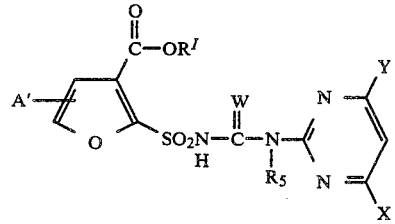

| A' | R^I | W | R_5 | X | Y | m.p. (°C.) |
|---|---|---|---|---|---|---|
| H | CH_3 | O | H | CH_3 | Cl | |
| H | CH_3 | O | H | H | H | |
| H | CH_3 | O | H | Cl | Cl | |
| H | CH_3 | O | H | OCH_2CH_3 | CH_2CH_3 | |
| H | CH_3 | O | H | CH_3 | CH(CH_3)_2 | |
| H | CH_3 | O | H | CH_3 | CH_2CH_3 | |
| H | CH_3 | O | H | CH_3 | CH_2OCH_3 | |
| H | CH_3 | O | H | CH_3 | CH_3CH_2OCH_3 | |
| H | CH_3 | O | H | CH_3 | (CH_2)_4OCH_3 | |
| H | CH_3 | O | H | CH_3 | (CH_2)_2OC_2H_5 | |
| H | CH_3 | O | H | OCH_3 | CH_2CN | |
| H | CH_3 | O | H | OCH_3 | CH—CN \| CH_3 | |
| H | CH_3 | O | H | OCH_3 | (CH_2)_3CO_2CH_3 | |
| H | CH_3 | O | H | OCH_3 | CH_2CO_2C_2H_5 | |
| H | CH_3 | O | H | OCH_3 | CH_2CH_3 | |
| H | CH_3 | O | H | OCH_3 | CH_2CH_2Cl | |
| H | CH_3 | O | H | OCH_3 | CF_3 | |
| H | CH_3 | O | H | OCH_3 | CH_2CCl_3 | |
| H | CH_3 | O | H | OCH_3 | (CH_2)_4Cl | |
| H | CH_3 | O | H | OCH_3 | (CH_2)_3Br | |
| H | CH_3 | O | H | OCH_3 | CH_2CH=CH_2 | |
| H | CH_3 | O | H | OCH_3 | CH_2CH=CHCH_2 | |
| H | CH_3 | O | H | CH_3 | O(CH_2)_2OCH_3 | |
| H | CH_3 | O | H | CH_3 | O(CH_2)_3OC_2H_5 | |
| H | CH_3 | O | H | CH_3 | O(CH_2)_2OCH(CH_3)_2 | |
| H | CH_3 | O | H | CH_3 | CH_3 | 194–196 |
| H | CH_3 | O | H | CH_3 | OCH_3 | 162–165 |
| H | CH_3 | O | H | OCH_3 | OCH_3 | 205–207 |

TABLE I-h

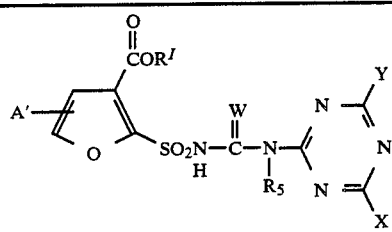

| A' | R^I | W | R_5 | X | Y | m.p. (°C.) |
|---|---|---|---|---|---|---|
| H | CH_3 | O | H | CH_3 | Cl | |
| H | CH_3 | O | H | H | H | |
| H | CH_3 | O | H | Cl | Cl | |
| H | CH_3 | O | H | OCH_2CH_3 | CH_2CH_3 | |
| H | CH_3 | O | H | CH_3 | CH(CH_3)_2 | |
| H | CH_3 | O | H | CH_3 | CH_2CH_3 | |
| H | CH_3 | O | H | CH_3 | CH_2OCH_3 | |
| H | CH_3 | O | H | CH_3 | CH_3CH_2OCH_3 | |
| H | CH_3 | O | H | CH_3 | (CH_2)_4OCH_3 | |
| H | CH_3 | O | H | CH_3 | (CH_2)_2OC_2H_5 | |
| H | CH_3 | O | H | OCH_3 | CH_2CN | |
| H | CH_3 | O | H | OCH_3 | CH—CN \| CH_3 | |
| H | CH_3 | O | H | OCH_3 | (CH_2)_3CO_2CH_3 | |
| H | CH_3 | O | H | OCH_3 | CH_2CO_2C_2H_5 | |
| H | CH_3 | O | H | OCH_3 | CH_2CH_3 | |
| H | CH_3 | O | H | OCH_3 | CH_2CH_2Cl | |
| H | CH_3 | O | H | OCH_3 | CF_3 | |
| H | CH_3 | O | H | OCH_3 | CH_2CCl_3 | |
| H | CH_3 | O | H | OCH_3 | (CH_2)_4Cl | |
| H | CH_3 | O | H | OCH_3 | (CH_2)_3Br | |
| H | CH_3 | O | H | OCH_3 | CH_2CH=CH_2 | |
| H | CH_3 | O | H | OCH_3 | CH_2CH=CHCH_2 | |
| H | CH_3 | O | H | CH_3 | O(CH_2)_2OCH_3 | |
| H | CH_3 | O | H | CH_3 | O(CH_2)_3OC_2H_5 | |
| H | CH_3 | O | H | CH_3 | O(CH_2)_2OCH(CH_3)_2 | |
| H | CH_3 | O | H | OCH_3 | CH_3 | 168–170 |
| H | CH_3 | O | H | OCH_3 | OCH_3 | 164–167 |

TABLE I-i

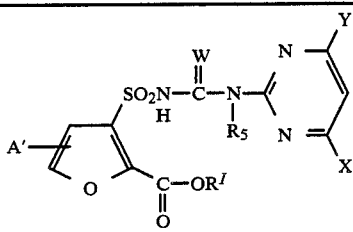

| A' | R^I | W | R_5 | X | Y | m.p. (°C.) |
|---|---|---|---|---|---|---|
| H | CH_3 | O | H | CH_3 | Cl | |
| H | CH_3 | O | H | H | H | |
| H | CH_3 | O | H | Cl | Cl | |
| H | CH_3 | O | H | OCH_2CH_3 | CH_2CH_3 | |
| H | CH_3 | O | H | CH_3 | CH(CH_3)_2 | |
| H | CH_3 | O | H | CH_3 | CH_2CH_3 | |
| H | CH_3 | O | H | CH_3 | CH_2OCH_3 | |
| H | CH_3 | O | H | CH_3 | CH_3CH_2OCH_3 | |
| H | CH_3 | O | H | CH_3 | (CH_2)_4OCH_3 | |
| H | CH_3 | O | H | CH_3 | (CH_2)_2OC_2H_5 | |
| H | CH_3 | O | H | OCH_3 | CH_2CN | |
| H | CH_3 | O | H | OCH_3 | CH—CN \| CH_3 | |
| H | CH_3 | O | H | OCH_3 | (CH_2)_3CO_2CH_3 | |

TABLE I-i-continued

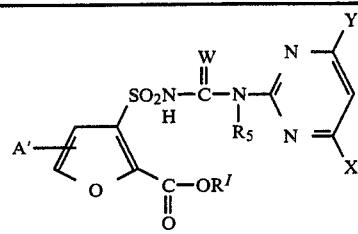

| A' | R^I | W | R_5 | X | Y | m.p. (°C.) |
|---|---|---|---|---|---|---|
| H | CH_3 | O | H | OCH_3 | CH_2CO_2C_2H_5 | |
| H | CH_3 | O | H | OCH_3 | CH_2CH_3 | |
| H | CH_3 | O | H | OCH_3 | CH_2CH_2Cl | |
| H | CH_3 | O | H | OCH_3 | CF_3 | |
| H | CH_3 | O | H | OCH_3 | CH_2CCl_3 | |
| H | CH_3 | O | H | OCH_3 | (CH_2)_4Cl | |
| H | CH_3 | O | H | OCH_3 | (CH_2)_3Br | |
| H | CH_3 | O | H | OCH_3 | CH_2CH=CH_2 | |
| H | CH_3 | O | H | OCH_3 | CH_2CH=CHCH_2 | |
| H | CH_3 | O | H | CH_3 | O(CH_2)_2OCH_3 | |
| H | CH_3 | O | H | CH_3 | O(CH_2)_3OC_2H_5 | |
| H | CH_3 | O | H | CH_3 | O(CH_2)_2OCH(CH_3)_2 | |
| H | CH_3 | O | H | CH_3 | CH_3 | 189–190 |
| H | CH_3 | O | H | OCH_3 | CH_3 | 189–190 |
| H | CH_3 | O | H | OCH_3 | OCH_3 | 180–182 |

TABLE I-j

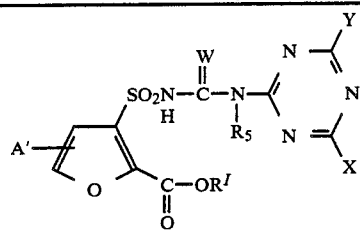

| A' | R^I | W | R_5 | X | Y | m.p. (°C.) |
|---|---|---|---|---|---|---|
| H | CH_3 | O | H | CH_3 | Cl | |
| H | CH_3 | O | H | H | H | |
| H | CH_3 | O | H | Cl | Cl | |
| H | CH_3 | O | H | OCH_2CH_3 | CH_2CH_3 | |
| H | CH_3 | O | H | CH_3 | CH(CH_3)_2 | |
| H | CH_3 | O | H | CH_3 | CH_2CH_3 | |
| H | CH_3 | O | H | CH_3 | CH_2OCH_3 | |
| H | CH_3 | O | H | CH_3 | CH_3CH_2OCH_3 | |
| H | CH_3 | O | H | CH_3 | (CH_2)_4OCH_3 | |
| H | CH_3 | O | H | CH_3 | (CH_2)_2OC_2H_5 | |
| H | CH_3 | O | H | OCH_3 | CH_2CN | |
| H | CH_3 | O | H | OCH_3 | CH—CN \| CH_3 | |
| H | CH_3 | O | H | OCH_3 | (CH_2)_3CO_2CH_3 | |
| H | CH_3 | O | H | OCH_3 | CH_2CO_2C_2H_5 | |
| H | CH_3 | O | H | OCH_3 | CH_2CF_3 | |
| H | CH_3 | O | H | OCH_3 | CH_2CH_2Cl | |
| H | CH_3 | O | H | OCH_3 | CF_3 | |
| H | CH_3 | O | H | OCH_3 | CH_2CCl_3 | |
| H | CH_3 | O | H | OCH_3 | (CH_2)_4Cl | |
| H | CH_3 | O | H | OCH_3 | (CH_2)_3Br | |
| H | CH_3 | O | H | OCH_3 | CH_2CH=CH_2 | |
| H | CH_3 | O | H | OCH_3 | CH_2CH=CHCH_2 | |
| H | CH_3 | O | H | CH_3 | O(CH_2)_2OCH_3 | |
| H | CH_3 | O | H | CH_3 | O(CH_2)_3OC_2H_5 | |
| H | CH_3 | O | H | CH_3 | O(CH_2)_2OCH(CH_3)_2 | |
| H | CH_3 | O | H | OCH_3 | OCH_3 | 160–163 |
| H | CH_3 | O | H | OCH_3 | OCH_3 | 173– |

TABLE I-j-continued

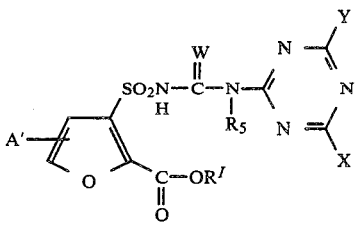

| A' | R^I | W | R_5 | X | Y | m.p. (°C.) |
|----|-----|---|-----|---|---|------------|
| H | CH_3 | O | H | CH_3 | CH_3 | 175 174–176 |

TABLE I-k

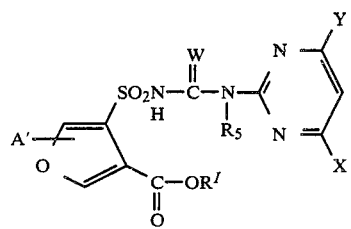

| A' | R^I | W | R_5 | X | Y | m.p. (°C.) |
|----|-----|---|-----|---|---|------------|
| H | CH_3 | O | H | CH_3 | Cl | |
| H | CH_3 | O | H | H | H | |
| H | CH_3 | O | H | Cl | Cl | |
| H | CH_3 | O | H | OCH_2CH_3 | CH_2CH_3 | |
| H | CH_3 | O | H | CH_3 | CH(CH_3)_2 | |
| H | CH_3 | O | H | CH_3 | CH_2CH_3 | |
| H | CH_3 | O | H | CH_3 | CH_2OCH_3 | |
| H | CH_3 | O | H | CH_3 | CH_3CH_2OCH_3 | |
| H | CH_3 | O | H | CH_3 | (CH_2)_4OCH_3 | |
| H | CH_3 | O | H | CH_3 | (CH_2)_2OC_2H_5 | |
| H | CH_3 | O | H | OCH_3 | CH_2CN | |
| H | CH_3 | O | H | OCH_3 | CH—CN \| CH_3 | |
| H | CH_3 | O | H | OCH_3 | (CH_2)_3CO_2CH_3 | |
| H | CH_3 | O | H | OCH_3 | CH_2CO_2C_2H_5 | |
| H | CH_3 | O | H | OCH_3 | CH_2CF_3 | |
| H | CH_3 | O | H | OCH_3 | CH_2CH_2Cl | |
| H | CH_3 | O | H | OCH_3 | CF_3 | |
| H | CH_3 | O | H | OCH_3 | CH_2CCl_3 | |
| H | CH_3 | O | H | OCH_3 | (CH_2)_4Cl | |
| H | CH_3 | O | H | OCH_3 | (CH_2)_3Br | |
| H | CH_3 | O | H | OCH_3 | CH_2CH=CH_2 | |
| H | CH_3 | O | H | OCH_3 | CH_2CH=CHCH_2 | |
| H | CH_3 | O | H | CH_3 | O(CH_2)_2OCH_3 | |
| H | CH_3 | O | H | CH_3 | O(CH_2)_3OC_2H_5 | |
| H | CH_3 | O | H | CH_3 | O(CH_2)_2OCH(CH_3)_2 | |

TABLE I-l

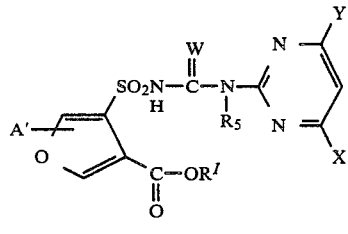

| A' | R^I | W | R_5 | X | Y | m.p. (°C.) |
|----|-----|---|-----|---|---|------------|
| H | CH_3 | O | H | CH_3 | Cl | |
| H | CH_3 | O | H | H | H | |
| H | CH_3 | O | H | Cl | Cl | |
| H | CH_3 | O | H | OCH_2CH_3 | CH_2CH_3 | |
| H | CH_3 | O | H | CH_3 | CH(CH_3)_2 | |
| H | CH_3 | O | H | CH_3 | CH_2CH_3 | |
| H | CH_3 | O | H | CH_3 | CH_2OCH_3 | |
| H | CH_3 | O | H | CH_3 | CH_3CH_2OCH_3 | |
| H | CH_3 | O | H | CH_3 | (CH_2)_4OCH_3 | |
| H | CH_3 | O | H | CH_3 | (CH_2)_2OC_2H_5 | |
| H | CH_3 | O | H | OCH_3 | CH_2CN | |
| H | CH_3 | O | H | OCH_3 | CH—CN \| CH_3 | |
| H | CH_3 | O | H | OCH_3 | (CH_2)_3CO_2CH_3 | |
| H | CH_3 | O | H | OCH_3 | CH_2CO_2C_2H_5 | |
| H | CH_3 | O | H | OCH_3 | CH_2CH_3 | |
| H | CH_3 | O | H | OCH_3 | CH_2CH_2Cl | |
| H | CH_3 | O | H | OCH_3 | CF_3 | |
| H | CH_3 | O | H | OCH_3 | CH_2CCl_3 | |
| H | CH_3 | O | H | OCH_3 | (CH_2)_4Cl | |
| H | CH_3 | O | H | OCH_3 | (CH_2)_3Br | |
| H | CH_3 | O | H | OCH_3 | CH_2CH=CH_2 | |
| H | CH_3 | O | H | OCH_3 | CH_2CH=CHCH_2 | |
| H | CH_3 | O | H | CH_3 | O(CH_2)_2OCH_3 | |
| H | CH_3 | O | H | CH_3 | O(CH_2)_3OC_2H_5 | |
| H | CH_3 | O | H | CH_3 | O(CH_2)_2OCH(CH_3)_2 | |

TABLE II-a

| A' | R^I | W | R_5 | X_1 | Y_1 | m.p. (°C.) |
|----|-----|---|-----|-----|-----|------------|
| H | CH_3 | O | H | H | H | |
| H | CH_3 | O | H | H | OCH_3 | |
| H | CH_3 | O | H | H | CH_3 | |
| H | CH_3 | O | H | Cl | H | |
| H | CH_3 | O | H | Cl | OCH_3 | |
| H | CH_3 | O | H | Cl | CH_3 | |
| H | CH_3 | O | H | OCH_3 | H | |
| H | CH_3 | O | H | OCH_3 | OCH_3 | |
| H | CH_3 | O | H | OCH_3 | CH_3 | |
| H | CH_3 | O | H | OC_2H_5 | H | |
| H | CH_3 | O | H | OC_2H_5 | OCH_3 | |
| H | CH_3 | O | H | OC_2H_5 | CH_3 | |
| H | CH_3 | O | H | CH_3 | H | |
| H | CH_3 | O | H | CH_3 | OCH_3 | |
| H | CH_3 | O | H | CH_3 | CH_3 | |
| H | CH_3 | O | H | OCH_3 | OCH_3 | |
| 5-Cl | CH_3 | O | H | OCH_3 | OCH_3 | |
| 5-CH_3 | CH_3 | O | H | OCH_3 | OCH_3 | |
| 5-Br | CH_3 | O | H | OCH_3 | OCH_3 | |
| 5-C_2H_5 | CH_3 | O | H | OCH_3 | OCH_3 | |
| H | CH(CH_3)_2 | O | CH | OCH_3 | OCH_3 | |

TABLE II-a-continued

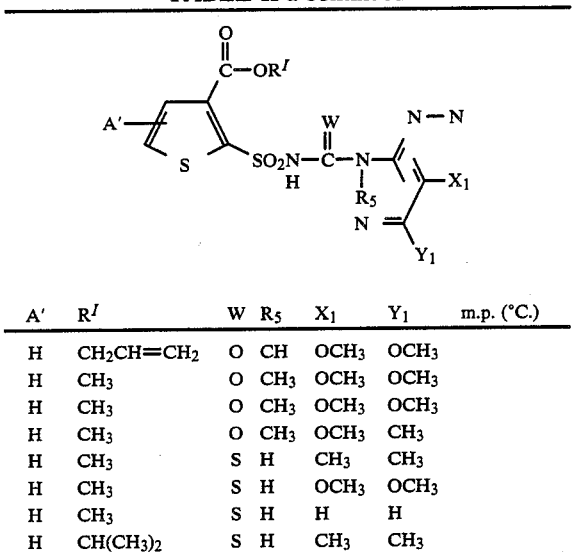

| A' | R^I | W | R_5 | X_1 | Y_1 | m.p. (°C.) |
|---|---|---|---|---|---|---|
| H | CH_2CH=CH_2 | O | CH | OCH_3 | OCH_3 | |
| H | CH_3 | O | CH_3 | OCH_3 | OCH_3 | |
| H | CH_3 | O | CH_3 | OCH_3 | OCH_3 | |
| H | CH_3 | O | CH_3 | OCH_3 | CH_3 | |
| H | CH_3 | S | H | CH_3 | CH_3 | |
| H | CH_3 | S | H | OCH_3 | OCH_3 | |
| H | CH_3 | S | H | H | H | |
| H | CH(CH_3)_2 | S | H | CH_3 | CH_3 | |

TABLE II-b

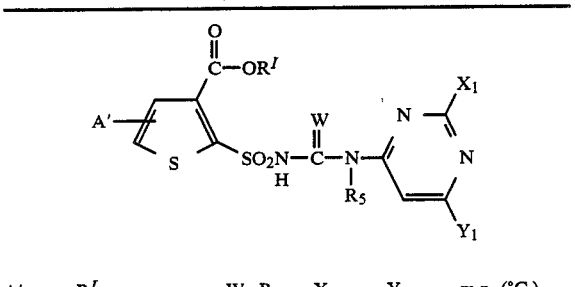

| A' | R^I | W | R_5 | X_1 | Y_1 | m.p. (°C.) |
|---|---|---|---|---|---|---|
| H | CH_3 | O | H | H | H | |
| H | CH_3 | O | H | H | OCH_3 | |
| H | CH_3 | O | H | H | CH_3 | |
| H | CH_3 | O | H | Cl | H | |
| H | CH_3 | O | H | Cl | OCH_3 | |
| H | CH_3 | O | H | Cl | CH_3 | |
| H | CH_3 | O | H | OCH_3 | H | |
| H | CH_3 | O | H | OCH_3 | OCH_3 | |
| H | CH_3 | O | H | OCH_3 | CH_3 | |
| H | CH_3 | O | H | OC_2H_5 | H | |
| H | CH_3 | O | H | OC_2H_5 | OCH_3 | |
| H | CH_3 | O | H | OC_2H_5 | CH_3 | |
| H | CH_3 | O | H | CH_3 | H | |
| H | CH_3 | O | H | CH_3 | OCH_3 | |
| H | CH_3 | O | H | CH_3 | CH_3 | |
| H | CH_3 | O | H | OCH_3 | OCH_3 | |
| 5-Cl | CH_3 | O | H | OCH_3 | OCH_3 | |
| 5-CH_3 | CH_3 | O | H | OCH_3 | OCH_3 | |
| 5-Br | CH_3 | O | H | OCH_3 | OCH_3 | |
| 5-C_2H_5 | CH_3 | O | H | OCH_3 | OCH_3 | |
| H | CH(CH_3)_2 | O | CH | OCH_3 | OCH_3 | |
| H | CH_2CH=CH_2 | O | CH | OCH_3 | OCH_3 | |
| H | CH_3 | O | CH_3 | OCH_3 | OCH_3 | |
| H | CH_3 | O | CH_3 | OCH_3 | OCH_3 | |
| H | CH_3 | O | CH_3 | OCH_3 | CH_3 | |
| H | CH_3 | S | H | CH_3 | CH_3 | |
| H | CH_3 | S | H | OCH_3 | OCH_3 | |
| H | CH_3 | S | H | H | H | |
| H | CH(CH_3)_2 | S | H | CH_3 | CH_3 | |

TABLE II-c

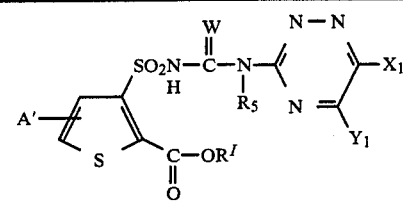

| A' | R^I | W | R_5 | X_1 | Y_1 | m.p. (°C.) |
|---|---|---|---|---|---|---|
| H | CH_3 | O | H | H | H | |
| H | CH_3 | O | H | H | OCH_3 | |
| H | CH_3 | O | H | H | CH_3 | |
| H | CH_3 | O | H | Cl | H | |
| H | CH_3 | O | H | Cl | OCH_3 | |
| H | CH_3 | O | H | Cl | CH_3 | |
| H | CH_3 | O | H | OCH_3 | H | |
| H | CH_3 | O | H | OCH_3 | OCH_3 | |
| H | CH_3 | O | H | OCH_3 | CH_3 | |
| H | CH_3 | O | H | OC_2H_5 | H | |
| H | CH_3 | O | H | OC_2H_5 | OCH_3 | |
| H | CH_3 | O | H | OC_2H_5 | CH_3 | |
| H | CH_3 | O | H | CH_3 | H | |
| H | CH_3 | O | H | CH_3 | OCH_3 | |
| H | CH_3 | O | H | CH_3 | CH_3 | 129° (d) |
| H | CH_3 | O | H | OCH_3 | OCH_3 | |
| 5-Cl | CH_3 | O | H | OCH_3 | OCH_3 | |
| 5-CH_3 | CH_3 | O | H | OCH_3 | OCH_3 | |
| 5-Br | CH_3 | O | H | OCH_3 | OCH_3 | |
| 5-C_2H_5 | CH_3 | O | H | OCH_3 | OCH_3 | |
| H | CH(CH_3)_2 | O | CH | OCH_3 | OCH_3 | |
| H | CH_2CH=CH_2 | O | CH | OCH_3 | OCH_3 | |
| H | CH_3 | O | CH_3 | OCH_3 | OCH_3 | |
| H | CH_3 | O | CH_3 | OCH_3 | OCH_3 | |
| H | CH_3 | O | CH_3 | OCH_3 | CH_3 | |
| H | CH_3 | S | H | CH_3 | CH_3 | |
| H | CH_3 | S | H | OCH_3 | OCH_3 | |
| H | CH_3 | S | H | H | H | |
| H | CH(CH_3)_2 | S | H | CH_3 | CH_3 | |

TABLE II-d

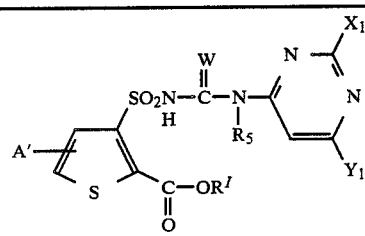

| A' | R^I | W | R_5 | X_1 | Y_1 | m.p. (°C.) |
|---|---|---|---|---|---|---|
| H | CH_3 | O | H | H | H | |
| H | CH_3 | O | H | H | OCH_3 | |
| H | CH_3 | O | H | H | CH_3 | |
| H | CH_3 | O | H | Cl | H | |
| H | CH_3 | O | H | Cl | OCH_3 | |
| H | CH_3 | O | H | Cl | CH_3 | |
| H | CH_3 | O | H | OCH_3 | H | |
| H | CH_3 | O | H | OCH_3 | OCH_3 | |
| H | CH_3 | O | H | OCH_3 | CH_3 | |
| H | CH_3 | O | H | OC_2H_5 | H | |
| H | CH_3 | O | H | OC_2H_5 | OCH_3 | |
| H | CH_3 | O | H | OC_2H_5 | CH_3 | |
| H | CH_3 | O | H | CH_3 | H | |
| H | CH_3 | O | H | CH_3 | OCH_3 | |
| H | CH_3 | O | H | CH_3 | CH_3 | |
| H | CH_3 | O | H | OCH_3 | OCH_3 | 126–133° |
| 5-Cl | CH_3 | O | H | OCH_3 | OCH_3 | |
| 5-CH_3 | CH_3 | O | H | OCH_3 | OCH_3 | |
| 5-Br | CH_3 | O | H | OCH_3 | OCH_3 | |
| 5-C_2H_5 | CH_3 | O | H | OCH_3 | OCH_3 | |
| H | CH(CH_3)_2 | O | CH | OCH_3 | OCH_3 | |
| H | CH_2CH=CH_2 | O | CH | OCH_3 | OCH_3 | |
| H | CH_3 | O | CH_3 | OCH_3 | OCH_3 | |
| H | CH_3 | O | CH_3 | OCH_3 | OCH_3 | |

TABLE II-d-continued

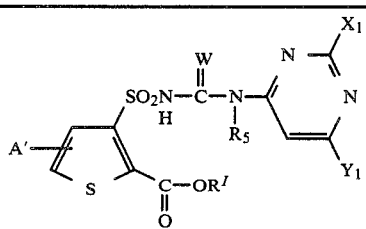

| A' | R^I | W | R5 | X1 | Y1 | m.p. (°C.) |
|---|---|---|---|---|---|---|
| H | CH3 | O | CH3 | OCH3 | CH3 | |
| H | CH3 | S | H | CH3 | CH3 | |
| H | CH3 | S | H | OCH3 | OCH3 | |
| H | CH3 | S | H | H | H | |
| H | CH(CH3)2 | S | H | CH3 | CH3 | |

TABLE II-e

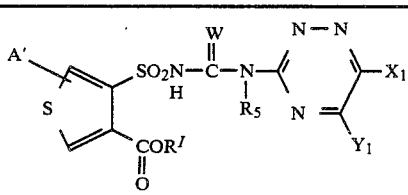

| A' | R^I | W | R5 | X1 | Y1 | m.p. (°C.) |
|---|---|---|---|---|---|---|
| H | CH3 | O | H | H | H | |
| H | CH3 | O | H | H | OCH3 | |
| H | CH3 | O | H | H | CH3 | |
| H | CH3 | O | H | Cl | H | |
| H | CH3 | O | H | Cl | OCH3 | |
| H | CH3 | O | H | Cl | CH3 | |
| H | CH3 | O | H | OCH3 | H | |
| H | CH3 | O | H | OCH3 | OCH3 | |
| H | CH3 | O | H | OCH3 | CH3 | |
| H | CH3 | O | H | OC2H5 | H | |
| H | CH3 | O | H | OC2H5 | OCH3 | |
| H | CH3 | O | H | OC2H5 | CH3 | |
| H | CH3 | O | H | CH3 | H | |
| H | CH3 | O | H | CH3 | OCH3 | |
| H | CH3 | O | H | CH3 | CH3 | |
| H | CH3 | O | H | OCH3 | OCH3 | |
| 5-Cl | CH3 | O | H | OCH3 | OCH3 | |
| 5-CH3 | CH3 | O | H | OCH3 | OCH3 | |
| 5-Br | CH3 | O | H | OCH3 | OCH3 | |
| 5-C2H5 | CH3 | O | H | OCH3 | OCH3 | |
| H | CH(CH3)2 | O | CH | OCH3 | OCH3 | |
| H | CH2CH=CH2 | O | CH | OCH3 | OCH3 | |
| H | CH3 | O | CH3 | OCH3 | OCH3 | |
| H | CH3 | O | CH3 | OCH3 | OCH3 | |
| H | CH3 | O | CH3 | OCH3 | CH3 | |
| H | CH3 | S | H | CH3 | CH3 | |
| H | CH3 | S | H | OCH3 | OCH3 | |
| H | CH3 | S | H | H | H | |
| H | CH(CH3)2 | S | H | CH3 | CH3 | |

TABLE II-f

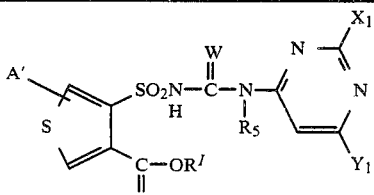

| A' | R^I | W | R5 | X1 | Y1 | m.p. (°C.) |
|---|---|---|---|---|---|---|
| H | CH3 | O | H | H | H | |
| H | CH3 | O | H | H | OCH3 | |
| H | CH3 | O | H | H | CH3 | |

TABLE II-f-continued

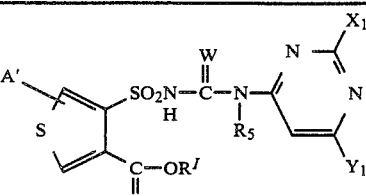

| A' | R^I | W | R5 | X1 | Y1 | m.p. (°C.) |
|---|---|---|---|---|---|---|
| H | CH3 | O | H | Cl | H | |
| H | CH3 | O | H | Cl | OCH3 | |
| H | CH3 | O | H | Cl | CH3 | |
| H | CH3 | O | H | OCH3 | H | |
| H | CH3 | O | H | OCH3 | OCH3 | |
| H | CH3 | O | H | OCH3 | CH3 | |
| H | CH3 | O | H | OC2H5 | H | |
| H | CH3 | O | H | OC2H5 | OCH3 | |
| H | CH3 | O | H | OC2H5 | CH3 | |
| H | CH3 | O | H | CH3 | H | |
| H | CH3 | O | H | CH3 | OCH3 | |
| H | CH3 | O | H | CH3 | CH3 | |
| H | CH3 | O | H | OCH3 | OCH3 | |
| 5-Cl | CH3 | O | H | OCH3 | OCH3 | |
| 5-CH3 | CH3 | O | H | OCH3 | OCH3 | |
| 5-Br | CH3 | O | H | OCH3 | OCH3 | |
| 5-C2H5 | CH3 | O | H | OCH3 | OCH3 | |
| H | CH(CH3)2 | O | CH | OCH3 | OCH3 | |
| H | CH2CH=CH2 | O | CH | OCH3 | OCH3 | |
| H | CH3 | O | CH3 | OCH3 | OCH3 | |
| H | CH3 | O | CH3 | OCH3 | OCH3 | |
| H | CH3 | O | CH3 | OCH3 | CH3 | |
| H | CH3 | S | H | CH3 | CH3 | |
| H | CH3 | S | H | OCH3 | OCH3 | |
| H | CH3 | S | H | H | H | |
| H | CH(CH3)2 | S | H | CH3 | CH3 | |

TABLE II-g

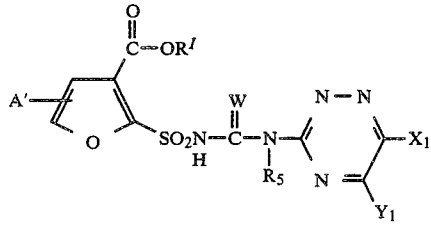

| A' | R^I | W | R5 | X1 | Y1 | m.p. (°C.) |
|---|---|---|---|---|---|---|
| H | CH3 | O | H | H | H | |
| H | CH3 | O | H | H | OCH3 | |
| H | CH3 | O | H | H | CH3 | |
| H | CH3 | O | H | Cl | H | |
| H | CH3 | O | H | Cl | OCH3 | |
| H | CH3 | O | H | Cl | CH3 | |
| H | CH3 | O | H | OCH3 | H | |
| H | CH3 | O | H | OCH3 | OCH3 | |
| H | CH3 | O | H | OCH3 | CH3 | |
| H | CH3 | O | H | OC2H5 | H | |
| H | CH3 | O | H | OC2H5 | OCH3 | |
| H | CH3 | O | H | OC2H5 | CH3 | |
| H | CH3 | O | H | CH3 | H | |
| H | CH3 | O | H | CH3 | OCH3 | |
| H | CH3 | O | H | CH3 | CH3 | |
| H | CH3 | O | H | OCH3 | OCH3 | |
| 5-Cl | CH3 | O | H | OCH3 | OCH3 | |
| 5-CH3 | CH3 | O | H | OCH3 | OCH3 | |
| 5-Br | CH3 | O | H | OCH3 | OCH3 | |
| 5-C2H5 | CH3 | O | H | OCH3 | OCH3 | |
| H | CH(CH3)2 | O | CH | OCH3 | OCH3 | |
| H | CH2CH=CH2 | O | CH | OCH3 | OCH3 | |
| H | CH3 | O | CH3 | OCH3 | OCH3 | |
| H | CH3 | O | CH3 | OCH3 | OCH3 | |
| H | CH3 | S | H | CH3 | CH3 | |

TABLE II-g-continued

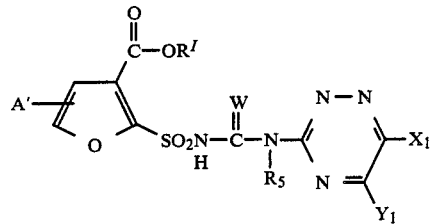

| A' | R^I | W | R5 | X1 | Y1 | m.p. (°C.) |
|---|---|---|---|---|---|---|
| H | CH3 | S | H | OCH3 | OCH3 | |
| H | CH3 | S | H | H | H | |
| H | CH(CH3)2 | S | H | CH3 | CH3 | |

TABLE II-h

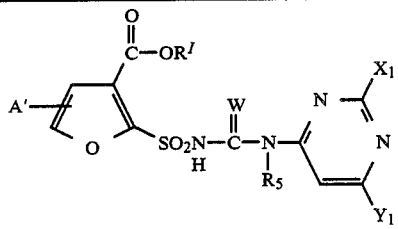

| A' | R^I | W | R5 | X1 | Y1 | m.p. (°C.) |
|---|---|---|---|---|---|---|
| H | CH3 | O | H | H | H | |
| H | CH3 | O | H | H | OCH3 | |
| H | CH3 | O | H | H | CH3 | |
| H | CH3 | O | H | Cl | H | |
| H | CH3 | O | H | Cl | OCH3 | |
| H | CH3 | O | H | Cl | CH3 | |
| H | CH3 | O | H | OCH3 | H | |
| H | CH3 | O | H | OCH3 | OCH3 | |
| H | CH3 | O | H | OCH3 | CH3 | |
| H | CH3 | O | H | OC2H5 | H | |
| H | CH3 | O | H | OC2H5 | OCH3 | |
| H | CH3 | O | H | OC2H5 | CH3 | |
| H | CH3 | O | H | CH3 | H | |
| H | CH3 | O | H | CH3 | OCH3 | |
| H | CH3 | O | H | CH3 | CH3 | |
| H | CH3 | O | H | OCH3 | OCH3 | |
| 5-Cl | CH3 | O | H | OCH3 | OCH3 | |
| 5-CH3 | CH3 | O | H | OCH3 | OCH3 | |
| 5-Br | CH3 | O | H | OCH3 | OCH3 | |
| 5-C2H5 | CH3 | O | H | OCH3 | OCH3 | |
| H | CH(CH3)2 | O | CH | OCH3 | OCH3 | |
| H | CH2CH=CH2 | O | CH | OCH3 | OCH3 | |
| H | CH3 | O | CH3 | OCH3 | OCH3 | |
| H | CH3 | O | CH3 | OCH3 | CH3 | |
| H | CH3 | O | CH3 | OCH3 | CH3 | |
| H | CH3 | S | H | CH3 | CH3 | |
| H | CH3 | S | H | OCH3 | OCH3 | |
| H | CH3 | S | H | H | H | |
| H | CH(CH3)2 | S | H | CH3 | CH3 | |

TABLE II-i

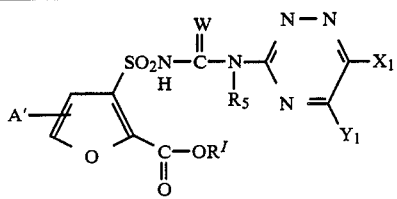

| A' | R^I | W | R5 | X1 | Y1 | m.p. (°C.) |
|---|---|---|---|---|---|---|
| H | CH3 | O | H | H | H | |
| H | CH3 | O | H | H | OCH3 | |
| H | CH3 | O | H | H | CH3 | |
| H | CH3 | O | H | Cl | H | |

TABLE II-i-continued

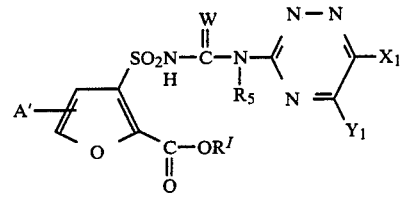

| A' | R^I | W | R5 | X1 | Y1 | m.p. (°C.) |
|---|---|---|---|---|---|---|
| H | CH3 | O | H | Cl | OCH3 | |
| H | CH3 | O | H | Cl | CH3 | |
| H | CH3 | O | H | OCH3 | H | |
| H | CH3 | O | H | OCH3 | OCH3 | |
| H | CH3 | O | H | OCH3 | CH3 | |
| H | CH3 | O | H | OC2H5 | H | |
| H | CH3 | O | H | OC2H5 | OCH3 | |
| H | CH3 | O | H | OC2H5 | CH3 | |
| H | CH3 | O | H | CH3 | H | |
| H | CH3 | O | H | CH3 | OCH3 | |
| H | CH3 | O | H | CH3 | CH3 | |
| H | CH3 | O | H | OCH3 | OCH3 | |
| 5-Cl | CH3 | O | H | OCH3 | OCH3 | |
| 5-CH3 | CH3 | O | H | OCH3 | OCH3 | |
| 5-Br | CH3 | O | H | OCH3 | OCH3 | |
| 5-C2H5 | CH3 | O | H | OCH3 | OCH3 | |
| H | CH(CH3)2 | O | CH | OCH3 | OCH3 | |
| H | CH2CH=CH2 | O | CH | OCH3 | OCH3 | |
| H | CH3 | O | CH3 | OCH3 | OCH3 | |
| H | CH3 | O | CH3 | OCH3 | CH3 | |
| H | CH3 | S | H | CH3 | CH3 | |
| H | CH3 | S | H | OCH3 | OCH3 | |
| H | CH3 | S | H | H | H | |
| H | CH(CH3)2 | S | H | CH3 | CH3 | |

TABLE II-j

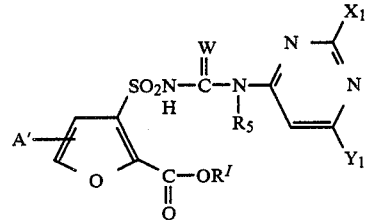

| A' | R^I | W | R5 | X1 | Y1 | m.p. (°C.) |
|---|---|---|---|---|---|---|
| H | CH3 | O | H | H | H | |
| H | CH3 | O | H | H | OCH3 | |
| H | CH3 | O | H | H | CH3 | |
| H | CH3 | O | H | Cl | H | |
| H | CH3 | O | H | Cl | OCH3 | |
| H | CH3 | O | H | Cl | CH3 | |
| H | CH3 | O | H | OCH3 | H | |
| H | CH3 | O | H | OCH3 | OCH3 | |
| H | CH3 | O | H | OCH3 | CH3 | |
| H | CH3 | O | H | OC2H5 | H | |
| H | CH3 | O | H | OC2H5 | OCH3 | |
| H | CH3 | O | H | OC2H5 | CH3 | |
| H | CH3 | O | H | CH3 | H | |
| H | CH3 | O | H | CH3 | OCH3 | |
| H | CH3 | O | H | CH3 | CH3 | |
| H | CH3 | O | H | OCH3 | OCH3 | |
| 5-Cl | CH3 | O | H | OCH3 | OCH3 | |
| 5-CH3 | CH3 | O | H | OCH3 | OCH3 | |
| 5-Br | CH3 | O | H | OCH3 | OCH3 | |
| 5-C2H5 | CH3 | O | H | OCH3 | OCH3 | |
| H | CH(CH3)2 | O | CH | OCH3 | OCH3 | |
| H | CH2CH=CH2 | O | CH | OCH3 | OCH3 | |
| H | CH3 | O | CH3 | OCH3 | OCH3 | |
| H | CH3 | O | CH3 | OCH3 | CH3 | |
| H | CH3 | O | CH3 | OCH3 | CH3 | |
| H | CH3 | S | H | CH3 | CH3 | |
| H | CH3 | S | H | OCH3 | OCH3 | |
| H | CH3 | S | H | H | H | |

TABLE II-j-continued

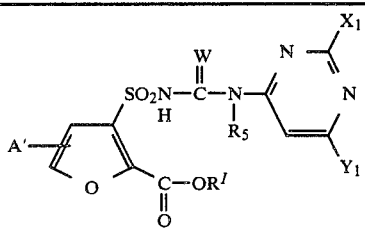

| A' | R$^I$ | W | R$_5$ | X$_1$ | Y$_1$ | m.p. (°C.) |
|---|---|---|---|---|---|---|
| H | CH(CH$_3$)$_2$ | S | H | CH$_3$ | CH$_3$ | |

TABLE II-k

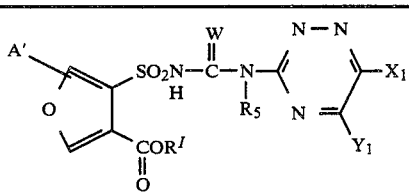

| A' | R$^I$ | W | R$_5$ | X$_1$ | Y$_1$ | m.p. (°C.) |
|---|---|---|---|---|---|---|
| H | CH$_3$ | O | H | H | H | |
| H | CH$_3$ | O | H | H | OCH$_3$ | |
| H | CH$_3$ | O | H | H | CH$_3$ | |
| H | CH$_3$ | O | H | Cl | H | |
| H | CH$_3$ | O | H | Cl | OCH$_3$ | |
| H | CH$_3$ | O | H | Cl | CH$_3$ | |
| H | CH$_3$ | O | H | OCH$_3$ | H | |
| H | CH$_3$ | O | H | OCH$_3$ | OCH$_3$ | |
| H | CH$_3$ | O | H | OCH$_3$ | CH$_3$ | |
| H | CH$_3$ | O | H | OC$_2$H$_5$ | H | |
| H | CH$_3$ | O | H | OC$_2$H$_5$ | OCH$_3$ | |
| H | CH$_3$ | O | H | OC$_2$H$_5$ | CH$_3$ | |
| H | CH$_3$ | O | H | CH$_3$ | H | |
| H | CH$_3$ | O | H | CH$_3$ | OCH$_3$ | |
| H | CH$_3$ | O | H | CH$_3$ | CH$_3$ | |
| H | CH$_3$ | O | H | OCH$_3$ | OCH$_3$ | |
| 5-Cl | CH$_3$ | O | H | OCH$_3$ | OCH$_3$ | |
| 5-CH$_3$ | CH$_3$ | O | H | OCH$_3$ | OCH$_3$ | |
| 5-Br | CH$_3$ | O | H | OCH$_3$ | OCH$_3$ | |
| 5-C$_2$H$_5$ | CH$_3$ | O | H | OCH$_3$ | OCH$_3$ | |
| H | CH(CH$_3$)$_2$ | O | CH | OCH$_3$ | OCH$_3$ | |
| H | CH$_2$CH=CH$_2$ | O | CH | OCH$_3$ | OCH$_3$ | |
| H | CH$_3$ | O | CH$_3$ | OCH$_3$ | OCH$_3$ | |
| H | CH$_3$ | O | CH$_3$ | OCH$_3$ | OCH$_3$ | |
| H | CH$_3$ | O | CH$_3$ | OCH$_3$ | CH$_3$ | |
| H | CH$_3$ | S | H | CH$_3$ | CH$_3$ | |
| H | CH$_3$ | S | H | OCH$_3$ | OCH$_3$ | |
| H | CH$_3$ | S | H | H | H | |
| H | CH(CH$_3$)$_2$ | S | H | CH$_3$ | CH$_3$ | |

TABLE II-l

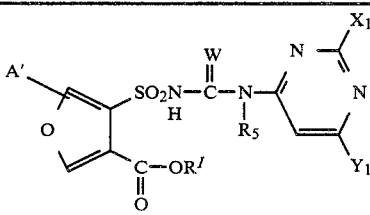

| A' | R$^I$ | W | R$_5$ | X$_1$ | Y$_1$ | m.p. (°C.) |
|---|---|---|---|---|---|---|
| H | CH$_3$ | O | H | H | H | |
| H | CH$_3$ | O | H | H | OCH$_3$ | |
| H | CH$_3$ | O | H | H | CH$_3$ | |
| H | CH$_3$ | O | H | Cl | H | |
| H | CH$_3$ | O | H | Cl | OCH$_3$ | |
| H | CH$_3$ | O | H | Cl | CH$_3$ | |
| H | CH$_3$ | O | H | OCH$_3$ | H | |
| H | CH$_3$ | O | H | OCH$_3$ | OCH$_3$ | |

TABLE II-l-continued

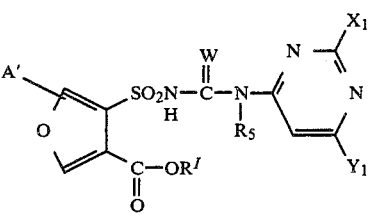

| A' | R$^I$ | W | R$_5$ | X$_1$ | Y$_1$ | m.p. (°C.) |
|---|---|---|---|---|---|---|
| H | CH$_3$ | O | H | OCH$_3$ | CH$_3$ | |
| H | CH$_3$ | O | H | OC$_2$H$_5$ | H | |
| H | CH$_3$ | O | H | OC$_2$H$_5$ | OCH$_3$ | |
| H | CH$_3$ | O | H | OC$_2$H$_5$ | CH$_3$ | |
| H | CH$_3$ | O | H | CH$_3$ | H | |
| H | CH$_3$ | O | H | CH$_3$ | OCH$_3$ | |
| H | CH$_3$ | O | H | CH$_3$ | CH$_3$ | |
| H | CH$_3$ | O | H | OCH$_3$ | OCH$_3$ | |
| 5-Cl | CH$_3$ | O | H | OCH$_3$ | OCH$_3$ | |
| 5-CH$_3$ | CH$_3$ | O | H | OCH$_3$ | OCH$_3$ | |
| 5-Br | CH$_3$ | O | H | OCH$_3$ | OCH$_3$ | |
| 5-C$_2$H$_5$ | CH$_3$ | O | H | OCH$_3$ | OCH$_3$ | |
| H | CH(CH$_3$)$_2$ | O | CH | OCH$_3$ | OCH$_3$ | |
| H | CH$_2$CH=CH$_2$ | O | CH | OCH$_3$ | OCH$_3$ | |
| H | CH$_3$ | O | CH$_3$ | OCH$_3$ | OCH$_3$ | |
| H | CH$_3$ | O | CH$_3$ | OCH$_3$ | OCH$_3$ | |
| H | CH$_3$ | O | CH$_3$ | OCH$_3$ | CH$_3$ | |
| H | CH$_3$ | S | H | CH$_3$ | CH$_3$ | |
| H | CH$_3$ | S | H | OCH$_3$ | OCH$_3$ | |
| H | CH$_3$ | S | H | H | H | |
| H | CH(CH$_3$)$_2$ | S | H | CH$_3$ | CH$_3$ | |

TABLE III-a

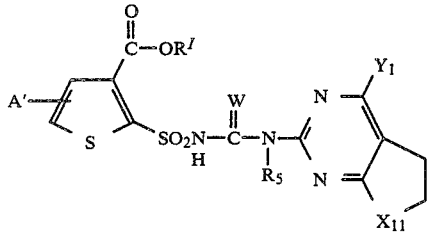

| A' | R$^I$ | W | R$_5$ | X$_{11}$ | Y$_1$ | m.p. (°C.) |
|---|---|---|---|---|---|---|
| H | CH$_3$ | O | H | CH$_2$ | H | |
| H | CH$_3$ | O | H | CH$_2$ | OCH$_3$ | |
| H | CH$_3$ | O | H | CH$_2$ | CH$_3$ | |
| H | CH$_3$ | O | H | O | H | |
| H | CH$_3$ | O | H | O | OCH$_3$ | |
| H | CH$_3$ | O | H | O | CH$_3$ | |
| 5-CH$_3$ | CH$_3$ | O | H | O | CH$_3$ | |
| 5-CH$_3$ | CH$_3$ | O | H | O | CH$_3$ | |
| 5-Cl | CH$_3$ | O | H | O | CH$_3$ | |
| 5-Cl | CH$_3$ | O | H | O | CH$_3$ | |
| H | CH$_3$ | S | H | CH$_2$ | OCH$_3$ | |
| H | CH$_3$ | S | H | O | CH$_3$ | |
| H | CH(CH$_3$)$_2$ | S | H | O | CH$_3$ | |
| H | CH(CH$_3$)$_2$ | O | H | O | CH$_3$ | |
| H | CH$_3$ | O | CH$_3$ | O | CH$_3$ | |
| H | CH(CH$_3$)$_2$ | O | CH$_3$ | O | CH$_3$ | |

TABLE III-b

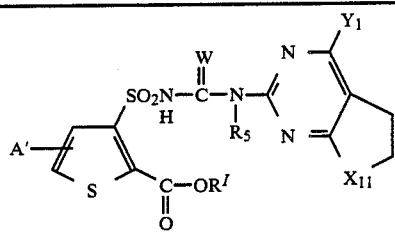

| A' | R^I | W | R_5 | X_11 | Y_1 | m.p. (°C.) |
|---|---|---|---|---|---|---|
| H | CH_3 | O | H | CH_2 | H | |
| H | CH_3 | O | H | CH_2 | OCH_3 | |
| H | CH_3 | O | H | CH_2 | CH_3 | |
| H | CH_3 | O | H | O | H | |
| H | CH_3 | O | H | O | OCH_3 | |
| H | CH_3 | O | H | O | CH_3 | 147–155 (d) |
| 5-CH_3 | CH_3 | O | H | O | CH_3 | |
| 5-CH_3 | CH_3 | O | H | O | CH_3 | |
| 5-Cl | CH_3 | O | H | O | CH_3 | |
| 5-Cl | CH_3 | O | H | O | CH_3 | |
| H | CH_3 | S | H | CH_2 | OCH_3 | |
| H | CH_3 | S | H | O | CH_3 | |
| H | CH_3 | S | H | O | CH_3 | |
| H | CH(CH_3)_2 | S | H | O | CH_3 | |
| H | CH(CH_3)_2 | O | H | O | CH_3 | |
| H | CH_3 | O | CH_3 | O | CH_3 | |
| H | CH(CH_3)_2 | O | CH_3 | O | CH_3 | |

TABLE III-c

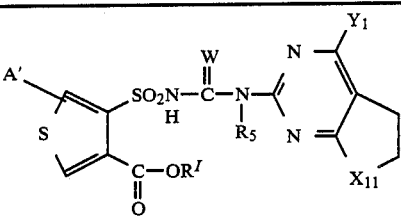

| A' | R^I | W | R_5 | X_11 | Y_1 | m.p. (°C.) |
|---|---|---|---|---|---|---|
| H | CH_3 | O | H | CH_2 | H | |
| H | CH_3 | O | H | CH_2 | OCH_3 | |
| H | CH_3 | O | H | CH_2 | CH_3 | |
| H | CH_3 | O | H | O | H | |
| H | CH_3 | O | H | O | OCH_3 | |
| H | CH_3 | O | H | O | CH_3 | |
| 5-CH_3 | CH_3 | O | H | O | CH_3 | |
| 5-CH_3 | CH_3 | O | H | O | CH_3 | |
| 5-Cl | CH_3 | O | H | O | CH_3 | |
| 5-Cl | CH_3 | O | H | O | CH_3 | |
| H | CH_3 | S | H | CH_2 | OCH_3 | |
| H | CH_3 | S | H | O | CH_3 | |
| H | CH_3 | S | H | O | CH_3 | |
| H | CH(CH_3)_2 | S | H | O | CH_3 | |
| H | CH(CH_3)_2 | O | H | O | CH_3 | |
| H | CH_3 | O | CH_3 | O | CH_3 | |
| H | CH(CH_3)_2 | O | CH_3 | O | CH_3 | |

TABLE III-d

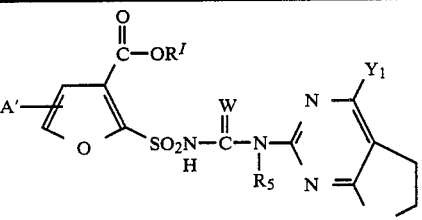

| A' | R^I | W | R_5 | X_11 | Y_1 | m.p. (°C.) |
|---|---|---|---|---|---|---|
| H | CH_3 | O | H | CH_2 | H | |

TABLE III-d-continued

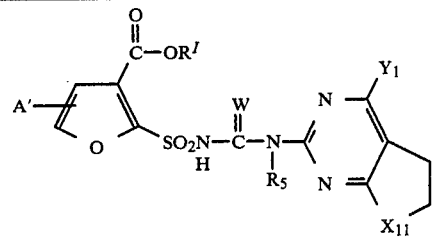

| A' | R^I | W | R_5 | X_11 | Y_1 | m.p. (°C.) |
|---|---|---|---|---|---|---|
| H | CH_3 | O | H | CH_2 | OCH_3 | |
| H | CH_3 | O | H | CH_2 | CH_3 | |
| H | CH_3 | O | H | O | H | |
| H | CH_3 | O | H | O | OCH_3 | |
| H | CH_3 | O | H | O | CH_3 | 180–182° |
| 5-CH_3 | CH_3 | O | H | O | CH_3 | |
| 5-CH_3 | CH_3 | O | H | O | CH_3 | |
| 5-Cl | CH_3 | O | H | O | CH_3 | |
| 5-Cl | CH_3 | O | H | O | CH_3 | |
| H | CH_3 | S | H | CH_2 | OCH_3 | |
| H | CH_3 | S | H | O | CH_3 | |
| H | CH_3 | S | H | O | CH_3 | |
| H | CH(CH_3)_2 | S | H | O | CH_3 | |
| H | CH(CH_3)_2 | O | H | O | CH_3 | |
| H | CH_3 | O | CH_3 | O | CH_3 | |
| H | CH(CH_3)_2 | O | CH_3 | O | CH_3 | |

TABLE III-e

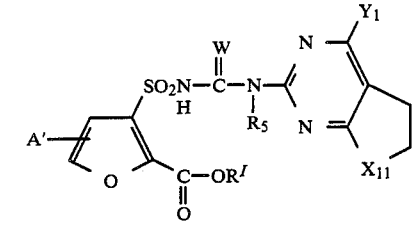

| A' | R^I | W | R_5 | X_11 | Y_1 | m.p. (°C.) |
|---|---|---|---|---|---|---|
| H | CH_3 | O | H | CH_2 | H | |
| H | CH_3 | O | H | CH_2 | OCH_3 | |
| H | CH_3 | O | H | CH_2 | CH_3 | |
| H | CH_3 | O | H | O | H | |
| H | CH_3 | O | H | O | OCH_3 | |
| H | CH_3 | O | H | O | CH_3 | 175° (d) |
| 5-CH_3 | CH_3 | O | H | O | CH_3 | |
| 5-CH_3 | CH_3 | O | H | O | CH_3 | |
| 5-Cl | CH_3 | O | H | O | CH_3 | |
| 5-Cl | CH_3 | O | H | O | CH_3 | |
| H | CH_3 | S | H | CH_2 | OCH_3 | |
| H | CH_3 | S | H | O | CH_3 | |
| H | CH_3 | S | H | O | CH_3 | |
| H | CH(CH_3)_2 | S | H | O | CH_3 | |
| H | CH(CH_3)_2 | O | H | O | CH_3 | |
| H | CH_3 | O | CH_3 | O | CH_3 | |
| H | CH(CH_3)_2 | O | CH_3 | O | CH_3 | |

TABLE III-f

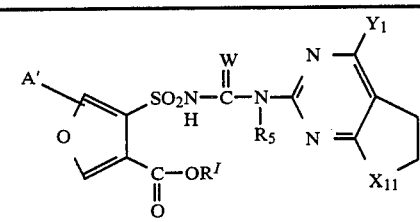

| A' | R^I | W | R_5 | X_11 | Y_1 | m.p. (°C.) |
|---|---|---|---|---|---|---|
| H | CH_3 | O | H | CH_2 | H | |
| H | CH_3 | O | H | CH_2 | OCH_3 | |

TABLE III-f-continued

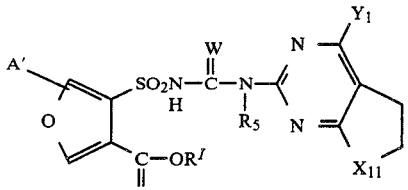

| A' | R$^I$ | W | R$_5$ | X$_{11}$ | Y$_1$ | m.p. (°C.) |
|---|---|---|---|---|---|---|
| H | CH$_3$ | O | H | CH$_2$ | CH$_3$ | |
| H | CH$_3$ | O | H | O | H | |
| H | CH$_3$ | O | H | O | OCH$_3$ | |
| H | CH$_3$ | O | H | O | CH$_3$ | |
| 5-CH$_3$ | CH$_3$ | O | H | O | CH$_3$ | |
| 5-CH$_3$ | CH$_3$ | O | H | O | CH$_3$ | |
| 5-Cl | CH$_3$ | O | H | O | CH$_3$ | |
| 5-Cl | CH$_3$ | O | H | O | CH$_3$ | |
| H | CH$_3$ | S | H | CH$_2$ | OCH$_3$ | |
| H | CH$_3$ | S | H | O | OCH$_3$ | |
| H | CH$_3$ | S | H | O | CH$_3$ | |
| H | CH(CH$_3$)$_2$ | S | H | O | CH$_3$ | |
| H | CH(CH$_3$)$_2$ | O | H | O | CH$_3$ | |
| H | CH$_3$ | O | CH$_3$ | O | CH$_3$ | |
| H | CH(CH$_3$)$_2$ | O | CH$_3$ | O | CH$_3$ | |

TABLE IV-a

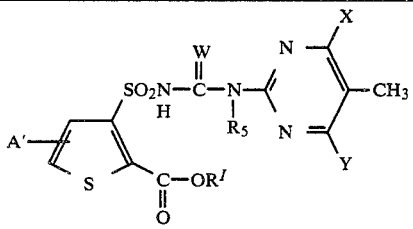

| A' | R$^I$ | W | R$_5$ | X | Y | m.p. (°C.) |
|---|---|---|---|---|---|---|
| H | CH$_3$ | O | H | CH$_3$ | CH$_3$ | |
| H | CH$_3$ | O | H | OCH$_3$ | CH$_3$ | |
| H | CH$_3$ | O | H | OCH$_3$ | OCH$_3$ | |
| H | CH$_3$ | O | H | CH$_3$ | CH$_2$OCH$_3$ | |
| H | CH$_3$ | O | H | OC$_2$H$_5$ | C$_2$H$_5$ | |
| H | CH$_3$ | S | H | OCH$_3$ | CH$_3$ | |
| H | CH$_3$ | S | H | CH$_3$ | CH$_3$ | |
| H | CH$_3$ | O | CH$_3$ | CH$_3$ | OCH$_3$ | |
| H | CH$_3$ | O | CH$_3$ | OCH$_3$ | OCH$_3$ | |
| 5-Cl | CH$_3$ | O | H | OCH$_3$ | OCH$_3$ | |
| 5-CH$_3$ | CH$_3$ | O | H | CH$_3$ | CH$_3$ | |
| 5-CH$_3$ | CH$_3$ | O | H | OCH$_3$ | OCH$_3$ | |
| H | C$_2$H$_5$ | O | H | OCH$_3$ | OCH$_3$ | |
| H | CH(CH$_3$)$_2$ | O | H | OCH$_3$ | OCH$_3$ | |
| H | CH$_2$CH=CH$_2$ | O | H | OCH$_3$ | OCH$_3$ | |

TABLE IV-b

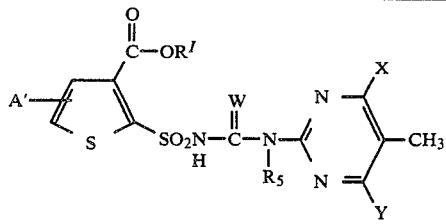

| A' | R$^I$ | W | R$_5$ | X | Y | m.p. (°C.) |
|---|---|---|---|---|---|---|
| H | CH$_3$ | O | H | CH$_3$ | CH$_3$ | |
| H | CH$_3$ | O | H | OCH$_3$ | CH$_3$ | |
| H | CH$_3$ | O | H | OCH$_3$ | OCH$_3$ | |
| H | CH$_3$ | O | H | CH$_3$ | CH$_2$OCH$_3$ | |

TABLE IV-b-continued

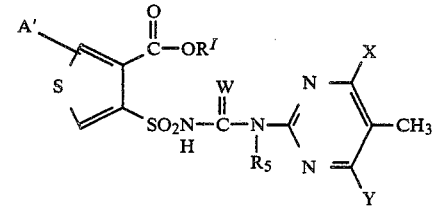

| A' | R$^I$ | W | R$_5$ | X | Y | m.p. (°C.) |
|---|---|---|---|---|---|---|
| H | CH$_3$ | O | H | OC$_2$H$_5$ | C$_2$H$_5$ | |
| H | CH$_3$ | S | H | OCH$_3$ | CH$_3$ | |
| H | CH$_3$ | S | H | CH$_3$ | CH$_3$ | |
| H | CH$_3$ | O | CH$_3$ | CH$_3$ | OCH$_3$ | |
| H | CH$_3$ | O | CH$_3$ | OCH$_3$ | OCH$_3$ | |
| 5-Cl | CH$_3$ | O | H | OCH$_3$ | OCH$_3$ | |
| 5-CH$_3$ | CH$_3$ | O | H | CH$_3$ | CH$_3$ | |
| 5-CH$_3$ | CH$_3$ | O | H | OCH$_3$ | OCH$_3$ | |
| H | C$_2$H$_5$ | O | H | OCH$_3$ | OCH$_3$ | |
| H | CH(CH$_3$)$_2$ | O | H | OCH$_3$ | OCH$_3$ | |
| H | CH$_2$CH=CH$_2$ | O | H | OCH$_3$ | OCH$_3$ | |

TABLE IV-c

| A' | R$^I$ | W | R$_5$ | X | Y | m.p. (°C.) |
|---|---|---|---|---|---|---|
| H | CH$_3$ | O | H | CH$_3$ | CH$_3$ | |
| H | CH$_3$ | O | H | OCH$_3$ | CH$_3$ | |
| H | CH$_3$ | O | H | OCH$_3$ | OCH$_3$ | |
| H | CH$_3$ | O | H | CH$_3$ | CH$_2$OCH$_3$ | |
| H | CH$_3$ | O | H | OC$_2$H$_5$ | C$_2$H$_5$ | |
| H | CH$_3$ | S | H | OCH$_3$ | CH$_3$ | |
| H | CH$_3$ | S | H | CH$_3$ | CH$_3$ | |
| H | CH$_3$ | O | CH$_3$ | CH$_3$ | OCH$_3$ | |
| H | CH$_3$ | O | CH$_3$ | OCH$_3$ | OCH$_3$ | |
| 5-Cl | CH$_3$ | O | H | OCH$_3$ | OCH$_3$ | |
| 5-CH$_3$ | CH$_3$ | O | H | CH$_3$ | CH$_3$ | |
| 5-CH$_3$ | CH$_3$ | O | H | OCH$_3$ | OCH$_3$ | |
| H | C$_2$H$_5$ | O | H | OCH$_3$ | OCH$_3$ | |
| H | CH(CH$_3$)$_2$ | O | H | OCH$_3$ | OCH$_3$ | |
| H | CH$_2$CH=CH$_2$ | O | H | OCH$_3$ | OCH$_3$ | |

TABLE IV-d

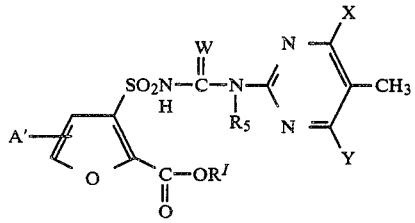

| A' | R$^I$ | W | R$_5$ | X | Y | m.p. (°C.) |
|---|---|---|---|---|---|---|
| H | CH$_3$ | O | H | CH$_3$ | CH$_3$ | |
| H | CH$_3$ | O | H | OCH$_3$ | CH$_3$ | |
| H | CH$_3$ | O | H | OCH$_3$ | OCH$_3$ | |
| H | CH$_3$ | O | H | CH$_3$ | CH$_2$OCH$_3$ | |
| H | CH$_3$ | O | H | OC$_2$H$_5$ | C$_2$H$_5$ | |
| H | CH$_3$ | S | H | OCH$_3$ | CH$_3$ | |
| H | CH$_3$ | S | H | CH$_3$ | CH$_3$ | |

TABLE IV-d-continued

| A' | R¹ | W | R₅ | X | Y | m.p. (°C.) |
|---|---|---|---|---|---|---|
| H | CH₃ | O | CH₃ | CH₃ | OCH₃ | |
| H | CH₃ | O | CH₃ | OCH₃ | OCH₃ | |
| 5-Cl | CH₃ | O | H | OCH₃ | OCH₃ | |
| 5-CH₃ | CH₃ | O | H | CH₃ | CH₃ | |
| 5-CH₃ | CH₃ | O | H | OCH₃ | OCH₃ | |
| H | C₂H₅ | O | H | OCH₃ | OCH₃ | |
| H | CH(CH₃)₂ | O | H | OCH₃ | OCH₃ | |
| H | CH₂CH=CH₂ | O | H | OCH₃ | OCH₃ | |

TABLE IV-e

| A' | R¹ | W | R₅ | X | Y | m.p. (°C.) |
|---|---|---|---|---|---|---|
| H | CH₃ | O | H | CH₃ | CH₃ | |
| H | CH₃ | O | H | OCH₃ | CH₃ | |
| H | CH₃ | O | H | OCH₃ | OCH₃ | |
| H | CH₃ | O | H | CH₃ | CH₂OCH₃ | |
| H | CH₃ | O | H | OC₂H₅ | C₂H₅ | |
| H | CH₃ | S | H | OCH₃ | CH₃ | |
| H | CH₃ | S | H | CH₃ | CH₃ | |
| H | CH₃ | O | CH₃ | CH₃ | OCH₃ | |
| H | CH₃ | O | CH₃ | OCH₃ | OCH₃ | |
| 5-Cl | CH₃ | O | H | OCH₃ | OCH₃ | |
| 5-CH₃ | CH₃ | O | H | CH₃ | CH₃ | |
| 5-CH₃ | CH₃ | O | H | OCH₃ | OCH₃ | |
| H | C₂H₅ | O | H | OCH₃ | OCH₃ | |
| H | CH(CH₃)₂ | O | H | OCH₃ | OCH₃ | |
| H | CH₂CH=CH₂ | O | H | OCH₃ | OCH₃ | |

TABLE IV-f

| A' | R¹ | W | R₅ | X | Y | m.p. (°C.) |
|---|---|---|---|---|---|---|
| H | CH₃ | O | H | CH₃ | CH₃ | |
| H | CH₃ | O | H | OCH₃ | CH₃ | |
| H | CH₃ | O | H | OCH₃ | OCH₃ | |
| H | CH₃ | O | H | CH₃ | CH₂OCH₃ | |
| H | CH₃ | O | H | OC₂H₅ | C₂H₅ | |
| H | CH₃ | S | H | OCH₃ | CH₃ | |
| H | CH₃ | S | H | CH₃ | CH₃ | |
| H | CH₃ | O | CH₃ | CH₃ | OCH₃ | |
| H | CH₃ | O | CH₃ | OCH₃ | OCH₃ | |
| 5-Cl | CH₃ | O | H | OCH₃ | OCH₃ | |

TABLE IV-f-continued

| A' | R¹ | W | R₅ | X | Y | m.p. (°C.) |
|---|---|---|---|---|---|---|
| 5-CH₃ | CH₃ | O | H | CH₃ | CH₃ | |
| 5-CH₃ | CH₃ | O | H | OCH₃ | OCH₃ | |
| H | C₂H₅ | O | H | OCH₃ | OCH₃ | |
| H | CH(CH₃)₂ | O | H | OCH₃ | OCH₃ | |
| H | CH₂CH=CH₂ | O | H | OCH₃ | OCH₃ | |

TABLE V

| A' | R¹ | R₅ | X | Y | Z | m.p. (°C.) |
|---|---|---|---|---|---|---|
| H | CH₃ | H | CH₃ | CH₃ | CH | |
| H | CH₃ | H | CH₃ | OCH₃ | CH | |
| H | CH₃ | H | CH₃ | OC₂H₅ | CH | |
| H | CH₃ | H | OCH₃ | OCH₃ | CH | |
| H | CH(CH₃)₂ | H | OCH₃ | OCH₃ | N | |
| H | CH₂CH₂Cl | H | OCH₃ | OCH₃ | N | |
| H | CH₃ | H | CH₃ | CH₃ | N | |
| H | CH₃ | H | CH₃ | CH₃ | CCH₃ | |
| H | CH₃ | H | CH₃ | OCH₃ | CCH₃ | |

TABLE VI

| A' | R¹ | WR^IV | X | Y | Z | m.p. (°C.) |
|---|---|---|---|---|---|---|
| H | CH₃ | OCH₃ | CH₃ | CH₃ | N | |
| H | CH₃ | OC₂H₅ | OCH₃ | CH₃ | N | |
| H | CH₃ | OCH₂CH=CH₂ | OCH₃ | CH₃ | N | |
| H | CH₃ | OCH₃ | OCH₃ | CH₃ | CH | |
| H | CH₃ | OCH₃ | CH₃ | CH₃ | CH | |
| H | CH₃ | OCH(CH₃)₂ | CH₃ | CH₃ | CH | |
| H | CH₃ | OC₂H₅ | CH₃ | CH₃ | CH | |
| H | CH₃ | OCH₃ | CH₃ | CH₃ | CH | |
| H | CH₃ | O(CH₂)₃CH₃ | CH₃ | CH₃ | CH | |
| H | CH₃ | OCH₂CH=CHCH₃ | CH₃ | CH₃ | CH | |
| H | CH₃ | OC₂H₅ | CH₃ | CH₃ | CCH₃ | |
| H | CH₃ | SCH₃ | CH₃ | OCH₃ | N | |
| H | CH₃ | SC₂H₅ | CH₃ | OCH₃ | N | |
| H | CH₃ | SCH₂CH=CH₂ | CH₃ | CH₃ | CH | |
| H | CH₃ | S(CH₂)₄CH₃ | CH₃ | CH₃ | CH | |

TABLE VII-a

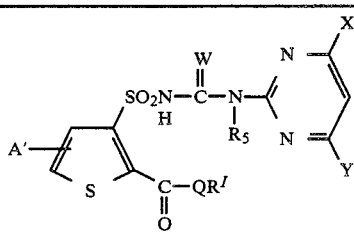

| A' | QR^I | W | R5 | X | Y | m.p. (°C.) |
|---|---|---|---|---|---|---|
| H | SCH3 | O | H | CH3 | OCH3 | |
| H | SCH(CH3)2 | O | H | CH3 | OCH3 | |
| H | SCH—C2H5 / CH3 | O | H | CH3 | OCH3 | |
| H | SCH—CH(CH3)2 / CH3 | O | H | CH3 | OCH3 | |
| H | SCH2CH=CH2 | O | H | CH3 | OCH3 | |
| H | SCH2CH—CHC2H5 | O | H | CH3 | OCH3 | |
| H | SCH2—C≡C—C2H5 | O | H | CH3 | OCH3 | |
| H | S(CH2)4Cl | O | H | CH3 | OCH3 | |
| H | SCH2CN | O | H | CH3 | OCH3 | |
| 5-Cl | S(CH2)3OCH3 | O | H | CH3 | OCH3 | |
| 5-Cl | S(CH2)4OCH3 | O | H | CH3 | OCH3 | |
| 5-CH3 | SCH2CH=CHCH2Cl | O | H | CH3 | OCH3 | |
| 5-C2H5 | SCH2C≡CCH2CH2Cl | O | H | CH3 | OCH3 | |
| H | S-cyclohexyl | O | H | CH3 | OCH3 | |
| H | S-cyclohexenyl | O | H | CH3 | OCH3 | |
| H | S-cyclohexyl | O | H | CH3 | OCH3 | |
| H | S—CH2-cyclopropyl | O | H | CH3 | OCH3 | |
| H | SCHCH2-C6H4-CH3 / CH3 | O | H | CH3 | OCH3 | |
| H | NH2 | O | H | CH3 | OCH3 | |
| H | N—CH3 / CH3 | O | H | CH3 | OCH3 | |
| H | N(CH2CN)2 | O | H | CH3 | OCH3 | |
| H | N(CH2CH2CN)2 | O | H | CH3 | OCH3 | |
| H | N(C2H5)2 | O | H | CH3 | OCH3 | |
| H | N(CH3)(CH(CH3)2) | O | H | CH3 | OCH3 | |
| H | N(CH2CH=CH2)2 | O | H | CH3 | OCH3 | |
| 5-Cl | piperidinyl | O | H | CH3 | OCH3 | |

TABLE VII-a-continued

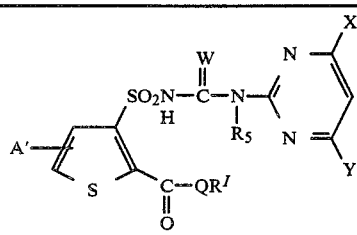

| A' | QR^I | W | R5 | X | Y | m.p. (°C.) |
|---|---|---|---|---|---|---|
| 5-Cl | morpholinyl | O | H | CH3 | OCH3 | |
| 5-Br | NHCH3 | O | H | CH3 | CH3 | |
| 5-CH3 | NHC2H5 | O | H | CH3 | CH3 | |
| 5-CH3 | NHCH(CH3)2 | O | H | CH3 | CH3 | |
| H | NHCH(CH3)(C2H5) | O | H | CH3 | CH3 | |
| H | NH(CH2)3CH3 | O | H | CH3 | CH3 | |
| H | NH(CH2)OCH3 | O | H | CH3 | CH3 | |
| H | NH(CH2)3OC2H5 | O | H | CH3 | CH3 | |
| H | NH(CH2)2OCH(CH3)2 | O | H | CH3 | CH3 | |
| H | NHCH2CH2O-C6H5 | O | H | CH3 | CH3 | |
| H | NHCH2CH=CH2 | O | CH3 | CH3 | CH3 | |
| H | NHCH2CH=CHC2H5 | O | H | CH3 | CH3 | |
| H | NH-cyclopropyl | O | H | CH3 | CH3 | |
| H | NH-cyclohexyl | O | CH3 | CH3 | CH3 | |
| H | NH-cyclopentyl | O | H | CH3 | CH3 | |
| H | NH-cyclopentenyl | O | H | CH3 | CH3 | |
| H | NH-cyclohexenyl | O | H | CH3 | CH3 | |
| H | NH-cyclohexyl(OCH3)(OCH3) | O | H | CH3 | CH3 | |
| H | NH-cyclohexyl-CH3 | O | H | CH3 | CH3 | |
| H | NH-cyclohexyl-CF3 | O | H | CH3 | CH3 | |
| H | NH-cyclohexyl-C2H5 | O | H | CH3 | CH3 | |

TABLE VII-a-continued

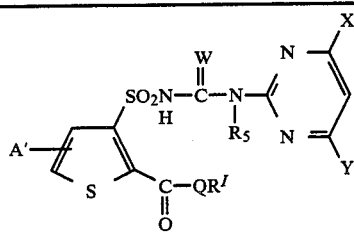

| A' | QR$^I$ | W | R$_5$ | X | Y | m.p. (°C.) |
|---|---|---|---|---|---|---|
| H | CH$_3$<br>N—CH$_2$CN | O | H | CH$_3$ | CH$_3$ | |
| H | CH$_3$<br>N—C(CH$_3$)$_2$CN | O | H | CH$_3$ | CH$_3$ | |
| H | CH$_3$<br>N—OCH$_3$ | O | H | CH$_3$ | CH$_3$ | |
| H | NH—C$_6$H$_4$—CH$_3$ (p) | O | H | CH$_3$ | OCH$_3$ | |
| H | NH—C$_6$H$_4$—Cl (o) | O | H | CH$_3$ | OCH$_3$ | |
| H | NH—C$_6$H$_4$—Cl (m) | O | H | CH$_3$ | OCH$_3$ | |
| H | NH—C$_6$H$_4$—OCH$_3$ (p) | O | H | CH$_3$ | OCH$_3$ | |
| H | NH—CH$_2$—C$_6$H$_4$—Cl (m) | O | H | CH$_3$ | OCH$_3$ | |
| H | NH—CH(CH$_3$)—C$_6$H$_4$—CH$_3$ | O | H | CH$_3$ | OCH$_3$ | |
| H | NH—CH(CH$_3$)—C$_6$H$_4$—OCH$_3$ | O | H | CH$_3$ | OCH$_3$ | |
| H | NH—CH(CH$_3$)—C$_6$H$_3$(CH$_3$)(Cl) | O | H | CH$_3$ | OCH$_3$ | |
| H | N-pyrrolidinyl | O | H | CH$_3$ | CH$_3$ | |
| H | N-pyrrolidinyl | O | H | OCH$_3$ | CH$_3$ | |
| H | NHOC$_2$H$_5$ | O | H | OCH$_3$ | CH$_3$ | 159– |

TABLE VII-a-continued

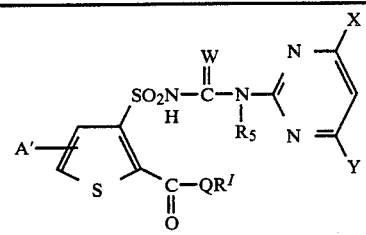

| A' | QR$^I$ | W | R$_5$ | X | Y | m.p. (°C.) |
|---|---|---|---|---|---|---|
| H | N(CH$_3$)OCH$_3$ | O | H | OCH$_3$ | OCH$_3$ | 162<br>177–179(d) |
| H | NHOCH$_3$ | O | H | CH$_3$ | CH$_3$ | 172–174 |
| H | N(CH$_3$)OCH$_3$ | O | H | CH$_3$ | CH$_3$ | 150–154 |
| H | NH—C$_6$H$_3$(Cl)(F) | O | H | CH$_3$ | CH$_3$ | 205–205.5 |
| H | N-piperidinyl | O | H | CH$_3$ | CH$_3$ | 167–170 |
| H | S-cyclohexyl | O | H | CH$_3$ | CH$_3$ | |

TABLE VII-b

| A' | QR$^I$ | W | R$_5$ | X | Y | m.p. (°C.) |
|---|---|---|---|---|---|---|
| H | SCH$_3$ | O | H | CH$_3$ | OCH$_3$ | |
| H | SCH(CH$_3$)$_2$ | O | H | CH$_3$ | OCH$_3$ | |
| H | SCH(CH$_3$)—C$_2$H$_5$ | O | H | CH$_3$ | OCH$_3$ | |
| H | SCH(CH$_3$)—CH(CH$_3$)$_2$ | O | H | CH$_3$ | OCH$_3$ | |
| H | SCH$_2$CH=CH$_2$ | O | H | CH$_3$ | OCH$_3$ | |
| H | SCH$_2$CH=CHC$_2$H$_5$ | O | H | CH$_3$ | OCH$_3$ | |
| H | SCH$_2$—C≡C—C$_2$H$_5$ | O | H | CH$_3$ | OCH$_3$ | |
| H | S(CH$_2$)$_4$Cl | O | H | CH$_3$ | OCH$_3$ | |
| H | SCH$_2$CN | O | H | CH$_3$ | OCH$_3$ | |
| 5-Cl | S(CH$_2$)$_3$OCH$_3$ | O | H | CH$_3$ | OCH$_3$ | |
| 5-Cl | S(CH$_2$)$_4$OCH$_3$ | O | H | CH$_3$ | OCH$_3$ | |
| 5-CH$_3$ | SCH$_2$CH=CHCH$_2$Cl | O | H | CH$_3$ | OCH$_3$ | |
| 5-C$_2$H$_5$ | SCH$_2$C≡CCH$_2$CH$_2$Cl | O | H | CH$_3$ | OCH$_3$ | |
| H | S-cyclohexyl | O | H | CH$_3$ | OCH$_3$ | |

TABLE VII-b-continued

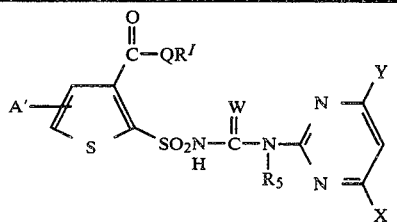

| A' | QR$^I$ | W | R$_5$ | X | Y | m.p. (°C.) |
|---|---|---|---|---|---|---|
| H | S—cyclohexenyl | O | H | CH$_3$ | OCH$_3$ | |
| H | S—cyclohexyl | O | H | CH$_3$ | OCH$_3$ | |
| H | S—CH$_2$—cyclopropyl | O | H | CH$_3$ | OCH$_3$ | |
| H | SCH(CH$_3$)CH$_2$—C$_6$H$_4$—CH$_3$ | O | H | CH$_3$ | OCH$_3$ | |
| H | NH$_2$ | O | H | CH$_3$ | OCH$_3$ | |
| H | N(CH$_3$)$_2$ | O | H | CH$_3$ | OCH$_3$ | |
| H | N(CH$_2$CN)$_2$ | O | H | CH$_3$ | OCH$_3$ | |
| H | N(CH$_2$CH$_2$CN)$_2$ | O | H | CH$_3$ | OCH$_3$ | |
| H | N(C$_2$H$_5$)$_2$ | O | H | CH$_3$ | OCH$_3$ | |
| H | N(CH$_3$)CH(CH$_3$)$_2$ | O | H | CH$_3$ | OCH$_3$ | |

TABLE VII-c

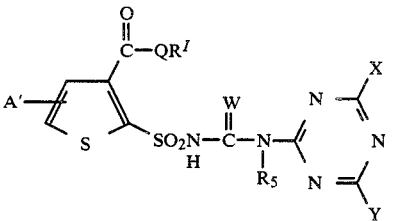

| A' | QR$^I$ | W | R$_5$ | X | Y | m.p. (°C.) |
|---|---|---|---|---|---|---|
| H | SCH$_3$ | O | H | CH$_3$ | OCH$_3$ | |
| H | SCH(CH$_3$)$_2$ | O | H | CH$_3$ | OCH$_3$ | |
| H | SCH(CH$_3$)—C$_2$H$_5$ | O | H | CH$_3$ | OCH$_3$ | |
| H | SCH(CH$_3$)—CH(CH$_3$)$_2$ | O | H | CH$_3$ | OCH$_3$ | |
| H | SCH$_2$CH=CH$_2$ | O | H | CH$_3$ | OCH$_3$ | |
| H | SCH$_2$CH=CHC$_2$H$_5$ | O | H | CH$_3$ | OCH$_3$ | |
| H | SCH$_2$—C≡C—C$_2$H$_5$ | O | H | CH$_3$ | OCH$_3$ | |
| H | S(CH$_2$)$_4$Cl | O | H | CH$_3$ | OCH$_3$ | |
| H | SCH$_2$CN | O | H | CH$_3$ | OCH$_3$ | |
| 5-Cl | S(CH$_2$)$_3$OCH$_3$ | O | H | CH$_3$ | OCH$_3$ | |
| 5-Cl | S(CH$_2$)$_4$OCH$_3$ | O | H | CH$_3$ | OCH$_3$ | |

TABLE VII-c-continued

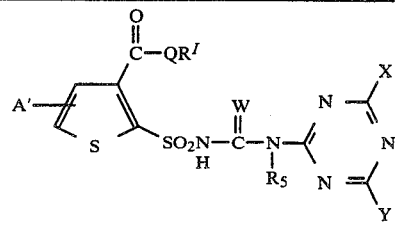

| A' | QR$^I$ | W | R$_5$ | X | Y | m.p. (°C.) |
|---|---|---|---|---|---|---|
| 5-CH$_3$ | SCH$_2$CH=CHCH$_2$Cl | O | H | CH$_3$ | OCH$_3$ | |
| 5-C$_2$H$_5$ | SCH$_2$C≡CCH$_2$CH$_2$Cl | O | H | CH$_3$ | OCH$_3$ | |
| H | S—cyclohexyl | O | H | CH$_3$ | OCH$_3$ | |
| H | S—cyclohexyl | O | H | CH$_3$ | OCH$_3$ | |
| H | S—cyclohexyl | O | H | CH$_3$ | OCH$_3$ | |
| H | S—CH$_2$—cyclopropyl | O | H | CH$_3$ | OCH$_3$ | |
| H | SCH(CH$_3$)CH$_2$—C$_6$H$_4$—CH$_3$ | O | H | CH$_3$ | OCH$_3$ | |
| H | NH$_2$ | O | H | CH$_3$ | OCH$_3$ | |
| H | N(CH$_3$)$_2$ | O | H | CH$_3$ | OCH$_3$ | |
| H | N(CH$_2$CN)$_2$ | O | H | CH$_3$ | OCH$_3$ | |
| H | N(CH$_2$CH$_2$CN)$_2$ | O | H | CH$_3$ | OCH$_3$ | |
| H | N(C$_2$H$_5$)$_2$ | O | H | CH$_3$ | OCH$_3$ | |
| H | N(CH$_3$)CH(CH$_3$)$_2$ | O | H | CH$_3$ | OCH$_3$ | |

TABLE VII-d

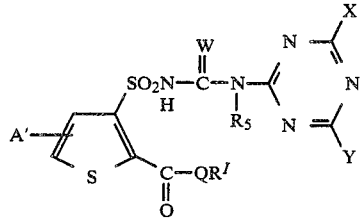

| A' | QR$^I$ | W | R$_5$ | X | Y | m.p. (°C.) |
|---|---|---|---|---|---|---|
| H | SCH$_3$ | O | H | CH$_3$ | OCH$_3$ | |
| H | SCH(CH$_3$)$_2$ | O | H | CH$_3$ | OCH$_3$ | |
| H | SCH(CH$_3$)—C$_2$H$_5$ | O | H | CH$_3$ | OCH$_3$ | |
| H | SCH(CH$_3$)—CH(CH$_3$)$_2$ | O | H | CH$_3$ | OCH$_3$ | |

TABLE VII-d-continued

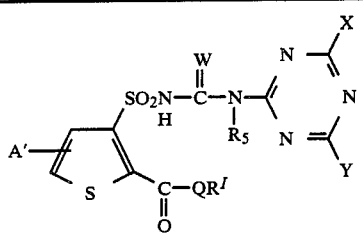

| A' | QR$^I$ | W | R$_5$ | X | Y | m.p. (°C.) |
|---|---|---|---|---|---|---|
| H | SCH$_2$CH—CH$_2$ | O | H | CH$_3$ | OCH$_3$ | |
| H | SCH$_2$CH—CHC$_2$H$_5$ | O | H | CH$_3$ | OCH$_3$ | |
| H | SCH$_2$—C≡C—C$_2$H$_5$ | O | H | CH$_3$ | OCH$_3$ | |
| H | S(CH$_2$)$_4$Cl | O | H | CH$_3$ | OCH$_3$ | |
| H | SCH$_2$CN | O | H | CH$_3$ | OCH$_3$ | |
| 5-Cl | S(CH$_2$)$_3$OCH$_3$ | O | H | CH$_3$ | OCH$_3$ | |
| 5-Cl | S(CH$_2$)$_4$OCH$_3$ | O | H | CH$_3$ | OCH$_3$ | |
| 5-CH$_3$ | SCH$_2$CH=CHCH$_2$Cl | O | H | CH$_3$ | OCH$_3$ | |
| 5-C$_2$H$_5$ | SCH$_2$C≡CCH$_2$CH$_2$Cl | O | H | CH$_3$ | OCH$_3$ | |
| H | S—cyclohexyl | O | H | CH$_3$ | OCH$_3$ | |
| H | S—cyclohexenyl | O | H | CH$_3$ | OCH$_3$ | |
| H | S—cyclohexyl | O | H | CH$_3$ | OCH$_3$ | |
| H | S—CH$_2$—cyclopropyl | O | H | CH$_3$ | OCH$_3$ | |
| H | SCH(CH$_3$)CH$_2$-C$_6$H$_4$-CH$_3$ | O | H | CH$_3$ | OCH$_3$ | |
| H | NH$_2$ | O | H | CH$_3$ | OCH$_3$ | |
| H | N(CH$_3$)$_2$ | O | H | CH$_3$ | OCH$_3$ | |
| H | N(CH$_2$CN)$_2$ | O | H | CH$_3$ | OCH$_3$ | |
| H | N(CH$_2$CH$_2$CN)$_2$ | O | H | CH$_3$ | OCH$_3$ | |
| H | N(C$_2$H$_5$)$_2$ | O | H | CH$_3$ | OCH$_3$ | |
| H | N(CH$_3$)CH(CH$_3$)$_2$ | O | H | CH$_3$ | OCH$_3$ | |
| H | pyrrolidinyl | O | H | CH$_3$ | CH$_3$ | 113–117° |

TABLE VII-e

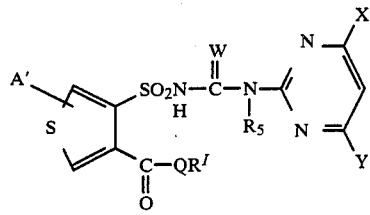

| A' | QR$^I$ | W | R$_5$ | X | Y | m.p. (°C.) |
|---|---|---|---|---|---|---|
| H | SCH$_3$ | O | H | CH$_3$ | OCH$_3$ | |
| H | SCH(CH$_3$)$_2$ | O | H | CH$_3$ | OCH$_3$ | |
| H | SCH(CH$_3$)C$_2$H$_5$ | O | H | CH$_3$ | OCH$_3$ | |
| H | SCH(CH$_3$)CH(CH$_3$)$_2$ | O | H | CH$_3$ | OCH$_3$ | |
| H | SCH$_2$CH—CH$_2$ | O | H | CH$_3$ | OCH$_3$ | |
| H | SCH$_2$CH—CHC$_2$H$_5$ | O | H | CH$_3$ | OCH$_3$ | |
| H | SCH$_2$—C≡C—C$_2$H$_5$ | O | H | CH$_3$ | OCH$_3$ | |
| H | S(CH$_2$)$_4$Cl | O | H | CH$_3$ | OCH$_3$ | |
| H | SCH$_2$CN | O | H | CH$_3$ | OCH$_3$ | |
| 5-Cl | S(CH$_2$)$_3$OCH$_3$ | O | H | CH$_3$ | OCH$_3$ | |
| 5-Cl | S(CH$_2$)$_4$OCH$_3$ | O | H | CH$_3$ | OCH$_3$ | |
| 5-CH$_3$ | SCH$_2$CH=CHCH$_2$Cl | O | H | CH$_3$ | OCH$_3$ | |
| 5-C$_2$H$_5$ | SCH$_2$C≡CCH$_2$CH$_2$Cl | O | H | CH$_3$ | OCH$_3$ | |
| H | S—cyclohexyl | O | H | CH$_3$ | OCH$_3$ | |
| H | S—cyclohexenyl | O | H | CH$_3$ | OCH$_3$ | |
| H | S—cyclohexyl | O | H | CH$_3$ | OCH$_3$ | |
| H | S—CH$_2$—cyclopropyl | O | H | CH$_3$ | OCH$_3$ | |
| H | SCH(CH$_3$)CH$_2$-C$_6$H$_4$-CH$_3$ | O | H | CH$_3$ | OCH$_3$ | |
| H | NH$_2$ | O | H | CH$_3$ | OCH$_3$ | |
| H | N(CH$_3$)$_2$ | O | H | CH$_3$ | OCH$_3$ | |
| H | N(CH$_2$CN)$_2$ | O | H | CH$_3$ | OCH$_3$ | |
| H | N(CH$_2$CH$_2$CN)$_2$ | O | H | CH$_3$ | OCH$_3$ | |
| H | N(C$_2$H$_5$)$_2$ | O | H | CH$_3$ | OCH$_3$ | |
| H | N(CH$_3$)CH(CH$_3$)$_2$ | O | H | CH$_3$ | OCH$_3$ | |

TABLE VII-f

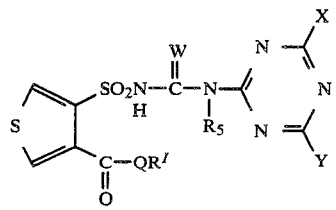

| A' | QR¹ | W | R₅ | X | Y | m.p. (°C.) |
|---|---|---|---|---|---|---|
| H | SCH₃ | O | H | CH₃ | OCH₃ | |
| H | SCH(CH₃)₂ | O | H | CH₃ | OCH₃ | |
| H | SCH—C₂H₅<br>\|<br>CH₃ | O | H | CH₃ | OCH₃ | |
| H | SCH—CH(CH₃)₂<br>\|<br>CH₃ | O | H | CH₃ | OCH₃ | |
| H | SCH₂CH=CH₂ | O | H | CH₃ | OCH₃ | |
| H | SCH₂CH=CHC₂H₅ | O | H | CH₃ | OCH₃ | |
| H | SCH₂—C≡C—C₂H₅ | O | H | CH₃ | OCH₃ | |
| H | S(CH₂)₄Cl | O | H | CH₃ | OCH₃ | |
| H | SCH₂CN | O | H | CH₃ | OCH₃ | |
| 5-Cl | S(CH₂)₃OCH₃ | O | H | CH₃ | OCH₃ | |
| 5-Cl | S(CH₂)₄OCH₃ | O | H | CH₃ | OCH₃ | |
| 5-CH₃ | SCH₂CH=CHCH₂Cl | O | H | CH₃ | OCH₃ | |
| 5-C₂H₅ | SCH₂C≡CCH₂CH₂Cl | O | H | CH₃ | OCH₃ | |
| H | S-cyclohexyl | O | H | CH₃ | OCH₃ | |
| H | S-cyclohexenyl | O | H | CH₃ | OCH₃ | |
| H | S-cyclohexenyl | O | H | CH₃ | OCH₃ | |
| H | S—CH₂-cyclopropyl | O | H | CH₃ | OCH₃ | |
| H | SCHCH₂—C₆H₄—CH₃<br>\|<br>CH₃ | O | H | CH₃ | OCH₃ | |
| H | NH₂ | O | H | CH₃ | OCH₃ | |
| H | N—CH₃<br>\|<br>CH₃ | O | H | CH₃ | OCH₃ | |
| H | N(CH₂CN)₂ | O | H | CH₃ | OCH₃ | |
| H | N(CH₂CH₂CN)₂ | O | H | CH₃ | OCH₃ | |
| H | N(C₂H₅)₂ | O | H | CH₃ | OCH₃ | |
| H | N(CH₃)(CH(CH₃)₂) | O | H | CH₃ | OCH₃ | |

TABLE VII-g

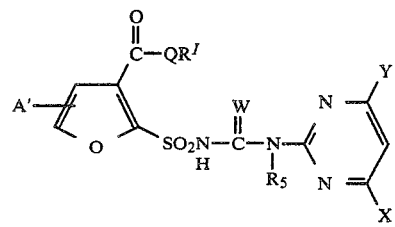

| A' | QR¹ | W | R₅ | X | Y | m.p. (°C.) |
|---|---|---|---|---|---|---|
| H | SCH₃ | O | H | CH₃ | OCH₃ | |
| H | SCH(CH₃)₂ | O | H | CH₃ | OCH₃ | |
| H | SCH—C₂H₅<br>\|<br>CH₃ | O | H | CH₃ | OCH₃ | |
| H | SCH—CH(CH₃)₂<br>\|<br>CH₃ | O | H | CH₃ | OCH₃ | |
| H | SCH₂CH=CH₂ | O | H | CH₃ | OCH₃ | |
| H | SCH₂CH=CHC₂H₅ | O | H | CH₃ | OCH₃ | |
| H | SCH₂—C≡C—C₂H₅ | O | H | CH₃ | OCH₃ | |
| H | S(CH₂)₄Cl | O | H | CH₃ | OCH₃ | |
| H | SCH₂CN | O | H | CH₃ | OCH₃ | |
| 5-Cl | S(CH₂)₃OCH₃ | O | H | CH₃ | OCH₃ | |
| 5-Cl | S(CH₂)₄OCH₃ | O | H | CH₃ | OCH₃ | |
| 5-CH₃ | SCH₂CH=CHCH₂Cl | O | H | CH₃ | OCH₃ | |
| 5-C₂H₅ | SCH₂C≡CCH₂CH₂Cl | O | H | CH₃ | OCH₃ | |
| H | S-cyclohexyl | O | H | CH₃ | OCH₃ | |
| H | S-cyclohexenyl | O | H | CH₃ | OCH₃ | |
| H | S-cyclohexenyl | O | H | CH₃ | OCH₃ | |
| H | S—CH₂-cyclopropyl | O | H | CH₃ | OCH₃ | |
| H | SCHCH₂—C₆H₄—CH₃<br>\|<br>CH₃ | O | H | CH₃ | OCH₃ | |
| H | NH₂ | O | H | CH₃ | OCH₃ | |
| H | N—CH₃<br>\|<br>CH₃ | O | H | CH₃ | OCH₃ | |
| H | N(CH₂CN)₂ | O | H | CH₃ | OCH₃ | |
| H | N(CH₂CH₂CN)₂ | O | H | CH₃ | OCH₃ | |
| H | N(C₂H₅)₂ | O | H | CH₃ | OCH₃ | |
| H | N(CH₃)(CH(CH₃)₂) | O | H | CH₃ | OCH₃ | |

TABLE VII-h

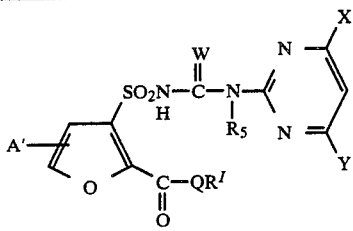

| A' | QR¹ | W | R₅ | X | Y | m.p. (°C.) |
|---|---|---|---|---|---|---|
| H | SCH₃ | O | H | CH₃ | OCH₃ | |
| H | SCH(CH₃)₂ | O | H | CH₃ | OCH₃ | |
| H | SCH(CH₃)—C₂H₅ | O | H | CH₃ | OCH₃ | |
| H | SCH(CH₃)—CH(CH₃)₂ | O | H | CH₃ | OCH₃ | |
| H | SCH₂CH=CH₂ | O | H | CH₃ | OCH₃ | |
| H | SCH₂CH=CHC₂H₅ | O | H | CH₃ | OCH₃ | |
| H | SCH₂—C≡C—C₂H₅ | O | H | CH₃ | OCH₃ | |
| H | S(CH₂)₄Cl | O | H | CH₃ | OCH₃ | |
| H | SCH₂CN | O | H | CH₃ | OCH₃ | |
| 5-Cl | S(CH₂)₃OCH₃ | O | H | CH₃ | OCH₃ | |
| 5-Cl | S(CH₂)₄OCH₃ | O | H | CH₃ | OCH₃ | |
| 5-CH₃ | SCH₂CH=CHCH₂Cl | O | H | CH₃ | OCH₃ | |
| 5-C₂H₅ | SCH₂C≡CCH₂Cl | O | H | CH₃ | OCH₃ | |
| H | S-cyclohexyl | O | H | CH₃ | OCH₃ | |
| H | S-cyclohexenyl | O | H | CH₃ | OCH₃ | |
| H | S-cyclohexyl | O | H | CH₃ | OCH₃ | |
| H | S—CH₂-cyclopropyl | O | H | CH₃ | OCH₃ | |
| H | SCH(CH₃)CH₂-(4-methylphenyl) | O | H | CH₃ | OCH₃ | |
| H | NH₂ | O | H | CH₃ | OCH₃ | |
| H | N(CH₃)₂ | O | H | CH₃ | OCH₃ | |
| H | N(CH₂CN)₂ | O | H | CH₃ | OCH₃ | |
| H | N(CH₂CH₂CN)₂ | O | H | CH₃ | OCH₃ | |
| H | N(C₂H₅)₂ | O | H | CH₃ | OCH₃ | |
| H | N(CH₃)(CH(CH₃)₂) | O | H | CH₃ | OCH₃ | |

TABLE VII-i

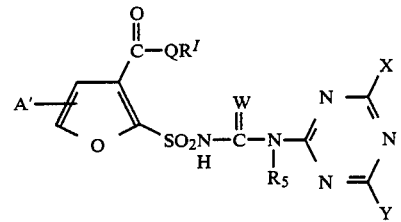

| A' | QR¹ | W | R₅ | X | Y | m.p. (°C.) |
|---|---|---|---|---|---|---|
| H | SCH₃ | O | H | CH₃ | OCH₃ | |
| H | SCH(CH₃)₂ | O | H | CH₃ | OCH₃ | |
| H | SCH(CH₃)—C₂H₅ | O | H | CH₃ | OCH₃ | |
| H | SCH(CH₃)—CH(CH₃)₂ | O | H | CH₃ | OCH₃ | |
| H | SCH₂CH=CH₂ | O | H | CH₃ | OCH₃ | |
| H | SCH₂CH=CHC₂H₅ | O | H | CH₃ | OCH₃ | |
| H | SCH₂—C≡C—C₂H₅ | O | H | CH₃ | OCH₃ | |
| H | S(CH₂)₄Cl | O | H | CH₃ | OCH₃ | |
| H | SCH₂CN | O | H | CH₃ | OCH₃ | |
| 5-Cl | S(CH₂)₃OCH₃ | O | H | CH₃ | OCH₃ | |
| 5-Cl | S(CH₂)₄OCH₃ | O | H | CH₃ | OCH₃ | |
| 5-CH₃ | SCH₂CH=CHCH₂Cl | O | H | CH₃ | OCH₃ | |
| 5-C₂H₅ | SCH₂C≡CCH₂Cl | O | H | CH₃ | OCH₃ | |
| H | S-cyclohexyl | O | H | CH₃ | OCH₃ | |
| H | S-cyclohexenyl | O | H | CH₃ | OCH₃ | |
| H | S-cyclohexyl | O | H | CH₃ | OCH₃ | |
| H | S—CH₂-cyclopropyl | O | H | CH₃ | OCH₃ | |
| H | SCH(CH₃)CH₂-(4-methylphenyl) | O | H | CH₃ | OCH₃ | |
| H | NH₂ | O | H | CH₃ | OCH₃ | |
| H | N(CH₃)₂ | O | H | CH₃ | OCH₃ | |
| H | N(CH₂CN)₂ | O | H | CH₃ | OCH₃ | |
| H | N(CH₂CH₂CN)₂ | O | H | CH₃ | OCH₃ | |
| H | N(C₂H₅)₂ | O | H | CH₃ | OCH₃ | |
| H | N(CH₃)(CH(CH₃)₂) | O | H | CH₃ | OCH₃ | |

TABLE VII-j

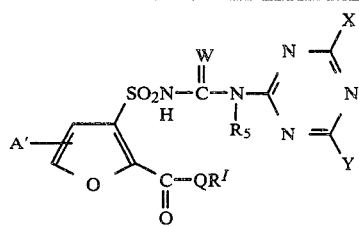

| A' | QR$^I$ | W | R$_5$ | X | Y | m.p. (°C.) |
|---|---|---|---|---|---|---|
| H | SCH$_3$ | O | H | CH$_3$ | OCH$_3$ | |
| H | SCH(CH$_3$)$_2$ | O | H | CH$_3$ | OCH$_3$ | |
| H | SCH(CH$_3$)—C$_2$H$_5$ | O | H | CH$_3$ | OCH$_3$ | |
| H | SCH(CH$_3$)—CH(CH$_3$)$_2$ | O | H | CH$_3$ | OCH$_3$ | |
| H | SCH$_2$CH=CH$_2$ | O | H | CH$_3$ | OCH$_3$ | |
| H | SCH$_2$CH=CHC$_2$H$_5$ | O | H | CH$_3$ | OCH$_3$ | |
| H | SCH$_2$—C≡C—C$_2$H$_5$ | O | H | CH$_3$ | OCH$_3$ | |
| H | S(CH$_2$)$_4$Cl | O | H | CH$_3$ | OCH$_3$ | |
| H | SCH$_2$CN | O | H | CH$_3$ | OCH$_3$ | |
| 5-Cl | S(CH$_2$)$_3$OCH$_3$ | O | H | CH$_3$ | OCH$_3$ | |
| 5-Cl | S(CH$_2$)$_4$OCH$_3$ | O | H | CH$_3$ | OCH$_3$ | |
| 5-CH$_3$ | SCH$_2$CH=CHCH$_2$Cl | O | H | CH$_3$ | OCH$_3$ | |
| 5-C$_2$H$_5$ | SCH$_2$C≡CCH$_2$CH$_2$Cl | O | H | CH$_3$ | OCH$_3$ | |
| H | S-cyclohexyl | O | H | CH$_3$ | OCH$_3$ | |
| H | S-cyclohexenyl | O | H | CH$_3$ | OCH$_3$ | |
| H | S-cyclohexyl | O | H | CH$_3$ | OCH$_3$ | |
| H | S—CH$_2$-cyclopropyl | O | H | CH$_3$ | OCH$_3$ | |
| H | SCH(CH$_3$)CH$_2$-(4-CH$_3$-C$_6$H$_4$) | O | H | CH$_3$ | OCH$_3$ | |
| H | NH$_2$ | O | H | CH$_3$ | OCH$_3$ | |
| H | N(CH$_3$)$_2$ | O | H | CH$_3$ | OCH$_3$ | |
| H | N(CH$_2$CN)$_2$ | O | H | CH$_3$ | OCH$_3$ | |
| H | N(CH$_2$CH$_2$CN)$_2$ | O | H | CH$_3$ | OCH$_3$ | |
| H | N(C$_2$H$_5$)$_2$ | O | H | CH$_3$ | OCH$_3$ | |
| H | N(CH$_3$)(CH(CH$_3$)$_2$) | O | H | CH$_3$ | OCH$_3$ | |

TABLE VII-k

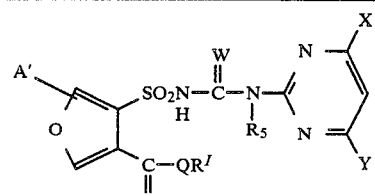

| A' | QR$^I$ | W | R$_5$ | X | Y | m.p. (°C.) |
|---|---|---|---|---|---|---|
| H | SCH$_3$ | O | H | CH$_3$ | OCH$_3$ | |
| H | SCH(CH$_3$)$_2$ | O | H | CH$_3$ | OCH$_3$ | |
| H | SCH(CH$_3$)—C$_2$H$_5$ | O | H | CH$_3$ | OCH$_3$ | |
| H | SCH(CH$_3$)—CH(CH$_3$)$_2$ | O | H | CH$_3$ | OCH$_3$ | |
| H | SCH$_2$CH=CH$_2$ | O | H | CH$_3$ | OCH$_3$ | |
| H | SCH$_2$CH=CHC$_2$H$_5$ | O | H | CH$_3$ | OCH$_3$ | |
| H | SCH$_2$—C≡C—C$_2$H$_5$ | O | H | CH$_3$ | OCH$_3$ | |
| H | S(CH$_2$)$_4$Cl | O | H | CH$_3$ | OCH$_3$ | |
| H | SCH$_2$CN | O | H | CH$_3$ | OCH$_3$ | |
| 5-Cl | S(CH$_2$)$_2$OCH$_3$ | O | H | CH$_3$ | OCH$_3$ | |
| 5-Cl | S(CH$_2$)$_4$OCH$_3$ | O | H | CH$_3$ | OCH$_3$ | |
| 5-CH$_3$ | SCH$_2$CH=CHCH$_2$Cl | O | H | CH$_3$ | OCH$_3$ | |
| 5-C$_2$H$_5$ | SCH$_2$C≡CCH$_2$CH$_2$Cl | O | H | CH$_3$ | OCH$_3$ | |
| H | S-cyclohexyl | O | H | CH$_3$ | OCH$_3$ | |
| H | S-cyclohexenyl | O | H | CH$_3$ | OCH$_3$ | |
| H | S-cyclohexyl | O | H | CH$_3$ | OCH$_3$ | |
| H | S—CH$_2$-cyclopropyl | O | H | CH$_3$ | OCH$_3$ | |
| H | SCH(CH$_3$)CH$_2$-(4-CH$_3$-C$_6$H$_4$) | O | H | CH$_3$ | OCH$_3$ | |
| H | NH$_2$ | O | H | CH$_3$ | OCH$_3$ | |
| H | N(CH$_3$)$_2$ | O | H | CH$_3$ | OCH$_3$ | |
| H | N(CH$_2$CN)$_2$ | O | H | CH$_3$ | OCH$_3$ | |
| H | N(CH$_2$CH$_2$CN)$_2$ | O | H | CH$_3$ | OCH$_3$ | |
| H | N(C$_2$H$_5$)$_2$ | O | H | CH$_3$ | OCH$_3$ | |
| H | N(CH$_3$)(CH(CH$_3$)$_2$) | O | H | CH$_3$ | OCH$_3$ | |

TABLE VII-l

| A' | QR^I | W | R_5 | X | Y | m.p. (°C.) |
|---|---|---|---|---|---|---|
| H | SCH_3 | O | H | CH_3 | OCH_3 | |
| H | SCH(CH_3)_2 | O | H | CH_3 | OCH_3 | |
| H | SCH(CH_3)—C_2H_5 | O | H | CH_3 | OCH_3 | |
| H | SCH(CH_3)—CH(CH_3)_2 | O | H | CH_3 | OCH_3 | |
| H | SCH_2CH=CH_2 | O | H | CH_3 | OCH_3 | |
| H | SCH_2CH=CHC_2H_5 | O | H | CH_3 | OCH_3 | |
| H | SCH_2—C≡C—C_2H_5 | O | H | CH_3 | OCH_3 | |
| H | S(CH_2)_4Cl | O | H | CH_3 | OCH_3 | |
| H | SCH_2CN | O | H | CH_3 | OCH_3 | |
| 5-Cl | S(CH_2)_2OCH_3 | O | H | CH_3 | OCH_3 | |
| 5-Cl | S(CH_2)_4OCH_3 | O | H | CH_3 | OCH_3 | |
| 5-CH_3 | SCH_2CH=CHCH_2Cl | O | H | CH_3 | OCH_3 | |
| 5-C_2H_5 | SCH_2C≡CCH_2Cl | O | H | CH_3 | OCH_3 | |
| H | S-cyclohexyl | O | H | CH_3 | OCH_3 | |
| H | S-cyclohexenyl | O | H | CH_3 | OCH_3 | |
| H | S-cyclohexyl | O | H | CH_3 | OCH_3 | |
| H | S—CH_2-cyclopropyl | O | H | CH_3 | OCH_3 | |
| H | SCH(CH_3)CH_2-(4-CH_3-C_6H_4) | O | H | CH_3 | OCH_3 | |
| H | NH_2 | O | H | CH_3 | OCH_3 | |
| H | N(CH_3)_2 | O | H | CH_3 | OCH_3 | |
| H | N(CH_2CN)_2 | O | H | CH_3 | OCH_3 | |
| H | N(CH_2CH_2CN)_2 | O | H | CH_3 | OCH_3 | |
| H | N(C_2H_5)_2 | O | H | CH_3 | OCH_3 | |
| H | N(CH_3)(CH(CH_3)_2) | O | H | CH_3 | OCH_3 | |

TABLE VIII-a

| A' | QR^1 | W | R_5 | X_1 | Y_1 | m.p.(°C.) |
|---|---|---|---|---|---|---|
| H | SCH(CH_3)_2 | O | H | CH_3 | CH_3 | |
| H | SCH_3 | O | H | CH_3 | CH_3 | |
| H | SCH_2CH_3 | O | H | CH_3 | CH_3 | |
| H | S(CH_2)_3CH_3 | O | H | CH_3 | CH_3 | |
| H | NH(CH_2)_3CH_3 | O | H | CH_3 | CH_3 | |
| H | NHCH(CH_3)_2 | O | H | CH_3 | CH_3 | |
| H | N(CH_3)_2 | O | H | OCH_3 | OCH_3 | |
| H | N(C_2H_5)_2 | O | H | OCH_3 | OCH_3 | |
| H | N(OCH_3)(CH_3) | O | H | OCH_3 | OCH_3 | |
| H | N-pyrrolidinyl | O | H | OCH_3 | OCH_3 | |

TABLE VIII-b

| A' | QR^I | W | R_5 | X_1 | Y_1 | m.p.(°C.) |
|---|---|---|---|---|---|---|
| H | SCH(CH_3)_2 | O | H | CH_3 | CH_3 | |
| H | SCH_3 | O | H | CH_3 | CH_3 | |
| H | SCH_2CH_3 | O | H | CH_3 | CH_3 | |
| H | S(CH_2)_3CH_3 | O | H | CH_3 | CH_3 | |
| H | NH(CH_2)_3CH_3 | O | H | CH_3 | CH_3 | |
| H | NHCH(CH_3)_2 | O | H | CH_3 | CH_3 | |
| H | N(CH_3)_2 | O | H | OCH_3 | OCH_3 | |
| H | N(C_2H_5)_2 | O | H | OCH_3 | OCH_3 | |
| H | N(OCH_3)(CH_3) | O | H | OCH_3 | OCH_3 | |
| H | N-pyrrolidinyl | O | H | OCH_3 | OCH_3 | |

TABLE VIII-c

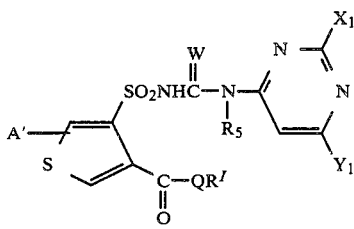

| A' | QR^I | W | R5 | X1 | Y1 | m.p.(°C.) |
|---|---|---|---|---|---|---|
| H | SCH(CH3)2 | O | H | CH3 | CH3 | |
| H | SCH3 | O | H | CH3 | CH3 | |
| H | SCH3CH3 | O | H | CH3 | CH3 | |
| H | S(CH2)3CH3 | O | H | CH3 | CH3 | |
| H | NH(CH2)3CH3 | O | H | CH3 | CH3 | |
| H | NHCH(CH3)2 | O | H | CH3 | CH3 | |
| H | N(CH3)2 | O | H | OCH3 | OCH3 | |
| H | N(C2H5)2 | O | H | OCH3 | OCH3 | |
| H | N—OCH3 / CH3 | O | H | OCH3 | OCH3 | |
| H | N (pyrrolidinyl) | O | H | OCH3 | OCH3 | |

TABLE VIII-d

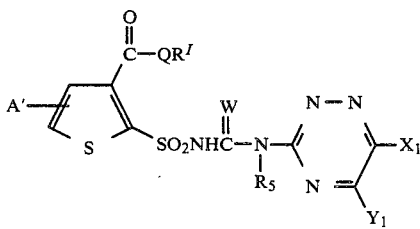

| A' | QR^I | W | R5 | X1 | Y1 | m.p.(°C.) |
|---|---|---|---|---|---|---|
| H | SCH(CH3)2 | O | H | CH3 | CH3 | |
| H | SCH3 | O | H | CH3 | CH3 | |
| H | SCH3CH3 | O | H | CH3 | CH3 | |
| H | S(CH2)3CH3 | O | H | CH3 | CH3 | |
| H | NH(CH2)3CH3 | O | H | CH3 | CH3 | |
| H | NHCH(CH3)2 | O | H | CH3 | CH3 | |
| H | N(CH3)2 | O | H | OCH3 | OCH3 | |
| H | N(C2H5)2 | O | H | OCH3 | OCH3 | |
| H | N—OCH3 / CH3 | O | H | OCH3 | OCH3 | |
| H | N (pyrrolidinyl) | O | H | OCH3 | OCH3 | |

TABLE VIII-e

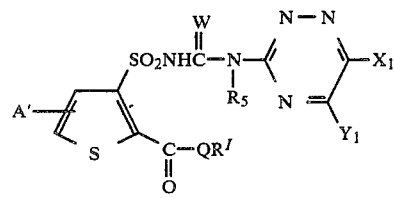

| A' | QR^I | W | R5 | X1 | Y1 | m.p.(°C.) |
|---|---|---|---|---|---|---|
| H | SCH(CH3)2 | O | H | CH3 | CH3 | |
| H | SCH3 | O | H | CH3 | CH3 | |
| H | SCH3CH3 | O | H | CH3 | CH3 | |
| H | S(CH2)3CH3 | O | H | CH3 | CH3 | |
| H | NH(CH2)3CH3 | O | H | CH3 | CH3 | |
| H | NHCH(CH3)2 | O | H | CH3 | CH3 | |
| H | N(CH3)2 | O | H | OCH3 | OCH3 | |
| H | N(C2H5)2 | O | H | OCH3 | OCH3 | |
| H | N—OCH3 / CH3 | O | H | OCH3 | OCH3 | |
| H | N (pyrrolidinyl) | O | H | OCH3 | OCH3 | |

TABLE VIII-f

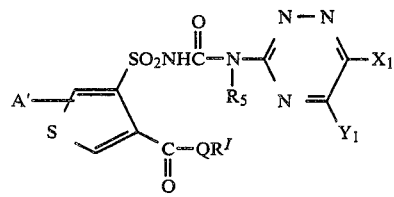

| A' | QR^I | W | R5 | X1 | Y1 | m.p.(°C.) |
|---|---|---|---|---|---|---|
| H | SCH(CH3)2 | O | H | CH3 | CH3 | |
| H | SCH3 | O | H | CH3 | CH3 | |
| H | SCH3CH3 | O | H | CH3 | CH3 | |
| H | S(CH2)3CH3 | O | H | CH3 | CH3 | |
| H | NH(CH2)3CH3 | O | H | CH3 | CH3 | |
| H | NHCH(CH3)2 | O | H | CH3 | CH3 | |
| H | N(CH3)2 | O | H | OCH3 | OCH3 | |
| H | N(C2H5)2 | O | H | OCH3 | OCH3 | |
| H | N—OCH3 / CH3 | O | H | OCH3 | OCH3 | |
| H | N (pyrrolidinyl) | O | H | OCH3 | OCH3 | |

TABLE VIII-g

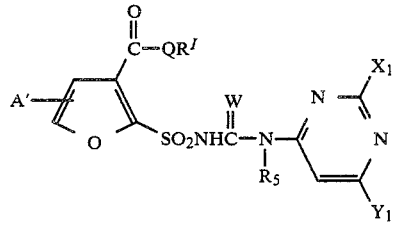

| A' | QR^I | W | R5 | X1 | Y1 | m.p.(°C.) |
|---|---|---|---|---|---|---|
| H | SCH(CH3)2 | O | H | CH3 | CH3 | |

TABLE VIII-g-continued

Structure: furan with C(=O)-QR^I at one position, A' substituent, SO₂NHC(W)N(R₅)-pyrimidine (X₁, Y₁)

| A' | QR^I | W | R₅ | X₁ | Y₁ | m.p.(°C.) |
|---|---|---|---|---|---|---|
| H | SCH₃ | O | H | CH₃ | CH₃ | |
| H | SCH₃CH₃ | O | H | CH₃ | CH₃ | |
| H | S(CH₂)₃CH₃ | O | H | CH₃ | CH₃ | |
| H | NH(CH₂)₃CH₃ | O | H | CH₃ | CH₃ | |
| H | NHCH(CH₃)₂ | O | H | CH₃ | CH₃ | |
| H | N(CH₃)₂ | O | H | OCH₃ | OCH₃ | |
| H | N(C₂H₅)₂ | O | H | OCH₃ | OCH₃ | |
| H | N(—OCH₃)CH₃ | O | H | OCH₃ | OCH₃ | |
| H | pyrrolidinyl | O | H | OCH₃ | OCH₃ | |

TABLE VIII-h

| A' | QR^I | W | R₅ | X₁ | Y₁ | m.p.(°C.) |
|---|---|---|---|---|---|---|
| H | SCH(CH₃)₂ | O | H | CH₃ | CH₃ | |
| H | SCH₃ | O | H | CH₃ | CH₃ | |
| H | SCH₃CH₃ | O | H | CH₃ | CH₃ | |
| H | S(CH₂)₃CH₃ | O | H | CH₃ | CH₃ | |
| H | NH(CH₂)₃CH₃ | O | H | CH₃ | CH₃ | |
| H | NHCH(CH₃)₂ | O | H | CH₃ | CH₃ | |
| H | N(CH₃)₂ | O | H | OCH₃ | OCH₃ | |
| H | N(C₂H₅)₂ | O | H | OCH₃ | OCH₃ | |
| H | N(—OCH₃)CH₃ | O | H | OCH₃ | OCH₃ | |
| H | pyrrolidinyl | O | H | OCH₃ | OCH₃ | |

TABLE VIII-i

| A' | QR^I | W | R₅ | X₁ | Y₁ | m.p.(°C.) |
|---|---|---|---|---|---|---|
| H | SCH(CH₃)₂ | O | H | CH₃ | CH₃ | |
| H | SCH₃ | O | H | CH₃ | CH₃ | |
| H | SCH₃CH₃ | O | H | CH₃ | CH₃ | |
| H | S(CH₂)₃CH₃ | O | H | CH₃ | CH₃ | |
| H | NH(CH₂)₃CH₃ | O | H | CH₃ | CH₃ | |
| H | NHCH(CH₃)₂ | O | H | CH₃ | CH₃ | |
| H | N(CH₃)₂ | O | H | OCH₃ | OCH₃ | |
| H | N(C₂H₅)₂ | O | H | OCH₃ | OCH₃ | |
| H | N(—OCH₃)CH₃ | O | H | OCH₃ | OCH₃ | |
| H | pyrrolidinyl | O | H | OCH₃ | OCH₃ | |

TABLE VIII-j

| A' | QR^I | W | R₅ | X₁ | Y₁ | m.p.(°C.) |
|---|---|---|---|---|---|---|
| H | SCH(CH₃)₂ | O | H | CH₃ | CH₃ | |
| H | SCH₃ | O | H | CH₃ | CH₃ | |
| H | SCH₃CH₃ | O | H | CH₃ | CH₃ | |
| H | S(CH₂)₃CH₃ | O | H | CH₃ | CH₃ | |
| H | NH(CH₂)₃CH₃ | O | H | CH₃ | CH₃ | |
| H | NHCH(CH₃)₂ | O | H | CH₃ | CH₃ | |
| H | N(CH₃)₂ | O | H | OCH₃ | OCH₃ | |
| H | N(C₂H₅)₂ | O | H | OCH₃ | OCH₃ | |
| H | N(—OCH₃)CH₃ | O | H | OCH₃ | OCH₃ | |
| H | pyrrolidinyl | O | H | OCH₃ | OCH₃ | |

TABLE VIII-k

| A' | QR^I | W | R_5 | X_1 | Y_1 | m.p.(°C.) |
|---|---|---|---|---|---|---|
| H | SCH(CH_3)_2 | O | H | CH_3 | CH_3 | |
| H | SCH_3 | O | H | CH_3 | CH_3 | |
| H | SCH_3CH_3 | O | H | CH_3 | CH_3 | |
| H | S(CH_2)_3CH_3 | O | H | CH_3 | CH_3 | |
| H | NH(CH_2)_3CH_3 | O | H | CH_3 | CH_3 | |
| H | NHCH(CH_3)_2 | O | H | CH_3 | CH_3 | |
| H | N(CH_3)_2 | O | H | OCH_3 | OCH_3 | |
| H | N(C_2H_5)_2 | O | H | OCH_3 | OCH_3 | |
| H | N(—OCH_3)CH_3 | O | H | OCH_3 | OCH_3 | |
| H | N(pyrrolidinyl) | O | H | OCH_3 | OCH_3 | |

TABLE VIII-l

| A' | QR^I | W | R_5 | X_1 | Y_1 | m.p.(°C.) |
|---|---|---|---|---|---|---|
| H | SCH(CH_3)_2 | O | H | CH_3 | CH_3 | |
| H | SCH_3 | O | H | CH_3 | CH_3 | |
| H | SCH_3CH_3 | O | H | CH_3 | CH_3 | |
| H | S(CH_2)_3CH_3 | O | H | CH_3 | CH_3 | |
| H | NH(CH_2)_3CH_3 | O | H | CH_3 | CH_3 | |
| H | NHCH(CH_3)_2 | O | H | CH_3 | CH_3 | |
| H | N(CH_3)_2 | O | H | OCH_3 | OCH_3 | |
| H | N(C_2H_5)_2 | O | H | OCH_3 | OCH_3 | |
| H | N(—OCH_3)CH_3 | O | H | OCH_3 | OCH_3 | |
| H | N(pyrrolidinyl) | O | H | OCH_3 | OCH_3 | |

TABLE IX-a

| A' | QR^I | W | R_5 | Y_1 | X_{II} | m.p.(°C.) |
|---|---|---|---|---|---|---|
| H | SCH_3 | O | H | CH_3 | CH_2 | |
| H | SC_2H_5 | O | H | CH_3 | CH_2 | |

TABLE IX-a-continued

| A' | QR^I | W | R_5 | Y_1 | X_{II} | m.p.(°C.) |
|---|---|---|---|---|---|---|
| H | SCH(CH_3)_2 | O | H | CH_3 | CH_2 | |
| H | SCH_2CH=CH_2 | O | H | CH_3 | CH_2 | |
| H | NHC_2H_5 | O | H | CH_3 | CH_2 | |
| H | NHCH(CH_3)_2 | O | H | CH_3 | O | |
| H | NH(CH_2)_5CH_3 | O | H | CH_3 | O | |
| H | NH(CH_2)_8CH_3 | O | H | CH_3 | O | |
| H | N(CH_3)_2 | O | H | CH_3 | O | |

TABLE IX-b

| A' | QR^I | W | R_5 | Y_1 | X_{II} | m.p.(°C.) |
|---|---|---|---|---|---|---|
| H | SCH_3 | O | H | CH_3 | CH_2 | |
| H | SC_2H_5 | O | H | CH_3 | CH_2 | |
| H | SCH(CH_3)_2 | O | H | CH_3 | CH_2 | |
| H | SCH_2CH=CH_2 | O | H | CH_3 | CH_2 | |
| H | NHC_2H_5 | O | H | CH_3 | CH_2 | |
| H | NHCH(CH_3)_2 | O | H | CH_3 | O | |
| H | NH(CH_2)_5CH_3 | O | H | CH_3 | O | |
| H | NH(CH_2)_8CH_3 | O | H | CH_3 | O | |
| H | N(CH_3)_2 | O | H | CH_3 | O | |

TABLE IX-c

| A' | QR^I | W | R_5 | Y_1 | X_{II} | m.p. (°C.) |
|---|---|---|---|---|---|---|
| H | SCH_3 | O | H | CH_3 | CH_2 | |
| H | SC_2H_5 | O | H | CH_3 | CH_2 | |
| H | SCH(CH_3)_2 | O | H | CH_3 | CH_2 | |
| H | SCH_2CH=CH_2 | O | H | CH_3 | CH_2 | |
| H | NHC_2H_5 | O | H | CH_3 | CH_2 | |
| H | NHCH(CH_3)_2 | O | H | CH_3 | O | |
| H | NH(CH_2)_5CH_3 | O | H | CH_3 | O | |
| H | NH(CH_2)_8CH_3 | O | H | CH_3 | O | |
| H | N(CH_3)_2 | O | H | CH_3 | O | |

TABLE IX-d

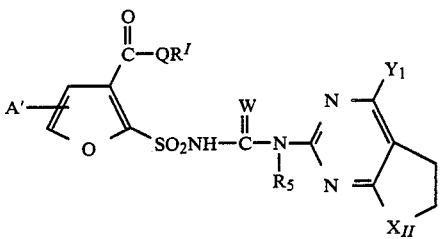

| A' | QR$^I$ | W | R$_5$ | Y$_1$ | X$_{II}$ | m.p. (°C.) |
|---|---|---|---|---|---|---|
| H | SCH$_3$ | O | H | CH$_3$ | CH$_2$ | |
| H | SC$_2$H$_5$ | O | H | CH$_3$ | CH$_2$ | |
| H | SCH(CH$_3$)$_2$ | O | H | CH$_3$ | CH$_2$ | |
| H | SCH$_2$CH=CH$_2$ | O | H | CH$_3$ | CH$_2$ | |
| H | NHC$_2$H$_5$ | O | H | CH$_3$ | CH$_3$ | |
| H | NHCH(CH$_3$)$_2$ | O | H | CH$_3$ | O | |
| H | NH(CH$_2$)$_5$CH$_3$ | O | H | CH$_3$ | O | |
| H | NH(CH$_2$)$_8$CH$_3$ | O | H | CH$_3$ | O | |
| H | N(CH$_3$)$_2$ | O | H | CH$_3$ | O | |

TABLE X-a

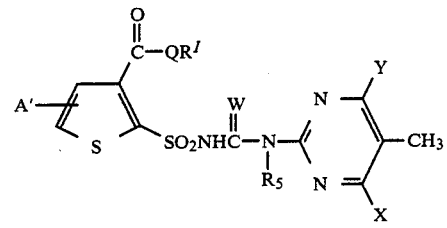

| A' | QR$^I$ | W | R$_5$ | X | Y | m.p. (°C.) |
|---|---|---|---|---|---|---|
| H | SCH$_3$ | O | H | CH$_3$ | CH$_3$ | |
| H | SC$_2$H$_5$ | O | H | CH$_3$ | CH$_3$ | |
| H | SCH(CH$_3$)$_2$ | O | H | CH$_3$ | CH$_3$ | |
| H | S(CH$_2$)$_3$CH$_3$ | O | H | CH$_3$ | CH$_3$ | |
| H | SCH$_2$CH=CH$_2$ | O | H | CH$_3$ | CH$_3$ | |
| H | S(CH$_2$)—CH$_3$ | O | H | CH$_3$ | CH$_3$ | |
| H | NHCH(CH$_3$)$_2$ | O | H | CH$_3$ | CH$_3$ | |
| H | NHC$_2$H$_5$ | O | H | CH$_3$ | CH$_3$ | |
| H | N(CH$_3$)$_2$ | O | H | CH$_3$ | CH$_3$ | |
| H | N(C$_2$H$_5$)$_2$ | O | H | CH$_3$ | CH$_3$ | |

TABLE IX-e

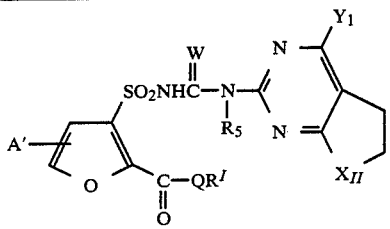

| A' | QR$^I$ | W | R$_5$ | Y$_1$ | X$_{II}$ | m.p. (°C.) |
|---|---|---|---|---|---|---|
| H | SCH$_3$ | O | H | CH$_3$ | CH$_2$ | |
| H | SC$_2$H$_5$ | O | H | CH$_3$ | CH$_2$ | |
| H | SCH(CH$_3$)$_2$ | O | H | CH$_3$ | CH$_2$ | |
| H | SCH$_2$CH=CH$_2$ | O | H | CH$_3$ | CH$_2$ | |
| H | NHC$_2$H$_5$ | O | H | CH$_3$ | CH$_2$ | |
| H | NHCH(CH$_3$)$_2$ | O | H | CH$_3$ | O | |
| H | NH(CH$_2$)$_5$CH$_3$ | O | H | CH$_3$ | O | |
| H | NH(CH$_2$)$_8$CH$_3$ | O | H | CH$_3$ | O | |
| H | N(CH$_3$)$_2$ | O | H | CH$_3$ | O | |

TABLE X-b

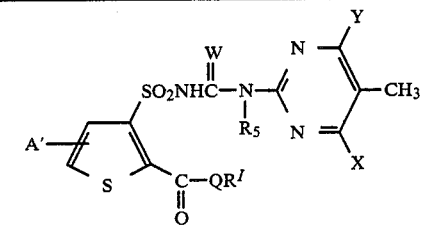

| A' | QR$^I$ | W | R$_5$ | X | Y | m.p. (°C.) |
|---|---|---|---|---|---|---|
| H | SCH$_3$ | O | H | CH$_3$ | CH$_3$ | |
| H | SC$_2$H$_5$ | O | H | CH$_3$ | CH$_3$ | |
| H | SCH(CH$_3$)$_2$ | O | H | CH$_3$ | CH$_3$ | |
| H | S(CH$_2$)$_3$CH$_3$ | O | H | CH$_3$ | CH$_3$ | |
| H | SCH$_2$CH=CH$_2$ | O | H | CH$_3$ | CH$_3$ | |
| H | S(CH$_3$)—CH$_3$ | O | H | CH$_3$ | CH$_3$ | |
| H | NHCH(CH$_3$)$_2$ | O | H | CH$_3$ | CH$_3$ | |
| H | NHC$_2$H$_5$ | O | H | CH$_3$ | CH$_3$ | |
| H | N(CH$_3$)$_2$ | O | H | CH$_3$ | CH$_3$ | |
| H | N(C$_2$H$_5$)$_2$ | O | H | CH$_3$ | CH$_3$ | |

TABLE IX-f

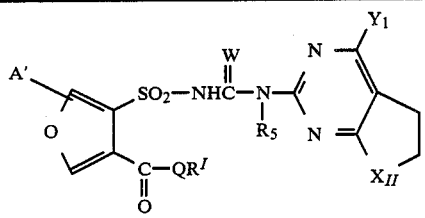

| A' | QR$^I$ | W | R$_5$ | Y$_1$ | X$_{II}$ | m.p. (°C.) |
|---|---|---|---|---|---|---|
| H | SCH$_3$ | O | H | CH$_3$ | CH$_2$ | |
| H | SC$_2$H$_5$ | O | H | CH$_3$ | CH$_2$ | |
| H | SCH(CH$_3$)$_2$ | O | H | CH$_3$ | CH$_2$ | |
| H | SCH$_2$CH=CH$_2$ | O | H | CH$_3$ | CH$_2$ | |
| H | NHC$_2$H$_5$ | O | H | CH$_3$ | CH$_2$ | |
| H | NHCH(CH$_3$)$_2$ | O | H | CH$_3$ | O | |
| H | NH(CH$_2$)$_8$CH$_3$ | O | H | CH$_3$ | O | |
| H | NH(CH$_2$)$_8$CH$_3$ | O | H | CH$_3$ | O | |
| H | N(CH$_3$)$_2$ | O | H | CH$_3$ | O | |

TABLE X-c

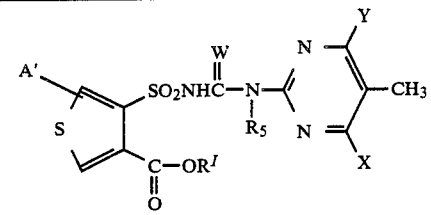

| A' | QR$^I$ | W | R$_5$ | X | Y | m.p. (°C.) |
|---|---|---|---|---|---|---|
| H | SCH$_3$ | O | H | CH$_3$ | CH$_3$ | |
| H | SC$_2$H$_5$ | O | H | CH$_3$ | CH$_3$ | |
| H | SCH(CH$_3$)$_2$ | O | H | CH$_3$ | CH$_3$ | |
| H | S(CH$_2$)$_3$CH$_3$ | O | H | CH$_3$ | CH$_3$ | |
| H | SCH$_2$CH=CH$_2$ | O | H | CH$_3$ | CH$_3$ | |
| H | S(CH$_2$)—CH$_3$ | O | H | CH$_3$ | CH$_3$ | |
| H | NHCH(CH$_3$)$_2$ | O | H | CH$_3$ | CH$_3$ | |
| H | NHC$_2$H$_5$ | O | H | CH$_3$ | CH$_3$ | |
| H | N(CH$_3$)$_2$ | O | H | CH$_3$ | CH$_3$ | |
| H | N(C$_2$H$_5$)$_2$ | O | H | CH$_3$ | CH$_3$ | |

TABLE X-d

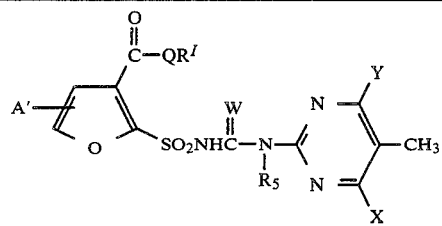

| A' | QR$^I$ | W | R$_5$ | X | Y | m.p. (°C.) |
|---|---|---|---|---|---|---|
| H | SCH$_3$ | O | H | CH$_3$ | CH$_3$ | |
| H | SC$_2$H$_5$ | O | H | CH$_3$ | CH$_3$ | |
| H | SCH(CH$_3$)$_2$ | O | H | CH$_3$ | CH$_3$ | |
| H | S(CH$_2$)$_3$CH$_3$ | O | H | CH$_3$ | CH$_3$ | |
| H | SCH$_2$CH=CH$_2$ | O | H | CH$_3$ | CH$_3$ | |
| H | S(CH$_2$)—CH$_3$ | O | H | CH$_3$ | CH$_3$ | |
| H | NHCH(CH$_3$)$_2$ | O | H | CH$_3$ | CH$_3$ | |
| H | NHC$_2$H$_5$ | O | H | CH$_3$ | CH$_3$ | |
| H | N(CH$_3$)$_2$ | O | H | CH$_3$ | CH$_3$ | |
| H | N(C$_2$H$_5$)$_2$ | O | H | CH$_3$ | CH$_3$ | |

TABLE X-e

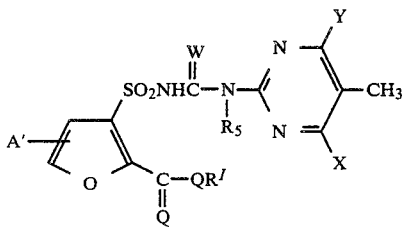

| A' | QR$^I$ | W | R$_5$ | X | Y | m.p. (°C.) |
|---|---|---|---|---|---|---|
| H | SCH$_3$ | O | H | CH$_3$ | CH$_3$ | |
| H | SC$_2$H$_5$ | O | H | CH$_3$ | CH$_3$ | |
| H | SCH(CH$_3$)$_2$ | O | H | CH$_3$ | CH$_3$ | |
| H | S(CH$_2$)$_3$CH$_3$ | O | H | CH$_3$ | CH$_3$ | |
| H | SCH$_2$CH=CH$_2$ | O | H | CH$_3$ | CH$_3$ | |
| H | S(CH$_2$)—CH$_3$ | O | H | CH$_3$ | CH$_3$ | |
| H | NHCH(CH$_3$)$_2$ | O | H | CH$_3$ | CH$_3$ | |
| H | NHC$_2$H$_5$ | O | H | CH$_3$ | CH$_3$ | |
| H | N(CH$_3$)$_2$ | O | H | CH$_3$ | CH$_3$ | |
| H | N(C$_2$H$_5$)$_2$ | O | H | CH$_3$ | CH$_3$ | |

TABLE X-f

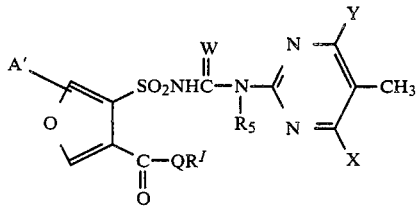

| A' | QR$^I$ | W | R$_5$ | X | Y | m.p. (°C.) |
|---|---|---|---|---|---|---|
| H | SCH$_3$ | O | H | CH$_3$ | CH$_3$ | |
| H | SC$_2$H$_5$ | O | H | CH$_3$ | CH$_3$ | |
| H | SCH(CH$_3$)$_2$ | O | H | CH$_3$ | CH$_3$ | |
| H | S(CH$_2$)$_3$CH$_3$ | O | H | CH$_3$ | CH$_3$ | |
| H | SCH$_2$CH=CH$_2$ | O | H | CH$_3$ | CH$_3$ | |
| H | S(CH$_2$)—CH$_3$ | O | H | CH$_3$ | CH$_3$ | |
| H | NHCH(CH$_3$)$_2$ | O | H | CH$_3$ | CH$_3$ | |
| H | NHC$_2$H$_5$ | O | H | CH$_3$ | CH$_3$ | |
| H | N(CH$_3$)$_2$ | O | H | CH$_3$ | CH$_3$ | |
| H | N(C$_2$H$_5$)$_2$ | O | H | CH$_3$ | CH$_3$ | |

TABLE XI-a

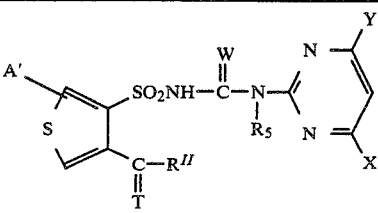

| A' | $-\overset{T}{\underset{}{C}}-R^{II}$ | W | R$_5$ | X | Y | m.p. (°C.) |
|---|---|---|---|---|---|---|
| H | —C(O)—CH$_3$ | O | H | CH$_3$ | CH$_3$ | |
| H | —C(O)—(CH$_2$)$_5$CH$_3$ | O | CH$_3$ | CH$_3$ | CH$_3$ | |
| H | —C(O)CH(CH$_3$)$_2$ | O | H | CH$_3$ | CH$_3$ | |
| H | —C(O)CH$_2$CH=CH$_2$ | O | CH$_3$ | CH$_3$ | CH$_3$ | |
| H | —C(O)CH$_2$CH=CHC$_2$H$_5$ | O | H | CH$_3$ | CH$_3$ | |
| H | —C(O)—C$_6$H$_5$ | O | CH$_3$ | CH$_3$ | CH$_3$ | |
| H | —C(O)—CH$_2$—C$_6$H$_5$ | O | CH$_3$ | CH$_3$ | CH$_3$ | |
| H | —C(O)—C$_6$H$_4$—Cl (4-) | O | CH$_3$ | CH$_3$ | CH$_3$ | |
| H | —C(O)—C$_6$H$_3$Cl$_2$ (3,5-) | O | CH$_3$ | CH$_3$ | CH$_3$ | |
| H | —C(O)—C$_6$H$_4$—OCH$_3$ | O | CH$_3$ | CH$_3$ | CH$_3$ | |
| H | —C(O)—C$_6$H$_4$—CH$_3$ | O | CH$_3$ | CH$_3$ | CH$_3$ | |
| H | —C(O)—CH$_2$—C$_6$H$_4$—CH$_3$ | O | CH$_3$ | CH$_3$ | CH$_3$ | |
| H | —C(O)—cyclohexyl | O | CH$_3$ | CH$_3$ | CH$_3$ | |
| H | —C(O)—CH$_2$—cyclopropyl | O | H | CH$_3$ | CH$_3$ | |

TABLE XI-a-continued

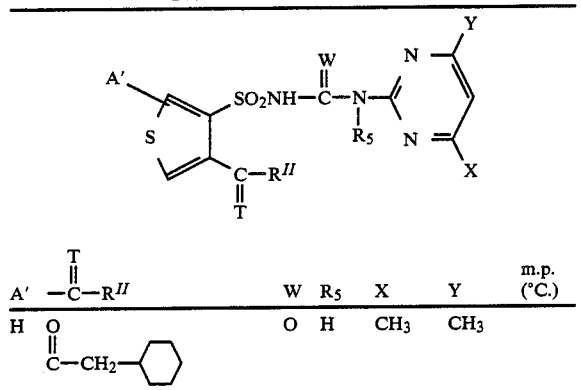

| A' | T‖ —C—R^II | W | R5 | X | Y | m.p. (°C.) |
|---|---|---|---|---|---|---|
| H | O‖ —C—CH2—cyclohexyl | O | H | CH3 | CH3 | |
| H | NOH‖ C—CH3 | O | H | CH3 | CH3 | |
| H | NOCH3‖ C—C2H5 | O | H | CH3 | CH3 | |
| H | NOCH(CH3)2‖ C—C2H5 | O | H | CH3 | CH3 | |
| H | NOCH2CH=CH2‖ C—CH3 | O | H | CH3 | CH3 | |
| H | O‖ CH | O | H | CH3 | CH3 | |
| H | O‖ CH | O | H | CH3 | CH3 | |
| H | O‖ CH | O | H | OCH3 | OCH3 | |

TABLE XI-b

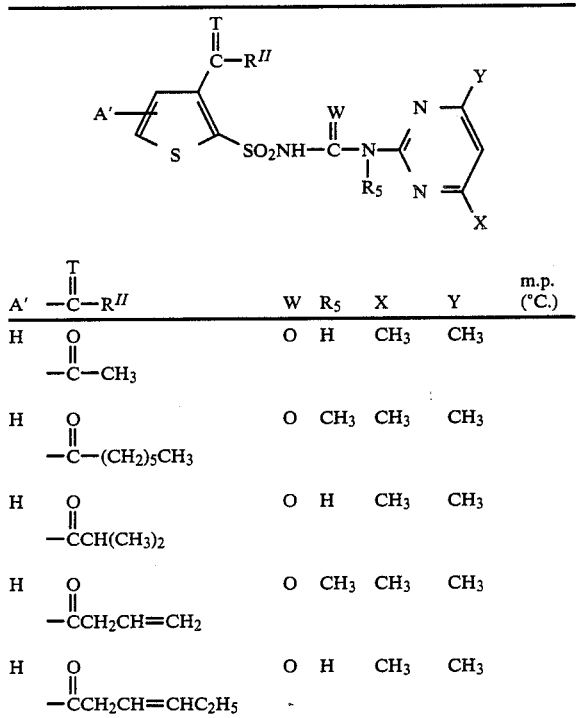

| A' | T‖ —C—R^II | W | R5 | X | Y | m.p. (°C.) |
|---|---|---|---|---|---|---|
| H | O‖ —C—CH3 | O | H | CH3 | CH3 | |
| H | O‖ —C—(CH2)5CH3 | O | CH3 | CH3 | CH3 | |
| H | O‖ —CCH(CH3)2 | O | H | CH3 | CH3 | |
| H | O‖ —CCH2CH=CH2 | O | CH3 | CH3 | CH3 | |
| H | O‖ —CCH2CH=CHC2H5 | O | H | CH3 | CH3 | |

TABLE XI-b-continued

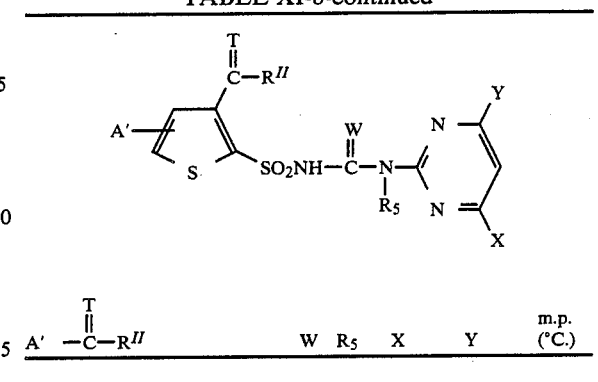

| A' | T‖ —C—R^II | W | R5 | X | Y | m.p. (°C.) |
|---|---|---|---|---|---|---|
| H | O‖ —C—phenyl | O | CH3 | CH3 | CH3 | |
| H | O‖ —CCH2—phenyl | O | CH3 | CH3 | CH3 | |
| H | O‖ —C—(4-Cl-phenyl) | O | CH3 | CH3 | CH3 | |
| H | O‖ —C—(3,5-diCl-phenyl) | O | CH3 | CH3 | CH3 | |
| H | O‖ —C—(3-OCH3-phenyl) | O | CH3 | CH3 | CH3 | |
| H | O‖ —C—(3-CH3-phenyl) | O | CH3 | CH3 | CH3 | |
| H | O‖ —C—CH2—(4-CH3-phenyl) | O | CH3 | CH3 | CH3 | |
| H | O‖ —C—cyclohexyl | O | CH3 | CH3 | CH3 | |
| H | O‖ —C—CH2—cyclopropyl | O | H | CH3 | CH3 | |
| H | O‖ —C—CH2—cyclohexyl | O | H | CH3 | CH3 | |
| H | O‖ CH | O | H | CH3 | OCH3 | |

TABLE XI-c

| A' | T, -C-R(II) | W | R5 | X | Y | m.p. (°C.) |
|---|---|---|---|---|---|---|
| H | -C(O)-CH3 | O | H | CH3 | CH3 | |
| H | -C(O)-(CH2)5CH3 | O | CH3 | CH3 | CH3 | |
| H | -CC(O)H(CH3)2 | O | H | CH3 | CH3 | |
| H | -CC(O)H2CH=CH2 | O | CH3 | CH3 | CH3 | |
| H | -CC(O)H2CH=CHC2H5 | O | H | CH3 | CH3 | |
| H | -C(O)-C6H5 | O | CH3 | CH3 | CH3 | |
| H | -CC(O)H2-C6H5 | O | CH3 | CH3 | CH3 | |
| H | -C(O)-C6H4-Cl | O | CH3 | CH3 | CH3 | |
| H | -C(O)-C6H3(Cl)2 | O | CH3 | CH3 | CH3 | |
| H | -C(O)-C6H4-OCH3 | O | CH3 | CH3 | CH3 | |
| H | -C(O)-C6H4-CH3 | O | CH3 | CH3 | CH3 | |
| H | -C(O)-CH2-C6H4-CH3 | O | CH3 | CH3 | CH3 | |
| H | -C(O)-cyclohexyl | O | CH3 | CH3 | CH3 | |
| H | -C(O)-CH2-cyclopropyl | O | H | CH3 | CH3 | |

TABLE XI-c-continued

| A' | T, -C-R(II) | W | R5 | X | Y | m.p. (°C.) |
|---|---|---|---|---|---|---|
| H | -C(O)-CH2-cyclohexyl | O | H | CH3 | CH3 | |
| H | -C(O)H | O | H | CH3 | OCH3 | |

TABLE XI-d

| A' | T, -C-R(II) | W | R5 | X | Y | m.p. (°C.) |
|---|---|---|---|---|---|---|
| H | -C(O)-CH3 | O | H | CH3 | CH3 | |
| H | -C(O)-(CH2)5CH3 | O | CH3 | CH3 | CH3 | |
| H | -CC(O)H(CH3)2 | O | H | CH3 | CH3 | |
| H | -CC(O)H2CH=CH2 | O | CH3 | CH3 | CH3 | |
| H | -CC(O)H2CH=CHC2H5 | O | H | CH3 | CH3 | |
| H | -C(O)-C6H5 | O | CH3 | CH3 | CH3 | |
| H | -CC(O)H2-C6H5 | O | CH3 | CH3 | CH3 | |
| H | -C(O)-C6H4-Cl | O | CH3 | CH3 | CH3 | |
| H | -C(O)-C6H3(Cl)2 | O | CH3 | CH3 | CH3 | |

TABLE XI-d-continued

Structure: A'-thiophene with SO₂NH-C(W)-N(R₅)-C(=N-)(triazine with X, Y) and C(T)-R^II substituent

| A' | —C(T)—R^II | W | R₅ | X | Y | m.p. (°C.) |
|---|---|---|---|---|---|---|
| H | —C(=O)—(3-methoxyphenyl) | O | CH₃ | CH₃ | CH₃ | |
| H | —C(=O)—(2-methylphenyl) | O | CH₃ | CH₃ | CH₃ | |
| H | —C(=O)—CH₂—(4-methylphenyl) | O | CH₃ | CH₃ | CH₃ | |
| H | —C(=O)—cyclohexyl | O | CH₃ | CH₃ | CH₃ | |
| H | —C(=O)—CH₂—cyclopropyl | O | H | CH₃ | CH₃ | |
| H | —C(=O)—CH₂—cyclohexyl | O | H | CH₃ | CH₃ | |
| H | —CH=O | O | H | CH₃ | OCH₃ | |
| H | —CH=O | O | H | CH₃ | CH₃ | 155–158° |

TABLE XI-e

| A' | —C(T)—R^II | W | R₅ | X | Y | m.p. (°C.) |
|---|---|---|---|---|---|---|
| H | —C(=O)—CH₃ | O | H | CH₃ | CH₃ | |
| H | —C(=O)—(CH₂)₃CH₃ | O | CH₃ | CH₃ | CH₃ | |
| H | —C(=O)—CH(CH₃)₂ | O | H | CH₃ | CH₃ | |
| H | —C(=O)—CH₂CH=CH₂ | O | CH₃ | CH₃ | CH₃ | |
| H | —C(=O)—CH₂CH=CHC₂H₅ | O | H | CH₃ | CH₃ | |
| H | —C(=O)—phenyl | O | CH₃ | CH₃ | CH₃ | |
| H | —C(=O)—CH₂—phenyl | O | CH₃ | CH₃ | CH₃ | |
| H | —C(=O)—(4-chlorophenyl) | O | CH₃ | CH₃ | CH₃ | |
| H | —C(=O)—(3,5-dichlorophenyl) | O | CH₃ | CH₃ | CH₃ | |
| H | —C(=O)—(3-methoxyphenyl) | O | CH₃ | CH₃ | CH₃ | |
| H | —C(=O)—(2-methylphenyl) | O | CH₃ | CH₃ | CH₃ | |
| H | —C(=O)—CH₂—(4-methylphenyl) | O | CH₃ | CH₃ | CH₃ | |
| H | —C(=O)—cyclohexyl | O | CH₃ | CH₃ | CH₃ | |
| H | —C(=O)—CH₂—cyclopropyl | O | H | CH₃ | CH₃ | |
| H | —C(=O)—CH₂—cyclohexyl | O | H | CH₃ | CH₃ | |
| H | —CH=O | O | H | CH₃ | OCH₃ | |

TABLE XI-f

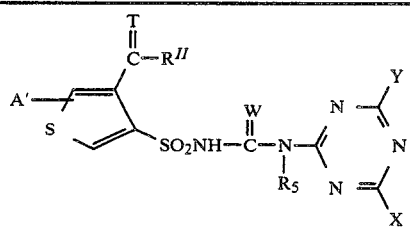

| A' | —C(T)—R^II | W | R_5 | X | Y | m.p. (°C.) |
|---|---|---|---|---|---|---|
| H | —C(=O)—CH_3 | O | H | CH_3 | CH_3 | |
| H | —C(=O)—(CH_2)_3CH_3 | O | CH_3 | CH_3 | CH_3 | |
| H | —C(=O)CH(CH_3)_2 | O | H | CH_3 | CH_3 | |
| H | —C(=O)CH_2CH=CH_2 | O | CH_3 | CH_3 | CH_3 | |
| H | —C(=O)CH_2CH=CHC_2H_5 | O | H | CH_3 | CH_3 | |
| H | —C(=O)—C_6H_5 | O | CH_3 | CH_3 | CH_3 | |
| H | —C(=O)CH_2—C_6H_5 | O | CH_3 | CH_3 | CH_3 | |
| H | —C(=O)—C_6H_4—Cl | O | CH_3 | CH_3 | CH_3 | |
| H | —C(=O)—C_6H_3(Cl)_2 | O | CH_3 | CH_3 | CH_3 | |
| H | —C(=O)—C_6H_4—OCH_3 | O | CH_3 | CH_3 | CH_3 | |
| H | —C(=O)—C_6H_4—CH_3 | O | CH_3 | CH_3 | CH_3 | |
| H | —C(=O)—CH_2—C_6H_4—CH_3 | O | CH_3 | CH_3 | CH_3 | |
| H | —C(=O)—cyclohexyl | O | CH_3 | CH_3 | CH_3 | |
| H | —C(=O)—CH_2—cyclopropyl | O | H | CH_3 | CH_3 | |

TABLE XI-f-continued

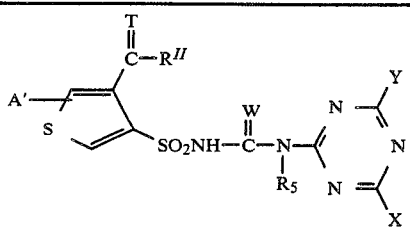

| A' | —C(T)—R^II | W | R_5 | X | Y | m.p. (°C.) |
|---|---|---|---|---|---|---|
| H | —C(=O)—CH_2—cyclohexyl | O | H | CH_3 | CH_3 | |
| H | —C(=O)H | O | H | CH_3 | OCH_3 | |

TABLE XI-g

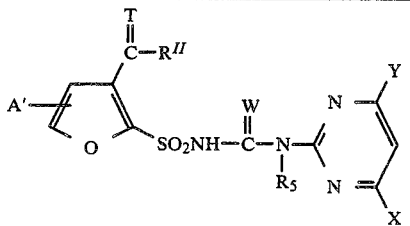

| A' | —C(T)—R^II | W | R_5 | X | Y | m.p. (°C.) |
|---|---|---|---|---|---|---|
| H | —C(=O)—CH_3 | O | H | CH_3 | CH_3 | |
| H | —C(=O)—(CH_2)_3CH_3 | O | CH_3 | CH_3 | CH_3 | |
| H | —C(=O)CH(CH_3)_2 | O | H | CH_3 | CH_3 | |
| H | —C(=O)CH_2CH=CH_2 | O | CH_3 | CH_3 | CH_3 | |
| H | —C(=O)CH_2CH=CHC_2H_5 | O | H | CH_3 | CH_3 | |
| H | —C(=O)—C_6H_5 | O | CH_3 | CH_3 | CH_3 | |
| H | —C(=O)CH_2—C_6H_5 | O | CH_3 | CH_3 | CH_3 | |
| H | —C(=O)—C_6H_4—Cl | O | CH_3 | CH_3 | CH_3 | |
| H | —C(=O)—C_6H_3(Cl)_2 | O | CH_3 | CH_3 | CH_3 | |

TABLE XI-g-continued

Structure: furan with A' substituent, T=C(R^II) group, SO_2NH-C(W)-N(R_5)-pyrimidine with X, Y substituents

| A' | —C(=T)—R^II | W | R_5 | X | Y | m.p. (°C.) |
|---|---|---|---|---|---|---|
| H | —C(=O)—(3-methoxyphenyl) | O | CH_3 | CH_3 | CH_3 | |
| H | —C(=O)—(2-methylphenyl) | O | CH_3 | CH_3 | CH_3 | |
| H | —C(=O)—CH_2—(4-methylphenyl) | O | CH_3 | CH_3 | CH_3 | |
| H | —C(=O)—cyclohexyl | O | CH_3 | CH_3 | CH_3 | |
| H | —C(=O)—CH_2—cyclopropyl | O | H | CH_3 | CH_3 | |
| H | —C(=O)—CH_2—cyclohexyl | O | H | CH_3 | CH_3 | |
| H | —CH(=O) | O | H | OCH_3 | OCH_3 | |

TABLE XI-h

Structure: furan with A' substituent, SO_2NH-C(W)-N(R_5)-pyrimidine (Y,X); C(=T)R^II on furan

| A' | —C(=T)—R^II | W | R_5 | X | Y | m.p. (°C.) |
|---|---|---|---|---|---|---|
| H | —C(=O)—CH_3 | O | H | CH_3 | CH_3 | |
| H | —C(=O)—(CH_2)_3CH_3 | O | CH_3 | CH_3 | CH_3 | |
| H | —C(=O)CH(CH_3)_2 | O | H | CH_3 | CH_3 | |
| H | —C(=O)CH_2CH=CH_2 | O | CH_3 | CH_3 | CH_3 | |

TABLE XI-h-continued

| A' | —C(=T)—R^II | W | R_5 | X | Y | m.p. (°C.) |
|---|---|---|---|---|---|---|
| H | —C(=O)CH_2CH=CHC_2H_5 | O | H | CH_3 | CH_3 | |
| H | —C(=O)—phenyl | O | CH_3 | CH_3 | CH_3 | |
| H | —C(=O)CH_2—phenyl | O | CH_3 | CH_3 | CH_3 | |
| H | —C(=O)—(4-chlorophenyl) | O | CH_3 | CH_3 | CH_3 | |
| H | —C(=O)—(3,5-dichlorophenyl) | O | CH_3 | CH_3 | CH_3 | |
| H | —C(=O)—(3-methoxyphenyl) | O | CH_3 | CH_3 | CH_3 | |
| H | —C(=O)—(3-methylphenyl) | O | CH_3 | CH_3 | CH_3 | |
| H | —C(=O)—CH_2—(4-methylphenyl) | O | CH_3 | CH_3 | CH_3 | |
| H | —C(=O)—cyclohexyl | O | CH_3 | CH_3 | CH_3 | |
| H | —C(=O)—CH_2—cyclopropyl | O | H | CH_3 | CH_3 | |
| H | —C(=O)—CH_2—cyclohexyl | O | H | CH_3 | CH_3 | |
| H | —CH(=O) | O | H | CH_3 | OCH_3 | |

TABLE XI-i

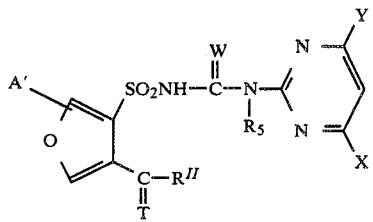

| A' | —C(T)—R^II | W | R₅ | X | Y | m.p. (°C.) |
|---|---|---|---|---|---|---|
| H | —C(=O)—CH₃ | O | H | CH₃ | CH₃ | |
| H | —C(=O)—(CH₂)₃CH₃ | O | CH₃ | CH₃ | CH₃ | |
| H | —CCH(CH₃)₂ (C=O) | O | H | CH₃ | CH₃ | |
| H | —CCH₂CH=CH₂ (C=O) | O | CH₃ | CH₃ | CH₃ | |
| H | —CCH₂CH=CHC₂H₅ (C=O) | O | H | CH₃ | CH₃ | |
| H | —C(=O)—C₆H₅ | O | CH₃ | CH₃ | CH₃ | |
| H | —CCH₂—C₆H₅ (C=O) | O | CH₃ | CH₃ | CH₃ | |
| H | —C(=O)—C₆H₄—Cl (4-Cl) | O | CH₃ | CH₃ | CH₃ | |
| H | —C(=O)—C₆H₃—Cl₂ (3,5-Cl₂) | O | CH₃ | CH₃ | CH₃ | |
| H | —C(=O)—C₆H₄—OCH₃ (3-OCH₃) | O | CH₃ | CH₃ | CH₃ | |
| H | —C(=O)—C₆H₄—CH₃ (3-CH₃) | O | CH₃ | CH₃ | CH₃ | |
| H | —C(=O)—CH₂—C₆H₄—CH₃ (4-CH₃) | O | CH₃ | CH₃ | CH₃ | |
| H | —C(=O)—C₆H₁₁ (cyclohexyl) | O | CH₃ | CH₃ | CH₃ | |
| H | —C(=O)—CH₂—cyclopropyl | O | H | CH₃ | CH₃ | |

TABLE XI-i-continued

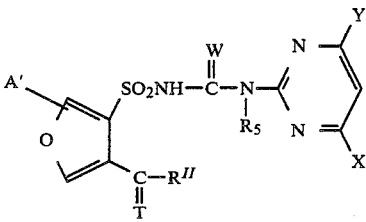

| A' | —C(T)—R^II | W | R₅ | X | Y | m.p. (°C.) |
|---|---|---|---|---|---|---|
| H | —C(=O)—CH₂—cyclohexyl | O | H | CH₃ | CH₃ | |
| H | —C(=O)—CH (formyl) | O | H | CH₃ | OCH₃ | |

TABLE XI-j

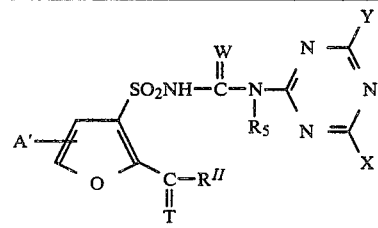

| A' | —C(T)—R^II | W | R₅ | X | Y | m.p. (°C.) |
|---|---|---|---|---|---|---|
| H | —C(=O)—CH₃ | O | H | CH₃ | CH₃ | |
| H | —C(=O)—(CH₂)₃CH₃ | O | CH₃ | CH₃ | CH₃ | |
| H | —CCH(CH₃)₂ (C=O) | O | H | CH₃ | CH₃ | |
| H | —CCH₂CH=CH₂ (C=O) | O | CH₃ | CH₃ | CH₃ | |
| H | —CCH₂CH=CHC₂H₅ (C=O) | O | H | CH₃ | CH₃ | |
| H | —C(=O)—C₆H₅ | O | CH₃ | CH₃ | CH₃ | |
| H | —CCH₂—C₆H₅ (C=O) | O | CH₃ | CH₃ | CH₃ | |
| H | —C(=O)—C₆H₄—Cl (4-Cl) | O | CH₃ | CH₃ | CH₃ | |
| H | —C(=O)—C₆H₃—Cl₂ (3,5-Cl₂) | O | CH₃ | CH₃ | CH₃ | |

TABLE XI-j-continued

Structure:
SO2NH-C(=W)-N(R5)-[triazine with X, Y]
Furan with A' and -C(=T)-R^II substituent

| A' | -C(=T)-R^II | W | R5 | X | Y | m.p. (°C.) |
|---|---|---|---|---|---|---|
| H | -C(=O)-(3-methoxyphenyl) | O | CH3 | CH3 | CH3 | |
| H | -C(=O)-(3-methylphenyl) | O | CH3 | CH3 | CH3 | |
| H | -C(=O)-CH2-(4-methylphenyl) | O | CH3 | CH3 | CH3 | |
| H | -C(=O)-cyclohexyl | O | CH3 | CH3 | CH3 | |
| H | -C(=O)-CH2-cyclopropyl | O | H | CH3 | CH3 | |
| H | -C(=O)-CH2-cyclohexyl | O | H | CH3 | CH3 | |
| H | -CH(=O) | O | H | CH3 | OCH3 | |

TABLE XI-k

Structure:
Furan with A' and -C(=T)-R^II; -SO2NH-C(=W)-N(R5)-[triazine with X, Y]

| A' | -C(=T)-R^II | W | R5 | X | Y | m.p. (°C.) |
|---|---|---|---|---|---|---|
| H | -C(=O)-CH3 | O | H | CH3 | CH3 | |
| H | -C(=O)-(CH2)3CH3 | O | CH3 | CH3 | CH3 | |
| H | -CCH(CH3)2 (=O) | O | H | CH3 | CH3 | |
| H | -CCH2CH=CH2 (=O) | O | CH3 | CH3 | CH3 | |

TABLE XI-k-continued

| A' | -C(=T)-R^II | W | R5 | X | Y | m.p. (°C.) |
|---|---|---|---|---|---|---|
| H | -CCH2CH=CHC2H5 (=O) | O | H | CH3 | CH3 | |
| H | -C(=O)-phenyl | O | CH3 | CH3 | CH3 | |
| H | -CCH2-phenyl (=O) | O | CH3 | CH3 | CH3 | |
| H | -C(=O)-(4-chlorophenyl) | O | CH3 | CH3 | CH3 | |
| H | -C(=O)-(3,5-dichlorophenyl) | O | CH3 | CH3 | CH3 | |
| H | -C(=O)-(3-methoxyphenyl) | O | CH3 | CH3 | CH3 | |
| H | -C(=O)-(3-methylphenyl) | O | CH3 | CH3 | CH3 | |
| H | -C(=O)-CH2-(4-methylphenyl) | O | CH3 | CH3 | CH3 | |
| H | -C(=O)-cyclohexyl | O | CH3 | CH3 | CH3 | |
| H | -C(=O)-CH2-cyclopropyl | O | H | CH3 | CH3 | |
| H | -C(=O)-CH2-cyclohexyl | O | H | CH3 | CH3 | |
| H | -CH(=O) | O | H | CH3 | OCH3 | |

TABLE XI-1

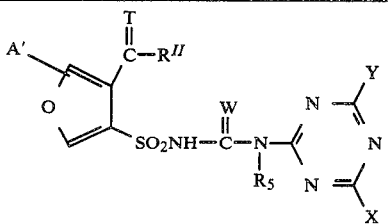

| A' | —C(T)R^II | W | R5 | X | Y | m.p. (°C.) |
|---|---|---|---|---|---|---|
| H | —C(O)—CH$_3$ | O | H | CH$_3$ | CH$_3$ | |
| H | —C(O)—(CH$_2$)$_3$CH$_3$ | O | CH$_3$ | CH$_3$ | CH$_3$ | |
| H | —C(O)CH(CH$_3$)$_2$ | O | H | CH$_3$ | CH$_3$ | |
| H | —C(O)CH$_2$CH=CH$_2$ | O | CH$_3$ | CH$_3$ | CH$_3$ | |
| H | —C(O)CH$_2$CH=CHC$_2$H$_5$ | O | H | CH$_3$ | CH$_3$ | |
| H | —C(O)—C$_6$H$_5$ | O | CH$_3$ | CH$_3$ | CH$_3$ | |
| H | —C(O)CH$_2$—C$_6$H$_5$ | O | CH$_3$ | CH$_3$ | CH$_3$ | |
| H | —C(O)—C$_6$H$_4$—Cl | O | CH$_3$ | CH$_3$ | CH$_3$ | |
| H | —C(O)—C$_6$H$_3$Cl$_2$ | O | CH$_3$ | CH$_3$ | CH$_3$ | |
| H | —C(O)—C$_6$H$_4$—OCH$_3$ | O | CH$_3$ | CH$_3$ | CH$_3$ | |
| H | —C(O)—C$_6$H$_4$—CH$_3$ | O | CH$_3$ | CH$_3$ | CH$_3$ | |
| H | —C(O)—CH$_2$—C$_6$H$_4$—CH$_3$ | O | CH$_3$ | CH$_3$ | CH$_3$ | |
| H | —C(O)—C$_6$H$_{11}$ | O | CH$_3$ | CH$_3$ | CH$_3$ | |
| H | —C(O)—CH$_2$-cyclopropyl | O | H | CH$_3$ | CH$_3$ | |

TABLE XI-1-continued

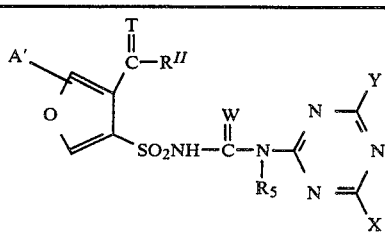

| A' | —C(T)R^II | W | R5 | X | Y | m.p. (°C.) |
|---|---|---|---|---|---|---|
| H | —C(O)—CH$_2$—C$_6$H$_{11}$ | O | H | CH$_3$ | CH$_3$ | |
| H | —C(O)CH | O | H | CH$_3$ | OCH$_3$ | |

TABLE XII

Other compounds within the scope of this invention include:

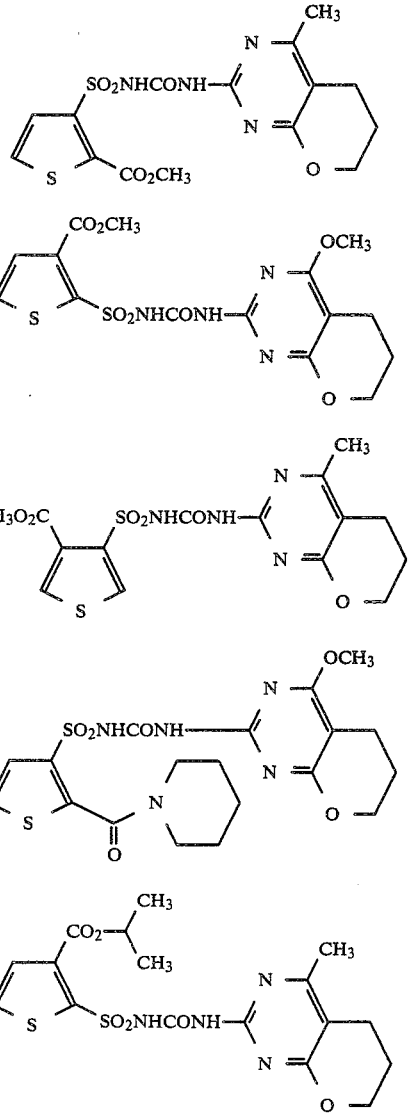

TABLE XII-continued
Other compounds within the scope of this invention include:
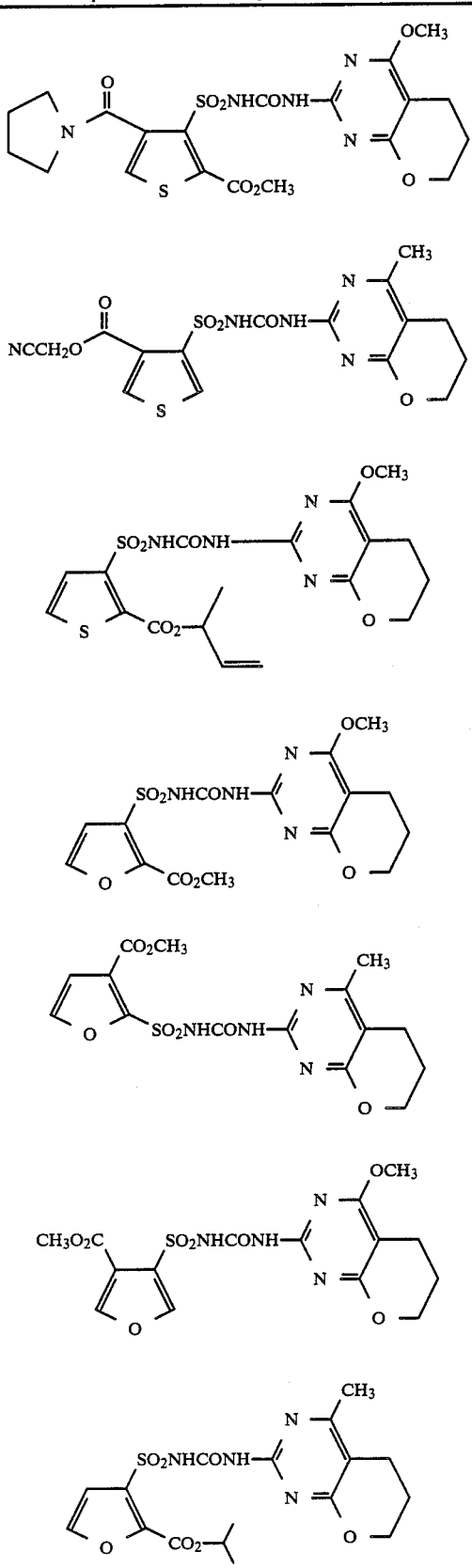
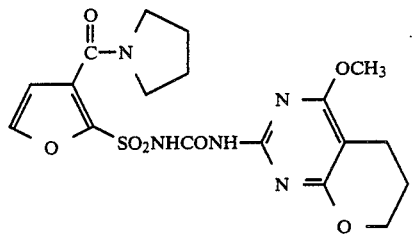
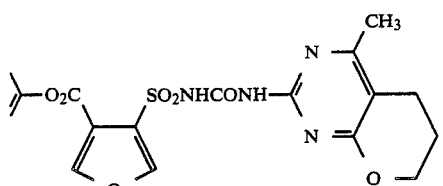
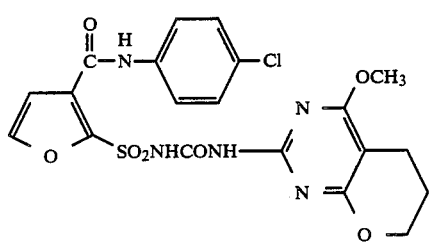
TABLE XII-a
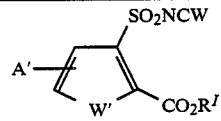
| A' | W' | W | R$^I$ |
|---|---|---|---|
| H | S | O | C$_2$H$_5$ |
| H | S | O | CH(CH$_3$)$_2$ |
| H | S | O | CH$_2$CH$_2$Cl |
| H | S | O | (CH$_2$)$_6$H |
| H | S | O | CH—CH$_2$CH$_3$<br>    |<br>    CH$_3$ |
| H | S | O | CH$_2$—CH=CH$_2$ |
| H | S | O | CH$_2$—CH=CH—CH$_3$ |
| H | S | O | CH$_2$CH=CH—CH$_2$CH$_3$ |

TABLE XII-a-continued

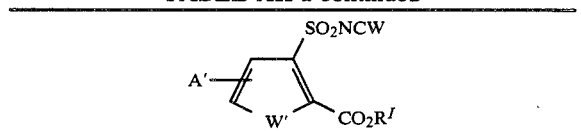

| A' | W' | W | R$^I$ |
|---|---|---|---|
| H | S | O | CH$_2$—C(=CH$_2$)—CH$_3$ |
| H | S | O | CH$_2$CH(CH$_3$)$_2$ |
| H | S | O | CH$_2$CH(CH$_2$CH$_3$)$_2$ |
| H | S | O | CH$_2$CH$_2$Cl |
| H | S | O | CH$_2$CH(CH$_2$Cl)$_2$ |
| H | S | O | CH$_2$CCl$_3$ |
| H | S | O | (CH$_2$)$_6$Cl |
| H | S | O | (CH$_2$)$_6$Br |
| H | S | O | CH$_2$CH$_2$Br |
| H | S | O | (CH$_2$)$_6$F |
| H | S | O | (CH$_2$)$_4$F |
| H | S | O | CH$_2$CN |
| H | S | O | CH$_2$CH$_2$CN |
| H | S | O | CH$_2$CH$_2$OCH$_3$ |
| H | S | O | (CH$_2$)$_6$OCH$_3$ |
| H | S | O | (CH$_2$)$_3$OCH$_3$ |
| H | S | O | CH(CH$_3$)—CH$_2$OCH$_3$ |
| H | S | O | CH(CH$_3$)CH$_2$OCH$_3$ |
| H | S | O | CH(CH$_3$)—CH$_2$OCH(CH$_3$)$_2$ |
| H | S | O | CH(CH$_3$)—CH$_2$OCH$_2$OCl$_3$ |
| H | S | O | CH$_2$CN |
| H | S | O | 3-methyltetrahydropyran |
| H | S | O | 3-methyltetrahydrofuran |
| H | S | O | (tetrahydropyran-3-yl)methyl |
| H | S | O | (tetrahydropyran-2-yl)methyl |
| H | S | O | (tetrahydropyran-4-yl)methyl |
| H | S | O | (tetrahydrofuran-3-yl)methyl |
| H | S | O | (tetrahydrofuran-2-yl)methyl |
| H | S | O | oxiranylmethyl |
| H | S | O | CH$_2$OCH$_3$ |
| H | S | O | CH$_2$OC$_2$H$_5$ |
| H | S | O | CH$_2$O(CH$_2$)$_4$H |
| H | S | O | CH$_2$CH=CHCl |
| H | S | O | CH$_2$CH=CH—CH$_2$Cl |
| H | S | O | CH$_2$CH=CH(CH$_2$)$_3$Cl |
| H | S | O | CH$_2$C≡C—CH$_3$ |
| H | S | O | CH$_2$C≡C—CH$_2$Cl |
| H | S | O | CH$_2$C≡CH$_2$CH$_2$—Cl |
| H | S | O | cyclopentyl |
| H | S | O | cyclohexyl |
| H | S | O | cyclohex-1-enyl |
| H | S | O | 3,5-dimethylcyclohexyl |
| H | S | O | 1,2-dimethylcyclohexyl |
| H | S | O | 2,5-dimethylcyclohexyl |
| H | S | O | cyclopropylmethyl |
| H | S | O | cyclopentylmethyl |

TABLE XII-a-continued

Structure: A'-[ring with W']-SO₂NCW / CO₂R^I

| A' | W' | W | R^I |
|---|---|---|---|
| H | S | O | —H₂C-cyclohexyl |
| H | S | O | CH₂-phenyl |
| H | S | O | CH₂CH₂-phenyl |
| H | S | O | CH(CH₃)-phenyl |
| H | S | O | H₂C-(4-Cl-phenyl) |
| H | S | O | H₂C-(3,4-di-CH₃-phenyl) |
| H | S | O | H₂C-(4-OCH₃-phenyl) |
| H | S | O | CH₂CH₂OCH₂CH₃ |
| H | S | O | CH₂CH₂OCH(CH₃)₂ |
| H | S | O | CH₂CH₂O-phenyl |
| H | S | O | CH₂CH₂OCH₂CH₂Cl |
| H | S | O | CH₂CH₂OCH₂CCl₃ |
| H | S | O | CH(CH₃)CH₂OC₂H₅ |
| H | S | O | CH(CH₃)—CH₂OCH(CH₃)₂ |
| H | S | O | (CH₂)₃OCH(CH₃)₂ |
| H | S | O | (CH₂)₃OCH₂CH₃ |
| H | S | O | CH₂CH₂OCH₂CH₂OCH₃ |
| H | S | O | CH₂CH₂(OCH₂CH₂)₂OC₂H₅ |
| 5-CH₃ | S | O | CH₃ |
| H | O | O | CH₃ |
| H | S | S | CH₃ |
| 4-CH₃ | S | O | CH₃ |
| 4-Cl | S | O | CH₃ |
| 4-Br | S | O | CH₃ |
| 5-Br | S | O | CH₃ |
| 4-NO₂ | S | O | CH₃ |
| 4-C₂H₅ | S | O | CH₃ |
| 5-C₂H₅ | S | O | CH₃ |
| 5-n-C₇H₉ | S | O | CH₃ |
| 5-CH(CH₃)₂ | S | O | CH₃ |
| 4-CF₃ | S | O | CH₃ |
| 5-OCH₃ | S | O | CH₃ |

TABLE XII-b

Structure: R^I O₂C / SO₂NCW on ring with A' and W'

| A' | W' | W | R^I |
|---|---|---|---|
| H | S | O | C₂H₅ |
| H | S | O | CH(CH₃)₂ |
| H | S | O | CH₂CH₂Cl |
| H | S | O | (CH₂)₆H |
| H | S | O | CH(CH₃)—CH₂CH₃ |
| H | S | O | CH₂—CH=CH₂ |
| H | S | O | CH₂—CH=CH—CH₃ |
| H | S | O | CH₂CH=CH—CH₂CH₃ |
| H | S | O | CH₂—C(=CH₂)—CH₃ |
| H | S | O | CH₂CH(CH₃)₂ |
| H | S | O | CH₂CH(CH₂CH₃)₂ |
| H | S | O | CH₂CH₂Cl |
| H | S | O | CH₂CH(CH₂Cl)₂ |
| H | S | O | CH₂OCl₃ |
| H | S | O | (CH₂)₆Cl |
| H | S | O | (CH₂)₆Br |
| H | S | O | CH₂CH₂Br |
| H | S | O | (CH₂)₆F |
| H | S | O | (CH₂)₄F |
| H | S | O | CH₂CN |
| H | S | O | CH₂CH₂CN |
| H | S | O | CH₂CH₂OCH₃ |
| H | S | O | (CH₂)₆OCH₃ |
| H | S | O | (CH₂)₃OCH₃ |
| H | S | O | CH(CH₃)—CH₂OCH₃ |
| H | S | O | CH(CH₃)CH₂OCH₃ |
| H | S | O | CH(CH₃)—CH₂OCH(CH₃)₂ |
| H | S | O | CH(CH₃)—CH₂OCH₂OCl |
| H | S | O | CH₂CN |

TABLE XII-b-continued $$R^IO_2C \quad SO_2NCW$$
(structure with A', W')

| A' | W' | W | R$^I$ |
|----|----|----|----|
| H | S | O | 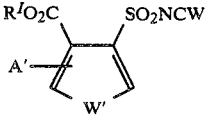 (3-tetrahydropyranyl) |
| H | S | O | 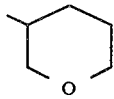 (3-tetrahydrofuranyl) |
| H | S | O |  (tetrahydropyran-3-ylmethyl) |
| H | S | O | 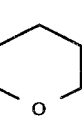 (tetrahydropyran-2-ylmethyl) |
| H | S | O | 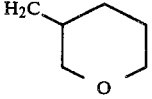 (tetrahydropyran-4-ylmethyl) |
| H | S | O | 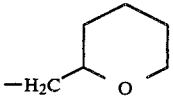 (tetrahydrofuran-3-ylmethyl) |
| H | S | O | 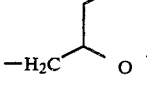 (tetrahydrofuran-2-ylmethyl) |
| H | S | O | —H$_2$C—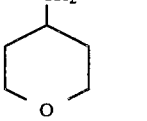 (oxiranylmethyl) |
| H | S | O | CH$_2$OCH$_3$ |
| H | S | O | CH$_2$OC$_2$H$_5$ |
| H | S | O | CH$_2$O(CH$_2$)$_4$H |
| H | S | O | CH$_2$CH=CHCl |
| H | S | O | CH$_2$CH=CH—CH$_2$Cl |
| H | S | O | CH$_2$CH=CH(CH$_2$)$_3$Cl |
| H | S | O | CH$_2$C≡C—CH$_3$ |
| H | S | O | CH$_2$C≡C—CH$_2$Cl |
| H | S | O | CH$_2$C≡C—CH$_2$CH$_2$—Cl |
| H | S | O | 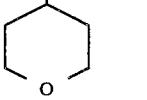 (cyclopentyl) |
| H | S | O | 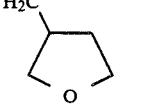 (cyclohexyl) |
| H | S | O | 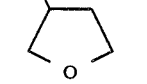 (cyclohexenyl) |
| H | S | O | 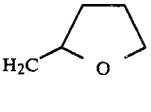 (3-methylcyclohexyl) |
| H | S | O | 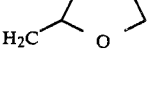 (2-methylcyclohexyl with CH$_3$) |
| H | S | O | 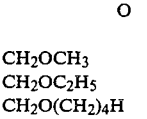 (dimethylcyclohexyl) |
| H | S | O | —H$_2$C—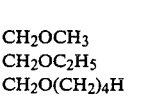 (cyclopropylmethyl) |
| H | S | O | —H$_2$C—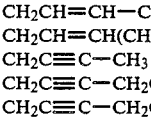 (cyclopentylmethyl) |
| H | S | O | —H$_2$C—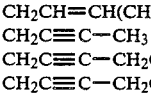 (cyclohexylmethyl) |
| H | S | O | CH$_2$—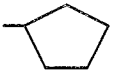 (benzyl) |
| H | S | O | CH$_2$CH$_2$—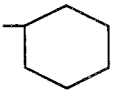 (phenethyl) |
| H | S | O | CH(CH$_3$)—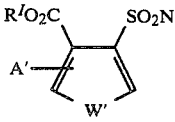 (1-phenylethyl) |
| H | S | O | H$_2$C—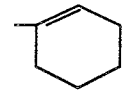—Cl (4-chlorobenzyl) |
| H | S | O | H$_2$C—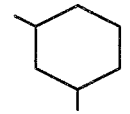(CH$_3$)$_2$ (dimethylbenzyl) |

TABLE XII-b-continued

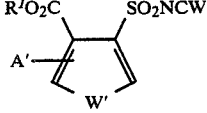

| A' | W' | W | R^I |
|---|---|---|---|
| H | S | O | 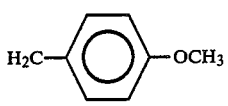 H₂C—⟨⟩—OCH₃ |
| H | S | O | CH₂CH₂OCH₂CH₃ |
| H | S | O | CH₂CH₂OCH(CH₃)₂ |
| H | S | O | 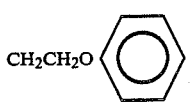 CH₂CH₂O—⟨⟩ |
| H | S | O | CH₂CH₂OCH₂CH₂Cl |
| H | S | O | CH₂CH₂OCH₂OCl₃ |
| H | S | O | CHCH₂OC₂H₅ \| CH₃ |
| H | S | O | CH—CH₂OCH(CH₃)₂ \| CH₃ |
| H | S | O | (CH₂)₃OCH(CH₃)₂ |
| H | S | O | (CH₂)₃OCH₂CH₃ |
| H | S | O | CH₂CH₂OCH₂CH₂OCH₃ |
| H | S | O | CH₂CH₂(OCH₂CH₂)₂OC₂H₅ |
| 5-CH₃ | S | O | CH₃ |
| H | O | O | CH₃ |
| H | S | S | CH₃ |
| 2-CH₃ | S | O | CH₃ |
| 2-Cl | S | O | CH₃ |
| 2-Br | S | O | CH₃ |
| 5-Br | S | O | CH₃ |
| 2-NO₂ | S | O | CH₃ |
| 2-C₂H₅ | S | O | CH₃ |
| 5-C₂H₅ | S | O | CH₃ |
| 5-n-C₇H₉ | S | O | CH₃ |
| 5-CH(CH₃)₂ | S | O | CH₃ |
| 2-CF₃ | S | O | CH₃ |
| 5-OCH₃ | S | O | CH₃ |

TABLE XII-c

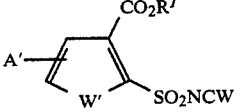

| A' | W' | W | R^I |
|---|---|---|---|
| H | S | O | C₂H₅ |
| H | S | O | CH(CH₃)₂ |
| H | S | O | CH₂CH₂Cl |
| H | S | O | (CH₂)₆H |
| H | S | O | CH—CH₂CH₃ \| CH₃ |
| H | S | O | CH₂—CH=CH₂ |
| H | S | O | CH₂—CH=CH—CH₃ |
| H | S | O | CH₂CH=CH—CH₂CH₃ |
| H | S | O | CH₂ ‖ CH₂—C—CH₃ |

TABLE XII-c-continued

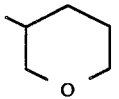

| A' | W' | W | R^I |
|---|---|---|---|
| H | S | O | CH₂CH(CH₃)₂ |
| H | S | O | CH₂CH(CH₂CH₃)₂ |
| H | S | O | CH₂CH₂Cl |
| H | S | O | CH₂CH(CH₂Cl)₂ |
| H | S | O | CH₂OCl₃ |
| H | S | O | (CH₂)₆Cl |
| H | S | O | (CH₂)₆Br |
| H | S | O | CH₂CH₂Br |
| H | S | O | (CH₂)₆F |
| H | S | O | (CH₂)₄F |
| H | S | O | CH₂CN |
| H | S | O | CH₂CH₂CN |
| H | S | O | CH₂CH₂OCH₃ |
| H | S | O | (CH₂)₆OCH₃ |
| H | S | O | (CH₂)₃OCH₃ |
| H | S | O | CH—CH₂OCH₃ \| CH₃ |
| H | S | O | CHCH₂OCH₃ \| CH₃ |
| H | S | O | CH—CH₂OCH(CH₃)₂ \| CH₃ |
| H | S | O | CH—CH₂OCH₂OCl₃ \| CH₃ |
| H | S | O | CH₂CN |
| H | S | O | 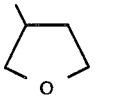 |
| H | S | O | 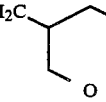 |
| H | S | O | 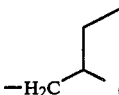 H₂C—⟨⟩ |
| H | S | O | 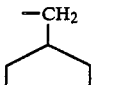 —H₂C—⟨⟩ |
| H | S | O | 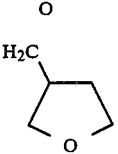 —CH₂—⟨⟩ |
| H | S | O | 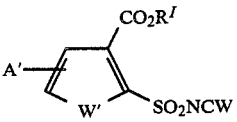 H₂C—⟨⟩ |

TABLE XII-c-continued $$\text{structure: } A'\text{-(W')-}[CO_2R^I][SO_2NCW]$$

| A' | W' | W | R^I |
|---|---|---|---|
| H | S | O | (tetrahydrofuran-2-yl)methyl (H₂C-furanyl-O) |
| H | S | O | -H₂C-oxiranyl |
| H | S | O | CH₂OCH₃ |
| H | S | O | CH₂OC₂H₅ |
| H | S | O | CH₂O(CH₂)₄H |
| H | S | O | CH₂CH=CHCl |
| H | S | O | CH₂CH=CH—CH₂Cl |
| H | S | O | CH₂CH=CH(CH₂)₃Cl |
| H | S | O | CH₂C≡C—CH₃ |
| H | S | O | CH₂C≡C—CH₂Cl |
| H | S | O | CH₂C≡C—CH₂CH₂—Cl |
| H | S | O | cyclopentyl |
| H | S | O | cyclohexyl |
| H | S | O | cyclohex-1-enyl |
| H | S | O | 3-methylcyclohexyl |
| H | S | O | 2-methylcyclohexyl |
| H | S | O | 2,5-dimethylcyclohexyl |
| H | S | O | —H₂C-cyclopropyl |
| H | S | O | —H₂C-cyclopentyl |
| H | S | O | —H₂C-cyclohexyl |
| H | S | O | CH₂—C₆H₅ (benzyl) |
| H | S | O | CH₂CH₂—C₆H₅ |
| H | S | O | CH(CH₃)—C₆H₅ |
| H | S | O | H₂C—C₆H₄—Cl (4-Cl benzyl) |
| H | S | O | H₂C—C₆H₃(CH₃)₂ (2,4-dimethylbenzyl) |
| H | S | O | H₂C—C₆H₄—OCH₃ (4-methoxybenzyl) |
| H | S | O | CH₂CH₂OCH₂CH₃ |
| H | S | O | CH₂CH₂OCH(CH₃)₂ |
| H | S | O | CH₂CH₂O—C₆H₅ |
| H | S | O | CH₂CH₂OCH₂CH₂Cl |
| H | S | O | CH₂CH₂OCH₂OCl₃ |
| H | S | O | CH(CH₃)CH₂OC₂H₅ |
| H | S | O | CH(CH₃)—CH₂OCH(CH₃)₂ |
| H | S | O | (CH₂)₃OCH(CH₃)₂ |
| H | S | O | (CH₂)₃OCH₂CH₃ |
| H | S | O | CH₂CH₂OCH₂CH₂OCH₃ |
| H | S | O | CH₂CH₂(OCH₂CH₂)₂OC₂H₅ |
| 5-CH₃ | S | O | CH₃ |
| H | O | O | CH₃ |
| H | S | S | CH₃ |
| 4-CH₃ | S | O | CH₃ |
| 4-Cl | S | O | CH₃ |
| 4-Br | S | O | CH₃ |
| 5-Br | S | O | CH₃ |
| 4-NO₂ | S | O | CH₃ |
| 4-C₂H₅ | S | O | CH₃ |
| 5-C₂H₅ | S | O | CH₃ |
| 5-n-C₇H₉ | S | O | CH₃ |
| 5-CH(CH₃)₂ | S | O | CH₃ |

TABLE XII-c-continued

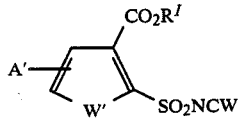

| A' | W' | W | R$^I$ |
|---|---|---|---|
| 4-CF$_3$ | S | O | CH$_3$ |
| 5-OCH$_3$ | S | O | CH$_3$ |

TABLE XII-d

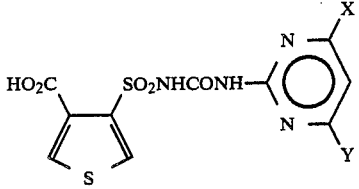

| X | Y | m.p. (°C.) |
|---|---|---|
| CH$_3$ | OCH$_3$ | 182–187 (d) |
| OCH$_3$ | OCH$_3$ | 195–197 |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions set forth in Table XVIII.

TABLE XVIII

| | Active Ingredient | Weight Percent* Diluent(s) | Surfactant(s) |
|---|---|---|---|
| Wettable Powders | 20–90 | 0–74 | 1–10 |
| Oil Suspensions, Emulsions, Solutions (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredients can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers," 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual," MC Publishing Corp., Ridgewood, N.J., as well as Sisely and Wood, "Encyclopedia of Surface Active Agents," Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration," *Chemical Engineering*, Dec. 4, 1967, pp. 147ff. and "Perry's Chemical Engineer's Handbook," 4th Ed., McGraw-Hill, New York, 1963, pp. 8–59ff.

For further information regarding the art of formulation, see for example:

H. M. Loux, U.S. Pat. No. 3,235,361, Feb. 15, 1966, Col. 6, line 16 through Col. 7, line 19 and Examples 10 through 41.

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167, 169–182.

H. Gysin and E. Knusli, U.S. Pat. No. 2,891,855, June 23, 1959, Col. 3, line 66 through Col. 5, line 17 and Examples 1–4.

G. C. Klingman, "Weed Control as a Science", John Wiley & Sons, Inc., New York, 1961, pp. 81–96.

J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 7

Wettable Powder methyl 3-[[(4,6-dimethylpyrimidin-2-yl)aminocarbonyl]aminosulfonyl]-2-thiophenecarboxylate: 80%
sodium alkylnaphthalenesulfonate: 2%
sodium ligninsulfonate: 2%
synthetic amorphous silica: 3%
kaolinite: 13%

The ingredients are blended, hammer-milled until all the solids are essentially under 50 microns, reblended, and packaged.

EXAMPLE 8

Wettable Powder methyl 3-[[(4,6-dimethoxypyrimidin-2-yl)aminocarbonyl]aminosulfonyl]-2-thiophenecarboxylate: 50%
sodium alkylnaphthalenesulfonate: 2%
low viscosity methyl cellulose: 2%
diatomaceous earth: 46%

The ingredients are blended, coarsely hammer-milled and then air-milled to produce particles essentially all below 10 microns in diameter. The product is reblended before packaging.

EXAMPLE 9

Granule wettable powder of Example 8: 5%
attapulgite granules (U.S.S. 20–40 mesh; 0.84–0.42 mm): 95%

A slurry of wettable powder containing ≈25% solids is sprayed on the surface of attapulgite granules in a double-cone blender. The granules are dried and packaged.

EXAMPLE 10

Extruded Pellet methyl 3-[[(4-methoxy-6-methylpyrimidin-2-yl)aminocarbonyl]aminosulfonyl]-2-thiophenecarboxylate: 25%
anhydrous sodium sulfate: 10%
crude calcium ligninsulfonate: 5%
sodium alkylnaphthalenesulfonate: 1%
calcium/magnesium bentonite: 59%

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 11

Oil Suspension methyl 3-[[(4,6-dimethylpyrimidin-2-yl)aminocarbonyl]aminosulfonyl]-2-thiophenecarboxylate: 25%
polyoxyethylene sorbitol hexaoleate: 5%
highly aliphatic hydrocarbon oil: 70%

The ingredients are ground together in a sand mill until the solid particles have been reduced to under about 5 microns. The resulting suspension may be applied directly, but preferably after being extended with oils or emulsified in water.

EXAMPLE 12

Wettable Powder methyl 3-[[(4,6-dimethoxypyrimidin-2-yl)aminocarbonyl]aminosulfonyl]-2-thiophenecarboxylate: 20%
sodium alkylnaphthalenesulfonate: 4%
sodium ligninsulfonate: 4%
low viscosity methyl cellulose: 3%
attapulgite: 69%

The ingredients are thoroughly blended. After grinding in a hammer mill to produce particles essentially all below 100 microns, the material is reblended and sifted through a U.S.S. No. 50 sieve (0.3 mm opening) and packaged.

EXAMPLE 13

Oil Suspension methyl 3-[[(4-methoxy-6-methylpyrimidin-2-yl)aminocarbonyl]aminosulfonyl]-2-thiophenecarboxylate: 35%
blend of polyalcohol carboxylic esters and oil soluble petroleum sulfonates: 6%
xylene: 59%

The ingredients are combined and ground together in a sand mill to produce particles essentially all below 3 microns. The product can be used directly, extended with oils, or emulsified in water.

EXAMPLE 14

High Strength Concentrate methyl 3-[[(4,6-dimethylpyrimidin-2-yl)aminocarbonyl]aminosulfonyl]-2-thiophenecarboxylate: 99%
silica aerogel: 0.5%
synthetic amorphous silica: 0.5%

The ingredients are blended and ground in a hammer mill to produce a material essentially all passing a U.S.S. No. 50 screen (0.3 mm opening). The concentrate may be formulated further if necessary.

EXAMPLE 15

Low Strength Granule methyl 3-[[(4,6-dimethoxypyrimidin-2-yl)aminocarbonyl]aminosulfonyl]-2-thiophenecarboxylate: 1%
N,N-dimethylformamide: 9%
attapulgite granules (U.S.S. 20–40 mesh): 90%

The active ingredient is dissolved in the solvent and the solution is sprayed upon dedusted granules in a rotating blender. After spraying of the solution has been completed, the blender is allowed to run for a short period and then the granules are packaged.

EXAMPLE 16

Aqueous Suspension methyl 3-[[(4-methoxy-6-methylpyrimidin-2-yl)aminocarbonyl]aminosulfonyl]-2-thiophenecarboxylate: 40%
polyacrylic acid thickener: 0.3%
dodecylphenol polyethylene glycol ether: 0.5%
disodium phosphate: 1%
monosodium phosphate: 0.5%
polyvinyl alcohol: 1.0%
water: 56.7%

The ingredients are blended and ground together in a sand mill to produce particles essentially all under 5 microns in size.

EXAMPLE 17

Solution methyl 3-[[(4,6-dimethylpyrimidin-2-yl)aminocarbonyl]aminosulfonyl]-2-thiopuenecarboxylate: 5%
water: 95%

The salt is added directly to the water with stirring to produce the solution, which may then be packaged for use.

EXAMPLE 18

Granule methyl 3-[[(4,6-dimethoxypyrimidin-2-yl)aminocarbonyl]aminosulfonyl]-2-thiophenecarboxylate: 80%
wetting agent: 1%
crude ligninsulfonate salt (containing 5–20% of the natural sugars): 10%
attapulgite clay: 9%

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 19

Low Strength Granule methyl 3-[[(4-methoxy-6-methylpyrimidin-2-yl)aminocarbonyl]aminosulfonyl]-2-thiophenecarboxylate: 0.1%
attapulgite granules (U.S.S. 20–40 mesh): 99.9%

The active ingredient is dissolved in a solvent and the solution is sprayed upon dedusted granules in a double cone blender. After spraying of the solution has been completed, the material is warmed to evaporate the solvent. The material is allowed to cool and then packaged.

UTILITY

The compounds of the present invention are powerful herbicides. They have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Alternatively, the subject compounds are useful for the selective pre- or post-emergence weed control in crops, such as wheat and soybeans.

The rates of application for the compounds of the invention are determined by a number of factors, including their use as selective or general herbicides, the crop species involved, the types of weeds to be controlled, weather and climate, formulations selected, mode of application, amount of foliage present, etc. In general terms, the subject compounds should be applied at levels of around 0.06 to 10 kg/ha, the lower rates being suggested for use on lighter soils and/or those having a low organic matter content, for selective weed control or for situations where only short-term persistence is required.

The compounds of the invention may be used in combination with any other commercial herbicide examples of which are those of the triazine, triazole, uracil, urea, amide, diphenylether, carbamate and bipyridylium types.

The herbicidal properties of the subject compounds were discovered in a number of greenhouse tests. The test procedures are results follow.

TEST A

Seeds of crabgrass (Digitaria spp.), barnyardgrass (*Echinochloa crusgalli*), wild oats (*Avena fatua*), *Cassia tora*, morningglory (Ipomoea spp.), cocklebur (Xanthium spp.), sorghum, corn, soybean, rice, wheat as well as nutsedge tubers were planted in a growth medium and treated preemergence with the chemicals dissolved in a non-phytotoxic solvent. At the same time, cotton having five leaves (including cotyledonary ones), bush beans with the third trifoliate leaf expanding, crabgrass, barnyardgrass and wild oats with two leaves, cassia with three leaves (including cotyledonary ones), morningglory and cocklebur with four leaves (including the cotyledonary ones), sorghum and corn with four leaves, soybean with two cotyledonary leaves, rice with three leaves, wheat with one leaf, and nutsedge with three-five leaves were sprayed. Treated plants and controls were maintained in a greenhouse for sixteen days, whereupon all species were compared to controls and visually rated for response to treatment. The ratings are based on a numerical scale extending from 0=no injury, to 10=complete kill. The accompanying descriptive symbols have the following meanings: B=burn; G=growth retardation; C=chlorosis/necrosis; D=defoliation; 6Y=abscised buds or flowers; 6F=delayed flowering; U=unusual pigmentation; S=albinism; E=emergence inhibition; and H=formative effects. The ratings for the compounds tested by this procedure are presented in Table A. It will be seen that certain of the compounds tested have utility for selective pre- and post-emergence weed control in soybeans and wheat.

TABLE A
| | kg/ha | BUSH-BEAN | COT-TON | MORNING-GLORY | COCKLE-BUR | CAS-SIA | NUT-SEDGE | CRAB-GRASS | BARN-YARD-GRASS | WILD OATS | WHEAT | CORN | SOY-BEAN | RICE | SOR-GHUM |
|---|---|---|---|---|---|---|---|---|---|---|---|---|---|---|---|
| | | | | | POST-EMERGENCE | | | | | | | | | | |
| 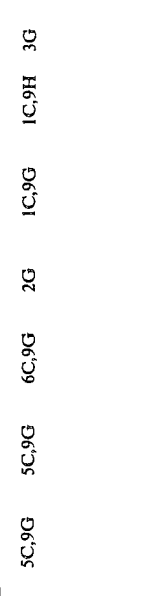 | 0.1 | 6C,9G, 6Y | 3U,9G | 9C | 5C,9G | 0 | 5C,9G | 5C,9G | 6C,9G | 2G | 1C,9G | 1C,9H | 3G | 2C,9G | 1C,9G |
| 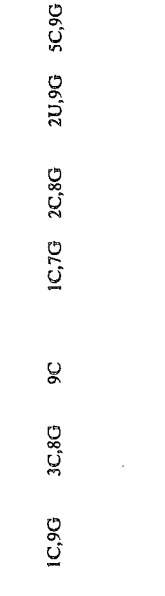 | 0.1 | 5C,8G, 6Y | 7C,9G | 10C | 9C | 2C | 1C,9G | 3C,8G | 9C | 1C,7G | 2C,8G | 2U,9G | 5C,9G | 5C,9G | 5U,9G |
| 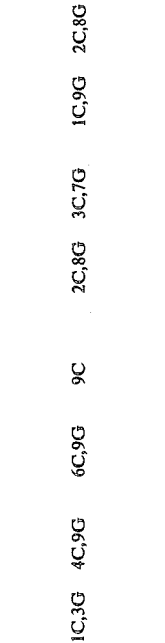 | 0.1 | 8D,9G, 6Y | 7C,9G | 10C | 3C,9G | 1C,3G | 4C,9G | 6C,9G | 9C | 2C,8G | 3C,7G | 1C,9G | 2C,8G | 3C,9G | 3C,9G |
| | | | | | PRE-EMERGENCE | | | | | | | | | | |
|  | 0.1 | | | 9G | 9G | 6G | 10E | 1C,7G | 1C,9H | 1C,6G | 1C,9G | 1C,9H | 0. | 10E | 10H |

TABLE A-continued
| Structure | kg/ha | BUSH-BEAN | COT-TON | MORNING-GLORY | COCKLE-BUR | CAS-SIA | NUT-SEDGE | CRAB-GRASS | BARN-YARD GRASS | WILD OATS | WHEAT | CORN | SOY-BEAN | RICE | SOR-GHUM |
|---|---|---|---|---|---|---|---|---|---|---|---|---|---|---|---|
|  | 0.1 | | 9C | 9G | 9H | 8G | 10E | 1C,7G | 1C,9H | 1C,8G | 1C,9G | 9G | 6H | 10E | 10E |
|  | 0.1 | | 3C,7G | 9G | 9H | 8G | 10E | 1C,8G | 1C,9H | 1C,8G | 1C,9H | 9G | 6H | 10E | 1C,9H |
| POST-EMERGENCE |
|  | 0.1 | | 3C,3H | 5C,8G | 10C | 1C | 0 | 1C,5G | 2C,8H | 0 | 0 | 2C,8H | 1C,2H | — | 1C,9G |
| 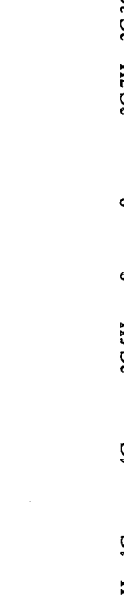 | 0.4 | 6C,9G | 3C,3H | 1C,3H | 1C,5G | 2C,2H | 1C | 4G | 2C,5H | 0 | 0 | 2C,7H | 2C,3G | 1C,5G | 2C,9H |
|  | 0.1 | 2C,8G, 6Y | 9C | 10C | 10C | 2C,7H | 1C | 1C | 2C,9H | 1H | 1H | 9H | 5C,9G | 2C,8G | 2C,7H |

TABLE A-continued

| Structure | kg/ha | BUSH-BEAN | COT-TON | MORNING-GLORY | COCKLE-BUR | CAS-SIA | NUT-SEDGE | CRAB-GRASS | BARN-YARD-GRASS | WILD OATS | WHEAT | CORN | SOY-BEAN | RICE | SOR-GHUM |
|---|---|---|---|---|---|---|---|---|---|---|---|---|---|---|---|
| *Structure 1: pyrimidine with CH₃, CH₃, SO₂NHCNH, CO₂CH₃, thiophene* | 0.1 | | 9C | 9G | 8H | 2C | 0 | 0 | 1C,5G | 0 | 0 | 1C,4G | 0 | 10E | 1C,9H |
| *Structure 2: triazine with CH₃, CH₃, SO₂NHCNH, CO₂CH₃, thiophene* | 0.4 | | | 5G | 9G | 2G | 10E | 3C | 3C | 0 | 0 | | 1C,1H | 10E | 3C,9H |
| *Structure 3: pyrimidine with OCH₃, OCH₃, SO₂NHCNH, CO₂CH₃, thiophene* | 0.1 | | | 9H | 9H | 6G | 7G | 5G | 2C,7G | 0 | 0 | 1C,5H | 2C,5H | 10E | 1C,7H |
| | | | | | POST-EMERGENCE | | | | | | | | | | |
| *Structure 4: pyrimidine with OCH₃, CH₃, SO₂NHCNH, CO₂CH₃, thiophene* | 0.1 | 9C | 9C | 10C | 6C | 1C | 1C | 3C | 10C | 0 | 0 | 7C | 2C | 5C | 9G |
| *Structure 5: dihydrofuran-pyrimidine with CH₃, SO₂NHCONH, CO₂CH₃, thiophene* | 0.4 | 3C,4G, 6F | 1C,7G | 10C | 10C | 0 | 5C,5G | 10C | 10C | 2C,3G | 3C,5G | 3U,5G | 4G | 3C,4G | 3C,4G |

TABLE A-continued

| Structure | kg/ha | BUSH-BEAN | COT-TON | MORNING-GLORY | COCKLE-BUR | CAS-SIA | NUT-SEDGE | CRAB-GRASS | BARN-YARD-GRASS | WILD OATS | WHEAT | CORN | SOY-BEAN | RICE | SOR-GHUM |
|---|---|---|---|---|---|---|---|---|---|---|---|---|---|---|---|
| (structure with pyrrolidine carbonyl, dimethylpyrimidine) | 0.05 | 3C | 4C,8G | 4C,9H | 2C,9G | 2C | 0 | 0 | 1C | 1C | 2C | 1C,2G | 1H | 1C,2G | 1C,5H |
| PRE-EMERGENCE | | | | | | | | | | | | | | | |
| (structure with OCH₃ pyrimidine, CO₂CH₃ thiophene) | 0.1 | | | 9G | 8H | 8G | 3G | 2C | 2C,8G | 0 | 3G | 1C,8G | 2C,4G | 9H | 1C,9H |
| (structure with dihydrofuran pyrimidine, CO₂CH₃ thiophene) | 0.4 | | | 5G,3C | 6C,5G | 4G | 10E | 4C,7G | 5C,8G | 3C,4G | 10E | | | 10E | 7C,8G |
| POST-EMERGENCE | | | | | | | | | | | | | | | |
| (structure with pyrrolidine carbonyl, dimethylpyrimidine) | 0.05 | | | 0 | 0 | 0 | 0 | 0 | 0 | 0 | 0 | 0 | 1C,3G | 0 | 0 |

TABLE A-continued

| Structure | kg/ha | BUSH-BEAN | COTTON | MORNING-GLORY | COCKLE-BUR | CAS-SIA | NUT-SEDGE | CRAB-GRASS | BARN-YARD GRASS | WILD OATS | WHEAT | CORN | SOY-BEAN | RICE | SOR-GHUM |
|---|---|---|---|---|---|---|---|---|---|---|---|---|---|---|---|
| (OCH₃/CH₃ pyrimidine, SO₂NHCONH, pyrrolidine-carbonyl thiophene) | 0.05 | 6Y,7C,9G | 6C,9G | 10C | 6C,9G | 1C,4G | 2C,8G | 2C | 3C,7H | 2C | 2C,9G | 2C,8H | 2C,8G | 2C,9G | 2C,9H |
| (CH₃ pyrimidine, SO₂NHCONH, CO₂CH₃ cyclopentene-thiophene) | 0.05 | 2B | 0 | 1C,3G | 1C | 1C | 0 | 0 | 0 | 0 | 0 | 0 | 1H | 5G | 2C,8H |
| (OCH₃ pyrimidine, SO₂NHCONH, CO₂CH₃ cyclopentene-thiophene) | 0.05 | 1B | 3G | 0 | 0 | 0 | 0 | 0 | 0 | 0 | 0 | 0 | 0 | 0 | 0 |
| PRE-EMERGENCE | | | | | | | | | | | | | | | |
| (OCH₃/CH₃ pyrimidine, SO₂NHCONH, pyrrolidine-carbonyl thiophene) | 0.05 | | | 9H | 9H | 5G | 10E | 1C | 9H,3C | 2C,7G | 9G | 1C,9H | 1C,3H | 4C,9H | 2C,8H |

TABLE A-continued

| | kg/ha | BUSH-BEAN | COT-TON | MORNING-GLORY | COCKLE-BUR | CAS-SIA | NUT-SEDGE | CRAB-GRASS | BARN-YARD-GRASS | WILD OATS | WHEAT | CORN | SOY-BEAN | RICE | SOR-GHUM |
|---|---|---|---|---|---|---|---|---|---|---|---|---|---|---|---|
| structure 1 | 0.05 | 0 | 0 | 0 | 9H | 2C | 0 | 0 | 1C | 0 | 0 | 1C,5G | 0 | 2C | 6H |
| structure 2 | 0.05 | 0 | 0 | 0 | 9H | 0 | 0 | 0 | 0 | 0 | 0 | 0 | 0 | 0 | 0 |
| POST-EMERGENCE | | | | | | | | | | | | | | | |
| structure 3 | 0.05 | 6Y,1B, 2H | 4C,9G | 3C,9G | 3C,9H | 2C | 2C,5G | 1C | 2C,6H | 0 | 0 | 2C,8H | 2C,9G | 1C,3G | 1C,9G |
| structure 4 | 0.05 | 0 | 0 | 0 | 0 | 0 | 0 | 0 | 0 | 0 | 0 | 0 | 0 | 0 | 0 |

TABLE A-continued

| Structure | kg/ha | BUSH-BEAN | COT-TON | MORNING-GLORY | COCKLE-BUR | CAS-SIA | NUT-SEDGE | CRAB-GRASS | BARN-YARD-GRASS | WILD OATS | WHEAT | CORN | SOY-BEAN | RICE | SOR-GHUM |
|---|---|---|---|---|---|---|---|---|---|---|---|---|---|---|---|
| Structure 1 (CH₃/CH₃ pyrimidine, SO₂NHCONH-thiophene-CHO) | 0.05 | 3D,6Y | 0 | 0 | 0 | 0 | 2G | 0 | 2G | 0 | 0 | 2C,7H | 1H | 8G | 2C,9G |
| | | | | | | PRE-EMERGENCE | | | | | | | | | |
| Structure 2 (OCH₃/CH₃ pyrimidine, SO₂NHCONH-thiophene-C(=NOEt)H) | 0.05 | | | 9G | 5G | 0 | 0 | 0 | 5H | 0 | 0 | 1C,5C | 2C,4H | 1C,6G | 2C |
| Structure 3 (CH₃/CH₃ pyrimidine, SO₂NHCONH-thiophene-COOCH₂-phenyl) | 0.05 | | | 0 | 0 | 0 | 0 | 0 | 0 | 0 | 0 | 0 | 0 | 0 | 0 |
| | | | | | | POST-EMERGENCE | | | | | | | | | |
| Structure 4 (CH₃/CH₃ pyrimidine, SO₂NHCONH-thiophene-CHO) | 0.05 | | | 0 | 3C,8H | 1H | 0 | 0 | 1H | 0 | 2G | 3H | 5G | 6H |

TABLE A-continued

| Structure | kg/ha | BUSH-BEAN | COT-TON | MORNING-GLORY | COCKLE-BUR | CAS-SIA | NUT-SEDGE | CRAB-GRASS | BARN-YARD-GRASS | WILD OATS | WHEAT | CORN | SOY-BEAN | RICE | SOR-GHUM |
|---|---|---|---|---|---|---|---|---|---|---|---|---|---|---|---|
| CH₃O₂C—[thiophene]—SO₂NHCONH—[pyrimidine(CH₃, CH₃)] | 0.4 | 9C | 10C | 10C | 10C | 9C | 7C,9G | 9C | 9C | 9C | 9C | 7U,9C | 9C | 8C | 9C |
| CH₃O₂C—[thiophene]—SO₂NHCONH—[pyrimidine(OCH₃, CH₃)] | 0.4 | 9C | 9C | 10C | 10C | 9C | 9C | 9C | 9C | 9C | 9C | 10C | 9C | 8C | 10C |
| CH₃O₂C—[thiophene]—SO₂NHCONH—[pyrimidine(OCH₃, CH₃)] | 0.4 | 9C | 9C | 10C | 9C | 9C | 6C,9G | 9C | 9C | 8C | 4C,8G | 5U,10C | 6C,9G | 5C,9G | 6C,9G |
| | | | | | PRE-EMERGENCE | | | | | | | | | | |
| CH₃O₂C—[thiophene]—SO₂NHCONH—[pyrimidine(CH₃, CH₃)] | 0.4 | | | 9H | 9H | 10C | 10E | 10E | 9H | 5C,9H | 10E | 10E | 9H | 10E | 10E |
| CH₃O₂C—[thiophene]—SO₂NHCONH—[pyrimidine(OCH₃, CH₃)] | 0.4 | | | 9H | 9H | 9H | 10E | 10E | 5C,9H | 5C,9H | 10E | 10E | 9H | 10E | 10E |

TABLE A-continued

| Structure | kg/ha | BUSH-BEAN | COT-TON | MORNING-GLORY | COCKLE-BUR | CAS-SIA | NUT-SEDGE | CRAB-GRASS | BARN-YARD GRASS | WILD OATS | WHEAT | CORN | SOY-BEAN | RICE | SOR-GHUM |
|---|---|---|---|---|---|---|---|---|---|---|---|---|---|---|---|
| ![structure with OCH3, CH3, thiophene-CO2CH3] | 0.4 | | 9C | 9G | 9H | 9G | 9G | 6C,9G | 5C,9H | 3C,9G | 3C,9G | 10E | 9H | 10E | 6C,9H |

POST-EMERGENCE

| Structure | kg/ha | BUSH-BEAN | COT-TON | MORNING-GLORY | COCKLE-BUR | CAS-SIA | NUT-SEDGE | CRAB-GRASS | BARN-YARD GRASS | WILD OATS | WHEAT | CORN | SOY-BEAN | RICE | SOR-GHUM |
|---|---|---|---|---|---|---|---|---|---|---|---|---|---|---|---|
| ![structure OCH3, OCH3, thiophene-CO2CH2] | 0.4 | 9C | 9C | 10C | 9C | 9C | 9C | 8C | 9C | 2C,8G | 1C,5G | 8U,9C | 5C,9G | 9C | 2C,9G |
| ![structure OCH3, OCH3 pyridine, thiophene-CO2CH(CH3)2] | 0.1 | 9C | 9C | 10C | 2C | 1C | 1C | 1C | 3C | 0 | 0 | 3C | 9C | 5C | 2C |
| ![structure OCH3, CH3 pyridine, thiophene-CO2CH2CH=CH2] | 0.05 | 7C,9G, 6Y | 6C,9G | 10C | 5C,9G | 1C | 9G | 5G | 4C,9H | 2G | 1C,6G | 5C,9G | 6H | 8G | 1C,9G |

PRE-EMERGENCE

TABLE A-continued

| Structure | kg/ha | BUSH-BEAN | COT-TON | MORNING-GLORY | COCKLE-BUR | CAS-SIA | NUT-SEDGE | CRAB-GRASS | BARN-YARD-GRASS | WILD OATS | WHEAT | CORN | SOY-BEAN | RICE | SOR-GHUM |
|---|---|---|---|---|---|---|---|---|---|---|---|---|---|---|---|
| (structure 1: CH₃O₂C-thiophene-SO₂NHCONH-pyrimidine(OCH₃)₂) | 0.4 | | | 9H | 9H | 3C,9G | 10E | 3C,9H | 5C,9H | 3C,9G | 1C,8H | 3C,9H | 9H | 10E | 6C,9H |
| (structure 2: thiophene-CO₂CH(CH₃)₂, SO₂NHCONH-pyrimidine(OCH₃)₂) | 0.1 | | | 9G | | 6G | 10E | 2G | 3C,9H | 2C,7G | 1C,3G | 3C,9G | 9H | 9H | 4C,9G |
| (structure 3: thiophene-CO₂CH₂CH=CH₂, SO₂NHCONH-pyrimidine(OCH₃,CH₃)) | 0.05 | | | 9G | 9H | 8G | 10E | 1C | 2C,9H | 1C,8G | 1C,9G | 1C,9G | 1C,3G | 10E | 3C,9G |
| POST-EMERGENCE | | | | | | | | | | | | | | | |
| (structure 4: CH₃O₂C-thiophene-SO₂NHCONH-pyrimidine(OCH₃)₂) | 0.4 | 9C | 9C | 10C | 9C | 9C | 9C | 9C | 9C | 9C | 9C | 6U,9C | 9C | 6C,9G | 9C |
| (structure 5: CH₃O₂C-thiophene-SO₂NHCONH-pyrimidine(CH₃)₂) | 0.4 | 9C | 9C | 10C | 9C | 6C,9G | 9C | 9C | 9C | 9C | 8C | 5U,9C | 9C | 6C,9G | 9C |

TABLE A-continued
| | kg/ha | BUSH-BEAN | COT-TON | MORNING-GLORY | COCKLE-BUR | CAS-SIA | NUT-SEDGE | CRAB-GRASS | BARN-YARD-GRASS | WILD OATS | WHEAT | CORN | SOY-BEAN | RICE | SOR-GHUM |
|---|---|---|---|---|---|---|---|---|---|---|---|---|---|---|---|
| 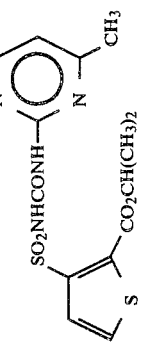 | 0.1 | 9C | 9C | 9C | 3C | 1C | 2C | 1C | 9C | 2C | 1C | 5C | 9C | 9C | 5C |
| PRE-EMERGENCE | | | | | | | | | | | | | | | |
| 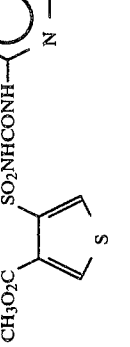 | 0.4 | | | 9G | 9H | 6C,9G | 10E | 10E | 3C,9H | 2C,9H | 10E | 10E | 9H | 10E | 2C,9G |
|  | 0.4 | | | 9G | 9H | 9G | 9G | 5C,9G | 5C,9H | 5C,9H | 1C,9G | 10E | 9H | 10E | 10E |
| 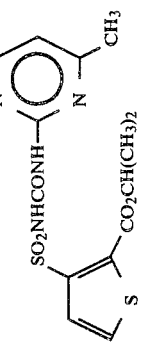 | 0.1 | | | 9H | | 9G | 9G | 2C,7G | 5C,9H | 3C,9G | 9G | 5C,9G | 9H | 10E | 5C,9H |
| POST-EMERGENCE | | | | | | | | | | | | | | | |

TABLE A-continued

| Structure | kg/ha | BUSH-BEAN | COT-TON | MORNING-GLORY | COCKLE-BUR | CAS-SIA | NUT-SEDGE | CRAB-GRASS | BARN-YARD-GRASS | WILD OATS | WHEAT | CORN | SOY-BEAN | RICE | SOR-GHUM |
|---|---|---|---|---|---|---|---|---|---|---|---|---|---|---|---|
| Structure with OCH₃, CH₃, SO₂NHCONH, thiophene with HO₂C | 1.0 | 0 | 0 | 0 | 0 | 0 | 0 | 0 | 0 | 0 | 0 | 0 | 0 | 0 | 0 |
| Structure with OCH₃, OCH₃, SO₂NHCONH, thiophene with CO₂H | 2.0 | 6C,9G, 6Y | 6C,9G, 7G | 6C,9G | 3C,9G | 2C,7G | 6C,7G | 9C | 10C | 9C | 9C | 7C,9C | 6C,9G | 4C,9G | 9C |
| Structure with OCH₃, CH₃, SO₂NHCONH, thiophene with CO₂CH(CH₃)(C₂H₅) | 0.05 | 2C,4G, 6Y | 3C,3H, 7G | 9C | 3C,9G | 1C | 2C,5G, 5X | 3G | 3C,8H | 2C | 1C,3G | 2C,8G | 2H,9G, 5X | 8G | 2H,9G |
|  |  |  |  |  | PRE-EMERGENCE |  |  |  |  |  |  |  |  |  |  |
| Structure with OCH₃, CH₃, SO₂NHCONH, thiophene with HO₂C | 1.0 | 0 | 0 | 0 | 0 | 0 | 0 | 0 | 0 | 0 | 0 | 0 | 0 | 0 | 0 |

TABLE A-continued

| | kg/ha | BUSH-BEAN | COTTON | MORNING-GLORY | COCKLE-BUR | CAS-SIA | NUT-SEDGE | CRAB-GRASS | BARN-YARD-GRASS | WILD OATS | WHEAT | CORN | SOY-BEAN | RICE | SOR-GHUM |
|---|---|---|---|---|---|---|---|---|---|---|---|---|---|---|---|
| ![structure with CO2H, thiophene, SO2NHCONH, pyrimidine with 2 OCH3] | 2.0 | | | 9C | 9H | 9G | 10E | 2C,9G | 2C,9H | 2C,9H | 4C,9H | 9H | 9H | 10E | 5C,9H |
| ![structure with CO2CH(C2H5)CH3, thiophene, SO2NHCONH, pyrimidine OCH3/CH3] | 0.05 | 3C,7G,6Y | 3C,4H,9G | 3C,9G | 9H | 2G | 2C,8G | 1C | 3C,8H | 2C,5G | 5G | 1C,8G | 2C,3G | 8H | 2C,9H |
| POST-EMERGENCE | | | | | | | | | | | | | | | |
| ![structure with CO2CH(CH3)CH2, thiophene, SO2NHCONH, pyrimidine OCH3/CH3] | 0.05 | | | | 2C,9G | 1C | 2C,7G | 1C | 3C,9H | 1C | 1C | 9H | 2C,8G | 8G,5I | 9G,5I |
| ![structure with CO2CH(CH3)C≡CH, methylthiophene, SO2NHCONH, pyrimidine CH3/OCH3] | 0.05 | 3C,8G,6Y | 4C,3H,9G | 9C | 9C | 1C | 2C,7G | 1C,5G | 9C | 1C | 1C,2G | 3H,9G | 3H,9G, 5X | 9C | 5C,9G |

TABLE A-continued

| Structure | kg/ha | BUSH-BEAN | COT-TON | MORNING-GLORY | COCKLE-BUR | CAS-SIA | NUT-SEDGE | CRAB-GRASS | BARN-YARD-GRASS | WILD OATS | WHEAT | CORN | SOY-BEAN | RICE | SOR-GHUM |
|---|---|---|---|---|---|---|---|---|---|---|---|---|---|---|---|
| [pyrimidine-CH3/OCH3, SO2NHCONH-thiophene-C(=O)-N-pyrrolidine] | 0.05 | 1C | 2C | 1C | 0 | 0 | 0 | 0 | 0 | 0 | 0 | 0 | 0 | 0 | 0 |
| PRE-EMERGENCE | | | | | | | | | | | | | | | |
| [pyrimidine-OCH3/CH3, SO2NHCONH-thiophene-CO2CH-CH3/CH-CH2] | 0.05 | | | 8G | 9H | 4G | 1C,8G | 1C | 9H,2C | 2C,7G | 2C,9G | 2C,9H | 8H | 9H | 1C,9G |
| [pyrimidine-CH3/OCH3, SO2NHCONH-thiophene-CO2-CH-CH3/C≡CH] | 0.05 | | | 3C,9G | 9H | 5G | 9G | 2C,8G | 9H | 2C,8G | 9H,2C | 1C,9H | 2C,6H | 10E | 7C,9H |
| [pyrimidine-CH3/OCH3, SO2NHCONH-thiophene-C(=O)-N-pyrrolidine] | 0.05 | | | 0 | | | 0 | 0 | 0 | 0 | 0 | | 0 | 0 | 0 |

TABLE A-continued

| Structure | kg/ha | BUSH-BEAN | COTTON | MORNING-GLORY | COCKLE-BUR | CASSIA | NUT-SEDGE | CRAB-GRASS | BARN-YARD-GRASS | WILD OATS | WHEAT | CORN | SOYBEAN | RICE | SORGHUM |
|---|---|---|---|---|---|---|---|---|---|---|---|---|---|---|---|
| POST-EMERGENCE | | | | | | | | | | | | | | | |
| SO₂NHCONH-pyrimidine(OCH₃,OCH₃), thiophene-C(=O)N(CH₃)(OCH₃) | 0.05 | 5C,9G, 6Y | 5C,9G | 4C,8G | 10C, | 1C,3H | 2C,9G | 1C | 2C,9H | 0 | 0 | 1C | 2C,9G | 2C,8G | 2C,9H |
| SO₂NHCONH-pyrimidine(CH₃,OCH₃), thiophene-C(=O)N(CH₃)(OCH₃) | 0.05 | 5C,9G, 6Y | 5C,9G | 6C,9G | 5C,9G | 2C,4G | 2C,9G | 7G | 9C | 1C,6G | 1C,6G | 1C,4G | 2C,2H,8G | 5C,9G | 4C,9G |
| SO₂NHCONH-pyrimidine(CH₃,CH₃), thiophene-CO₂CH₃ | 0.05 | 2C,9G, 6Y | 5C,9G | 5C,9G | 2H,9G | 1C,5G | 8G | 2C,6G | 2C,7H | 0 | 0 | 1C,3G | 0 | 6G | 2C,9H |
| PRE-EMERGENCE | | | | | | | | | | | | | | | |
| SO₂NHCONH-pyrimidine(OCH₃,OCH₃), thiophene-C(=O)N(CH₃)(OCH₃) | 0.05 | | | 8G | 9H | 0 | 9G | 2C | 2C,8H | 1C,5G | 1C,5G | 2C,7G | 1C | 9H | 2C,9H |

TABLE A-continued

| Structure | kg/ha | BUSH. BEAN | COT-TON | MORNING-GLORY | COCKLE-BUR | CAS-SIA | NUT-SEDGE | CRAB-GRASS | BARN-YARD GRASS | WILD OATS | WHEAT | CORN | SOY-BEAN | RICE | SOR-GHUM |
|---|---|---|---|---|---|---|---|---|---|---|---|---|---|---|---|
| Structure with CH3, OCH3, SO2NHCONH, C(O)N(CH3)OCH3, thiophene | 0.05 | | | 2C,9G | 9H | 6G,2C | 2C,9G | 3C,7G | 5C,9H | 2C,9G | 1C,9G | 2C,8G | 2C,6H | 10E | 9C,9H |
| Structure with CH3, CH3, SO2NHCONH, CO2CH3, thiophene | 0.05 | | | 9G | 9H | 0 | 9G | 1C | 2C,3G | 1C | 4G | 2C,7G | 0 | 2C,8H | 2C,9G |

POST-EMERGENCE

| Structure | kg/ha | BUSH. BEAN | COT-TON | MORNING-GLORY | COCKLE-BUR | CAS-SIA | NUT-SEDGE | CRAB-GRASS | BARN-YARD GRASS | WILD OATS | WHEAT | CORN | SOY-BEAN | RICE | SOR-GHUM |
|---|---|---|---|---|---|---|---|---|---|---|---|---|---|---|---|
| Structure with SCH3, CH3, SO2NHCONH, CO2CH3, thiophene | 0.05 | 1C,4G | 2C,2H, 8G | 1C,5G | 2G | 1C,2G | 1C,8G | 1C,5G | 1C,6G | 0 | 1G | 1C,2G | 1H | 8G | 7H |
| Structure with CH2OCH3, CH3, SO2NHCONH, CO2CH3, thiophene | 0.05 | 5C,9G, 6Y | 4C,7G | 2C,7G | 2C,9G | 1C | 4C,9G | 9G | 5C,9H | 0 | 2C,9G | 2C,9H | 0 | 9G | 1C,9G |

TABLE A-continued

| Structure | kg/ha | BUSH-BEAN | COT-TON | MORNING-GLORY | COCKLE-BUR | CAS-SIA | NUT-SEDGE | CRAB-GRASS | BARN-YARD-GRASS | WILD OATS | WHEAT | CORN | SOY-BEAN | RICE | SOR-GHUM |
|---|---|---|---|---|---|---|---|---|---|---|---|---|---|---|---|
| ![structure with N-OCH3, CH3, CH3, SO2NHCONH, CO2CH3, thiophene] | 2 | 1C,1H | 0 | 0 | 0 | 0 | 0 | 4G | 6H | 0 | 0 | 0 | 1C | 0 | 2G |
| ![structure with N-OCH3, CH3, CH3, SO2NHCONH, CO2CH3, thiophene] | 0.05 | 0 | 0 | 0 | 0 | 0 | 0 | 0 | 0 | 0 | 0 | 0 | 0 | 0 | 0 |
| PRE-EMERGENCE | | | | | | | | | | | | | | | |
| ![structure with SCH3, CH3, SO2NHCONH, CO2CH3, thiophene] | 0.05 | | | 1H | 8H | 1H | 9G | 1C | 3C,4G | 3G | 5G | 6G | 1H | 8H | 1C,7G |
| ![structure with CH2OCH3, CH3, SO2NHCONH, CO2CH3, thiophene] | 0.05 | | | 5G | 8H | 0 | 10E | 7G | 2C,8G | 2G | 9G | 2C,9H | 0 | 10E | 2C,9H |

TABLE A-continued

| Structure | kg/ha | BUSH-BEAN | COT-TON | MORNING-GLORY | COCKLE-BUR | CAS-SIA | NUT-SEDGE | CRAB-GRASS | BARN-YARD-GRASS | WILD OATS | WHEAT | CORN | SOY-BEAN | RICE | SOR-GHUM |
|---|---|---|---|---|---|---|---|---|---|---|---|---|---|---|---|
| Structure 1: CH₃(N-OCH₃)-pyrimidine(CH₃)-NH-SO₂-thiophene-CO₂CH₃ | 2 | 6H | | 6H | 6H | 0 | 0 | 2G | 0 | 0 | 0 | 0 | 0 | 1C | 2G |
| Structure 2: CH₃(N-OCH₃)-pyrimidine(CH₃)-NH-SO₂-thiophene-CO₂CH₃ | 0.05 | 0 | | 0 | 0 | 0 | 0 | 0 | 0 | 0 | 0 | 0 | 0 | 0 | 0 |
| | | | | | POST-EMERGENCE | | | | | | | | | | |
| Structure 3: Cl, OCH₃ pyrimidine-NH-SO₂-thiophene-CO₂CH₃ | 0.05 | 3C,5G, 6Y | 5C,9G | 10C | 5C,9G | 2C,6G | 9C | 3C | 2C,9H | 0 | 2C | 2C,7H | 1C,5H | 2C,8G | 9H |
| Structure 4: N(CH₃)₂, CH₃ pyrimidine-NH-SO₂-thiophene-CO₂CH₃ | 0.1 | 0 | 0 | 0 | 0 | 0 | 0 | 0 | 0 | 0 | 0 | 0 | 0 | 0 | 0 |

TABLE A-continued

| Structure | kg/ha | BUSH-BEAN | COT-TON | MORNING-GLORY | COCKLE-BUR | CAS-SIA | NUT-SEDGE | CRAB-GRASS | BARN-YARD-GRASS | WILD OATS | WHEAT | CORN | SOY-BEAN | RICE | SOR-GHUM |
|---|---|---|---|---|---|---|---|---|---|---|---|---|---|---|---|
| ![structure with N(CH3)2, Cl, SO2NHCONH, CO2CH3, thiophene] | 0.05 | 2H | 2C,7G | 1C | 5G | 1C | 2C,8G | 0 | 3C,9H | 0 | 0 | 2G | 0 | 5G | 9G |

PRE-EMERGENCE

| Structure | kg/ha | BUSH-BEAN | COT-TON | MORNING-GLORY | COCKLE-BUR | CAS-SIA | NUT-SEDGE | CRAB-GRASS | BARN-YARD-GRASS | WILD OATS | WHEAT | CORN | SOY-BEAN | RICE | SOR-GHUM |
|---|---|---|---|---|---|---|---|---|---|---|---|---|---|---|---|
| ![structure with Cl, OCH3, SO2NHCONH, CO2CH3, thiophene] | 0.05 | | | 9H | 9H | 1C | 8G | 3C | 3C,9H | 2C | 1C,4G | 3C,7G | 2G | 2C,9H | 2C,9H |
| ![structure with N(CH3)2, CH3, SO2NHCONH, CO2CH3, thiophene] | 0.1 | | | 0 | 0 | 0 | 0 | 0 | 0 | 0 | 0 | 0 | 0 | 0 | 0 |
| ![structure with N(CH3)2, Cl, SO2NHCONH, CO2CH3, thiophene] | 0.05 | | | 2G | 9H | 0 | 8G | 0 | 7H | 0 | 3G | 2C,6G | 0 | 3C,9H | 9H |

POST-EMERGENCE

TABLE A-continued

| | kg/ha | BUSH-BEAN | COT-TON | MORNING-GLORY | COCKLE-BUR | CAS-SIA | NUT-SEDGE | CRAB-GRASS | BARN-YARD-GRASS | WILD OATS | WHEAT | CORN | SOY-BEAN | RICE | SOR-GHUM |
|---|---|---|---|---|---|---|---|---|---|---|---|---|---|---|---|
| Structure 1 (Cl, CH$_3$ triazine; SO$_2$NHCONH-thiophene-CO$_2$CH$_3$) | 2.0 | 2C | 2C | 0 | 0 | 0 | 0 | 0 | 0 | 0 | 0 | 0 | 0 | 0 | 0 |
| Structure 2 (CH$_3$, OCH$_3$ triazine; SO$_2$NHCON(CH$_3$)-thiophene-CO$_2$CH$_3$) | 0.4 | 5S,7G, 6Y | 5C,9G | 3C,8G | 5C,9G | 0 | 5G | 2C,6G | 5C,9H | 0 | 0 | 2C,6H | 0 | 1C,7G | 1C,5H |
| Structure 3 (CH$_3$, CH$_3$ triazine; SO$_2$NHCON(CH$_3$)-thiophene-CO$_2$CH(CH$_3$)$_2$) | 0.1 | 0 | 2G,2C, 3H | 5G,2C | 8G | 2C | 0 | 0 | 0 | 0 | 0 | 0 | 0 | 0 | 0 |
| PRE-EMERGENCE | | | | | | | | | | | | | | | |
| Structure 4 (Cl, CH$_3$ triazine; SO$_2$NHCONH-thiophene-CO$_2$CH$_3$) | 2.0 | 0 | | 6G | 8H | 0 | 0 | 0 | 4C | 0 | 0 | 2C | 0 | 0 | 2G |
| Structure 5 (CH$_3$, OCH$_3$ triazine; SO$_2$NHCON(CH$_3$)-thiophene-CO$_2$CH$_3$) | 0.4 | | | 8G | 9H | 2C | | | 1C | 0 | 0 | 2C | 1C | 5H | 2C |

TABLE A-continued

| Structure | kg/ha | BUSH-BEAN | COTTON | MORNING-GLORY | COCKLE-BUR | CAS-SIA | NUT-SEDGE | CRAB-GRASS | BARN-YARD-GRASS | WILD OATS | WHEAT | CORN | SOY-BEAN | RICE | SOR-GHUM |
|---|---|---|---|---|---|---|---|---|---|---|---|---|---|---|---|
| ![structure with CH3, CH3 pyrimidine, SO2NHCONH, CO2CH(CH3)2, thiophene] | 0.1 | | 5G | 5G | 5G | 0 | 0 | 0 | 0 | 0 | 0 | 0 | 0 | 4G | 2G |
| POST-EMERGENCE |||||||||||||||
| ![structure with CH3, OCH3] | 0.1 | 10G, 8C | 10G, 7C | 10G,3C | 10G | 7G | 0 | 0 | 0 | 0 | 0 | 0 | 3G | 10G, 4C | 9G |
| ![structure with OCH3, OCH3] | 0.1 | 10G, 3C | 10G, 8C | 10C | 10C | 9G | 7G | 0 | 3G | 0 | 0 | 3G | 10G, 4H | 10G, 3C | 9G |
| ![structure with CH3, CH3] | 0.1 | 10G, 3H,2C | 9G,4H, 3C | 10G,3C | 10G,3H,2C | 3G | 9G,1C | 4G | 5G | 2G | 2G | 4G | 10G, 4H | 1C,9G | 7G |
| ![structure with CH3, CH3 pyridine] | 0.05 | | | | | | | | 9G,5H | 4G | 6G | 9G,2U, 2C | 9G | 10G, 2C | 10G |

PRE-EMERGENCE

TABLE A-continued

| Structure | kg/ha | BUSH BEAN | COTTON | MORNING GLORY | COCKLE BUR | CASSIA | NUT SEDGE | CRAB GRASS | BARN-YARD GRASS | WILD OATS | WHEAT | CORN | SOY BEAN | RICE | SORGHUM |
|---|---|---|---|---|---|---|---|---|---|---|---|---|---|---|---|
| Pyrimidine (CH$_3$/OCH$_3$), SO$_2$NHCONH-thiophene-CO$_2$CH(CH$_3$)$_2$ | 0.1 | 9C | 10C | 9G | 10E | 8G | 6G | 3G | 5G | 0 | 4G | 4G | 9G | 7G | 6G |
| Pyrimidine (OCH$_3$/OCH$_3$), SO$_2$NHCONH-thiophene-CO$_2$CH(CH$_3$)$_2$ | 0.1 | | | 9G | 6G | 8G | 5G | 1G | 3G | 2G | 2G | 2G | 9G | 7G | 6G |
| Pyridine (CH$_3$/CH$_3$), SO$_2$NHCONH-thiophene-CO$_2$CH(CH$_3$)$_2$ | 0.05 | | | 9G | 7G | 7G | 9G | 3G | 3H,9G | 6G | 7G | 2G | 9G | 7G | 9G |
| POST-EMERGENCE Pyrimidine (OCH$_3$/OCH$_3$), SO$_2$NHCNH-thiophene-CO$_2$CH$_3$ | 0.05 | 9C | | 9C | 10C | 1C | 9C | 9G | 6C | 1C | 1C | 3U | 6C | 5C | 10C |

TABLE A-continued
| Compound | kg/ha | BUSH-BEAN | COT-TON | MORNING-GLORY | COCKLE-BUR | CAS-SIA | NUT-SEDGE | CRAB-GRASS | BARN-YARD-GRASS | WILD OATS | WHEAT | CORN | SOY-BEAN | RICE | SOR-GHUM |
|---|---|---|---|---|---|---|---|---|---|---|---|---|---|---|---|
| 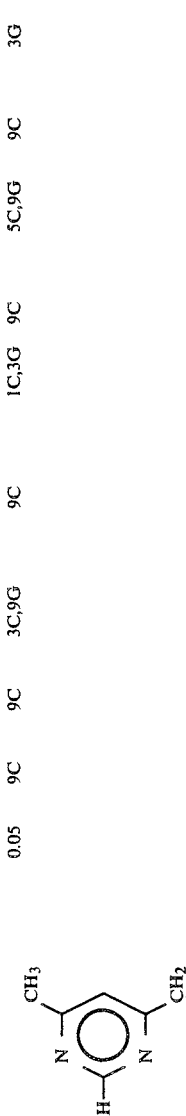 | 0.05 | 9C | 9C | 3C,9G | 9C | 1C,3G | 9C | 5C,9G | 9C | 3G | 3C,9G | 4U,9C | 3C,9H | 5C,9G | 5U,9G |
| 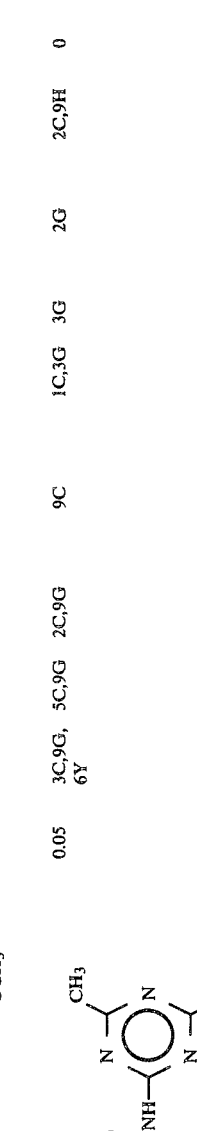 | 0.05 | 3C,9G, 6Y | 5C,9G | 2C,9G | 9C | 1C,3G | 3G | 2G | 2C,9H | 0 | 0 | 1U,9G | 3H,8H | 2C,9G | 1U,9G |
| PRE-EMERGENCE |
| 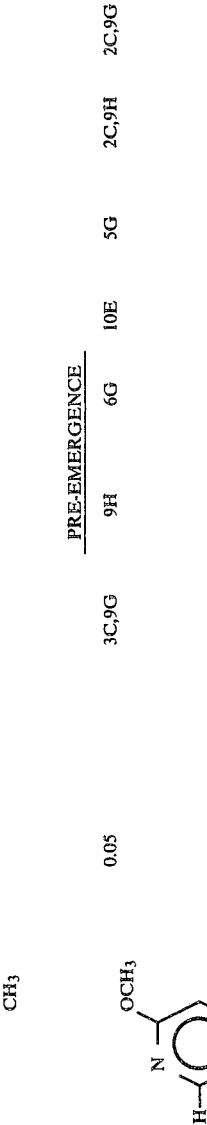 | 0.05 | | | 3C,9G | 9H | 6G | 10E | 5G | 2C,9H | 2C,9G | 2C,9G | 1U,9H | 9H | 10E | 10H |
| 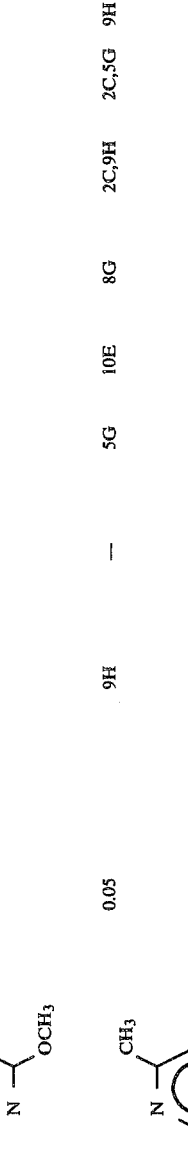 | 0.05 | | | 9H | — | 5G | 10E | 8G | 2C,9H | 2C,5G | 9H | 10E | 1C,7H | 10E | 4C,9H |

TABLE A-continued

| Structure | kg/ha | BUSH-BEAN | COT-TON | MORNING-GLORY | COCKLE-BUR | CAS-SIA | NUT-SEDGE | CRAB-GRASS | BARN-YARD-GRASS | WILD OATS | WHEAT | CORN | SOY-BEAN | RICE | SOR-GHUM |
|---|---|---|---|---|---|---|---|---|---|---|---|---|---|---|---|
| Structure with CO$_2$CH$_3$, thiophene, SO$_2$NHCNH, pyrimidine with 2 CH$_3$ groups | 0.05 | 9C | | 8H | 9H | 4G | 0 | 0 | 2C,6H | 0 | 3G | 1C,9G | 1C,5H | 10E | 2C,9H |
| | | | | | POST-EMERGENCE | | | | | | | | | | |
| Structure with CO$_2$CH$_3$, thiophene, SO$_2$NCN H H, pyrimidine with OCH$_3$ and CH$_3$ | 0.05 | 0 | 10C | 9C | 10C | 2C | 1C | 2G | 2C | 0 | 0 | 2C | 3C | 2C | 2C |
| Structure with CO$_2$CH$_3$, thiophene, SO$_2$NHCN CH$_3$, pyrimidine with OCH$_3$ and OCH$_3$ | 0.4 | 5C,8G | | 4C,9G | 2H,7G | 2C | 0 | 2G | 1H | 0 | 0 | 2G | 1G | 3G | 2G |
| Structure with CO$_2$CH$_2$CH=CH$_2$, thiophene, SO$_2$NHCNH, pyrimidine with CH$_3$ and CH$_3$ | 0.05 | 1C,5G, 6Y | 3C,5H, 9G | 2C,8G | 6G | 1C,4G | 3G | 2G | 2C,6H | 0 | 0 | 5H | 0 | 3C,9G | 2C,9G |
| | | | | | PRE-EMERGENCE | | | | | | | | | | |

TABLE A-continued

| Structure | kg/ha | BUSH-BEAN | COT-TON | MORNING-GLORY | COCKLE-BUR | CAS-SIA | NUT-SEDGE | CRAB-GRASS | BARN-YARD-GRASS | WILD OATS | WHEAT | CORN | SOY-BEAN | RICE | SOR-GHUM |
|---|---|---|---|---|---|---|---|---|---|---|---|---|---|---|---|
| Structure 1 | 0.05 | | | 10C | — | 2C,9G | 2C | 1C | 3C,9H | 1C,4G | 1C,4G | 9G | 2C,9H | 10E | 2C,9H |
| Structure 2 | 0.4 | | | 5G | 9H | 0 | 4G | 0 | 0 | 0 | 0 | 0 | 0 | | 3H |
| Structure 3 | 0.05 | | | 7G | 9G | 3G | 9G | 0 | 2C | 0 | 3G | 4G | 2C,8G | 2C,6G | 2C |
| | | | | | POST-EMERGENCE | | | | | | | | | | |
| Structure 4 | 0.05 | 3C,9G, 6Y | 6C,9G | 2C,9G | 10C | 1C,3G | 2C,8G | 4G | 2C,9H | 1C | 1C | 1C,6G | 2C,6H | | |
| Structure 5 | | | | | | | | | | | | 2C,8H | 2C,6H | 7G | 2C,9G |

TABLE A-continued

| Structure | kg/ha | BUSH-BEAN | COTTON | MORNING-GLORY | COCKLE-BUR | CASSIA | NUT-SEDGE | CRAB-GRASS | BARN-YARD-GRASS | WILD OATS | WHEAT | CORN | SOY-BEAN | RICE | SOR-GHUM |
|---|---|---|---|---|---|---|---|---|---|---|---|---|---|---|---|
| Compound with OCH$_3$/CH$_3$ pyrimidine, SO$_2$NHCNH, CO$_2$CH$_2$CH=CH$_2$ thiophene | 0.05 | 5C,9G, 6Y | 9G | 9C | 2C,9G | 1C,3G | 2G | 2G | 5H | 0 | 0 | 2G | 2H,6G | 6G | 1H,7G |
| Compound with OCH$_3$/OCH$_3$ pyrimidine | 0.05 | 5C,9G, 6Y | 6C,9G | 6C,9G | 6C,9G | 1C,3G | 2G | 0 | 1H | 0 | 0 | 2G | 7H | 5G | 5G |
| | | | | | | | | | PRE-EMERGENCE | | | | | | |
| Compound with OCH$_3$/OCH$_3$ pyrimidine | 0.05 | | | 8G | 9H | 1C,3G | 10E | 2C | 3C,7H | 0 | 0 | 2C,8H | 2H | 3C,7G | 2C,9H |
| Compound with OCH$_3$/CH$_3$ pyrimidine | 0.05 | | | 9G | 2C,9H | 6G | 2G | 1C | 0 | 0 | 1C,5G | 1C,3G | 1C,3G | 1C | 2C |

TABLE A-continued

| Structure | kg/ha | BUSH-BEAN | COTTON | MORNING-GLORY | COCKLE-BUR | CAS-SIA | NUT-SEDGE | CRAB-GRASS | BARN-YARD-GRASS | WILD OATS | WHEAT | CORN | SOY-BEAN | RICE | SOR-GHUM |
|---|---|---|---|---|---|---|---|---|---|---|---|---|---|---|---|
| Pyrimidine (OCH$_3$/OCH$_3$), SO$_2$NHCNH, CO$_2$CH$_2$CH=CH$_2$, thiophene | 0.05 | 3C,8G,6Y | 5C,9G | 3C,9G | 9H | 2C,6G | 1C,7G | 1C,4G | 1C,3H | 2C | 0 | 2C,5G | 2C,5H | 2C,4G | 1C,3G |

POST-EMERGENCE

| Structure | kg/ha | BUSH-BEAN | COTTON | MORNING-GLORY | COCKLE-BUR | CAS-SIA | NUT-SEDGE | CRAB-GRASS | BARN-YARD-GRASS | WILD OATS | WHEAT | CORN | SOY-BEAN | RICE | SOR-GHUM |
|---|---|---|---|---|---|---|---|---|---|---|---|---|---|---|---|
| Pyridine (CH$_3$/CH$_3$), SO$_2$NHCNH, CO$_2$CH$_3$, thiophene | 0.05 | 3C,6Y | — | 2C,9G | 7G | 1C | 0 | 0 | 7H | 0 | 0 | 0 | 0 | 0 | 6H |
| Pyrimidine (CH$_3$/C$_2$H$_5$), SO$_2$NHCNH, CO$_2$CH$_3$, thiophene | 0.05 | 3C,6Y | — | — | 1C | 1C | 9G | 6G | 9H | 0 | 2G | 2C,8H | 1C,2G | 7G | 9G |
| Pyrimidine (CH$_3$/CH(CH$_3$)$_2$), SO$_2$NHCNH, CO$_2$CH$_3$, thiophene | 0.05 | 2G,6F | — | 0 | 0 | 0 | 0 | 0 | 0 | 0 | 0 | 0 | 0 | 0 | 0 |

PRE-EMERGENCE

TABLE A-continued

| Structure | kg/ha | BUSH-BEAN | COTTON | MORNING-GLORY | COCKLE-BUR | CAS-SIA | NUT-SEDGE | CRAB-GRASS | BARN-YARD-GRASS | WILD OATS | WHEAT | CORN | SOY-BEAN | RICE | SOR-GHUM |
|---|---|---|---|---|---|---|---|---|---|---|---|---|---|---|---|
| $CH_3$/$CH_3$ pyridyl, $SO_2NHCNH$, $CO_2CH_3$ thiophene | 0.05 | 2C,5G, 6Y | 2C,3H, 8G | 5G | 3H | 0 | 0 | 0 | 5H,2C | 0 | 0 | 2G | 0 | 2C,4G | 2C,5G |
| $CH_3$/$C_2H_5$ pyridyl, $SO_2NHCNH$, $CO_2CH_3$ thiophene | 0.05 | | | 8H | 9H | 2C | 10E | 3G | 2C,6G | 2G | 8G | 8H | 0 | 9H | 3C,9H |
| $CH_3$/$CH(CH_3)_2$ pyridyl, $SO_2NHCNH$, $CO_2CH_3$ thiophene | 0.05 | | | 0 | 0 | 1C | 0 | 2G | 1C | 0 | 0 | 2G | 2G | 5G | 1C |

POST-EMERGENCE

| Structure | kg/ha | BUSH-BEAN | COTTON | MORNING-GLORY | COCKLE-BUR | CAS-SIA | NUT-SEDGE | CRAB-GRASS | BARN-YARD-GRASS | WILD OATS | WHEAT | CORN | SOY-BEAN | RICE | SOR-GHUM |
|---|---|---|---|---|---|---|---|---|---|---|---|---|---|---|---|
| $CH_3$/$CH_3$ pyridyl, $SO_2NHCNH$, $CNOCH_3$/$H$/$O$ thiophene | 0.05 | | | 2C | 1C | 1C,3G | 5G | 6G | 3C,9H | 0 | 0 | 1C | 1C,3G | 1C,7G | 5C,9H |

TABLE A-continued

| Structure | kg/ha | BUSH BEAN | COTTON | MORNING GLORY | COCKLE-BUR | CASSIA | NUT-SEDGE | CRAB-GRASS | BARN-YARD GRASS | WILD OATS | WHEAT | CORN | SOY-BEAN | RICE | SOR-GHUM |
|---|---|---|---|---|---|---|---|---|---|---|---|---|---|---|---|
| 191 | 0.05 | 0 | — | 0 | 0 | 0 | 0 | 0 | 0 | 0 | 0 | 0 | 0 | 0 | 0 |
| 192 | 0.05 | 2C,7G,6Y | 5C,8G | 4C,8G | 3G | 2C | 5G | 6G | 5C,9H | 4G | 3G | 3G | 2C,2H | 4C,9G | 3C,9H |

PRE-EMERGENCE

| Structure | kg/ha | BUSH BEAN | COTTON | MORNING GLORY | COCKLE-BUR | CASSIA | NUT-SEDGE | CRAB-GRASS | BARN-YARD GRASS | WILD OATS | WHEAT | CORN | SOY-BEAN | RICE | SOR-GHUM |
|---|---|---|---|---|---|---|---|---|---|---|---|---|---|---|---|
|  | 0.05 |  |  | 5G,3C | 7H | 2C | 8G | 1C,3G | 2C,4G | 1C | 3G | 1C,4G | 2G | 5C 9H | 4C,8G |

TABLE A-continued
| | kg/ha | BUSH-BEAN | COT-TON | MORNING-GLORY | COCKLE-BUR | CAS-SIA | NUT-SEDGE | CRAB-GRASS | BARN-YARD-GRASS | WILD OATS | WHEAT | CORN | SOY-BEAN | RICE | SOR-GHUM |
|---|---|---|---|---|---|---|---|---|---|---|---|---|---|---|---|
| 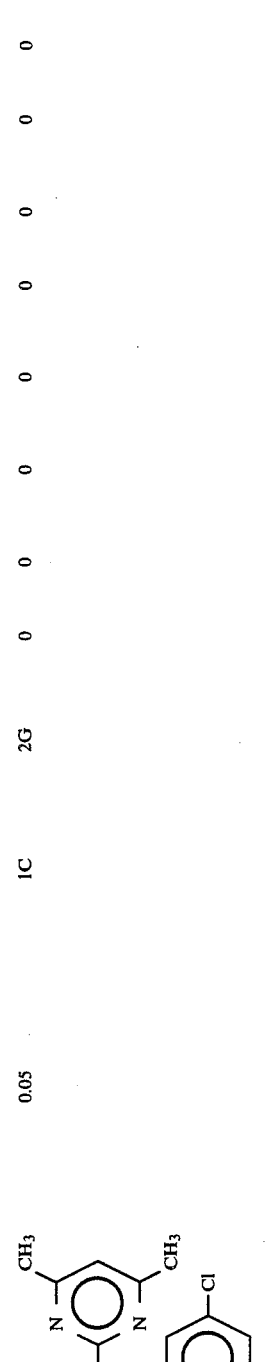 | 0.05 | 0 | — | 1C | 2G | 0 | 0 | 0 | 0 | 0 | 0 | 0 | 0 | 0 | 0 |
| 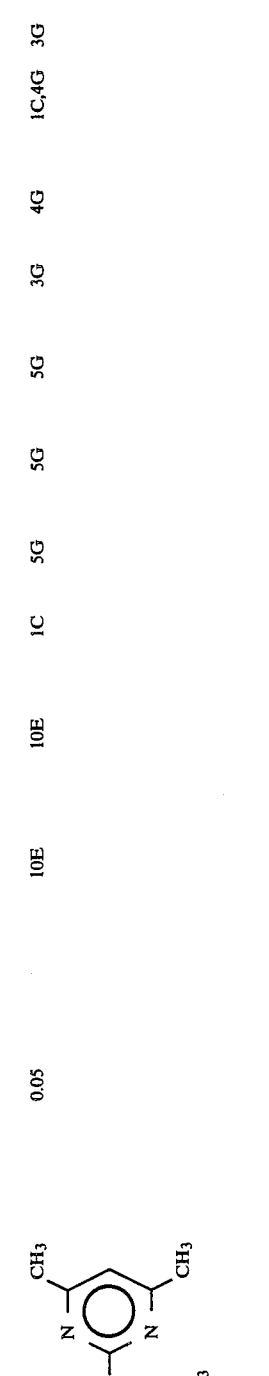 | 0.05 | | | 10E | 10E | 1C | 5G | 5G | 5G | 3G | 4G | 1C,4G | 3G | 3C,9H | 3C,9H |
| POST-EMERGENCE | | | | | | | | | | | | | | | |
| 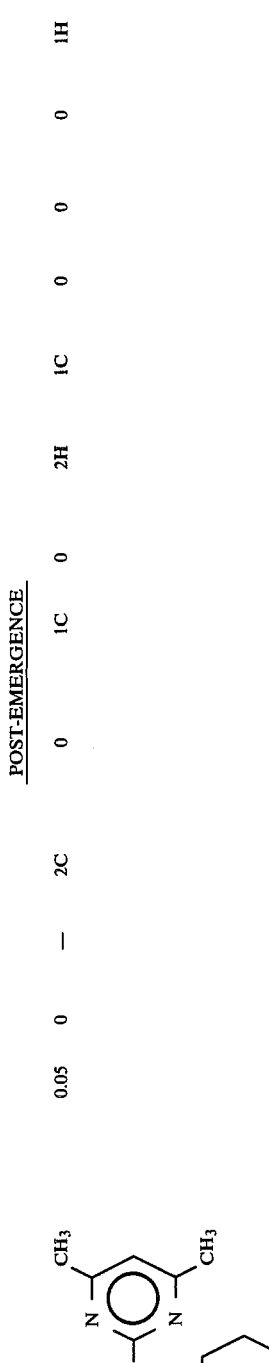 | 0.05 | 0 | | 2C | 0 | 1C | 0 | 2H | 1C | 0 | 0 | 0 | 1H | 0 | 1C |

TABLE A-continued

| Structure | kg/ha | BUSH-BEAN | COT-TON | MORNING-GLORY | COCKLE-BUR | CAS-SIA | NUT-SEDGE | CRAB-GRASS | BARN-YARD-GRASS | WILD OATS | WHEAT | CORN | SOY-BEAN | RICE | SOR-GHUM |
|---|---|---|---|---|---|---|---|---|---|---|---|---|---|---|---|
| Structure 1: pyrimidine-SO₂NHCNH-CO₂CH(CH₃)C≡CH, thiophene | 0.05 | 3C,7G, 6Y | — | 2C,7G | 2C,7H | 1C | 2C,7G | 3C,8H | 2C,9H | 0 | 9G | 2C,9H | 2C | 3C,9G | 1C,9G |
| Structure 2: pyrimidine-SO₂NHCNH-, cyclohexyl-S(=O), thiophene | 0.1 | 1C,6Y | 0 | 1C | 2G | 0 | 0 | 0 | 3H | 0 | 0 | 0 | 0 | 0 | 2C,7G |
| | | | | | PRE-EMERGENCE | | | | | | | | | | |
| Structure 3: pyrimidine-SO₂NHCNH-, piperidine-N(=O), thiophene | 0.05 | | | 0 | 2G | 0 | 0 | 0 | 2H | 2G | 2G | 1C,2G | 0 | 2G | 1C,5G |
| Structure 4: pyrimidine-SO₂NHCNH-CO₂CH(CH₃)C≡CH, thiophene | 0.05 | | | 8G | 9H | 0 | 4G | 1C | 3C,9H | 3G | 2C,7G | 9G | 0 | 10E | 1C,9G |

TABLE A-continued

| Structure | kg/ha | BUSH-BEAN | COT-TON | MORNING-GLORY | COCKLE-BUR | CAS-SIA | NUT-SEDGE | CRAB-GRASS | BARN-YARD-GRASS | WILD OATS | WHEAT | CORN | SOY-BEAN | RICE | SOR-GHUM |
|---|---|---|---|---|---|---|---|---|---|---|---|---|---|---|---|
| Structure with cyclohexyl-S-C(=O) and 4,6-dimethylpyrimidine | 0.1 | 0 | 0 | 0 | 0 | 0 | 0 | 0 | 0 | 0 | 0 | 0 | 0 | 0 | 0 |
| POST-EMERGENCE | | | | | | | | | | | | | | | |
| Structure with OCH₃/N(CH₃)₂ pyrimidine, CO₂CH₃ thiophene | 0.4 | 6C,9G, 6Y | 6C,9G | 10C | 10C | 2C,5G | 8G | 9C | 9C | 4C,9G | 4C,9G | 5U,9G | 2C,2H, 8G | 6C,9G | 5U,9G |
| Structure with OCH₃/CH₂OCH₃ pyrimidine, CO₂CH₃ thiophene | 0.05 | 2C,8G, 6Y | 3C,7G | 2C,7G | 2C,8G | 1C | 2G | 0 | 0 | 0 | 0 | 3H | 0 | 2C | 2C,9H |
| PRE-EMERGENCE | | | | | | | | | | | | | | | |
| Structure with 4,6-dimethylpyrimidine, CO₂CH₃ thiophene | 0.05 | 9C | 9C | 9C | 9C | 2C | 9C | 9C | 10C | 5C | 9C | 8U | 10C | 6C | 5C |

TABLE A-continued

| Structure | kg/ha | BUSH-BEAN | COTTON | MORNING-GLORY | COCKLE-BUR | CAS-SIA | NUT-SEDGE | CRAB-GRASS | BARN-YARD-GRASS | WILD OATS | WHEAT | CORN | SOY-BEAN | RICE | SOR-GHUM |
|---|---|---|---|---|---|---|---|---|---|---|---|---|---|---|---|
| Structure with OCH₃, N(CH₃)₂ on triazine | 0.4 | | | 9H | — | 7G | 2C,7G | 5C,9G | 6C,9H | 3C,9G | 2C,9G | 2C,9H | 1C,2H | 10E | 5C,9H |
| Structure with OCH₃, CH₂OCH₃ on pyrimidine | 0.05 | | | 0 | 8H | 0 | 0 | 0 | 0 | 0 | 0 | | 0 | 7H | 2C,8H |
| | | | | | | | | | | | | 2C,5G | | | |
| Structure with CH₃, CH₃ on pyrimidine | 0.05 | | | 9C | 9H | 9G | 10E | 5C,9G | 5C,9H | 2C,8G | 10E | 10E | 3C,9H | | 10E |
| POST-EMERGENCE | | | | | | | | | | | | | | | |
| Structure with OCH₃, CH₃ on pyrimidine | 0.05 | 9C | 6C,9G | 6C,9G | 9C | 3C,9G | 5C,8G | 5C,8G | 10C | 5C,9G | 9C | 7U,10C | 6C,9G | 5C,9G | 10C |

TABLE A-continued

| Structure | kg/ha | BUSH-BEAN | COT-TON | MORNING-GLORY | COCKLE-BUR | CAS-SIA | NUT-SEDGE | CRAB-GRASS | BARN-YARD-GRASS | WILD OATS | WHEAT | CORN | SOY-BEAN | RICE | SOR-GHUM |
|---|---|---|---|---|---|---|---|---|---|---|---|---|---|---|---|
| $CO_2CH_3$ / thiophene / $SO_2NHCNH$ / pyrimidine ($OCH_3$, $OCH_3$) | 0.05 | 9C | 5C,9G | 9C | 9C | 2C,3H | 2C,7G | 6G | 6C,9H | 0 | 0 | 7U,9H | 9C | 2C,7G | 2C,9G |
| $CO_2CH_3$ / thiophene-$C_2H_5$ / $SO_2NHCNH$ / pyrimidine ($CH_3$, $CH_3$) | 2.0 | 4S,7G, 6Y | — | 0 | 0 | 0 | 0 | 0 | 0 | 0 | 0 | 0 | 0 | 0 | 0 |
| | | | | | PRE-EMERGENCE | | | | | | | | | | |
| $CO_2CH_3$ / thiophene / $SO_2NHCNH$ / pyrimidine ($OCH_3$, $CH_3$) | 0.05 | 9C | 9C | 9H | 9G | 10E | 5C,9G | 2C,9H | 2C,9G | 10E | 10E | 9H | 10E | 10E |
| $CO_2CH_3$ / thiophene / $SO_2NHCNH$ / pyrimidine ($OCH_3$, $CH_3$) | 0.05 | 9C | | 9C | 9H | 3C,9G | 8G | 5G | 5C,9H | 2C,4G | 1C,6G | 2C,9H | 9H | 10E | 10E |
| $CO_2CH_3$ / thiophene-$C_2H_5$ / $SO_2NHCNH$ / pyrimidine ($CH_3$, $CH_3$) | 2.0 | | | 0 | 0 | 0 | 0 | 0 | 0 | 0 | 0 | 0 | 0 | 0 | 5C,9H |

TABLE A-continued

| | kg/ha | BUSH-BEAN | COT-TON | MORNING-GLORY | COCKLE-BUR | CAS-SIA | NUT-SEDGE | CRAB-GRASS | BARN-YARD-GRASS | WILD OATS | WHEAT | CORN | SOY-BEAN | RICE | SOR-GHUM |
|---|---|---|---|---|---|---|---|---|---|---|---|---|---|---|---|
| | | | | | POST-EMERGENCE | | | | | | | | | | |
| ![structure 1: CH3/OCH3 pyrimidine, CO2CH3, SO2NHCNH, C2H5, S] | 2.0 | 5S,9G,6Y | — | 1C | 0 | 0 | 0 | 2C | 2C,5H | 0 | 0 | 0 | 1C,4H | 3G | 2H |
| ![structure 2: OCH3/OCH3 pyrimidine] | 2.0 | 5S,8G,6Y | — | 2C,5G | 2C,8H | 2C | 0 | 3G | 1H | 0 | 0 | 2H | 2C,8G | 4G | 2G |
| | | | | | PRE-EMERGENCE | | | | | | | | | | |
| ![structure 3: CH3/OCH3 pyrimidine] | 2.0 | | | 5G | — | 1C | 0 | 3G | 0 | 0 | 0 | 0 | 0 | 0 | 0 |
| ![structure 4: OCH3/OCH3 pyrimidine] | 2.0 | | | 5G | 8H | 3H | 0 | 1C | 2C | 0 | 0 | 2G | 2C,5H | 2C,5H | 1C,3G |

TEST B

Two plastic bulb pans were filled with fertilized and limed Fallsington silt loam soil. One pan was planted with corn, sorghum, Kentucky bluegrass and several grassy weeds. The other pan was planted with cotton, soybeans, purple nutsedge (*Cyperus rotundus*), and several broadleaf weeds. The following grassy and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinum*), mustard (*Brassica arvensis*), cocklebur (*Xanthium pennsylvanicum*), pigweed (*Amaranthus retroflexus*), morningglory (*Ipomoea hederacea*), cassia (*Cassia tora*), teaweed (*Sida spinosa*), velvetleaf (*Abutilon theophrasti*), and jimsonweed (*Datura stramonium*). A 12.5 cm diameter plastic pot was also filled with prepared oil and planted with rice and wheat. Another 12.5 pot was planted with sugarbeets. The above four containers were treated preemergence with certain test compounds within the scope of the invention.

Twenty-eight days after treatment, the plants were evaluated and visually rated for response to the chemical treatments utilizing the rating system described previously for Test A. The data are summarized in Table B. Note that certain compounds are useful as pre-emergence treatments for weed control in crops such as soybeans and wheat.

TABLE B
PRE-EMERGENCE ON FALLSINGTON SILT LOAM

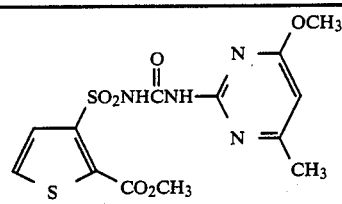

| Rate kg/ha | 0.03 | 0.12 |
|---|---|---|
| Crabgrass | 8G,7C | 10E |
| Barnyardgrass | 7G,3H | 8G,9C |
| Sorghum | 10E | 10E |
| Wild Oats | 2G | 5G |
| Johnsongrass | 7G,3H | 8G,5H |
| Dallisgrass | 3G | 4G |
| Giant foxtail | 8G,8C | 9G,9C |
| Ky. bluegrass | — | — |
| Cheatgrass | 8G | 7G |
| Sugarbeets | 8G,6C | 8G,7C |
| Corn | 5G,5H | 7G,5H |
| Mustard | 8G,8C | 9G,9C |
| Cocklebur | 6G,3H | 6G,3H |
| Pigweed | 10C | 10C |
| Nutsedge | 7G | 8G |
| Cotton | 8G | 8G |
| Morningglory | 7G | 8G |
| Cassia | 3G | 3G |
| Teaweed | 5G | 6G |
| Velvetleaf | 6G,3H | 7G,5C |
| Jimsonweed | 6G,6C | 6G,6C |
| Soybean | 0 | 4G |
| Rice | 10E | 10E |
| Wheat | 3G,3C | 4G,3C |

TABLE B-continued
PRE-EMERGENCE ON FALLSINGTON SILT LOAM

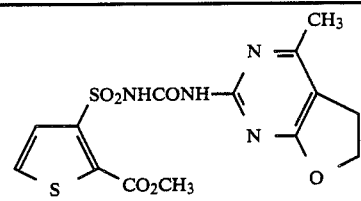

| Rate kg/ha | 0.03 | 0.12 |
|---|---|---|
| Crabgrass | 7G,5C | 10C |
| Barnyardgrass | 7G,6C | 8G,9C |
| Sorghum | 10E | 10E |
| Wild Oats | 5G | 7G |
| Johnsongrass | 6G,5H | 9G,8C |
| Dallisgrass | 7G | 8G |
| Giant foxtail | 6G,3C | 9G,3C |
| Ky. bluegrass | — | — |
| Cheatgrass | 8G | 10E |
| Sugarbeets | 8G,7C | 8G,7C |
| Corn | 5G,5H | 4G,3H |
| Mustard | 9G,9C | 9G,9C |
| Cocklebur | 7G,4C | 6G,5H |
| Pigweed | 9G,9C | 10C |
| Nutsedge | 7G | 9G |
| Cotton | 8G | 8G |
| Morningglory | 7G | 8G |
| Cassia | 3G | 4G |
| Teaweed | 4G | 5G,2C |
| Velvetleaf | 7G,7C | 10C |
| Jimsonweed | 5G | 5G,3C |
| Soybean | 0 | 6G,4C |
| Rice | 10E | 10E |
| Wheat | 7G,4C | 7G,4C |

| Rate kg/ha | 0.03 | 0.12 |
|---|---|---|
| Crabgrass | 3G | 4G |
| Barnyardgrass | 3G | 5G |
| Sorghum | 3G | 5G,3H |
| Wild Oats | 0 | 0 |
| Johnsongrass | 0 | 4G,3H |
| Dallisgrass | 3G | 4G |
| Giant foxtail | 0 | 3G |
| Ky. bluegrass | 0 | 5G |
| Cheatgrass | 3G | 5G |
| Sugarbeets | 0 | 3G |
| Corn | 2C | 2C,2U |
| Mustard | 5G | 7G |
| Cocklebur | 0 | 0 |
| Pigweed | 3G | 4G |
| Nutsedge | 0 | 0 |
| Cotton | 0 | 3G |
| Morningglory | 3G | 5G |
| Cassia | 0 | 0 |
| Teaweed | 0 | 0 |
| Velvetleaf | 0 | 0 |
| Jimsonweed | 0 | 0 |
| Soybean | 0 | 0 |
| Rice | 5G,3C | 7G,8C |
| Wheat | 0 | 3G |

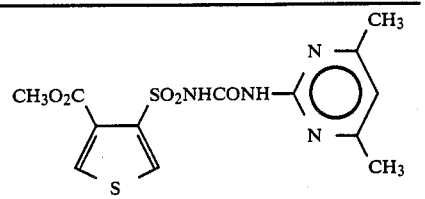

TABLE B-continued
PRE-EMERGENCE ON FALLSINGTON SILT LOAM

| Rate kg/ha | 0.03 | 0.12 | 0.007 |
|---|---|---|---|
| Crabgrass | 8G | 9G,8C | 6G |
| Barnyardgrass | 9G,7C | 9G,7C | 9G,9C |
| Sorghum | 10E | 10E | 8G,9C |
| Wild Oats | 6G,3H | 8G,8C | 6G,3H |
| Johnsongrass | 8G,3C | 9G,9C | 8G,5C |
| Dallisgrass | — | — | 5G |
| Giant foxtail | 6G,3H | 9G,8C | 3G |
| Ky. bluegrass | 7G,7C | 8G,9C | 7G |
| Cheatgrass | 10E | 10E | 10E |
| Sugarbeets | 9G,9C | 9G,9C | 7G,6C |
| Corn | 7G,5H | 9G,9C | 5G,2C |
| Mustard | 9G,9C | 9G,9C | 8G,8C |
| Cocklebur | 6G,3H | 7G,5H | 6G |
| Pigweed | 9G,8C | 10E | 10C |
| Nutsedge | 7G | 6G | 6G |
| Cotton | 7G | 8G,3C | 2G |
| Morningglory | 8G,3C | 9G,8C | 7G |
| Cassia | 7G | 7G | 5G |
| Teaweed | 6G | 7G | 2G |
| Velvetleaf | 8G,3C | 10C | 9G,5H |
| Jimsonweed | 7G | 8G,4C | 4G |
| Soybean | 4G | 7G,5H | 2G |
| Rice | 10E | 10E | 9G,9C |
| Wheat | 6G,3H | 8G,8C | 6G |

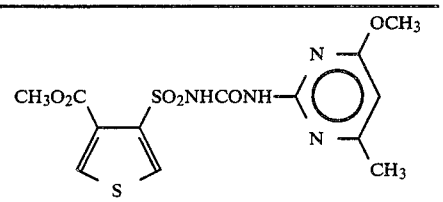

| Rate kg/ha | 0.03 | 0.12 | 0.007 |
|---|---|---|---|
| Crabgrass | 8G | 9G,8C | 7G |
| Barnyardgrass | 9G,8C | 9G,9C | 9C,8G |
| Sorghum | 10E | 10E | 9G,9C |
| Wild Oats | 7G,3H | 8G,6C | 4G |
| Johnsongrass | 8G,3C | 10C | 8G,3C |
| Dallisgrass | — | — | 5G |
| Giant foxtail | 9G,5H | 10C | 5G,2C |
| Ky. bluegrass | 9G,9C | 10C | 8G |
| Cheatgrass | 10E | 10E | 10E |
| Sugarbeets | 9G,9C | 9G,9C | 7G,8C |
| Corn | 7G,5H | 9G,9C | 7G,3H |
| Mustard | 9G,9C | 10C | 7G,8C |
| Cocklebur | 6G | 8G,5H | 4G |
| Pigweed | 10E | 10E | 9G,9C |
| Nutsedge | 5G | 7G | 5G |
| Cotton | 7G,3H | 9G,8C | 4G,2H |
| Morningglory | 8G,3C | 9G,6C | 7G,3C |
| Cassia | 7G | 7G | 4G |
| Teaweed | 7G | 7G,5C | 4G |
| Velvetleaf | 8G,6C | 10C | 8G,5H |
| Jimsonweed | 7G,5C | 9G,9C | 4G |
| Soybean | 7G,5H | 8G,5H | 3G |
| Rice | 10E | 10E | 9G,9C |
| Wheat | 6G | 8G,8C | 5G |

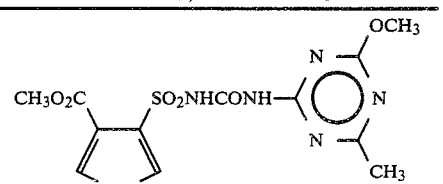

| Rate kg/ha | 0.03 | 0.12 | 0.007 |
|---|---|---|---|
| Crabgrass | 7G,3C | 9G,9C | 2G |
| Barnyardgrass | 6G,3C | 7G,3C | 4G |
| Sorghum | 8G,3C | 10C | 8G,3H |
| Wild Oats | 4G | 6G | 2G |
| Johnsongrass | 8G,4C | 8G,4C | 4G |
| Dallisgrass | 0 | 5G | 0 |
| Giant foxtail | 0 | 7G,3H | 0 |
| Ky. bluegrass | 8G,8C | 8G,8C | 0 |
| Cheatgrass | 5G | 7G,3H | 3G |
| Sugarbeets | 9G,9C | 10C | 10C |
| Corn | 9G,7C | 9G,9C | 7G,3H |
| Mustard | 10C | 10C | 10C |
| Cocklebur | 8G,5H | 9G,5H | 6G |
| Pigweed | 9G,9C | 10C | 9G,9C |
| Nutsedge | 6G | 6G | 3G |
| Cotton | 8G,5H | 8G,5H | 6G,3H |
| Morningglory | 8G,3H | 9G,5H | 9G,8C |
| Cassia | 9G,8C | — | 7G |
| Teaweed | 7G,3C | 7G,3C | 4G |
| Velvetleaf | 9G,9C | 10C | 8G |
| Jimsonweed | 6G,5H | 7G,7C | 5G |
| Soybean | 9G,5H | 9G,5H | 6G,3H |
| Rice | 10E | 10E | 6G |
| Wheat | 4G | 4G | 0 |

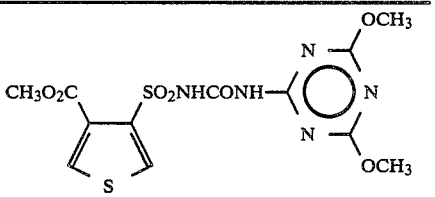

| Rate kg/ha | 0.03 | 0.12 | 0.007 |
|---|---|---|---|
| Crabgrass | 3G | 6G,3C | 0 |
| Barnyardgrass | 5G | 7G,4C | 4G |
| Sorghum | 8G,3H | 9G,9C | 7G,3H |
| Wild Oats | 2G | 4G | 0 |
| Johnsongrass | 5G,3H | 7G,3H | 5G |
| Dallisgrass | 0 | 6G | 2G |
| Giant foxtail | 0 | 3G | 0 |
| Ky. bluegrass | 6G | 8G,8C | 3G |
| Cheatgrass | 0 | 7G | 0 |
| Sugarbeets | 10C | 9G,9C | 9G,9C |
| Corn | 6G,3H | 6G,5H | 2G,1U |
| Mustard | 10C | 10C | 10E |
| Cocklebur | 6G | 7G,5H | 6G |
| Pigweed | 8G,8C | 10C | 7G,5E |
| Nutsedge | 2G | 7G | 6G |
| Cotton | 6G,5H | 9G,5H | 6G,3H |
| Morningglory | 8G,3H | 8G,3H | 9G,8C |
| Cassia | 6G | — | 4G |
| Teaweed | 6G,2C | 7G,3C | 3G |
| Velvetleaf | 8G,5H | 8G,8C | 6G |
| Jimsonweed | 5G | 6G,3C | 5G |
| Soybean | 5G | 9G,5H | 4G,3H |
| Rice | 7G | 10E | 5G |
| Wheat | 2G | 2G | 0 |

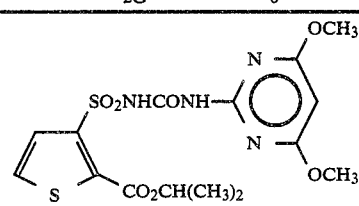

| Rate kg/ha | 0.03 | 0.12 |
|---|---|---|
| Crabgrass | 0 | 0 |
| Barnyardgrass | 3G | 3G |
| Sorghum | 0 | 6G,3H |
| Wild Oats | 0 | 0 |
| Johnsongrass | 0 | 5G,3H |
| Dallisgrass | 0 | 3G |
| Giant foxtail | 0 | 2H |
| Ky. bluegrass | 4G | 6G |
| Cheatgrass | 0 | 10E |
| Sugarbeets | 3G | 3G |
| Corn | 0 | 0 |
| Mustard | 8G,5C | 10C |
| Cocklebur | 0 | 0 |
| Pigweed | 4G | 8G,8C |
| Nutsedge | 0 | 7G |

TABLE B-continued
PRE-EMERGENCE ON FALLSINGTON SILT LOAM

| | | |
|---|---|---|
| Cotton | 0 | 3G |
| Morningglory | 3G | 4G |
| Cassia | 0 | 0 |
| Teaweed | 0 | 3G |
| Velvetleaf | 5G,3H | 6G,3H |
| Jimsonweed | 3G | 5G |
| Soybean | 0 | 2G |
| Rice | 4G | 5G,3H |
| Wheat | 0 | 0 |

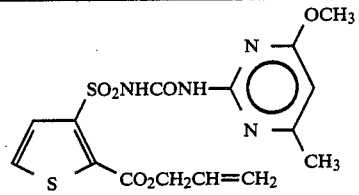

| Rate kg/ha | 0.03 | 0.12 |
|---|---|---|
| Crabgrass | 0 | 0 |
| Barnyardgrass | 6G | 6G,5H |
| Sorghum | 7G,3H | 10C |
| Wild Oats | 3G | 3G |
| Johnsongrass | 6G,3H | 8G,5E |
| Dallisgrass | 0 | 4G |
| Giant foxtail | 0 | 3G |
| Ky. bluegrass | 7G,4C | 7G,4C |
| Cheatgrass | 7G,5C | 9G,9C |
| Sugarbeets | 6G,3H | 10C |
| Corn | 4G,2U | 6G,5H |
| Mustard | 10C | 10C |
| Cocklebur | 2G | 3G |
| Pigweed | 8G,8C | 10C |
| Nutsedge | 7G | 7G |
| Cotton | 5G | 5G,2H |
| Morningglory | 5G | 4G |
| Cassia | 5G | 5G |
| Teaweed | 2G | 4G |
| Velvetleaf | 8G,5H | 9G,5H |
| Jimsonweed | 8G | 8G |
| Soybean | 4G | 4G |
| Rice | 7G | 8G |
| Wheat | 4G | 6G |

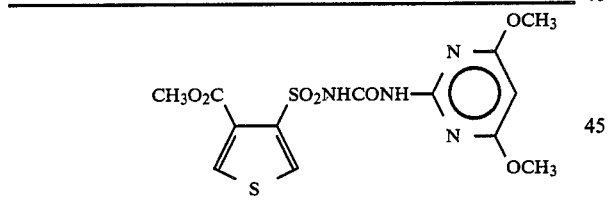

| Rate kg/ha | 0.03 | 0.12 |
|---|---|---|
| Crabgrass | 8G,5C | 9G,7C |
| Barnyardgrass | 9G,7C | 9G,7C |
| Sorghum | 10E | 10E |
| Wild Oats | 7G,3C | 8G,5E |
| Johnsongrass | 9G,7C | 9G,9C |
| Dallisgrass | 7G | 8G |
| Giant foxtail | 7G,3H | 9G,5H |
| Ky. bluegrass | 10C | 9G,9C |
| Cheatgrass | 10C | 10E |
| Sugarbeets | 9G,9C | 9G,9C |
| Corn | 7G,5H | 8G,3C |
| Mustard | 10C | 10E |
| Cocklebur | 6G | 7G |
| Pigweed | 10E | 10E |
| Nutsedge | 8G | 10E |
| Cotton | 3G | 7G,5H |
| Morningglory | 6G | 8G,3H |
| Cassia | 5G | 7G |
| Teaweed | 6G | 8G,4C |
| Velvetleaf | 8G,7C | 10C |
| Jimsonweed | 6G | 7G,7C |
| Soybean | 3G | 6G,3H |
| Rice | 10E | 10E |

TABLE B-continued
PRE-EMERGENCE ON FALLSINGTON SILT LOAM

| | | |
|---|---|---|
| Wheat | 7G,3C | 7G,5C |

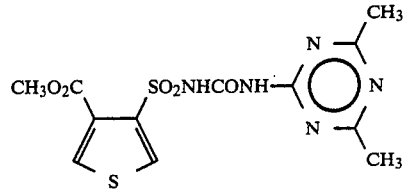

| Rate kg/ha | 0.03 | 0.12 | 0.007 |
|---|---|---|---|
| Crabgrass | 7G,3H | 8G,5C | 0 |
| Barnyardgrass | 6G,3H | 8G,4C | 0 |
| Sorghum | 9G,9C | 10E | 5G,3H |
| Wild Oats | 2G | 7G,3H | 0 |
| Johnsongrass | 8G,5H | 8G,5C | 0 |
| Dallisgrass | 6G | 0 | 0 |
| Giant foxtail | 5G,2H | 7G,5H | 0 |
| Ky. bluegrass | 7G,7C | 7G,5C | 0 |
| Cheatgrass | 7G,3C | 10C | 0 |
| Sugarbeets | 9G,9C | 9G,9C | 5G,3H |
| Corn | 10C | 10E | 3G |
| Mustard | 10C | 10C | 7G,3C |
| Cocklebur | 7G,5H | 8G,5H | 2G |
| Pigweed | 10C | 10C | 5G |
| Nutsedge | 6G | 7G | 0 |
| Cotton | 7G | 8G,5H | 0 |
| Morningglory | 8G,3H | 8G,3H | 6G,5H |
| Cassia | 6G | — | 0 |
| Teaweed | 6G | 7G,4C | 0 |
| Velvetleaf | 8G,5C | 8G,8C | 3G |
| Jimsonweed | 6G,4C | 6G,5C | 0 |
| Soybean | 2H | 7G,5H | 0 |
| Rice | 10E | 10E | 7G,3H |
| Wheat | 5G | 6G | 0 |

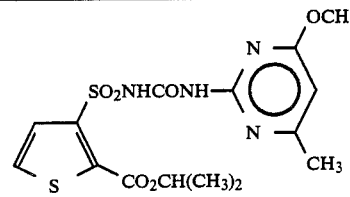

| Rate kg/ha | 0.03 | 0.12 |
|---|---|---|
| Crabgrass | 0 | 5G |
| Barnyardgrass | 5G,3H | 4G,2H |
| Sorghum | 8G,5H | 10C |
| Wild Oats | 0 | 3C |
| Johnsongrass | 7G,3H | 8G,5H |
| Dallisgrass | 0 | 4G |
| Giant foxtail | 0 | 4H |
| Ky. bluegrass | 7G | 8G,8C |
| Cheatgrass | 10E | 10E |
| Sugarbeets | 6G,3H | 10C |
| Corn | 5G,3H | 6G,5H |
| Mustard | 8G,5C | 10C |
| Cocklebur | 0 | 5G |
| Pigweed | 5G | 10E |
| Nutsedge | 0 | 5G |
| Cotton | 3G | 6G,3H |
| Morningglory | 4G | 5G |
| Cassia | 3G | 3G |
| Teaweed | 3G | 4G,2C |
| Velvetleaf | 3H | 6G,3H |
| Jimsonweed | 3G | 7G,3C |
| Soybean | 0 | 4G,3H |
| Rice | 6G | 7G,5H |
| Wheat | 3G | 3G |

TABLE B-continued
PRE-EMERGENCE ON FALLSINGTON SILT LOAM

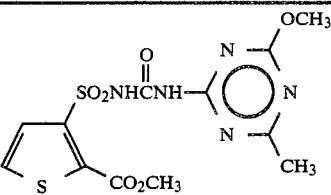

| Rate kg/ha | 0.12 | 0.5 |
|---|---|---|
| Crabgrass | 0 | 0 |
| Barnyardgrass | 0 | 0 |
| Sorghum | 0 | 7G,5H |
| Wild Oats | 0 | 4G |
| Johnsongrass | 0 | 5G |
| Dallisgrass | 0 | 3G |
| Giant foxtail | 0 | 2G |
| Ky. bluegrass | — | — |
| Cheatgrass | 0 | 5G |
| Sugarbeets | 2G | 6G |
| Corn | 0 | 4G |
| Mustard | 8G,5C | 10C |
| Cocklebur | 6G,3C | 6G,2C |
| Pigweed | 4G,4C | 7G,7C |
| Nutsedge | 0 | 5G |
| Cotton | 3G | 7G |
| Morningglory | 0 | 6G |
| Cassia | 0 | 3G |
| Teaweed | 0 | 0 |
| Velvetleaf | 4G,3C | 5G |
| Jimsonweed | 0 | 0 |
| Soybean | 0 | 4G,2H |
| Rice | 0 | 2G |
| Wheat | 0 | 3G |

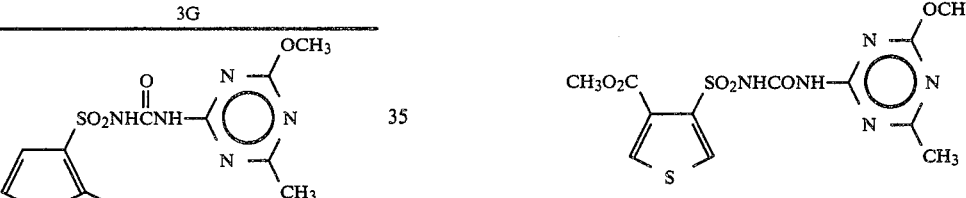

| Rate kg/ha | 0.06 | 0.12 | 0.5 |
|---|---|---|---|
| Crabgrass | 6G,7C | 4G | 7G |
| Barnyardgrass | 4G | 6G | 8G,4C |
| Sorghum | 9G,5C | 9G,8C | 10C |
| Wild Oats | 0 | 0 | 0 |
| Johnsongrass | 4G,3H | 4G | 7G,3H |
| Dallisgrass | 0 | 0 | 3G |
| Giant foxtail | 3G | 3G | 6G,3C |
| Ky. bluegrass | 3G | 3G | 5G |
| Cheatgrass | 3G | — | — |
| Sugarbeets | 9G,9C | 10C | 10C |
| Corn | 5G | 6G,3H | 9G,5H |
| Mustard | 10C | 8G | 10C |
| Cocklebur | 6G,3H | 7G,3H | 8G,5H |
| Pigweed | 8G,8C | 10C | 10E |
| Nutsedge | 3G | 7G | 8G |
| Cotton | 8G,3H | 9G,5C | 9G,5C |
| Morningglory | 8G,3H | 8G,3H | 9G,9C |
| Cassia | 6G | 5G | 7G |
| Teaweed | 5G,3H | 4G | 8G,5C |
| Velvetleaf | 8G,7C | 10C | 10C |
| Jimsonweed | 9G,9C | 7G | 10C |
| Soybean | 0 | 3G | 5G,3H |
| Rice | 10E | 8G,6C | 10E |
| Wheat | 0 | 0 | 0 |

Wheat and Barley Herbicide Screen

Two ten-inch in diameter plastic pans lined with polyethylene liners were filled with prepared Fallsington silt loam soil. One pan was planted with seeds of wheat (*Triticum aestivum*), barley (*Hordeum vulgare*), wild oats (*Avena fatua*), downy brome (*Bromus tectorum*), cheatgrass (*Bromus secalinus*), blackgrass (*Alopecurus myosuroides*), annual bluegrass (*Poa annua*), green foxtail (*Setaria viridis*), quackgrass (*Agropyron repens*), Italian ryegrass (*Lolium multiflorum*) and ripgut brome (*Bromus rigidus*). The other pan was planted with seeds of Russian thistle (*Salsola kali*), tansy mustard (*Descuraina pinnata*), smartweed (*Polygonum pennsylvanicum*), tumble mustard (*Sisymbrium altissium*), kochia (*Kochia scoparia*), shepherd's purse (*Capsella bursa-pastoris*), Matricaria indora, black nightshade (*Solanum nigrum*), yellow rocket (*Barbarea vulgaris*), wild mustard (*Brassica kaber*) and wild buckwheat (*Polygonum convolvulus*). The above two pans were treated preemergence. At the same time two pans in which the above plant species were growing were treated postemergence. Plant height at the time of treatment ranged from 1–15 cm depending on plant species.

The compounds applied were diluted with a non-pytotoxic solvent and sprayed over-the-top of the pans. An untreated control and a solvent alone control were included for comparison. All treatments were maintained in the greenhouse for 20 days at which time the treatments were compared to the controls and the effects visually rated. The recorded data are presented in Table C. It will be seen that the compounds have utility for selective weed control in cereal crops.

TABLE C

| | Post-emergence | Pre-emergence | Post-emergence | Pre-emergence |
|---|---|---|---|---|
| Rate kg/ha | 0.008 | 0.008 | 0.03 | 0.03 |
| wheat | 1C,1G | 0 | 6C,5G | 0 |
| barley | 1G | 1G | 2C,3G | 2G |
| wild oats | 1C,1G | 0 | 7C,5G | 0 |
| downy brome | 2G | 2G | 7C,7G | 5C,7G |
| cheatgrass | 1C,4G | 7G | 10C | 10C |
| blackgrass | 3C,3G | 5G | 9C,8G | 7C,7G |
| annual bluegrass | 8C,8G | 3C,6G | 10C | 7C,8G |
| green foxtail | 1C,3G | 1C,2G | 10C | 5C,6G |
| quackgrass | 2C,3G | 3G | 10C | 2C,5G |
| Italian ryegrass | 6C,7G | 1C,5G | 10C | 5C,7G |
| ripgut brome | 1C,2G | 0 | 3C,4G | 1C,3G |
| Russian thistle | 10C | 3G | 10C | 7C,6G |
| tansy mustard | 10C | 10C | 10C | 10C |
| smartweed | — | — | — | — |
| jimhill mustard | 10C | 10C | 10C | 10C |
| Kochia | 10C | 10C | 10C | 10C |
| shepherd's purse | 10C | 10C | 10C | 10C |
| false chamomile | 10C | 6C,7G | 10C | 10C |
| black nightshade | 10C | 7G | 10C | 7C,8G |
| yellow rocket | 10C | 10C | 10C | 10C |
| wild mustard | 10C | 10C | 10C | 10C |
| wild buckwheat | 10C | 7C,6G | 10C | 7C,7G |

TABLE C-continued

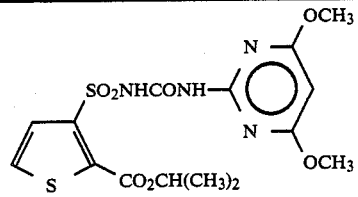

|  | Post-emergence | Pre-emergence | Post-emergence | Pre-emergence |
|---|---|---|---|---|
| Rate kg/ha | 0.015 | 0.015 | 0.06 | 0.06 |
| wheat | 0 | 0 | 2G | 0 |
| barley | 0 | 0 | 0 | 0 |
| wild oats | 0 | 2C,2G | 0 | 3C,4G |
| downy brome | 0 | 1C,3G | 0 | 4C,6G |
| cheatgrass | 0 | 1C,4G | 7C,5G | 10C |
| blackgrass | 0 | 3G | 7C,7G | 10C |
| annual bluegrass | 0 | 2G | 2G | 3C,5G |
| green foxtail | 0 | 0 | 1C,3G | 2C,4G |
| quackgrass | 0 | 0 | 0 | 2C,3G |
| Italian ryegrass | 0 | 0 | 0 | 0 |
| ripgut brome | 0 | 0 | 0 | 0 |
| Russian thistle | 10C | 0 | 10C | 7C,8G |
| tansy mustard | 10C | 10C | 10C | 10C |
| smartweed | — | — | — | — |
| jimhill mustard | 10C | 10C | 10C | 10C |
| Kochia | 10C | 2C,5G | 10C | 7C,7G |
| shepherd's purse | 10C | 10C | 10C | 10C |
| false chamomile | 10C | 4C,6G | 10C | 7C,9G |
| black nightshade | 0 | 2C,6G | 0 | 2C,7G |
| yellow rocket | 10C | 3C,8G | 10C | 9C,9G |
| wild mustard | 10C | 9C,9G | 10C | 10C |
| wild buckwheat | 3C,2G | 4G | 7C,6G | 2C,7G |

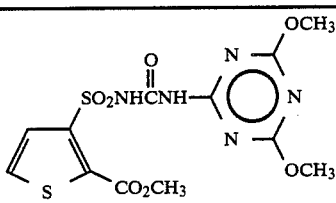

|  | Post-emergence | Pre-emergence | Post-emergence | Pre-emergence |
|---|---|---|---|---|
| Rate kg/ha | 0.015 | 0.015 | 0.06 | 0.06 |
| wheat | 0 | 0 | 0 | 0 |
| barley | 0 | 0 | 0 | 0 |
| wild oats | 0 | 0 | 0 | 0 |
| downy brome | 0 | 2G | 2C,3G | 2C,3G |
| cheatgrass | 0 | 1G | 2C,5G | 1C,5G |
| blackgrass | 0 | 3G | 1C,3G | 2C,7G |
| annual bluegrass | 0 | 2G | 1C,4G | 5G |
| green foxtail | 0 | 0 | 2G | 2C,3G |
| quackgrass | 0 | 0 | 0 | 1C,2G |
| Italian ryegrass | 0 | 0 | 3G | 3G |
| ripgut brome | 0 | 0 | 0 | 0 |
| Russian thistle | 10C | 2C,2G | 10C | 7C,8G |
| tansy mustard | 10C | 10C | 10C | 10C |
| smartweed | — | — | — | — |
| jimhill mustard | 10C | 10C | 10C | 10C |
| Kochia | 2C,4G | 3C,5G | 7C,7G | 7C,7G |
| shepherd's purse | 10C | 10C | 10C | 10C |
| false chamomile | 10C | 7C,8G | 10C | 9C,9G |
| black nightshade | 1C,3G | 1C,8G | 3C,6G | 2C,8G |
| yellow rocket | 2C,3G | 5C,6G | 10C | 6C,8G |
| wild mustard | 10C | 9C,9G | 10C | 9C,9G |
| wild buckwheat | 9C,8G | 4C,7G | 10C | 7C,7G |

TABLE C-continued

|  | Post-emergence | Pre-emergence | Post-emergence | Pre-emergence |
|---|---|---|---|---|
| Rate kg/ha | 0.008 | 0.008 | 0.03 | 0.03 |
| wheat | 0 | 0 | 0 | 0 |
| barley | 0 | 0 | 0 | 0 |
| wild oats | 0 | 0 | 0 | 0 |
| downy brome | 0 | 1C,2G | 1G | 2C,5G |
| cheatgrass | 0 | 3G | 2G | 2C,5G |
| blackgrass | 1G | 1C,3G | 1C,3G | 3C,7G |
| annual bluegrass | 1G | 5C,6G | 3G | 5C,7G |
| green foxtail | 2G | 0 | 2C,3G | 3G |
| quackgrass | 0 | 2G | 1G | 2C,7G |
| Italian ryegrass | 0 | 4G | 2G | 1G |
| ripgut brome | 0 | 0 | 0 |  |
| Russian thistle | 10C | 4C,5G | 10C | 10C |
| tansy mustard | 10C | 10C | 10C | 10C |
| smartweed | — | — | — | — |
| jimhill mustard | 10C | 10C | 10C | 10C |
| Kochia | 8C,8G | 7C,8G | 10C | 8C,9G |
| shepherd's purse | 9C,8G | 10C | 10C | 10C |
| false chamomile | 10C | 7C,8G | 10C | 9C,9G |
| black nightshade | 1G | 2C,5G | 2C,3G | 3C,8G |
| yellow rocket | 10C | 10C | 10C | 10C |
| wild mustard | 10C | 10C | 10C | 10C |
| wild buckwheat | 8C,7G | 4C,7G | 10C | 8C,8G |

What is claimed is:

1. A compound selected from

 I

 II or

 III wherein
W' is O or S;
A' is H, Cl, Br, $C_1$-$C_4$ alkyl, $OCH_3$, $NO_2$ or $CF_3$;

A is —C(O)QR$^I$ or —C(T)R$^{II}$ where Q is O, S or —N(R$_6$)—;

T is O or =N—OR$^{III}$ where R$^{III}$ is H, C$_1$-C$_4$ alkyl or C$_3$-C$_4$ alkenyl; when Q is O or S, then R$^1$ is C$_1$-C$_6$ alkyl, C$_3$-C$_6$ alkenyl, C$_3$-C$_6$ alkynyl, C$_2$-C$_6$ alkyl substituted with 1-3 Cl, F, or Br or one of CN or OCH$_3$, C$_3$-C$_6$ alkenyl substituted with 1∝3 Cl, C$_3$-C$_6$ alkynyl substituted with Cl, C$_5$-C$_6$ cycloalkyl, cyclohexenyl, cyclohexyl substituted with 1-3 CH$_3$, C$_4$-C$_7$ cycloalkylalkyl or

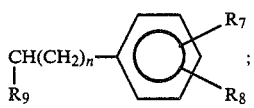

where R$_7$ and R$_8$ are independently H, Cl, CH$_3$ or OCH$_3$;

n is 0 or 1; and

R$_9$ is H or CH$_3$;

when Q is O, then R$^I$ is CH$_2$CH$_2$OR$_{15}$, CH$_2$CH$_2$CH$_2$OR$_{15}$, CH—CH$_2$OR$_{15}$, where R$_{15}$ is C$_2$H$_5$, CH(CH$_3$)$_2$, phenyl, CH$_2$CH$_2$Cl, CH$_2$CCl$_3$, (CH$_2$CH$_2$O)$_n$R$_{16}$,

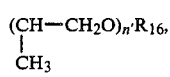

where R$_{16}$ is CH$_3$, C$_2$H$_5$, CH(CH$_3$)$_2$, phenyl, CH$_2$CH$_2$Cl, CH$_2$CCl$_3$, and n' is 2 or 3, CH$_2$CN,

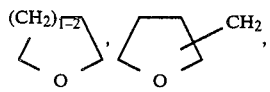

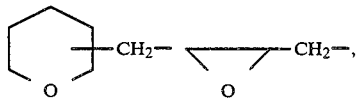

CH$_2$OR$_6'$, where R$_6'$ is C$_1$-C$_4$ alkyl provided R$^I$ has a total of ≦13 carbon atoms when Q is

then R$^I$ is H, C$_1$-C$_6$ alkyl, —CH$_2$CH$_2$OR$_{10}$, —CH$_2$CH$_2$CH$_2$OR$_{10}$, where R$_{10}$ is CH$_3$, CH$_3$CH$_2$, CH(CH$_3$)$_2$ or phenyl, C$_3$-C$_6$ alkenyl, C$_3$-C$_6$ cycloalkyl, C$_5$-C$_6$ cycloalkenyl, C$_6$ cycloalkyl substituted with any one of 1-2 OCH$_3$, 1-3 CH$_3$, —CH$_2$CH$_3$ or CF$_3$, C$_4$-C$_7$ cycloalkylalkyl, —CH$_2$CN, —CH$_2$CH$_2$CN,

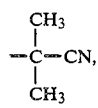

OCH$_3$, OCH$_2$CH$_3$,

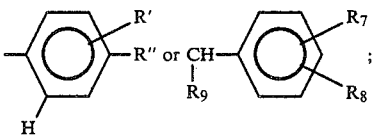

where

R' is H, C$_1$-C$_4$ alkyl, OCH$_3$, F, Cl, Br, CN, NO$_2$ or CF$_3$;

R" is H, CH$_3$, Cl, F or Br;

R$_7$, R$_8$ and R$_9$ are as previously defined;

R$_6$ is H, C$_1$-C$_3$ alkyl, CH$_2$CN, CH$_2$CH$_2$—CN or —CH$_2$—CH=CH$_2$ and R$_6$ and R$^I$ may be taken together to form —(CH$_2$)$_4$—, —(CH$_2$)$_5$— or —CH$_2$CH$_2$O—CH$_2$CH$_2$—;

with the proviso that when R$_6$ is CH$_2$CH$_2$CN or CH$_2$CN, then R$^I$ is CH$_2$CH$_2$CN or CH$_2$CN, and then R$^I$ and R$_6$ have a total carbon atom count of ≦13, and when R$^I$ is OCH$_3$ or OCH$_2$CH$_3$, then R$_6$ is H, or CH$_3$;

when A is

then R$^{II}$ is H, C$_1$-C$_6$ alkyl, C$_3$-C$_6$ alkenyl, phenyl, benzyl, benzyl or phenyl substituted with 1-2 Cl, 1-2 OCH$_3$, 1-2 CH$_3$, C$_5$-C$_6$ cycloalkyl, C$_4$-C$_7$ cycloalkylalkyl with the proviso that when T is =N—OR$^{III}$, then R$^{II}$ must be C$_1$-C$_6$ alkyl or C$_3$-C$_6$ alkenyl;

B is

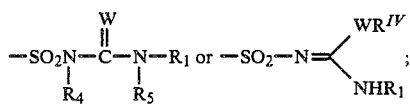

where

R$_4$ is H or CH$_3$;

W is O or S;

R$_5$ is H, or CH$_3$, with the proviso that either R$_4$ or R$_5$ must be H;

R$^{IV}$ is C$_1$-C$_6$ alkyl or C$_3$-C$_4$ alkenyl;

R$_1$ is

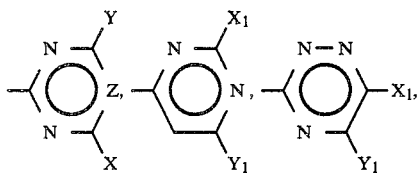

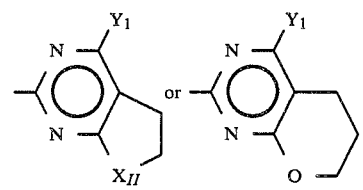

where

Z is CH or C—F;

X is H, Cl, —CH$_3$, —OCH$_3$ or —OCH$_2$CH$_3$;

Y is H, Cl, $C_1-C_4$ alkyl, $C_1-C_4$ alkyl substituted with —OCH₃, —OC₂H₅, —CN, —CO₂CH₃, —CO₂C₂H₅,

or 1-3 atoms of F, Cl, Br, $C_3-C_4$ alkenyl, —O—$(CH_2)_{n'}$O—$(C_1-C_3$ alkyl) where n' is 2 or 3,

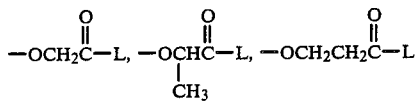

where L is OH, —NH₂,

—NH($C_1-C_4$ alkyl), —N($C_1-C_4$ alkyl)₂ or $C_1-C_6$ alkoxy, SCN, —N₃, $NR_{11}R_{12}$ where $R_{11}$ is H or CH₃ and $R_{12}$ is H, OCH₃, $C_1-C_4$ alkyl, $C_3-C_6$ cycloalkyl, —$C_3-C_4$ alkenyl, $C_2-C_3$ alkyl substituted with OCH₃ or OC₂H₅; $C_1-C_2$ alkyl substituted with —CN, CO₂H, CO₂CH₃ or CO₂C₂H₅, and $R_{11}$ and $R_{12}$ can be taken together to form —CH₂CH₂CH₂CH₂— or CH₂CH₂OCH₂CH₂—, —O—R₉ where R₉ is $C_1-C_4$ alkyl, $C_2-C_4$ alkyl substituted with 1-3 atoms of F, Cl or Br, $C_1-C_2$ alkyl substituted with cyano, $C_3-C_4$ alkenyl, —CH₂C≡CR₁₃,

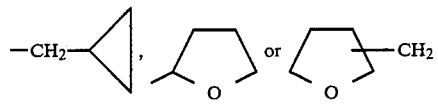

$R_{13}$ is H, CH₃ or CH₂Cl; $SR_{14}$;
where $R_{14}$ is $C_1-C_4$ alkyl, allyl, propargyl or $C_1-C_2$ alkyl substituted with CN; with the proviso that when X and Y are both H, then $R^I$ and $R^{II}$ are less than 5 carbons;
$X_I$ is H, Cl, OCH₃, OCH₂CH₃ or CH₃;
$Y_I$ is H, OCH₃ or CH₃; and
$X_{II}$ is O or CH₂
and further provided that when A contains greater than 5 carbon atoms, then Y must contain ≦4 carbon atoms; and their agriculturally suitable salts.

2. A compound of claim 1 in which B is

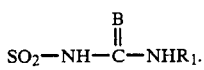

3. A compound of claim 2 in which W' is sulfur.
4. A compound of claim 3 in which T is oxygen.
5. A compound of claim 4 in which R₁ is

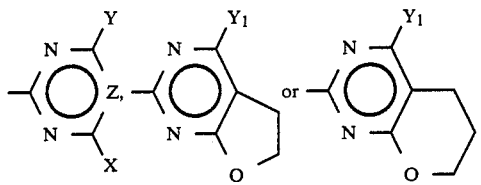

6. A compound of claim 5 where Q is O or S and $R^I$ is $C_1-C_4$ alkyl; $C_3-C_4$ alkenyl; $C_3-C_4$ alkynyl; $C_2-C_3$ alkyl substituted with CN, OCH₃ or 1-3F, Cl or Br; $C_3-C_4$ alkenyl substituted with Cl.

7. A compound of claim 5 in which Q is oxygen and $R^I$ is CH₂CH₂OR₁₅; CH₂CH₂CH₂OR₁₅;

where $R_{15}$ is CH₂CH₃; CH₂CN; CH₂OR₆' where $R_6'$ is CH₃ or CH₃CH₂; and

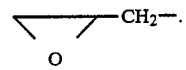

8. A compound of claim 5 in which Q is

and $R^I$ is H, $C_1-C_4$ alkyl, CH₂CH₂OR₁₀, CH₂CH₂CH₂OR₁₀ where $R_{10}$ is CH₃ or CH₃CH₂; $C_3-C_4$ alkenyl; CH₂CN; CH₂CH₂CN; OCH₃ or OCH₂CH₃; $R^6$ is H, $C_1-C_2$ alkyl, CH₂CN or CH₂CH₂CN and $R_6$ and $R^I$ can be taken together to form —CH₂—4.

9. A compound of claim 5 in which $R^{II}$ is H or $C_1-C_3$ alkyl.

10. A compound of claim 6 in which X is CH₃ or CH₃O; and Y is $C_1-C_2$ alkyl; $C_1-C_2$ alkyl substituted with OCH₃; OCH₂CH₃, CN or 1-3 atoms or F, Cl or Br;

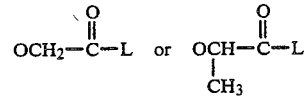

where L is NH₂, OH,

N(CH₃)₂, NHCH₃, $C_1-C_2$ alkoxy; SCN; N₃; $NR_{11}R_{12}$ where $R_{11}$ is H or CH₃; $R_{12}$ is H, CH₃, CH₃CH₂, OCH₃; OR₉ where R₉ is CH₃, CH₃CH₂; CH₂CH=CH₂; CH₂≡CH; or C₂ alkyl substituted with 1-3 F, Cl or Br; CH₃S.

11. A compound of claim 5 in which A' is H, Cl or Br.
12. A compound of claim 11 in which Q is O or S and $R^I$ is $C_1-C_4$ alkyl, CH₂CH=CH₂ or CH₂CH₂Cl.
13. A compound of claim 11 in which Q is O and $R^I$ is CH₂CH₂OCH₃,

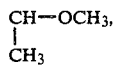
CH$_2$OCH$_3$ or CH$_2$OCH$_2$CH$_3$.

14. A compound of claim 11 in which Q is

and R$^I$ dis H; C$_1$-C$_3$ alkyl, OCH$_3$ or OCH$_2$CH$_3$ and R$_6$ is H or C$_1$-C$_2$ alkyl.

15. A compound of claim 11 in which R$^{II}$ is H or CH$_3$.

16. A compound of claim 2 in which A' is H; Y is CH$_3$, OCH$_3$, OCH$_2$CH$_3$, OCH$_2$CF$_3$, OCH$_2$CF$_3$, OCH$_2$CH—CH$_2$ or OCH$_2$C≡C.

17. A compound of claim 10 in which A is

and Q is oxygen or sulfur and R$^I$ is CH$_3$ or CH$_2$CH$_3$; Q is

and R$^I$ is H, CH$_3$ or OCH$_3$ and R$_6$ is CH$_3$; R$_1$ is

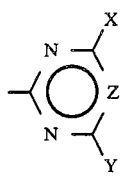

and Y is CH$_3$ or OCH$_3$.

18. A compound of claim 17 in which Formula I is utilized.

19. A compound of claim 17 in which Formula II is utilized.

20. A compound of claim 17 in which Formula III is utilized.

21. A compound of claim 2 in which W' is oxygen.

22. A compound of claim 21 in which T is oxygen.

23. A compound of claim 22 in which R$_1$ is

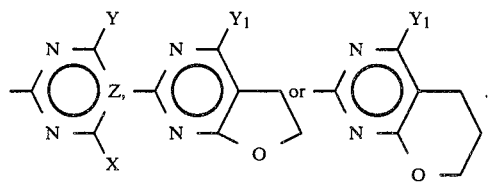

24. A compound of claim 22 where Q is O or S and R$_1$ is C$_1$-C$_4$ alkyl; C$_3$-C$_4$ alkenyl; C$_3$-C$_4$ alkynyl; C$_2$-C$_3$ alkyl substituted with CN, OCH$_3$ or 1-3 F, Cl or Br; C$_3$-C$_4$ alkenyl substituted with 1-3 Cl; C$_3$-C$_4$ alkynyl substituted with Cl.

25. A compound of claim 22 in which Q is oxygen and R$^I$ is CH$_2$CH$_2$OR$_{15}$; CH$_2$CH$_2$CH$_2$OR$_{15}$;

where R$_{15}$ is CH$_2$CH$_3$; CH$_2$CN; CH$_2$OR$_6$' wherein R$_6$' is CH$_3$, CH$_3$CH$_2$ or

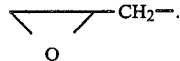

26. A compound of claim 22 in which Q is

and R$^I$ is H, C$_1$-C$_4$ alkyl, CH$_2$CH$_2$OR$_{10}$, CH$_2$CH$_2$CH$_2$OR$_{10}$ where R$_{10}$ is CH$_3$ or CH$_3$CH$_2$; C$_3$-C$_4$ alkenyl; CH$_2$CN; CH$_2$CH$_2$CN; OCH$_3$ or OCH$_2$CH$_3$; R$^6$ is H, C$_1$-C$_2$ alkyl, CH$_2$CN or CH$_2$CH$_2$CN and R$_6$ and R$^I$ can be taken together to form —CH$_2$—$_4$.

27. A compound of claim 23 in which R$^{II}$ is H or C$_1$-C$_3$ alkyl.

28. A compound of claim 24 in which Z is CH; X is CH$_3$ or CH$_3$O; and Y is C$_1$-C$_2$ alkyl; C$_1$-C$_2$ alkyl substituted with OCH$_3$; OCH$_2$CH$_3$, CN or 1-3 atoms of F, Cl or Br,

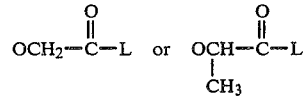

where L is NH$_2$, OH,

N(CH$_3$)$_2$, NHCH$_3$, C$_1$-C$_2$ alkoxy; SCN; N$_3$; NR$_{11}$R$_{12}$ where R$_{11}$ is H or CH$_3$; R$_{12}$ is H, CH$_3$, CH$_3$CH$_2$, OCH$_3$; OR$_9$ where R$_9$ is CH$_3$, CH$_3$CH$_2$, CH$_2$CH=CH$_2$, CH$_2$C≡CH, or C$_2$ alkyl substituted with 1-3 F, Cl or Br; CH$_3$S.

29. A compound of claim 23 in which A' is H, Cl or Br.

30. A compound of claim 29 in which Q is O or S and R$^I$ is C$_1$-C$_4$ alkyl, CH$_2$CH=CH$_2$ or CH$_2$CH$_2$Cl.

31. A compound of claim 29 in which Q is O and R$^I$ is CH$_2$CH$_2$OCH$_3$,

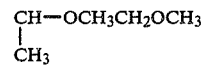

or CH$_2$OCH$_2$CH$_3$.

32. A compound of claim 29 in which Q is

and R$^I$ is H, C$_1$-C$_3$ alkyl, OCH$_3$ or OCH$_2$CH$_3$ and R$_6$ is H or C$_1$-C$_2$ alkyl.

33. A compound of claim 31 in which $R^{II}$ is H or $CH_3$.

34. A compound of claim 28 in which A' is H; Y is $CH_3$, $OCH_3$, $OCH_2CH_3$, $OCH_2CF_3$, $OCH_2CH=CH_2$ or $OCH_2C\equiv CH$.

35. A compound of claim 21 in which A is $$\underset{Q-R^I}{\overset{O}{\|}}$$

and Q is oxygen or sulfur and $R^I$ is $CH_3$ or $CH_2CH_3$; Q is $$-\underset{R_6}{\overset{}{N}}-$$

and and $R^I$ is H, $CH_3$ or $OCH_3$, $R_6$ is $CH_3$, and $R_1$ is

[structure]

and Y is $CH_3$ or $OCH_3$.

36. A compound of claim 35 in which Formula I is utilized.

37. A compound of claim 35 in which Formula I is utilized.

38. A compound of claim 35 in which Formula I is utilized.

39. A compound selected from

[structures I', II', III']

wherein
$R^I$ is H or M;
M is a cation of an alkali metal or of a tertiary amine of up to 12 carbon atoms;
W' is O or S;
A' is H, Cl, Br, $C_1$-$C_4$ alkyl, $OCH_3$, $NO_2$ or $CF_3$;
B is $$-SO_3N-\underset{\underset{R_4}{|}}{\overset{\overset{W}{\|}}{C}}-\underset{\underset{R_5}{|}}{N}-R_1 \text{ or } -SO_2-N=\underset{NH-R_1}{\overset{WR^{IV}}{\diagup}};$$

where
$R_4$ is H, $CH_3$; W is O or S;
$R_5$ is H, $CH_3$ or $CH_3O$; with the proviso that either $R_4$ or $R_5$ must be H;
$R^{IV}$ is $C_1$-$C_6$ alkyl or $C_3$-$C_4$ alkenyl;
$R_1$ is

[structures]

where
Z is CH or C—F
X is H, Cl, $-CH_3$, $-OCH_3$ or $-OCH_2CH_3$;
Y is H; Cl; $C_1$-$C_4$ alkyl; $C_1$-$C_4$ alkyl substituted with
$-OCH_3$, $-OC_2H_5$, $-CN$, $-CO_2CH_3$, $-CO_2C_2H_5$, $$\overset{O}{\underset{}{\|}}{C-L}$$

or 1-3 atoms of F, Cl, Br; $C_3$-$C_4$ alkenyl; $-O-(CH_2)_{n'}O-(C_1$-$C_3$ alkyl) where n' is 2 or 3'

$$-OCH_2\overset{O}{\underset{}{\|}}{C}-L;\ -O\underset{\underset{CH_3}{|}}{C}H\overset{O}{\underset{}{\|}}{C}-L;\ -OCH_2CH_2\overset{O}{\underset{}{\|}}{C}-L$$

where L is OH, $-NH_2$, $$-\underset{\underset{OCH_3}{|}}{N}CH_3,$$

$-NH(C_1$-$C_4$ alkyl), $-N(C_1$-$C_4$ alkyl)$_2$ or $C_1$-$C_6$ alkoxy; SCN; $-N_3$; $NR_{11}R_{12}$ where $R_{11}$ is H or $CH_3$ and $R_{12}$ is H, $-OCH_3$, $C_1$-$C_4$ alkyl, $C_3$-$C_6$ cycloalkyl, $C_3$-$C_4$ alkenyl, $C_2$-$C_3$ alkyl substituted with $OCH_3$ or $OC_2H_5$, $C_1$-$C_2$ alkyl substituted with $-CN$, $CO_2H$, $CO_2CH_3$ or $CO_2C_2H_5$, and $R_{11}$ and $R_{12}$ can be taken together to form $-CH_2CH_2CH_2CH_2-$ or $CH_2CH_2OCH_2CH_2-$; $-O-R_9$ where $R_9$ is $C_1$-$C_4$ alkyl, $C_2$-$C_4$ alkyl substituted with 1-3 atoms of F, Cl or Br, $C_1$-$C_2$ alkyl substituted with cyano, $C_3$-$C_4$ alkenyl, $-CH_2C\equiv CR_{13}$,

[structures]

$R_{13}$ is H, $CH_3$ or $CH_2Cl$; $SR_{14}$; where
$R_{14}$ is $C_1$-$C_4$ alkyl, allyl, propargyl or $C_1$-$C_2$ alkyl substituted with CN;
$X_1$ is H, Cl, $OCH_3$, $OCH_2CH_3$ or $CH_3$;
$Y_1$ is H, $OCH_3$ or $CH_3$; and
$X_{II}$ is O or $CH_2$.

40. A composition suitable for controlling the growth of undesired vegetation which comprises an effective amount of a compound of claim 1 and at least one of the following: surfactant, solid or liquid diluent.

41. A composition suitable for controlling the growth of undesired vegetation which comprises an effective amount of a compound of claim 2 and at least one of the following: surfactant, solid or liquid diluent.

42. A composition suitable for controlling the growth of undesired vegetation which comprises an effective amount of a compound of claim 3 and at least one of the following: surfactant, solid or liquid diluent.

43. A composition suitable for controlling the growth of undesired vegetation which comprises an effective amount of a compound of claim 4 and at least one of the following: surfactant, solid or liquid diluent.

44. A composition suitable for controlling the growth of undesired vegetation which comprises an effective amount of a compound of claim 5 and at least one of the following: surfactant, solid or liquid diluent.

45. A composition suitable for controlling the growth of undesired vegetation which comprises an effective amount of a compound of claim 6 and at least one of the following: surfactant, solid or liquid diluent.

46. A composition suitable for controlling the growth of undesired vegetation which comprises an effective amount of a compound of claim 7 and at least one of the following: surfactant, solid or liquid diluent.

47. A method for controlling the growth of undesired vegetation which comprises applying to the locus to be protected an effective amount of a compound of claim 1.

48. A method for controlling the growth of undesired vegetation which comprises applying to the locus to be protected an effective amount of a compound of claim 2.

49. A method for controlling the growth of undesired vegetation which comprises applying to the locus to be protected an effective amount of a compound of claim 3.

50. A method for controlling the growth of undesired vegetation which comprises applying to the locus to be protected an effective amount of a compound of claim 4.

51. A method for controlling the growth of undesired vegetation which comprises applying to the locus to be protected an effective amount of a compound of claim 5.

52. A method for controlling the growth of undesired vegetation which comprises applying to the locus to be protected an effective amount of a compound of claim 6.

53. A method for controlling the growth of undesired vegetation which comprises applying to the locus to be protected an effective amount of a compound of claim 7.

* * * * *